United States Patent
Lim et al.

(10) Patent No.: US 11,498,923 B2
(45) Date of Patent: Nov. 15, 2022

(54) SUBSTITUTED IMIDAZO[1,2-C]QUINAZOLINES AS A2A ANTAGONISTS

(71) Applicant: Merck Sharp & Dohme Corp., Rahway, NJ (US)

(72) Inventors: Yeon-Hee Lim, South San Francisco, CA (US); Gioconda V. Gallo-Etienne, Providence, NJ (US); Joseph Michael Kelly, Parlin, NJ (US); Michael Berlin, Flemington, NJ (US); Pauline Ting, New Providence, NJ (US); Hongwu Wang, Westfield, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/769,603

(22) PCT Filed: Dec. 10, 2018

(86) PCT No.: PCT/US2018/064649
§ 371 (c)(1),
(2) Date: Jun. 4, 2020

(87) PCT Pub. No.: WO2019/118313
PCT Pub. Date: Jun. 20, 2019

(65) Prior Publication Data
US 2021/0053973 A1    Feb. 25, 2021

Related U.S. Application Data

(60) Provisional application No. 62/597,962, filed on Dec. 13, 2017.

(51) Int. Cl.
C07D 487/04 (2006.01)
C07D 519/00 (2006.01)

(52) U.S. Cl.
CPC .......... *C07D 487/04* (2013.01); *C07D 519/00* (2013.01)

(58) Field of Classification Search
CPC .................................................. C07D 487/04
USPC ...................................................... 544/252
See application file for complete search history.

(56) References Cited

U.S. PATENT DOCUMENTS

| 5,565,460 | A | 10/1996 | Suzuki et al. |
| 6,630,475 | B2 | 10/2003 | Neustadt et al. |
| 6,897,217 | B2 | 5/2005 | Neustadt et al. |
| 7,572,802 | B2 | 8/2009 | Boyle et al. |
| RE44,205 | E | 5/2013 | Neustadt et al. |
| 8,435,994 | B2 * | 5/2013 | Harris .................. C07D 471/14 514/250 |
| 9,708,347 | B2 | 7/2017 | Ali et al. |
| 10,138,212 | B2 | 11/2018 | Ali et al. |
| 10,207,002 | B2 | 2/2019 | Gupta et al. |
| 10,472,347 | B2 | 11/2019 | Kuang et al. |
| 2012/0232086 | A1 | 9/2012 | Harris et al. |
| 2013/0184270 | A1 | 7/2013 | Liu |
| 2014/0110642 | A1 | 4/2014 | Stoessel et al. |
| 2018/0362530 | A1 | 12/2018 | Ali |

FOREIGN PATENT DOCUMENTS

| WO | 199501356 A1 | 1/1995 |
| WO | 199705138 A1 | 7/1996 |
| WO | 199852568 A1 | 11/1998 |

OTHER PUBLICATIONS

Antonioli, Luca et al., Immunity, inflammation and cancer: a leading role for adenosine, Nature Reviews Cancer, 2013, 842-857, 13.

Lukashev, Dmitriy et al., From "Hellstrom Paradox" to anti-adenosinergic cancer immunotherapy, Purinergic Signalling, 2007, 129-134, 3.

Suh, KJ, et al, EGFR or HER2 inhibition modulates the tumor microenvironment by suppression of PD-L1 and cytokines release, Oncotarget, 2017, 63901-63910, 8(38).

* cited by examiner

*Primary Examiner* — Douglas M Willis
(74) *Attorney, Agent, or Firm* — Sanjeev K. Mahanta; Alysia Finnegan

(57) ABSTRACT

Disclosed are compounds having the structure of Formula I, or a pharmaceutically acceptable salt of any thereof: wherein: "Z" and R1 are defined herein, which compounds are believed suitable for use in selectively antagonizing the A2a receptors, for example, those found in high density in the basal ganglia. Such compounds and pharmaceutical formulations are believed to be useful in treatment or management of neurodegenerative diseases, for example, Parkinson's disease, or movement disorders arising from use of certain medications used in the treatment or management of Parkinson's disease.

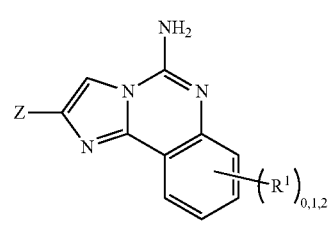

5 Claims, No Drawings

SUBSTITUTED IMIDAZO[1,2-C]QUINAZOLINES AS A2A ANTAGONISTS

CROSS-REFERENCE TO RELATED APPLICATIONS

This application is a U.S. National Phase application under 35 U.S.C. § 371 of PCT Application No. PCT/US2018/064649, filed Dec. 10, 2018, which published as WO2019/118313 A1 on Jun. 20, 2019 and claims priority under 35 U.S.C. § 365(b) from U.S. provisional patent application No. 62/597,962, filed Dec. 13, 2017.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Compounds which are selective antagonists for the $A_{2A}$ receptor specifically are of pharmacological interest because of their reduced level of side effects over A2a antagonists which effect a broader range of adenosine receptors. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in PCT International Application Publication No. WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the postsynaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

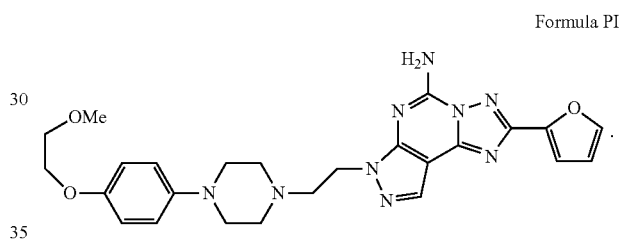

Formula PI

In the '475 patent example Schemes 1 to 5, along with preparative Schemes 1 to 4, show general methods of preparing compounds of Formula P. The '475 patent describes also that the compound of Formula I can be prepared as a pharmaceutically acceptable salt which may be useful for treating Parkinson's disease.

The use of $A_{2A}$ receptor antagonists in the potential treatment of central nervous system diseases, in particular Parkinson's disease, and to pharmaceutical compositions comprising said compounds has elevated the need for potent, moderately lipophilic, brain penetrant inhibitors of the $A_{2A}$ receptor. Such compounds would provide an expansion of the arsenal of compounds which are believed to have value in the treatment of central nervous system disorders, in particular treating or managing the progression of such diseases, for example, but not limited to, Parkinson's disease.

It has been shown that adenosine generated in the hypoxic environment of tumor cells can play a role in T-cell suppression preventing successful attack and rejection of solid tumors, and inhibition of A2a receptors in this environment, or genetic inactivation of A2aR receptors, leads to retardation of tumor growth and rejection of tumor tissue via suppression of the protective effect exerted by high levels of adenosine interacting with receptors on the surface of T-cells. See for example, Lukashev, D. et al., *Purinergic Signalling* (2007) 3:129-134; Antonioli, L. et al. *Nat. Rev. Cancer* (2013) 13:842-857.

SUMMARY OF THE INVENTION

In one aspect, the invention provides compounds, or pharmaceutically acceptable salts thereof, of Formula Ia:

Formula Ia

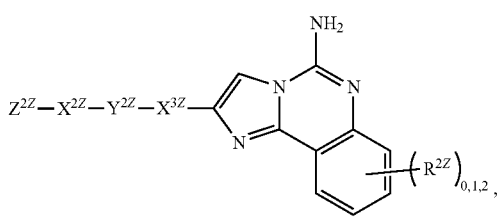

wherein:
$R^{2Z}$, if present, is selected independently for each occurrence from:
(1) $R^{2Za}_3C-O-$, wherein R is —H or —F;
(2) halo;
(3) heterocyclic, which is optionally substituted with alkyl or oxo
$X^{3Z}$ is $X^{3Za}-(CH_2)_{0-2}-$, wherein $X^{3Za}$ is selected from the group consisting of:
(1) —C(O)—; (2) —(CH$_2$)$_{0-2}$—NR'—, wherein R' is —H or a linear or branched alkyl of up to 4 carbon atoms;
(3) —C(O)—(CH$_2$)$_{0-2}$—NR'—, wherein R' is —H or a linear or branched alkyl of up to 4 carbon atoms; or (4) —(CH$_2$)$_{0-2}$—O—;
$Y^{2Z}$ is selected from the group consisting of:
(1) aryl; (2) heteroaryl; or (3) non-aromatic heterocyclic;
$X^{2Z}$ is selected from the group consisting of:
(1) a bond; (2) —(CH$_2$)$_{1-2}$—; (3) —O—; (4) —C(O)—(CH$_2$)$_{1-2}$—; (5) —C(O)—O—(CH$_2$)$_{1-2}$—; (6) —(CH$_2$)$_{0-2}$—C(O)NR"—(CH$_2$)$_{0-2}$— wherein R" is hydrogen or a linear or branched alkyl of up to 3 carbon atoms; or (7) —(CH$_2$)$_{0-2}$— NR"—C(O) (CH$_2$)$_{0-2}$— wherein R" is hydrogen or a linear or branched alkyl of up to 3 carbon atoms;
$Z^{2Z}$ is selected from the group consisting of:
(1) hydrogen; (2) halogen; (3) —OH; (4) linear or branched alkyl of up to 3 carbon atoms which is optionally substituted with halogen; (5) —NR'R", wherein R' and R" are independently hydrogen or a linear or branched alkyl of up to 3 carbon atoms; (6) aryl or a fused-ring aromatic moiety comprising up to 10 carbon atoms which is optionally substituted with
(a) halogen; (b) a linear or branched alkyl of up to 3 carbon atoms; (c) —CN; (d) a cycloalkyl comprising up to 8 carbon atoms in the ring; or (e) —O—(CH$_2$)$_{1-3}$—;
(7) heteroaryl which is optionally substituted with: (a) halogen; (b) linear or branched alkyl of up to 3 carbon atoms; (c) —CN; (d) a cycloalkyl of up to 8 ring carbon atoms; or (e) —O—(CH$_2$)$_{1-3}$—;
(8) a non-aromatic heterocyclic moiety comprising up to 10 ring carbon atoms which may include bridging carbon atoms and which is optionally substituted with:
(a) —C(O)—(CH$_2$)$_{1-3}$—H; (b) linear or branched alkyl of up to 3 carbon atoms which is optionally substituted with halogen or —OH; (c) )—O—(CH$_2$)$_{1-3}$—H; (d) oxo; (e) —C(O)NR'R", wherein R' and R" are independently hydrogen or a linear or branched alkyl of up to 3 carbon atoms; (f) —C(O)—O—(CH$_2$)$_{1-3}$—H; (g) H(CH$_2$)$_{1-3}$—C(O)NR"— wherein R" is hydrogen or a linear or branched alkyl of up to 3 carbon atoms; or
(9) heteroaryl, optionally substituted with:
(a) halogen; (b) —O—(CH$_2$)$_{1-3}$—H, which is optionally substituted with halogen; (c) —(CH$_2$)$_{1-3}$—H, which is optionally substituted with halogen; (d) —CN; or (e) a cycloalkyl comprising up to 8 ring carbon atoms.

In one aspect, the invention provides compounds, or pharmaceutically acceptable salts thereof, of Formula I:

Formula I

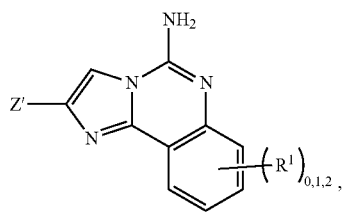

wherein:
$R^1$, if present, is selected independently for each occurrence from:
(1) $R^{1a}_3C-O-$, wherein $R^{1a}$ is —H or —F;
(2) fluoro;
(3) bromo;
(4) morpholino;
(5) a moiety of the formula:

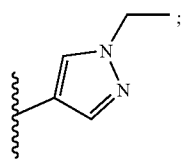 [SMILES: *c1cnn(CC)c1]

(6) a moiety of the formula:

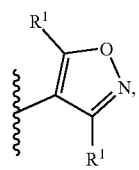

wherein, both of $R^1$ are either —H or methyl;
(7) a moiety of the formula:

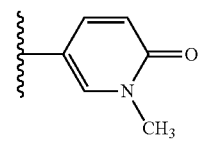

and $Z^1$ is:
(1) a moiety of the formula:

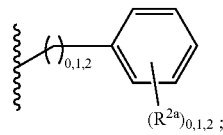

wherein, if present, $R^{2a}$ is independently for each occurrence:

(A)

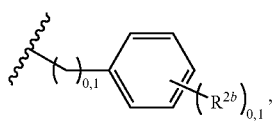

wherein, if present, $R^{2b}$ is:
(i) —O—CH$_3$; or (ii)

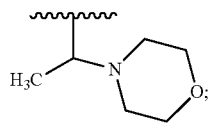 [SMILES: *C(C)N1CCOCC1]

(B) a linear or branched alkyl of up to 5 carbon atoms which is optionally substituted on one or more carbons thereof with one or more of:
(i) —F; (ii) 4-morpholine; or (iii) —OH, and in some embodiments, when selected to be a substituted alkyl, the alkyl is preferably —CH$_2$—OH, —CF$_3$, or

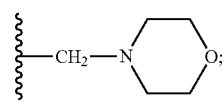

(C) —OH;
(D) Halogen, and in some embodiments, when selected to be halogen, is preferably: —Br, —Cl or —F;
(E) —N($R^{2c}$)$_2$, wherein $R^{2c}$ is independently for each occurrence —H or —CH$_3$;
(F)

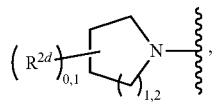

wherein, if present, $R^{2d}$ is 4-morpholine;
(G)

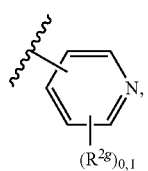

wherein $R^{2g}$, if present, is:
(i) —F; (ii) —CF$_3$; or (iii) 4-morpholine;
(H)

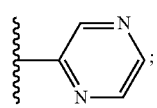

(I)

(J)

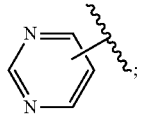

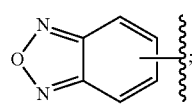

(K) a moiety of the formula:

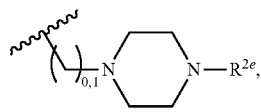

wherein $R^{2e}$ is:
(i) —CH$_2$—C(O)—CH$_3$;
(ii)

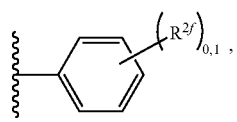

wherein, if present, $R^{2f}$ is —O—(CH$_2$)$_2$—O—CH$_3$; or
(iii)

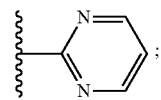

or
(iv)

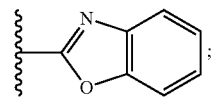

(L) —C(O)—$R^{2i}$ wherein, $R^{2i}$ is:

(i)

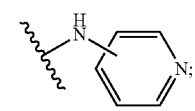

(ii)

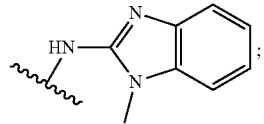

-continued (iii)
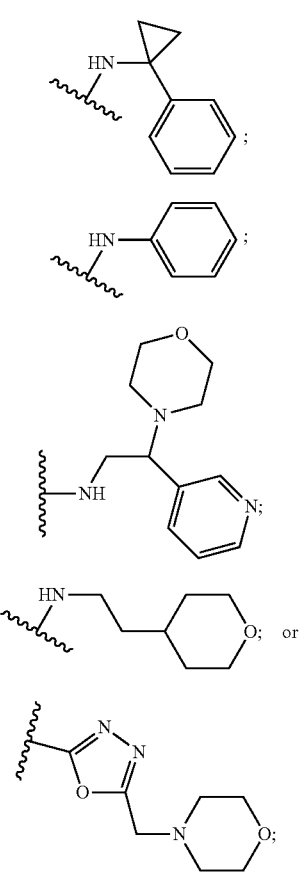

(iv)

(v)

(vi) or (vii)

(2) a moiety of the Formula:

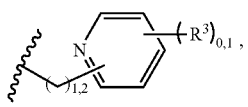

wherein, if present, $R^3$ is:
(A) linear, branched or cyclic alkyl of up to 4 carbon atoms, and in some embodiments, when selected to be alkyl, is preferably methyl;
(B) halogen, and if selected to be halogen, in some embodiments is preferably —Cl or —F;
(C)

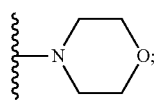

(D)

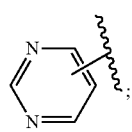

(E)

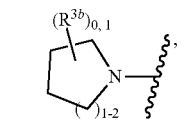

wherein, if present, $R^{3b}$ is aryl;
(F)

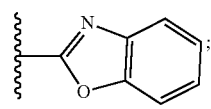 [SMILES: *c1nc2ccccc2o1]

wherein $R^{3a}$ is: (i) —CH$_3$; (ii) —C(O)—CH$_3$; or
(iii)

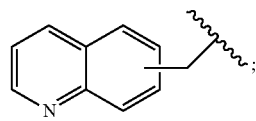

or
(3)

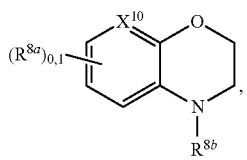

(4)

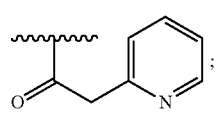 [SMILES: *C(=O)Cc1ccccn1]

wherein:
(A) $X^{10}$ is —CH═, $R^{8a}$ is present and is a bond from any available ring carbon to the 2-position of the imidazo[1,2-c]quinazolin-5-amine portion of the structure of Formula I, and $R^{8b}$ is:

or
(B) $X^{10}$ is selected from ═CH— or ═N—, $R^{8b}$ is a bond to the 2-position of the imidazo[1,2-c]quinazolin-5-amine portion of the structure of Formula I and $R^{8a}$ is not present; or (5)

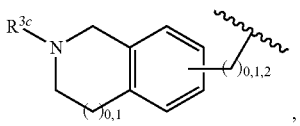, wherein $R^{3c}$ is:
(A) —H;
(B) —C(O)—$R^{3d}$, wherein $R^{3d}$ is: (i) —CRF3; (ii) —CH3; or
(iii)

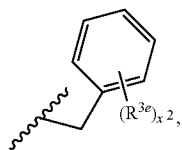

wherein: $x^2$ is 0, 1 or 2, and $R^{3e}$, if present, is (ai) —CN; or (aii) —F; or (C)

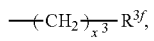

wherein: $x^3$ is 0, 1 or 2 and $R^{3f}$ is:
(i) —CH$_3$; or (ii)

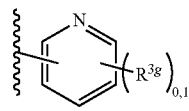

bonded via any available ring carbon, wherein $R^{3g}$, if present, is —CN; or (iii) aryl;

(6)

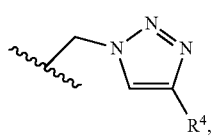

wherein $R^4$ is:
(A)

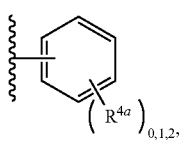

wherein $R^{4a}$, if present, is (i) —CF$_3$; (ii) —O—CF$_3$; (iii) —O—CH$_3$; (iv)

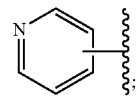

(B) —CH$_2$—O—C(O)—CH$_3$;
(C)

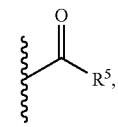

or
(D)

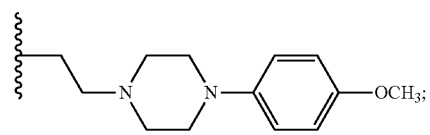 [SMILES: *CCN1CCN(c2ccc(OC)cc2)CC1]

(7)

wherein $R^5$ is:
(A)

(B) —N($R^{5b}$)$_2$, wherein $R^{5b}$ is independently for each occurrence:
(i) —H;
(ii) linear, branched or cyclic alkyl of up to 6 carbon atoms, which is optionally substituted on one or more carbon atoms thereof with:
(a) pyridine, which may be optionally substituted with methyl or bromine;
(b) morpholine, bonded via the ring nitrogen;
(c) pyridine, which may optionally be substituted on a ring carbon thereof with one or more of (bi) halogen, and in some embodiments when selected to be halogen is preferably —Br; or (bii) linear or branched alkyl of up to 4 carbon atoms, and in some embodiments when selected to be alkyl is preferably methyl;
and in some embodiments when selected to be alkyl or substituted alkyl, said alkyl is preferably: (ai) —CH$_3$; (aii)

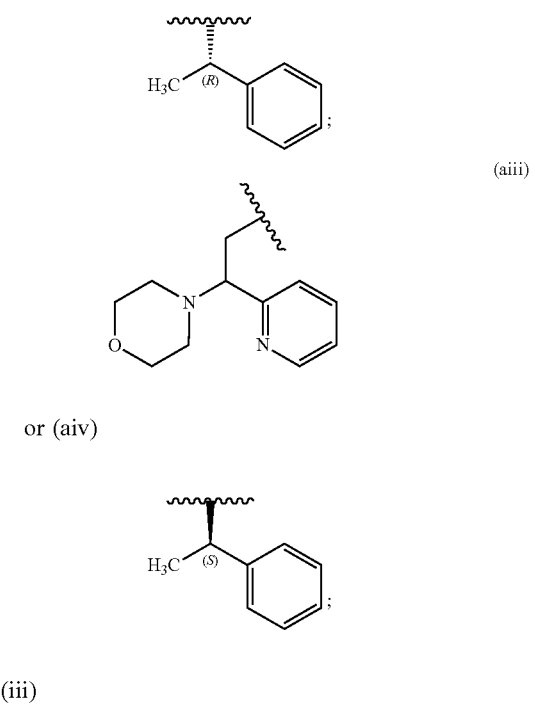

or (aiv)

(iii)

(iv) a moiety of the formula:

wherein R is:

(a)

(b) a moiety of the formula:

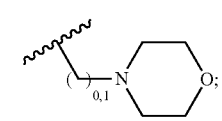

wherein $R^{5d}$ is: (ai) —H; (aii) —(CH$_2$)$_3$—OH; (aiii) —C(O)—C($R^{5da}$)$_3$; wherein $R^{5da}$ is independently for each occurrence —H or —CH$_3$; (aiv) pyridine; or (av) a moiety of the formula:

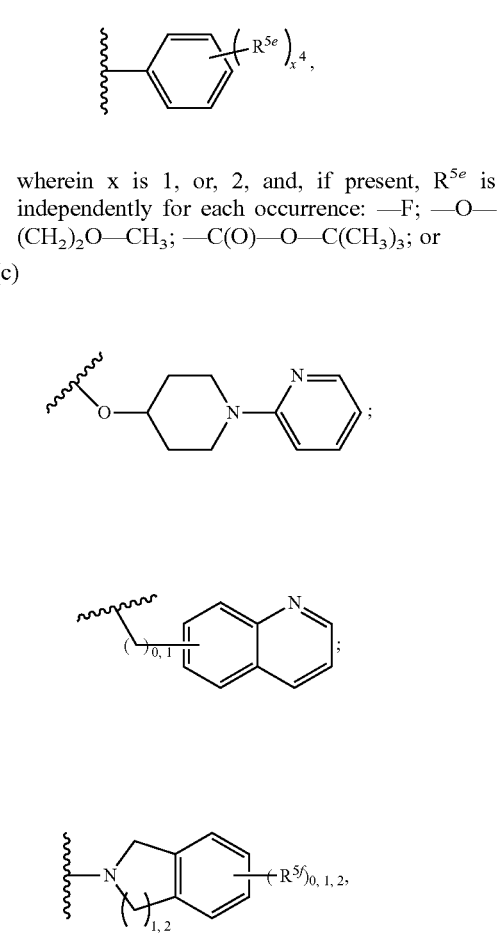

wherein x is 1, or, 2, and, if present, $R^{5e}$ is independently for each occurrence: —F; —O—(CH$_2$)$_2$O—CH$_3$; —C(O)—O—C(CH$_3$)$_3$; or (c)

(v)

(C)

wherein $R^{5f}$, if present, is independently for each occurrence:
(i) halogen, and when selected to be halogen, in some embodiments is preferably —Br;
(ii) —NH—C(O)—$R^{5n}$, wherein $R^{5n}$ is —CH$_3$ or pyridine;
(iii) a moiety of the formula:

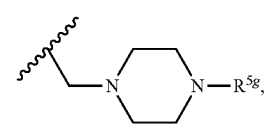

wherein $R^{5g}$ is a moiety of the formula:

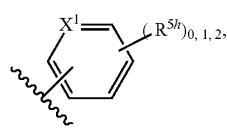

wherein $X^1$ is —N═, or —CH═ and if present $R^{5h}$ is independently for each occurrence —F;

(iv)

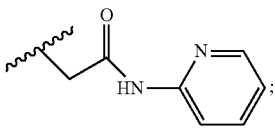 [SMILES: *CC(=O)Nc1ccccn1]

or
(v)

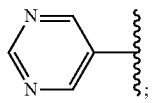

or (vi)

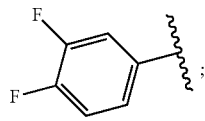 [SMILES: *c1ccc(F)c(F)c1]

(D)

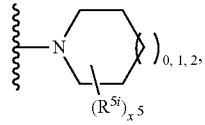

wherein $x^5$ is 0, 1 or 2, and wherein $R^{5i}$, if present, is independently for each occurrence:
  (i) halogen, and if selected to be halogen, in some embodiments is preferably —F;
  (ii) —OCH$_3$;
  (iii) linear or branched alkyl of up to 6 carbon atoms, and when selected to be alkyl, in some embodiments is preferably —CH$_3$ or isopropyl, and wherein said alkyl is optionally substituted on one or more carbons thereof with one or more substituents which are selected from:
    (a) —F; (b) —CF$_3$; (c) —OH; (d) —C(O)—N(R$^{5j}$)$_2$, wherein R$^{5j}$ is independently for each occurrence —H, —CH$_2$—CH$_3$; or
    (e) —C(O)—O—CH$_3$;
and wherein, when x=2 and both $R^{5i}$ are bonded to the same carbon atom, the two $R^{5i}$ may be taken together with the cycloamine to which they are bonded to form:
  (E) a carbonyl group, thereby providing a moiety of the formula:

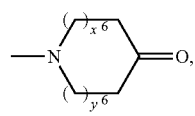

wherein one of $x^6$ and $y^6$ is 0 or 1 and the other is 1 or 2;

(F) an azaspirocycloalkyl moiety of the formula:

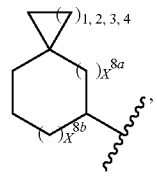

wherein $x^{8a}$ and $x^{8b}$ are independently 0, 1, or 2 and the sum of $x^{8a}$ and $x^{8b}$ is 4 or less;
(G) an oxa-azaspiro moiety or diazaspiro moiety of the formula:

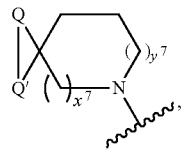

wherein, $x^7$=1 or 2, $y^7$=0 or 1, and $x^7+y^7 \geq 1$, and Q-Q' is:
  (i) —O—(CH$_2$)$_3$—; (ii) —O—CH$_2$—CH$_2$—C(CH$_3$)$_2$—; (iii) —(CH$_2$—O—CH$_2$); (iii) —CH$_2$—O—(CH$_2$)$_2$—; (iv) —O—(CH$_2$)$_4$—; (v) —O—(CH$_2$)$_2$—O—; (vi) —(CH$_2$)$_2$—C(O)—O—; (vii) —(C(R$^{7a}$)$_2$)$_2$—O—C(O)—, wherein R$^{7a}$ is independently for each occurrence —H or —CH$_3$; or (viii) —(CH$_2$)$_2$—Y$^{11}$—(CH$_2$)$_{1,2}$—, wherein, Y$^{11}$ is —N(R$^{5k}$)— or —N$^+$(R$^{5k}$)$_2$—, and R$^{5k}$ is independently for each occurrence:
    (a) —H; (b) linear or branched alkyl of up to 4 carbon atoms; (c) (CH$_3$)$_3$C—O—C(O)—; (d) CH$_3$—C(O)—; (e) —(C(O))$_{0,1}$—(CH$_2$)$_{1,2}$-aryl, wherein said aryl is optionally substituted with one or more substituents which are independently —F or —CN; or (avi) CH$_3$—C(O)—;
and wherein, when x=2 and each $R^{5i}$ is bonded to a different carbon atom, including adjacent carbon atoms, both $R^{5i}$ may be taken together with the cycloamine to which they are bonded, comprises a 5, 6, or 7 member cycloamine ring fused with or bridged by a 3, 4, 5, or 6-member alkyl ring thereby providing a fused-bicyclo structure or a bridged bicyclo structure wherein said two $R^{5i}$ together have the formula:
  (H) (—CH$_2$—)$_{x9}$ wherein "$x^9$" is 1, 2, 3, or 4;
  (I) [—(CH$_2$)$_{1,2}$—O—]; (l) —CH$_2$—SO$_2$—CH$_2$—; or
  (J) —CH$_2$—CH$_2$—, and wherein, one or more carbon atoms in said moiety may optionally be substituted with an alkyl or alkoxy moiety comprising up to four carbon atoms;
(K)

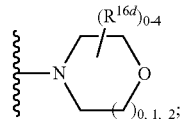

wherein, if present, $R^{16d}$ is independently for each occurrence a linear, branched or cyclic alkyl of up to 6 carbon atoms which is optionally substituted on one or more carbon atoms thereof with —F, and when present, in some embodiments is preferably —CH$_3$, isopropyl, or —CF$_3$ (L)

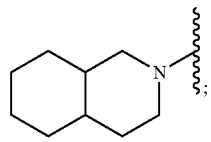 [SMILES: *N1CCC2CCCCC2C1]

(M)

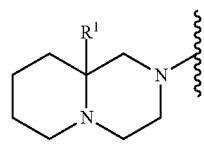

wherein R1 is: (a) ⵎ; or (b) ⵎ

(N) a moiety of the formula:

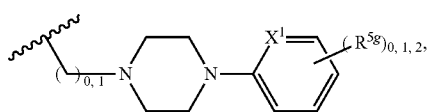

wherein $X^1$ is —N=, or —CH= and if present $R^{5g}$ is independently for each occurrence —F or

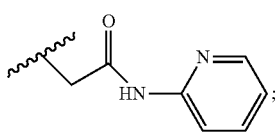

(8)

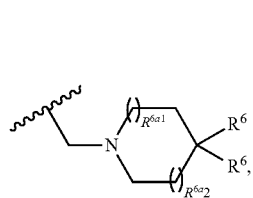

wherein: $R^{6a1}$ and $R^{6a2}$ are both 1 or both 2, and each $R^6$ is independently: (A) —H; (B) —OH; (C) —CH$_3$; (D) aryl which is optionally substituted on one or more ring carbon atoms with chlorine; or (E) —CH$_2$-aryl;

(9)

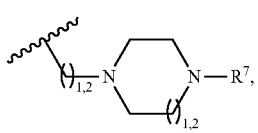

wherein $R^7$ is:
(A) CH$_2$—CH$_3$;
(B)

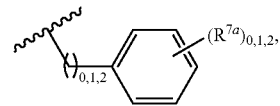

wherein, if present, $R^{7a}$ is independently for each occurrence from;
(i) —F; or (ii)

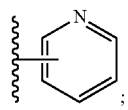

or (C)

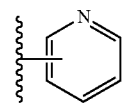

(10)

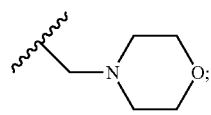

(11)

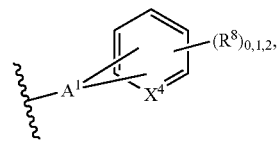

wherein, $X^4$ is —N= or —CH=, if present) $R^8$ is independently for each occurrence: (A) a halogen, and when selected to be a halogen, in some embodiments is preferably —F or —Br; (B) pyrimidine, which is bonded via one of carbon positions 2, 4, 5 or 6; (C) aryl, which is optionally substituted with one or two —F; (D) —NH—C(O)—R$^{8a}$, or —CH$_2$—C(O)—NH—R$^{8a}$, wherein R$^{8a}$ is:
(i) —CH$_3$; or (ii) pyridine; and
$A^1$ is a moiety bonded between two adjacent ring carbons which is of the formula selected from:

(A)

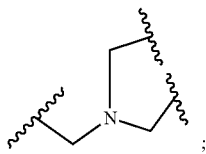

-continued (B)
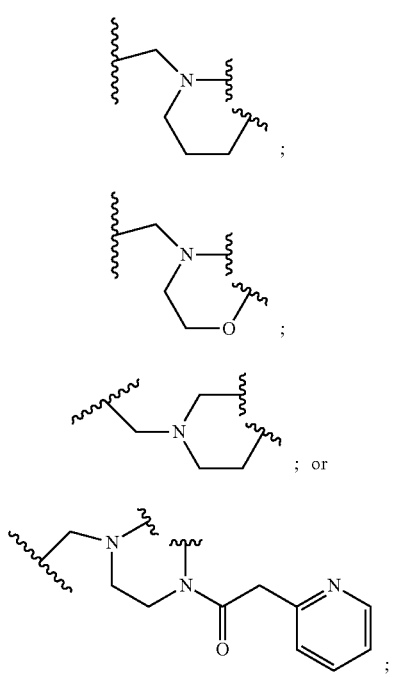

(12)

or
(13)

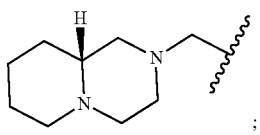

wherein R[9] is: (A) —H; (B)

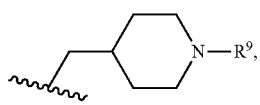

(C)

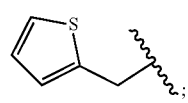

wherein, if present, R[9b] is —OCH$_3$ or —CH$_3$;

(D)
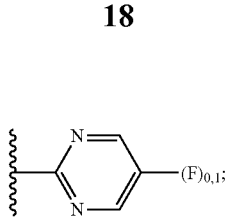

(E)
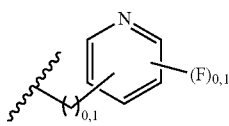

(F)
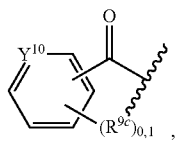

wherein, Y[10] is —CH= or —N=, and if present, R[9c] is —CH$_3$, methoxy, —F, or —Br;

(G) —CH$_2$R[9a], wherein R[9a] is (i) a linear, branched or cyclic alkyl of up to 4 carbon atoms; or (ii) a cyclic alkyl comprising an alkyl ring of up to 5 carbon atoms;

(H)
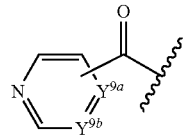

wherein, one of Y[9a] and Y[9b] is —CH= and the other is —N=; or (I)
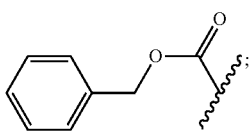

(14)

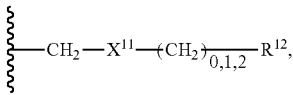

wherein, X[11] is —O— or —N(R[11a])—, and R[11a] is (A) aryl which is optionally substituted with one or two of (i) —F; (ii) —Cl; or (iii) —OH; or (B) pyridine; or (15)

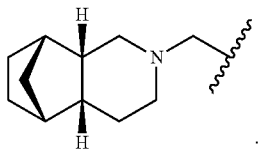 [SMILES: *CN1CC[C@@H]2[C@@H]3CC[C@@H](C3)[C@@H]2C1]

In some embodiments the present invention is a compound, or a pharmaceutically acceptable salt thereof, selected from:
2-benzyl-7-methoxyimidazo[1,2-c]quinazolin-5-amine;
2-benzylimidazo[1,2-c]quinazolin-5-amine;
2-benzyl-8-methoxyimidazo[1,2-c]quinazolin-5-amine;
2-benzyl-9-methoxyimidazo[1,2-c]quinazolin-5-amine;
2-benzyl-10-methoxyimidazo[1,2-c]quinazolin-5-amine;
2-benzyl-7-fluoroimidazo[1,2-c]quinazolin-5-amine;
2-benzyl-8-fluoroimidazo[1,2-c]quinazolin-5-amine;
2-benzyl-9-fluoroimidazo[1,2-c]quinazolin-5-amine;
2-benzyl-10-fluoroimidazo[1,2-c]quinazolin-5-amine;
2-benzyl-7-(trifluoromethoxy)imidazo[1,2-c]quinazolin-5-amine;
2-benzyl-8-fluoro-7-methoxyimidazo[1,2-c]quinazolin-5-amine;
2-benzyl-10-bromo-7-fluoroimidazo[1,2-c]quinazolin-5-amine;
2-benzyl-9-fluoro-8-morpholinoimidazo[1,2-c]quinazolin-5-amine;
2-(2-(trifluoromethyl)benzyl)imidazo[1,2-c]quinazolin-5-amine;
2-(quinolin-8-ylmethyl)imidazo[1,2-c]quinazolin-5-amine;
7-methoxy-2-(quinolin-8-ylmethyl)imidazo[1,2-c]quinazolin-5-amine;
7-methoxy-2-(2-(trifluoromethyl)benzyl)imidazo[1,2-c]quinazolin-5-amine;
2-(2,4-difluorobenzyl)-7-methoxyimidazo[1,2-c]quinazolin-5-amine;
7-methoxy-2-(2-morpholinobenzyl)imidazo[1,2-c]quinazolin-5-amine;
2-(2-(dimethylamino)benzyl)-7-methoxyimidazo[1,2-c]quinazolin-5-amine;
2-(4-fluorobenzyl)-7-methoxyimidazo[1,2-c]quinazolin-5-amine;
2-(3-fluorobenzyl)-7-methoxyimidazo[1,2-c]quinazolin-5-amine;
2-(2,6-dichlorobenzyl)-7-methoxyimidazo[1,2-c]quinazolin-5-amine;
2-([1,1'-biphenyl]-3-ylmethyl)-7-methoxyimidazo[1,2-c]quinazolin-5-amine;
2-(2-(morpholinomethyl)benzyl)imidazo[1,2-c]quinazolin-5-amine;
7-methoxy-2-(2-(morpholinomethyl)benzyl)imidazo[1,2-c]quinazolin-5-amine;
2-([1,1'-biphenyl]-2-ylmethyl)-7-fluoroimidazo[1,2-c]quinazolin-5-amine;
7-methoxy-2-(3-morpholinobenzyl)imidazo[1,2-c]quinazolin-5-amine;
7-methoxy-2-(2-(pyrrolidin-1-yl)benzyl)imidazo[1,2-c]quinazolin-5-amine;
7-methoxy-2-(2-morpholino-5-(trifluoromethyl)benzyl)imidazo[1,2-c]quinazolin-5-amine;
2-((5-amino-7-methoxyimidazo[1,2-c]quinazolin-2-yl)methyl)-3-fluorophenol;
7-fluoro-2-(quinolin-8-ylmethyl)imidazo[1,2-c]quinazolin-5-amine;
7-fluoro-2-(3-(morpholinomethyl)benzyl)imidazo[1,2-c]quinazolin-5-amine;
2-(3-benzylbenzyl)-7-fluoroimidazo[1,2-c]quinazolin-5-amine;
7-fluoro-2-(2-(morpholinomethyl)benzyl)imidazo[1,2-c]quinazolin-5-amine;
7-methoxy-2-(2-(piperidin-1-yl)benzyl)imidazo[1,2-c]quinazolin-5-amine;
2-((5-amino-7-fluoroimidazo[1,2-c]quinazolin-2-yl)methyl)-4-fluorophenol;
2-((2-chloropyridin-3-yl)methyl)-7-methoxyimidazo[1,2-c]quinazolin-5-amine;
7-methoxy-2-((6-morpholinopyridin-3-yl)methyl)imidazo[1,2-c]quinazolin-5-amine;
7-methoxy-2-((2-morpholinopyridin-4-yl)methyl)imidazo[1,2-c]quinazolin-5-amine;
7-methoxy-2-(4-morpholinobenzyl)imidazo[1,2-c]quinazolin-5-amine;
2-((2-fluoropyridin-3-yl)methyl)-7-methoxyimidazo[1,2-c]quinazolin-5-amine;
7-methoxy-2-((2-morpholinopyridin-3-yl)methyl)imidazo[1,2-c]quinazolin-5-amine;
1-(4-(4-((5-amino-7-methoxyimidazo[1,2-c]quinazolin-2-yl)methyl)phenyl)piperazin-1-yl)ethan-1-one;
1-(4-(5-((5-amino-7-methoxyimidazo[1,2-c]quinazolin-2-yl)methyl)pyridin-2-yl)piperazin-1-yl)ethan-1-one;
1-(4-(4-((5-amino-7-methoxyimidazo[1,2-c]quinazolin-2-yl)methyl)pyridin-2-yl)piperazin-1-yl)ethan-1-one;
1-(6-((5-amino-7-fluoroimidazo[1,2-c]quinazolin-2-yl)methyl)-3,4-dihydroisoquinolin-2(1H)-yl)ethan-1-one;
1-(7-((5-amino-7-fluoroimidazo[1,2-c]quinazolin-2-yl)methyl)-3,4-dihydroisoquinolin-2(1H)-yl)ethan-1-one;
7-methoxy-2-((2-(pyrrolidin-1-yl)pyridin-3-yl)methyl)imidazo[1,2-c]quinazolin-5-amine;
7-methoxy-2-((2-(piperidin-1-yl)pyridin-3-yl)methyl)imidazo[1,2-c]quinazolin-5-amine;
7-methoxy-2-((2-(4-methylpiperazin-1-yl)pyridin-3-yl)methyl)imidazo[1,2-c]quinazolin-5-amine;
7-fluoro-2-((1,2,3,4-tetrahydroisoquinolin-5-yl)methyl)imidazo-[1,2-c]quinazolin-5-amine;
1-(5-((5-amino-7-fluoroimidazo[1,2-c]quinazolin-2-yl)methyl)-3,4-dihydroisoquinolin-2(1H)-yl)ethan-1-one;
6-(5-((5-amino-7-fluoroimidazo[1,2-c]quinazolin-2-yl)methyl)-3,4-dihydroisoquinolin-2(1H)-yl)nicotinonitrile;
3-(2-(5-((5-amino-7-fluoroimidazo[1,2-c]quinazolin-2-yl)methyl)-3,4-dihydroisoquinolin-2(1H)-yl)-2-oxoethyl)benzonitrile;
7-fluoro-2-((2-propyl-1,2,3,4-tetrahydroisoquinolin-5-yl)methyl)imidazo-[1,2-c]quinazolin-5-amine;
7-fluoro-2-((2-(2-(pyridin-2-yl)ethyl)-1,2,3,4-tetrahydroisoquinolin-5-yl)methyl)imidazo[1,2-c]quinazolin-5-amine;
7-fluoro-2-((2-(pyridin-2-ylmethyl)-1,2,3,4-tetrahydroisoquinolin-5-yl)methyl)imidazo[1,2-c]quinazolin-5-amine;
1-(5-((5-amino-7-methoxyimidazo[1,2-c]quinazolin-2-yl)methyl)-3,4-dihydroisoquinolin-2(1H)-yl)-2-(3,4-difluorophenyl)ethan-1-one;
1-(5-((5-amino-7-methoxyimidazo[1,2-c]quinazolin-2-yl)methyl)-3,4-dihydroisoquinolin-2(1H)-yl)-4,4,4-trifluorobutan-1-one;
5-(5-amino-2-benzyl-7-fluoroimidazo[1,2-c]quinazolin-10-yl)-1-methylpyridin-2(1H)-one;
7-methoxy-2-((2-(4-phenylpiperidin-1-yl)pyridin-3-yl)methyl)imidazo[1,2-c]quinazolin-5-amine;
2-((2-(4-(benzo[d]oxazol-2-yl)piperazin-1-yl)pyridin-4-yl)methyl)-7-fluoroimidazo[1,2-c]quinazolin-5-amine;
1-(4-(4-((5-amino-7-methoxyimidazo[1,2-c]quinazolin-2-yl)methyl)pyridin-2-yl)piperazin-1-yl)ethan-1-one;
2-((2-benzylisoindolin-5-yl)methyl)-7-fluoroimidazo[1,2-c]quinazolin-5-amine;

7-methoxy-2-(2-((4-(4-(2-methoxyethoxy)phenyl)piper-azin-1-yl)methyl)benzyl)imidazo[1,2-c]quinazolin-5-amine;
7-methoxy-2-(2-((4-phenylpiperazin-1-yl)methyl)benzyl)imidazo[1,2-c]quinazolin-5-amine;
7-methoxy-2-(3-((4-phenylpiperazin-1-yl)methyl)benzyl)imidazo[1,2-c]quinazolin-5-amine;
7-methoxy-2-(4-((4-phenylpiperazin-1-yl)methyl)benzyl)imidazo[1,2-c]quinazolin-5-amine;
7-fluoro-2-(2-((4-(pyrimidin-2-yl)piperazin-1-yl)methyl)benzyl)imidazo[1,2-c]quinazolin-5-amine;
2-(2-((4-(benzo[d]oxazol-2-yl)piperazin-1-yl)methyl)benzyl)-7-fluoroimidazo[1,2-c]quinazolin-5-amine;
7-fluoro-2-(2-((4-morpholinopiperidin-1-yl)methyl)benzyl-)imidazo[1,2-c]quinazolin-5-amine;
7-fluoro-2-(3-(pyridin-3-yl)benzyl)imidazo[1,2-c]quinazolin-5-amine;
7-fluoro-2-((4'-(1-morpholinoethyl)-[1,1'-biphenyl]-3-yl)methyl)imidazo[1,2-c]quinazolin-5-amine;
7-fluoro-2-(4-(5-fluoropyridin-2-yl)benzyl)imidazo[1,2-c]quinazolin-5-amine;
2-(3-(benzo[c][1,2,5]oxadiazol-5-yl)benzyl)-7-fluoroimidazo[1,2-c]quinazolin-5-amine;
7-fluoro-2-((4'-methoxy-[1,1'-biphenyl]-4-yl)methyl)imidazo[1,2-c]quinazolin-5-amine;
2-(2-fluoro-6-(6-(trifluoromethyl)pyridin-3-yl)benzyl)-7-methoxyimidazo[1,2-c]quinazolin-5-amine;
7-methoxy-2-((2-(pyrimidin-5-yl)pyridin-3-yl)methyl)imidazo[1,2-c]quinazolin-5-amine;
7-fluoro-2-(5-fluoro-2-(pyrimidin-5-yl)benzyl)imidazo[1,2-c]quinazolin-5-amine;
7-fluoro-2-(4-(pyrazin-2-yl)benzyl)imidazo[1,2-c]quinazolin-5-amine;
7-fluoro-2-(5-fluoro-2-(2-morpholinopyridin-4-yl)benzyl)imidazo[1,2-c]quinazolin-5-amine;
4-((5-amino-7-fluoroimidazo[1,2-c]quinazolin-2-yl)methyl)-N-(pyridin-2-yl)benzamide;
3-((5-amino-7-fluoroimidazo[1,2-c]quinazolin-2-yl)methyl)-N-(pyridin-2-yl)benzamide;
5-amino-7-fluoro-2-(4-((1-methyl-1H-benzo[d]imidazol-2-yl)carbamoyl)benzyl)imidazo[1,2-c]quinazolin-6-ium formate;
4-((5-amino-7-fluoroimidazo[1,2-c]quinazolin-2-yl)methyl)-N-(1-phenylcyclopropyl)benzamide;
4-((5-amino-7-fluoroimidazo[1,2-c]quinazolin-2-yl)methyl)-N-(2-morpholino-2-(pyridin-3-yl)ethyl)benzamide;
4-((5-amino-7-methoxyimidazo[1,2-c]quinazolin-2-yl)methyl)-N-phenylbenzamide;
4-((5-amino-7-fluoroimidazo[1,2-c]quinazolin-2-yl)methyl)-N-(2-morpholinoethyl)benzamide;
7-fluoro-2-(4-(5-(morpholinomethyl)-1,3,4-oxadiazol-2-yl)benzyl)imidazo[1,2-c]quinazolin-5-amine;
1-(8-((5-amino-7-fluoroimidazo[1,2-c]quinazolin-2-yl)methyl)-2,3-dihydro-4H-benzo[b][1,4]oxazin-4-yl)-2-(pyridin-2-yl)ethan-1-one;
7-methoxy-2-((4-(4-methoxyphenyl)-1H-1,2,3-triazol-1-yl)methyl)imidazo[1,2-c]quinazolin-5-amine;
2-(4-(3,5-bis(trifluoromethyl)phenyl)-1H-1,2,3-triazol-1-yl)methyl)-7-fluoroimidazo[1,2-c]quinazolin-5-amine;
7-fluoro-2-((4-(4-(trifluoromethoxy)-phenyl)-1H-1,2,3-triazol-1-yl)methyl)-imidazo[1,2-c]-quinazolin-5-amine;
7-fluoro-2-((4-(pyridin-3-yl)-1H-1,2,3-triazol-1-yl)methyl)imidazo[1,2-c]quinazolin-5-amine;
7-fluoro-2-((4-(2-(4-(4-methoxyphenyl)piperazin-1-yl)ethyl)-1H-1,2,3-triazol-1-yl)methyl)imidazo[1,2-c]quinazolin-5-amine;
7-fluoro-2-((4-(4-(pyridin-3-yl)phenyl)-1H-1,2,3-triazol-1-yl)methyl)imidazo[1,2-c]quinazolin-5-amine;
(1-((5-amino-7-methoxyimidazo[1,2-c]quinazolin-2-yl)methyl)-1H-1,2,3-triazol-4-yl)methyl acetate;
7-fluoro-2-phenethylimidazo[1,2-c]quinazolin-5-amine;
7-fluoro-2-(2-(pyridin-2-yl)ethyl)imidazo[1,2-c]quinazolin-5-amine;
7-methoxy-2-phenethylimidazo[1,2-c]quinazolin-5-amine;
(5-amino-7-methoxyimidazo[1,2-c]quinazolin-2-yl)(phenyl)methanone;
2-(4-bromophenyl)imidazo[1,2-c]quinazolin-5-amine;
2-(3-bromophenyl)imidazo[1,2-c]quinazolin-5-amine;
7-fluoro-2-phenylimidazo[1,2-c]quinazolin-5-amine;
(2-(5-amino-7-fluoroimidazo[1,2-c]quinazolin-2-yl)phenyl)methanol;
N-(7-fluoro-2-(2-((4-(pyridin-2-yl)piperazin-1-yl)methyl)-phenyl)-imidazo[1,2-c]-quinazolin-5-yl)-methanesulfonamide;
1-((5-aminoimidazo[1,2-c]quinazolin-2-yl)methyl)-4-methylpiperidin-4-ol;
7-methoxy-2-((4-phenylpiperazin-1-yl)methyl)imidazo[1,2-c]quinazolin-5-amine;
2-((4-benzylpiperazin-1-yl)methyl)-7-fluoroimidazo[1,2-c]quinazolin-5-amine;
2-((4-ethylpiperazin-1-yl)methyl)-7-fluoroimidazo[1,2-c]quinazolin-5-amine;
7-fluoro-2-((4-phenethylpiperazin-1-yl)methyl)imidazo-[1,2-c]quinazolin-5-amine;
2-((4-benzylpiperidin-1-yl)methyl)-7-fluoroimidazo[1,2-c]quinazolin-5-amine;
7-fluoro-2-(morpholinomethyl)imidazo[1,2-c]quinazolin-5-amine;
2-((4-(2,4-difluorophenyl)piperazin-1-yl)methyl)imidazo[1,2-c]quinazolin-5-amine;
2-((2,3-dihydro-4H-benzo[b][1,4]oxazin-4-yl)methyl)-7-fluoroimidazo[1,2-c]quinazolin-5-amine;
2-((2,3-dihydro-4H-pyrido[3,2-b][1,4]oxazin-4-yl)methyl)-7-fluoroimidazo[1,2-c]quinazolin-5-amine;
7-fluoro-2-((4-(pyridin-2-yl)-1,4-diazepan-1-yl)methyl)imidazo[1,2-c]quinazolin-5-amine;
2-((5,8-dihydro-1,7-naphthyridin-7(6H)-yl)methyl)-7-methoxyimidazo[1,2-c]quinazolin-5-amine;
2-((3,4-dihydroisoquinolin-2(1H)-yl)methyl)-7-methoxyimidazo[1,2-c]quinazolin-5-amine;
2-((5,7-dihydro-6H-pyrrolo[3,4-b]pyridin-6-yl)methyl)-7-methoxyimidazo[1,2-c]quinazolin-5-amine;
2-((5-fluoroisoindolin-2-yl)methyl)-7-methoxyimidazo[1,2-c]quinazolin-5-amine;
7-fluoro-2-((5-fluoroisoindolin-2-yl)methyl)imidazo[1,2-c]quinazolin-5-amine;
2-((6-bromo-3,4-dihydroquinolin-1(2H)-yl)methyl)-7-fluoroimidazo[1,2-c]quinazolin-5-amine;
2-((5-bromoisoindolin-2-yl)methyl)-7-fluoroimidazo[1,2-c]quinazolin-5-amine;
N-(2-((5-amino-7-fluoroimidazo[1,2-c]quinazolin-2-yl)methyl)-1,2,3,4-tetrahydroisoquinolin-6-yl)picolinamide;
N-(2-((5-amino-7-fluoroimidazo[1,2-c]quinazolin-2-yl)methyl)-1,2,3,4-tetrahydroisoquinolin-6-yl)acetamide;
2-(2-((5-amino-7-fluoroimidazo[1,2-c]quinazolin-2-yl)methyl)-1,2,3,4-tetrahydroisoquinolin-6-yl)-N-(pyridin-2-yl)acetamide;
2-((6-(3,4-difluorophenyl)-3,4-dihydroisoquinolin-2(1H)-yl)methyl)-7-fluoroimidazo[1,2-c]quinazolin-5-amine;
2-(2-((5-amino-7-fluoroimidazo[1,2-c]quinazolin-2-yl)methyl)-1,2,3,4-tetrahydroisoquinolin-7-yl)-N-(pyridin-2-yl)acetamide;

(R)-7-methoxy-2-((octahydro-2H-pyrido[1,2-a]pyrazin-2-yl)methyl)imidazo[1,2-c]quinazolin-5-amine;
7-fluoro-2-((6-(pyrimidin-5-yl)-3,4-dihydroisoquinolin-2(1H)-yl)methyl)imidazo[1,2-c]quinazolin-5-amine;
7-methoxy-2-((7-(pyrimidin-5-yl)-3,4-dihydroisoquinolin-2(1H)-yl)methyl)imidazo[1,2-c]quinazolin-5-amine;
2-((7-(3,4-difluorophenyl)-3,4-dihydroisoquinolin-2(1H)-yl)methyl)-7-methoxyimidazo[1,2-c]quinazolin-5-amine;
1-(4-((5-amino-7-fluoroimidazo[1,2-c]quinazolin-2-yl)methyl)-3,4-dihydroquinoxalin-1(2H)-yl)-2-(pyridin-2-yl)ethan-1-one;
2-(2-(5,7-dihydro-6H-pyrrolo[3,4-b]pyridin-6-yl)ethyl)-7-methoxyimidazo[1,2-c]quinazolin-5-amine;
7-fluoro-2-(2-(4-(pyridin-2-yl)piperazin-1-yl)ethyl)imidazo[1,2-c]quinazolin-5-amine;
7-bromo-2-((phenylamino)methyl)imidazo[1,2-c]quinazolin-5-amine;
2-((benzylamino)methyl)-7-bromoimidazo[1,2-c]quinazolin-5-amine;
7-bromo-2-(((pyridin-3-ylmethyl)amino)methyl)imidazo[1,2-c]quinazolin-5-amine;
7-fluoro-2-(((4-fluorobenzyl)amino)methyl)imidazo[1,2-c]quinazolin-5-amine;
2-((benzylamino)-methyl)-7-methoxy-imidazo[1,2-c]-quinazolin-5-amine;
2-((3-(3-chlorophenyl)azetidin-1-yl)methyl)-7-methoxyimidazo[1,2-c]quinazolin-5-amine;
7-methoxy-2-(((pyridin-3-ylmethyl)amino)methyl)imidazo[1,2-c]quinazolin-5-amine;
7-fluoro-2-(phenoxymethyl)imidazo[1,2-c]quinazolin-5-amine;
7-fluoro-2-((3-methoxyphenoxy)methyl)imidazo[1,2-c]quinazolin-5-amine;
7-(1-ethyl-1H-pyrazol-4-yl)-2-(((4-fluorobenzyl)amino)methyl)imidazo[1,2-c]quinazolin-5-amine;
2-benzyl-7-(1-ethyl-1H-pyrazol-4-yl)imidazo[1,2-c]quinazolin-5-amine;
2-(((3-chlorobenzyl)-(methyl)amino)-methyl)-7-(1-ethyl-H-pyrazol-4-yl)imidazo[1,2-c]-quinazolin-5-amine;
2-benzyl-7-(3,5-dimethylisoxazol-4-yl)imidazo[1,2-c]quinazolin-5-amine;
2-((benzylamino)-methyl)-7-(3,5-dimethyl-isoxazol-4-yl)-imidazo[1,2-c]-quinazolin-5-amine;
7-(3,5-dimethylisoxazol-4-yl)-2-(4-fluorobenzyl)imidazo[1,2-c]quinazolin-5-amine;
7-(3,5-dimethylisoxazol-4-yl)-2-((2-methylpyridin-4-yl)methyl)imidazo[1,2-c]quinazolin-5-amine;
2-benzyl-7-(isoxazol-4-yl)imidazo[1,2-c]quinazolin-5-amine;
5-amino-7-methoxy-N-(quinolin-8-ylmethyl)imidazo[1,2-c]quinazoline-2-carboxamide;
5-amino-N-(2,4-difluorobenzyl)imidazo[1,2-c]quinazoline-2-carboxamide;
5-amino-7-methoxy-N-methyl-N-(quinolin-8-ylmethyl)imidazo[1,2-c]quinazoline-2-carboxamide;
5-amino-N-methyl-N-(quinolin-8-ylmethyl)imidazo[1,2-c]quinazoline-2-carboxamide;
5-amino-N-(quinolin-8-ylmethyl)-imidazo-[1,2-c]-quinazoline-2-carboxamide;
5-amino-7-fluoro-N-methyl-N-(quinolin-8-ylmethyl)imidazo[1,2-c]quinazoline-2-carboxamide;
5-amino-7-fluoro-N-(quinolin-8-ylmethyl)imidazo[1,2-c]quinazoline-2-carboxamide;
(5-bromoisoindolin-2-yl)(5-((2,4-dimethoxybenzyl)amino)-7-fluoroimidazo[1,2-c]quinazolin-2-yl)methanone;
(5-aminoimidazo[1,2-c]quinazolin-2-yl)(4-(2,4-difluorophenyl)piperazin-1-yl)methanone;
5-amino-7-fluoro-N-(2-morpholino-2-(pyridin-3-yl)ethyl)imidazo[1,2-c]quinazoline-2-carboxamide;
(5-amino-7-methoxyimidazo[1,2-c]quinazolin-2-yl)(3,5-dimethylpiperidin-1-yl)methanone;
(5-amino-7-methoxyimidazo[1,2-c]quinazolin-2-yl)(4,4-difluoropiperidin-1-yl)methanone;
(5-amino-7-methoxyimidazo[1,2-c]quinazolin-2-yl)(3-methoxypiperidin-1-yl)methanone;
(5-amino-7-methoxyimidazo[1,2-c]quinazolin-2-yl)(3-methylpiperidin-1-yl)methanone;
(5-amino-7-methoxyimidazo[1,2-c]quinazolin-2-yl)(3-fluoropiperidin-1-yl)methanone;
(5-amino-7-methoxyimidazo[1,2-c]quinazolin-2-yl)(3,3-difluoropiperidin-1-yl)methanone;
(5-amino-7-methoxyimidazo[1,2-c]quinazolin-2-yl)(3-(trifluoromethyl)piperidin-1-yl)methanone;
(5-amino-7-methoxyimidazo[1,2-c]quinazolin-2-yl)(5-azaspiro[2.5]octan-5-yl)methanone;
(5-amino-7-methoxyimidazo[1,2-c]quinazolin-2-yl)((3R,4R)-3,4-difluoropyrrolidin-1-yl)methanone;
(5-amino-7-methoxyimidazo[1,2-c]quinazolin-2-yl)(4-methylazepan-1-yl)methanone;
(5-amino-7-methoxyimidazo[1,2-c]quinazolin-2-yl)(1,4-oxazepan-4-yl)methanone;
(5-amino-7-methoxyimidazo[1,2-c]quinazolin-2-yl)(4,4-difluoroazepan-1-yl)methanone;
1-(5-amino-7-methoxyimidazo[1,2-c]quinazoline-2-carbonyl)azepan-4-one;
(5-amino-7-methoxyimidazo[1,2-c]quinazolin-2-yl)((2R,6S)-2,6-dimethylmorpholino)methanone;
(R)-(5-amino-7-methoxyimidazo[1,2-c]quinazolin-2-yl)(2-methylmorpholino)methanone;
(S)-(5-amino-7-methoxyimidazo[1,2-c]quinazolin-2-yl)(2-methylmorpholino)methanone;
(R)-(5-amino-7-methoxyimidazo[1,2-c]quinazolin-2-yl)(3-methylmorpholino)methanone;
(S)-(5-amino-7-methoxyimidazo[1,2-c]quinazolin-2-yl)(3-methylmorpholino)methanone;
(5-amino-7-methoxyimidazo[1,2-c]quinazolin-2-yl)(2-(trifluoromethyl)morpholino)-methanone;
(5-amino-7-methoxyimidazo[1,2-c]quinazolin-2-yl)(3-isobutylmorpholino)methanone;
(5-amino-7-methoxyimidazo[1,2-c]quinazolin-2-yl)(2,2-dimethylmorpholino)methanone;
(5-amino-7-methoxyimidazo[1,2-c]quinazolin-2-yl)(1,4-dioxa-8-azaspiro[4.5]decan-8-yl)methanone;
(5-amino-7-methoxyimidazo[1,2-c]quinazolin-2-yl)(3,3-dimethylpiperidin-1-yl)methanone;
(5-amino-7-methoxyimidazo[1,2-c]quinazolin-2-yl)(piperidin-1-yl)methanone;
(5-amino-7-methoxyimidazo[1,2-c]quinazolin-2-yl)(3-(hydroxymethyl)piperidin-1-yl)methanone;
(5-amino-7-methoxyimidazo[1,2-c]quinazolin-2-yl)(octahydroisoquinolin-2(1H)-yl)methanone;
(5-amino-7-methoxyimidazo[1,2-c]quinazolin-2-yl)(4-methylpiperidin-1-yl)methanone;
1-(5-amino-7-methoxyimidazo[1,2-c]quinazoline-2-carbonyl)-N,N-diethylpiperidine-3-carboxamide;
(5-amino-7-methoxyimidazo[1,2-c]quinazolin-2-yl)(2-methylpiperidin-1-yl)methanone;
(5-amino-7-methoxyimidazo[1,2-c]quinazolin-2-yl)(4-isopropylpiperidin-1-yl)methanone;
(5-amino-7-methoxyimidazo[1,2-c]quinazolin-2-yl)(2-oxa-8-azaspiro[4.5]decan-8-yl)methanone;
(5-amino-7-methoxyimidazo[1,2-c]quinazolin-2-yl)(4-azaspiro[2.5]octan-4-yl)methanone;

1-(5-amino-7-methoxyimidazo[1,2-c]quinazoline-2-carbonyl)-3-isopropylpiperidin-4-one;
(5-amino-7-methoxyimidazo[1,2-c]quinazolin-2-yl)(6-azaspiro[3.5]nonan-6-yl)methanone;
(5-amino-7-methoxyimidazo[1,2-c]quinazolin-2-yl)(6-azaspiro[2.5]octan-6-yl)methanone;
(5-amino-7-methoxyimidazo[1,2-c]quinazolin-2-yl)(8-azaspiro[4.5]decan-8-yl)methanone;
(5-amino-7-methoxyimidazo[1,2-c]quinazolin-2-yl)(2-oxa-6-azaspiro[3.5]nonan-6-yl)methanone;
(5-amino-7-methoxyimidazo[1,2-c]quinazolin-2-yl)(1-oxa-8-azaspiro[5.5]undecan-8-yl)methanone;
(5-amino-7-methoxyimidazo[1,2-c]quinazolin-2-yl)(1-oxa-7-azaspiro[4.5]decan-7-yl)methanone;
(5-amino-7-methoxyimidazo[1,2-c]quinazolin-2-yl)(2-oxa-7-azaspiro[3.5]nonan-7-yl)methanone;
(5-amino-7-methoxyimidazo[1,2-c]quinazolin-2-yl)(4,4-dimethylpiperidin-1-yl)methanone;
(5-amino-7-methoxyimidazo[1,2-c]quinazolin-2-yl)(8-azabicyclo[3.2.1]octan-8-yl)methanone;
(5-amino-7-methoxyimidazo[1,2-c]quinazolin-2-yl)(2-isopropylpyrrolidin-1-yl)methanone;
(5-amino-7-methoxyimidazo[1,2-c]quinazolin-2-yl)(2,5-dimethylpyrrolidin-1-yl)methanone;
(S)-(5-amino-7-methoxyimidazo[1,2-c]quinazolin-2-yl)(2-(trifluoromethyl)pyrrolidin-1-yl)methanone;
(S)-(5-amino-7-methoxyimidazo[1,2-c]quinazolin-2-yl)(3-methoxypyrrolidin-1-yl)methanone;
(R)-(5-amino-7-methoxyimidazo[1,2-c]quinazolin-2-yl)(3-methoxypyrrolidin-1-yl)methanone;
(R)-(5-amino-7-methoxyimidazo[1,2-c]quinazolin-2-yl)(3-(fluoromethyl)pyrrolidin-1-yl)methanone;
(S)-(5-amino-7-methoxyimidazo[1,2-c]quinazolin-2-yl)(3-fluoropyrrolidin-1-yl)methanone;
(S)-(5-amino-7-methoxyimidazo[1,2-c]quinazolin-2-yl)(2-methylpyrrolidin-1-yl)methanone;
(R)-(5-amino-7-methoxyimidazo[1,2-c]quinazolin-2-yl)(2-(trifluoromethyl)pyrrolidin-1-yl)methanone;
(5-amino-7-methoxyimidazo[1,2-c]quinazolin-2-yl)((1s,4s)-7-azabicyclo[2.2.1]heptan-7-yl)methanone;
(S)-(5-amino-7-methoxyimidazo[1,2-c]quinazolin-2-yl)(2-(fluoromethyl)pyrrolidin-1-yl)methanone;
(5-amino-7-methoxyimidazo[1,2-c]quinazolin-2-yl)(hexahydro-4H-furo[3,2-b]pyrrol-4-yl)methanone;
(5-amino-7-methoxyimidazo[1,2-c]quinazolin-2-yl)(3,3-difluoropyrrolidin-1-yl)methanone;
(5-amino-7-methoxyimidazo[1,2-c]quinazolin-2-yl)(2-azaspiro[4.4]nonan-2-yl)methanone;
(5-amino-7-methoxyimidazo[1,2-c]quinazolin-2-yl)(2,2,6,6-tetramethylmorpholino)methanone;
(5-amino-7-methoxyimidazo[1,2-c]quinazolin-2-yl)(3-oxa-8-azabicyclo[3.2.1]octan-8-yl)methanone;
(5-amino-7-methoxyimidazo[1,2-c]quinazolin-2-yl)((1S,4S)-2-oxa-5-azabicyclo[2.2.1]heptan-5-yl)methanone;
methyl 1-(5-amino-7-methoxyimidazo[1,2-c]quinazoline-2-carbonyl)piperidine-4-carboxylate;
8-(5-amino-7-methoxyimidazo[1,2-c]quinazoline-2-carbonyl)-1-oxa-8-azaspiro[4.5]decan-2-one;
8-(5-amino-7-methoxyimidazo[1,2-c]quinazoline-2-carbonyl)-2-oxa-8-azaspiro[4.5]decan-1-one;
7-(5-amino-7-methoxyimidazo[1,2-c]quinazoline-2-carbonyl)-3,3-dimethyl-2-oxa-7-azaspiro[4.5]decan-1-one;
(5-amino-7-methoxyimidazo[1,2-c]quinazolin-2-yl)(1-oxa-8-azaspiro[4.5]decan-8-yl)methanone;
(5-amino-7-methoxyimidazo[1,2-c]quinazolin-2-yl)(1,4-dioxa-7-azaspiro[4.5]decan-7-yl)methanone;
(5-amino-7-methoxyimidazo[1,2-c]quinazolin-2-yl)(3,3-dimethoxypiperidin-1-yl)methanone;
7-(5-amino-7-methoxyimidazo[1,2-c]quinazoline-2-carbonyl)-2-oxa-7-azaspiro[4.5]decan-1-one;
(5-amino-7-methoxyimidazo[1,2-c]quinazolin-2-yl)(4,4-dimethyl-1-oxa-8-azaspiro[4.5]decan-8-yl)methanone;
(5-amino-7-methoxyimidazo[1,2-c]quinazolin-2-yl)(3-azabicyclo[3.1.0]hexan-3-yl)methanone;
(5-amino-7-methoxyimidazo[1,2-c]quinazolin-2-yl)((3aR,4R,7S,7aS)-octahydro-2H-4,7-methanoisoindol-2-yl)methanone;
(5-amino-7-methoxyimidazo[1,2-c]quinazolin-2-yl)(3,3-dioxido-3-thia-6-azabicyclo[3.2.1]octan-6-yl)methanone;
1-(5-amino-7-methoxyimidazo[1,2-c]quinazoline-2-carbonyl)pyrrolidin-3-one;
(5-amino-7-methoxyimidazo[1,2-c]quinazolin-2-yl)((2R,6R)-2,6-dimethylmorpholino)methanone;
(5-amino-7-methoxyimidazo[1,2-c]quinazolin-2-yl)(3-methoxypiperidin-1-yl)methanone;
(5-amino-7-methoxyimidazo[1,2-c]quinazolin-2-yl)(3,3-difluoropiperidin-1-yl)methanone;
(5-amino-7-methoxyimidazo[1,2-c]quinazolin-2-yl)(5-azaspiro[2.5]octan-5-yl)methanone;
(S)-(5-amino-7-methoxyimidazo[1,2-c]quinazolin-2-yl)(3-(fluoromethyl)pyrrolidin-1-yl)methanone;
N-(2-(5-amino-7-fluoroimidazo[1,2-c]quinazoline-2-carbonyl)-1,2,3,4-tetrahydroisoquinolin-7-yl)acetamide;
(R)-(5-amino-7-methoxyimidazo[1,2-c]quinazolin-2-yl)(octahydro-2H-pyrido[1,2-a]pyrazin-2-yl)methanone;
5-amino-7-fluoro-N-(2-((4-(pyridin-2-yl)piperazin-1-yl)methyl)benzyl)imidazo[1,2-c]quinazoline-2-carboxamide;
(5-amino-7-fluoroimidazo[1,2-c]quinazolin-2-yl)(8-((4-(2,4-difluorophenyl)piperazin-1-yl)methyl)-3,4-dihydroisoquinolin-2(1H)-yl)methanone;
5-amino-7-fluoro-N-(1,2,3,4-tetrahydroquinolin-4-yl)imidazo[1,2-c]quinazoline-2-carboxamide;
5-amino-N-(2-((4-(2,4-difluorophenyl)piperazin-1-yl)methyl)benzyl)-7-fluoroimidazo[1,2-c]quinazoline-2-carboxamide;
5-amino-7-fluoro-N-(2-morpholinobenzyl)imidazo[1,2-c]quinazoline-2-carboxamide;
(5-amino-7-fluoroimidazo[1,2-c]quinazolin-2-yl)(8-((4-(pyridin-2-yl)piperazin-1-yl)methyl)-3,4-dihydroisoquinolin-2(1H)-yl)methanone;
5-amino-N-(3-(4-(2,4-difluorophenyl)piperazin-1-yl)benzyl)-7-fluoroimidazo[1,2-c]quinazoline-2-carboxamide;
5-amino-7-fluoro-N-(2-(4-(4-(2-methoxyethoxy)phenyl)piperazin-1-yl)benzyl)imidazo[1,2-c]quinazoline-2-carboxamide;
5-amino-7-fluoro-N-(3-(4-(4-(2-methoxyethoxy)phenyl)piperazin-1-yl)benzyl)imidazo[1,2-c]quinazoline-2-carboxamide;
5-amino-7-fluoro-N-(2-(morpholinomethyl)benzyl)imidazo[1,2-c]quinazoline-2-carboxamide;
tert-butyl 4-(2-(((5-amino-7-fluoroimidazo[1,2-c]quinazoline-2-carboxamido)methyl)phenyl)piperazine-1-carboxylate;
5-amino-7-fluoro-N-(3-morpholino-benzyl)imidazo-[1,2-c]-quinazoline-2-carboxamide;
5-amino-7-fluoro-N-(3-(morpholinomethyl)benzyl)imidazo[1,2-c]quinazoline-2-carboxamide;
tert-butyl 7-(5-amino-7-fluoroimidazo[1,2-c]quinazoline-2-carbonyl)-2,7-diazaspiro[4.4]nonane-2-carboxylate;
tert-butyl 7-(5-amino-7-fluoroimidazo[1,2-c]quinazoline-2-carbonyl)-2,7-diazaspiro[4.5]decane-2-carboxylate;

5-amino-7-fluoro-N-(2-(piperazin-1-yl)benzyl)imidazo[1,2-c]quinazoline-2-carboxamide;
tert-butyl 8-(5-amino-7-fluoroimidazo[1,2-c]quinazoline-2-carbonyl)-2,8-diazaspiro[4.5]decane-2-carboxylate;
5-amino-7-fluoro-N-(2-((1-(pyridin-2-yl)piperidin-4-yl)oxy)benzyl)imidazo[1,2-c]quinazoline-2-carboxamide;
N-(2-(4-acetylpiperazin-1-yl)benzyl)-5-amino-7-fluoroimidazo[1,2-c]quinazoline-2-carboxamide;
tert-butyl 9-(5-amino-7-fluoroimidazo[1,2-c]quinazoline-2-carbonyl)-2,9-diazaspiro[5.5]undecane-2-carboxylate;
(5-amino-7-fluoroimidazo[1,2-c]quinazolin-2-yl)(2,7-diazaspiro[4.5]decan-7-yl)methanone;
(5-amino-7-fluoroimidazo[1,2-c]quinazolin-2-yl)(2,8-diazaspiro[4.5]decan-8-yl)methanone;
1-(7-(5-amino-7-fluoroimidazo[1,2-c]quinazoline-2-carbonyl)-2,7-diazaspiro[4.5]decan-2-yl)ethan-1-one;
1-(8-(5-amino-7-fluoroimidazo[1,2-c]quinazoline-2-carbonyl)-2,8-diazaspiro[4.5]decan-2-yl)ethan-1-one;
(5-amino-7-fluoroimidazo[1,2-c]quinazolin-2-yl)(2,9-diazaspiro[5.5]undecan-9-yl)methanone;
5-amino-7-fluoro-N-(2-(4-(3-hydroxypropyl)piperazin-1-yl)benzyl)imidazo[1,2-c]quinazoline-2-carboxamide;
(5-amino-7-fluoroimidazo[1,2-c]quinazolin-2-yl)(2,7-diazaspiro[4.4]nonan-2-yl)methanone;
(5-amino-7-fluoroimidazo[1,2-c]quinazolin-2-yl)(7-(4-fluorobenzyl)-2,7-diazaspiro[4.4]nonan-2-yl)methanone;
1-(7-(5-amino-7-fluoroimidazo[1,2-c]quinazoline-2-carbonyl)-2,7-diazaspiro[4.4]nonan-2-yl)ethan-1-one;
4-(7-(5-amino-7-fluoroimidazo[1,2-c]quinazoline-2-carbonyl)-2,7-diazaspiro[4.4]nonan-2-yl)-3-fluorobenzonitrile;
(5-amino-7-fluoroimidazo[1,2-c]quinazolin-2-yl)(2-propyl-2,7-diazaspiro[4.5]decan-7-yl)methanone;
(5-amino-7-fluoroimidazo[1,2-c]quinazolin-2-yl)(2-propyl-2,8-diazaspiro[4.5]decan-8-yl)methanone;
1-(9-(5-amino-7-fluoroimidazo[1,2-c]quinazoline-2-carbonyl)-2,9-diazaspiro[5.5]undecan-2-yl)ethan-1-one;
(5-amino-7-fluoroimidazo[1,2-c]quinazolin-2-yl)(2-propyl-2,9-diazaspiro[5.5]undecan-9-yl)methanone;
(5-amino-7-fluoroimidazo[1,2-c]quinazolin-2-yl)(7-ethyl-2,7-diazaspiro[4.4]nonan-2-yl)methanone;
(5-amino-7-fluoroimidazo[1,2-c]quinazolin-2-yl)(7-(4-fluorophenethyl)-2,7-diazaspiro[4.4]nonan-2-yl)methanone;
1-(7-(5-amino-7-fluoroimidazo[1,2-c]quinazoline-2-carbonyl)-2,7-diazaspiro[4.4]nonan-2-yl)-2-(3,4-difluorophenyl)ethan-1-one;
2-(2-(5-amino-7-fluoroimidazo[1,2-c]quinazoline-2-carbonyl)-1,2,3,4-tetrahydroisoquinolin-6-yl)-N-(pyridin-2-yl)acetamide;
(R)-(5-amino-7-fluoroimidazo[1,2-c]quinazolin-2-yl)(octahydro-2H-pyrido[1,2-a]pyrazin-2-yl)methanone;
(S)-(5-amino-7-fluoroimidazo[1,2-c]quinazolin-2-yl)(octahydro-2H-pyrido[1,2-a]pyrazin-2-yl)methanone;
N-(2-(5-amino-7-fluoroimidazo[1,2-c]quinazoline-2-carbonyl)-1,2,3,4-tetrahydroisoquinolin-6-yl)picolinamide;
(5-amino-7-fluoroimidazo[1,2-c]quinazolin-2-yl)(6-(pyrimidin-5-yl)-3,4-dihydroisoquinolin-2(1H)-yl)methanone;
N-(2-(5-amino-7-fluoroimidazo[1,2-c]quinazoline-2-carbonyl)-1,2,3,4-tetrahydroisoquinolin-6-yl)acetamide;
(5-amino-7-fluoroimidazo[1,2-c]quinazolin-2-yl)(6-(3,4-difluorophenyl)-3,4-dihydroisoquinolin-2(1H)-yl)methanone;
2-(2-(5-amino-7-fluoroimidazo[1,2-c]quinazoline-2-carbonyl)-1,2,3,4-tetrahydroisoquinolin-7-yl)-N-(pyridin-2-yl)acetamide;
N-(2-(5-amino-7-fluoroimidazo[1,2-c]quinazoline-2-carbonyl)-1,2,3,4-tetrahydroisoquinolin-7-yl)picolinamide;
N-(2-(5-amino-7-fluoroimidazo[1,2-c]quinazoline-2-carbonyl)-1,2,3,4-tetrahydroisoquinolin-7-yl)acetamide;
(R)-(5-amino-7-methoxyimidazo[1,2-c]quinazolin-2-yl)(octahydro-2H-pyrido[1,2-a]pyrazin-2-yl)methanone;
5-amino-N-((6-bromopyridin-2-yl)methyl)-7-fluoroimidazo[1,2-c]quinazoline-2-carboxamide;
5-amino-7-fluoro-N-((6-methylpyridin-2-yl)methyl)imidazo[1,2-c]quinazoline-2-carboxamide;
(S)-5-amino-7-fluoro-N-(1-phenylethyl)imidazo[1,2-c]quinazoline-2-carboxamide;
(R)-5-amino-7-fluoro-N-(1-phenylethyl)imidazo[1,2-c]quinazoline-2-carboxamide;
5-amino-7-fluoro-N-(pyridin-2-ylmethyl)imidazo[1,2-c]quinazoline-2-carboxamide;
7-fluoro-2-(piperidin-4-ylmethyl)imidazo[1,2-c]quinazolin-5-amine;
7-fluoro-2-((1-(5-fluoropyrimidin-2-yl)piperidin-4-yl)methyl)imidazo[1,2-c]quinazolin-5-amine;
7-fluoro-2-((1-(thiophen-2-ylmethyl)piperidin-4-yl)methyl)imidazo[1,2-c]quinazolin-5-amine;
(4-((5-amino-7-fluoroimidazo[1,2-c]quinazolin-2-yl)methyl)piperidin-1-yl)(pyridin-3-yl)methanone;
7-fluoro-2-(piperidin-4-ylmethyl)-imidazo-[1,2-c]quinazolin-5-amine;
2-((1-benzylpiperidin-4-yl)methyl)-7-fluoroimidazo[1,2-c]quinazolin-5-amine;
2-((1-(cyclopropylmethyl)piperidin-4-yl)methyl)-7-fluoroimidazo[1,2-c]quinazolin-5-amine;
7-fluoro-2-((1-(thiophen-2-ylmethyl)piperidin-4-yl)methyl)imidazo[1,2-c]quinazolin-5-amine;
2-((1-ethylpiperidin-4-yl)methyl)-7-fluoroimidazo[1,2-c]quinazolin-5-amine;
7-fluoro-2-((1-phenethylpiperidin-4-yl)methyl)imidazo[1,2-c]quinazolin-5-amine;
7-fluoro-2-((1-(4-methoxybenzyl)piperidin-4-yl)methyl)imidazo[1,2-c]quinazolin-5-amine;
7-fluoro-2-((1-(3-methoxybenzyl)piperidin-4-yl)methyl)imidazo[1,2-c]quinazolin-5-amine;
7-fluoro-2-((1-(2-methoxybenzyl)piperidin-4-yl)methyl)-imidazo[1,2-c]-quinazolin-5-amine;
7-fluoro-2-((1-(4-methylbenzyl)piperidin-4-yl)methyl)-imidazo-[1,2-c]-quinazolin-5-amine;
7-fluoro-2-((1-(pyridin-3-ylmethyl)piperidin-4-yl)methyl)imidazo[1,2-c]quinazolin-5-amine;
(4-((5-amino-7-fluoroimidazo[1,2-c]quinazolin-2-yl)methyl)piperidin-1-yl)(phenyl)methanone;
benzyl 4-((5-amino-7-fluoroimidazo[1,2-c]quinazolin-2-yl)methyl)piperidine-1-carboxylate;
(4-((5-amino-7-fluoroimidazo[1,2-c]quinazolin-2-yl)methyl)piperidin-1-yl)(pyridin-3-yl)methanone;
(4-((5-amino-7-fluoroimidazo[1,2-c]quinazolin-2-yl)methyl)piperidin-1-yl)(pyridin-2-yl)methanone;
5-amino-7-fluoro-2-((1-(5-fluoropyridin-2-yl)piperidin-4-yl)methyl)imidazo[1,2-c]quinazolin-6-ium 2,2,2-trifluoroacetate;
(4-((5-amino-7-fluoroimidazo[1,2-c]quinazolin-2-yl)methyl)piperidin-1-yl)(4-methoxypyridin-2-yl)methanone;
(4-((5-amino-7-fluoroimidazo[1,2-c]quinazolin-2-yl)methyl)piperidin-1-yl)(pyrazin-2-yl)methanone;
(4-((5-amino-7-fluoroimidazo[1,2-c]quinazolin-2-yl)methyl)piperidin-1-yl)(6-bromopyridin-2-yl)methanone;
(4-((5-amino-7-fluoroimidazo[1,2-c]quinazolin-2-yl)methyl)piperidin-1-yl)(5-fluoropyridin-2-yl)methanone;
(4-((5-amino-7-fluoroimidazo[1,2-c]quinazolin-2-yl)methyl)piperidin-1-yl)(6-methylpyridin-2-yl)methanone;

(4-((5-amino-7-fluoroimidazo[1,2-c]quinazolin-2-yl)
methyl)piperidin-1-yl)(6-methoxypyridin-2-yl)methanone;

(4-((5-amino-7-fluoroimidazo[1,2-c]quinazolin-2-yl)
methyl)piperidin-1-yl)(pyrimidin-2-yl)methanone;

(4-((5-amino-7-fluoroimidazo[1,2-c]quinazolin-2-yl)
methyl)piperidin-1-yl)(5-methoxypyridin-2-yl)methanone;

In one aspect, the invention provides one or more compounds, or a pharmaceutically acceptable salt thereof, believed to have utility as an $A_{2A}$-receptor antagonist that is beneficial in the treatment or management of a disease implicating adenosine signaling, for example, the treatment of a movement disorder associated with Parkinson's disease and the provision of antiimmune suppression in the treatment of a tumor.

In another aspect, the invention is a pharmaceutical formulation comprising at least one compound, or a pharmaceutically acceptable salt thereof, of Formulae I, as described above.

In some aspects the present invention is the provision of a method of antagonizing A2a receptors in the treatment of solid tumors or central nervous system disorders by administering to a subject in need thereof a therapeutic amount of at least one compound of Formulae I, or a pharmaceutically acceptable salt of such compounds.

DETAILED DESCRIPTION OF THE INVENTION

As mentioned above, in one aspect the invention provides compounds of Formula I:

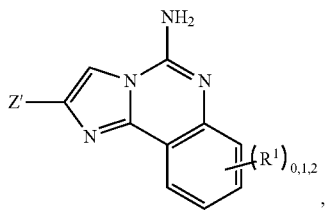

Formula I wherein Z' and $R^1$ are as defined herein.

In some embodiments, in the compound of Formula I, it is preferable to select $R^1$ to provide a compound of Formula Ia:

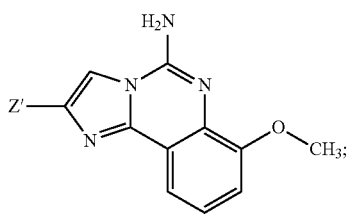

Formula IA wherein Z' is as defined above.

In some embodiments, in the compound of Formula I, it is preferable to select R to provide a compound of Formula IB:

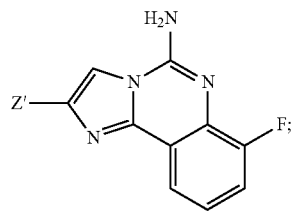

Formula IB wherein Z' is as defined above.

In some embodiments, in the compound of Formula I, it is preferable to select R to provide a compound of Formula IC:

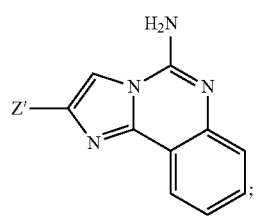

Formula IC wherein Z' is as defined above.

In the description that follows conventional structural representation is employed and includes conventional stereochemical notation for certain asymmetric carbon centers. This includes, for example, a solid black "wedge" bond representing a bond projecting from the plane of the reproduction medium, a "hashed wedge" bond representing a bond descending into the plane of the reproduction medium. Where there is an asymmetric carbon, a "wavey" line bond indicates both possible configurations, or where used in conjunction with a "doubly bonded" set of carbon atoms, indicates that both cis and trans orientations are included. As is conventional, plain solid lines represent all spatial configurations for the depicted bonding. Accordingly, where no specific stereochemical notation is supplied the representation contemplates all stereochemical and spatial orientations of the structural features.

For the most part, absolute configuration has not been determined for the example compounds, but has been assigned by analogy to specific example compounds which were prepared using the same or analogous reaction conditions and starting reagents of known stereochemical configuration, and wherein the products were isolated under similar chromatographic conditions as an analogous set of compounds wherein absolute stereochemical configuration was determined using X-ray crystallography. In some instances, products of similar reaction and chromatographic separation are assigned equivalent configurations for each enantiomer separated chromatographically although absolute stereochemical determination has not been made.

It will be appreciated that where isomeric mixtures are obtained, the preparation of individual stereoisomers in significant percentages of enantiomeric excess can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product.

Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. The present invention is meant to include all suitable isotopic variations of the compounds of Formula I.

Examples of isotopes that can be preferentially incorporated into compounds of the invention include isotopes of hydrogen, carbon, nitrogen, oxygen, phosphorus, iodine, fluorine and chlorine, for example, but not limited to: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, and $^{36}$Cl, $^{123}$I and $^{125}$I. It will be appreciated that other isotopes may be incorporated by known means also.

In particular, certain isotopically-labeled compounds of the invention (e.g., those labeled with $^3$H, $^{11}$C and $^{14}$C) are recognized as being particularly useful in compound and/or substrate tissue distribution assays using a variety of known techniques. Additionally, compounds of the invention contemplate isotopic substitution include different isotopic forms of hydrogen (H), including protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

In describing the compounds of the invention the term "linear-alkyl" or "branched-alkyl" means saturated carbon chains which may be linear or branched or combinations thereof, unless the carbon chain is defined otherwise. Examples of linear alkyl or branched alkyl groups include methyl, ethyl, propyl, isopropyl, butyl, sec- and tert-butyl, pentyl, hexyl, heptyl, octyl, nonyl, and the like. The term "Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl and the like. Where an alkyl moiety is specified by the number of carbon atoms, for example, " . . . a linear, branched, or cyclic alkyl of up to four carbon atoms" the meaning of the term includes all alkyl moieties which have 4 carbon atoms, and includes, in this example, methyl, ethyl, propyl, isopropyl, n-butyl, secondary-butyl, iso-butyl, tertiarybutyl, cyclo propyl, methyl-cyclopropyl-, -methylene-cyclopropyl and cyclobutyl.

The term "Oxo", as used herein, refers to a carbonyl moiety (>C=O) wherein the carbon atom is part of a cycloalkyl or heterocycloalkyl ring;

The term "heteroaryl", as used herein, represents a stable monocyclic, bicyclic or tricyclic ring of up to 10 atoms in each ring, wherein at least one ring is aromatic and includes from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "non-aromatic heterocycle" or "non-aromatic heterocyclic" as used herein is intended to mean a 5- to 10-membered nonaromatic ring, unless otherwise specified, containing from 1 to 4 heteroatoms selected from the group consisting of O, N, S, SO, or SO$_2$ and includes bicyclic groups. The term therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

"aryl" (sometimes abbreviated "ar") means an aromatic monocyclic or multicyclic ring system comprising 6 to 14 carbon atoms ("aryl moiety of up to 14 carbon atoms"), preferably 6 to 10 carbon atoms ("aryl moiety of up to 10 carbon atoms"); Non-limiting examples of suitable aryl groups include phenyl

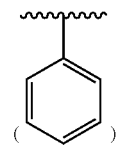

and naphthyl

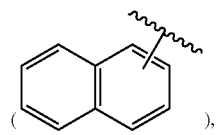

wherein bonding can be through any of the carbons in the aromatic ring, and wherein any ring carbon atoms not participating in a bond to the substrate may have bonded to it a substituent other than —H which provides a stable moiety;

Where a wavey line terminates a conventional bond (as opposed to connecting two atoms within a structure) it indicates a point of bonding to a structure, e.g.:

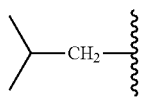

indicates a the secondary-butyl moiety is bonded via the methylene group via the bond terminated with the wavey line. Where an alphabetical notation is used to depict a substituent moiety, a dash is employed to indicate the point of bonding to the indicated substrate, e.g.: —CH$_2$—C(O)—CH$_2$Cl indicates the acetyl chloride moiety is bonded via the methylene portion of the moiety.

When any variable (e.g., n, R$^a$, R$^b$, etc.) occurs more than onetime in any constituent or in Formula I, its definition on each occurrence is independent of its definition at every other occurrence unless otherwise specified at the point of definition. One of ordinary skill in the art will recognize that choice of combinations of the various substituents defined in a structural representation, i.e. R$^1$, R$^A$, etc., are to be chosen in conformity with well-known principles of chemical structure connectivity and stability, and combinations of substituents and/or variables are permissible only if such combinations result in stable compounds.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

Where any variable or moiety is expressed in the form of a range, eg (—CH$_2$—)$_{1-4}$, both of the extrema of the specified range are included (i.e. 1 and 4 in the example) as well as all of the whole number values in between (i.e. 2 and 3 in the example).

The term "Halogen" includes fluorine, chlorine, bromine and iodine unless specified otherwise at the point where the term is used, and preferably, unless more narrowly defined at the point of use, halogen is selected from the group consisting of —F, —Cl, and —Br.

As the term is used herein, "subjects" (alternatively "patients") refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In some embodiments the subject is preferably a human. As used herein, the term "administration" and variants thereof (e.g., "administering" a compound) in reference to a compound of Formula I means providing the compound, or a pharmaceutically acceptable salt thereof, to a subject in need of treatment.

As mentioned above, in one aspect the present invention includes the provision of compounds of Formula I, which have properties that antagonize A2a receptors.

GENERAL SCHEMES AND EXAMPLES

The following is a list of abbreviations used in the description of the Schemes and synthesis of the Intermediates and Examples shown below.
DMF=dimethylformamide
DCM=dichloromethane
EtOAc=ethyl acetate
Hex=hexane
LiOH=lithium hydroxide
MgSO$_4$=magnesium sulfate
rt or RT=room temperature
THF=tetrahydrofuran
NMP=N-Methyl-2-pyrrolidone
TEA Triethyl Amine
TFA=Trifluoroacetic acid
HATU=2-(1H-7-Azabenzotriazol-1-yl)-1,1,3,3-tetramethyl uronium hexafluorophosphate Methanaminium
LAH=Lithium Aluminum Hydride
Pd$_2$(dppf) complex palladium(I) complexes with 1,1'-bis(diphenylphosphino)ferrocene (dppf)
Pd(Cl)$_2$(dppf) complex 1,1'-BIS(DIPHENYLPHOSPHINO)FERROCENE-PALLADIUM(II)DICHLORIDE DICHLOROMETHANE COMPLEX
mCPBA=meta-chloroperoxybenzoic acid
rt or RT=room temperature—about 25° C.

Example 1—Preparation of 2-benzyl-7-methoxyimidazo[1,2-c]quinazolin-5-amine Ex-01

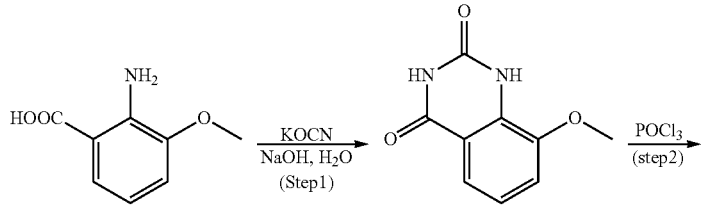

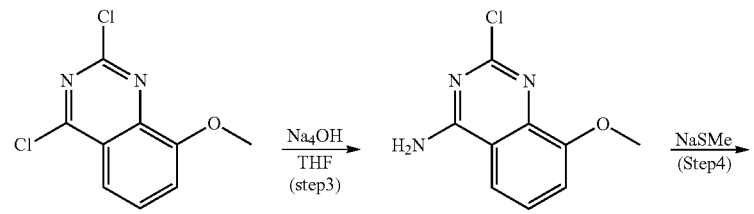

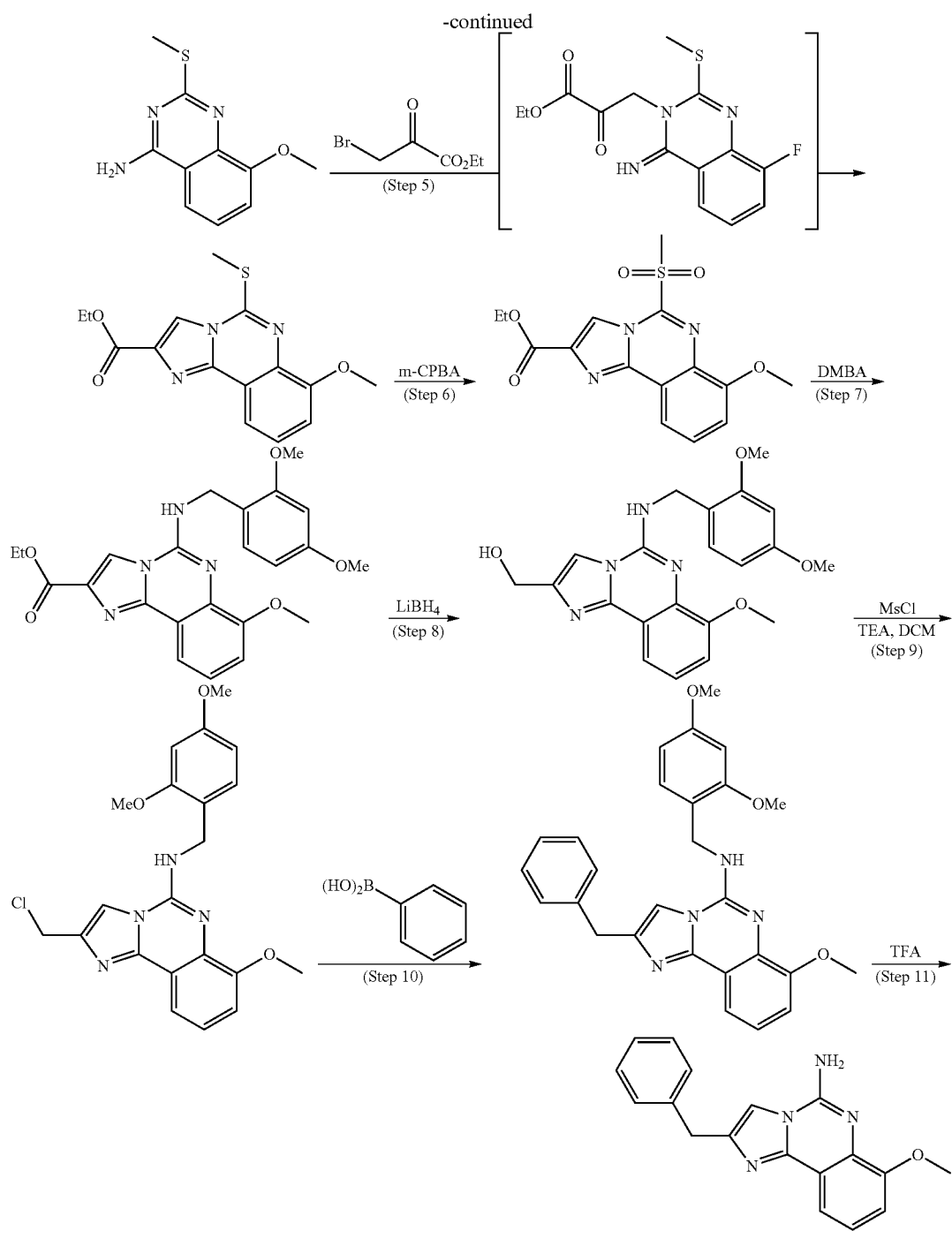

(Step 1) 8-Methoxyquinazoline-2,4-diol

To a suspension of 2-amino-3-methoxybenzoic acid (3 g, 17.95 mmol) in Water (100 ml) and acetic acid (1.099 ml, 19.20 mmol) at 55-60° C. was added a solution of potassium cyanate (3.49 g, 43.1 mmol) in water (7 mL). After 3-5 hr at 55-60° C., the reaction was cooled to RT. Solid NaOH (31.6 g, 790 mmol, 35-44 eq) as one portion was added quickly. Pale brownish cloudy solution became clear and then became white murky solution after 10 min. The reaction mixture was cooled down to 0° C. and then Conc. HCl (around 38 mL) was added to make pH 4-5 at 0° C. The white PPT was generated and filtered, washed with water (500 mL). The solid was dried under vac. oven overnight to afford the desired product, 8-methoxyquinazoline-2,4-diol (2.9 g). LC/MS=193 [M+1].

(Step 2) 2,4-Dichloro-8-methoxyquinazoline

A stirred suspension of 8-methoxyquinazoline-2,4-diol (2.0 g, 10.41 mmol) in POCl$_3$ (9.70 ml, 104 mmol) was heated to 105° C. overnight (16 hrs) resulting in the murky solution becoming clear. The reaction was cooled down and the POCl₃ was evaporated until solution became solid. The crude product was diluted with EtOAc (500 mL) and transferred into a beaker into which was added 2 L NaHCO₃(aq). The mixture was stirred for 30 minutes until the solids dissolved in EtOAc. Any remaining POCl₃ was quenched, and the organic layer was washed with aqueous NaHCO₃ and then brine solution. The organic layer was separated, dried over MgSO₄, filtered and concentrated to provide solid 2,4-dichloro-8-methoxyquinazoline, confirmed by LC/MS=230 [M+1].

(Step 3) 2-Chloro-8-methoxyquinazolin-4-amine

To a stirred solution of 2,4-dichloro-8-methoxyquinazoline (5 g, 23.0 mmol) in THF (50 ml) was added 28% aq. NH₄OH (46 ml, 331 mmol) at RT. The reaction mixture was stirred at RT for overnight. The white precipitate was generated, filtered and washed with water and dried in vacuum oven to afford the desired product, 2-chloro-8-methoxyquinazolin-4-amine (4.7 g). LC/MS=210 [M+1].

(Step 4) 8-Methoxy-2-(methylthio)quinazolin-4-amine

To a stirred suspension of 2-chloro-8-methoxyquinazolin-4-amine (3 g, 14.31 mmol) in anhydrous DMSO (28.6 ml) was added sodium thiomethoxide (1.505 g, 21.47 mmol) at room temperature. The reaction mixture was stirred at RT for 16 hrs. Iced-cold water was added into the reaction mixture and the precipitates were filtered and washed with cold water and dried under vac. oven to afford the desired product, 8-methoxy-2-(methylthio)quinazolin-4-amine (3.1 g). LC/MS=222 [M+1].

(Step 5) Ethyl 7-methoxy-5-(methylthio)imidazo[1,2-c]quinazoline-2-carboxylate

To a stirred suspension of 8-methoxy-2-(methylthio)quinazolin-4-amine (4.9 g, 22.37 mmol) in dry toluene was added Ethylbromopyruvate (6.25 ml, 44.7 mmol). The reaction mixture was heated to 150° C. overnight under Dean-Stark apparatus system. The solvent was evaporated and the crude was purified by column chromatography to give ethyl 7-methoxy-5-(methylthio)imidazo[1,2-c]quinazoline-2-carboxylate (3 g). LC/MS=318 [M+1].

(Step 6) Ethyl 7-methoxy-5-(methylsulfonyl)imidazo[1,2-c]quinazoline-2-carboxylate To a stirred solution of ethyl 7-methoxy-5-(methylthio)imidazo[1,2-c]quinazoline-2-carboxylate (2.8 g, 9.74 mmol) in CH₂Cl₂ (89 ml) was added mCPBA (4.80 g, 21.44 mmol) at room temperature. The clear solution became murky. The reaction mixture was stirred at room temp overnight. The solvent was evaporated and the crude product was used for the next step without further purification. Ethyl 7-methoxy-5-(methylsulfonyl)imidazo[1,2-c]quinazoline-2-carboxylate (3.1 g). LC/MS=350 [M+1].

(Step 7) Ethyl 5-((2,4-dimethoxybenzyl)amino)-7-methoxyimidazo[1,2-c]quinazoline-2-carboxylate To a stirred suspension of ethyl 7-methoxy-5-(methylsulfonyl)imidazo[1,2-c]quinazoline-2-carboxylate (3.1 g, 9.71 mmol) in Dioxane (81 ml) was added N,N-diisopropylethylamine (5.07 ml, 29.1 mmol) and 2,4-dimethoxybenzylamine (2.188 ml, 14.56 mmol). The stirred reaction mixture was heated to 100° C. for 4 hrs then cooled to ambient temperature, after which the solvent was evaporated and the residue was taken up in DCM and washed with 1N HCl solution then brine solution. The organic layer was separated and dried over MgSO4, filtered and concentrated. The crude product was purified by column chromatography. Pale yellowish solid was obtained ethyl 5-((2,4-dimethoxybenzyl)amino)-7-methoxyimidazo[1,2-c]quinazoline-2-carboxylate (3 g). LC/MS=437 [M+1].

(Step 8) (5-((2,4-dimethoxybenzyl)amino)-7-methoxyimidazo[1,2-c]quinazolin-2-yl)methanol To a stirred suspension of ethyl 5-((2,4-dimethoxybenzyl)amino)-7-methoxyimidazo[1,2-c]quinazoline-2-carboxylate (5.6 g, 10.56 mmol) in THF (106 ml) was added lithium borohydride (10.56 ml, 21.11 mmol) solution at RT. The reaction was monitored by TLC and LCMS for 16 hrs, until no starting material was detected by LCMS and TLC, then the reaction mixture was cooled on an ice bath and 10% HCl solution was added to the reaction (dropwise) until no bubbling was observed. The pH was measured and this process was repeated until a pH of 6-7 was observed. The treatments resulted in production of white material and MgSO4 was added, then the solution was then filtered and evaporated. The crude product thus obtained was was redissolved in DCM (250-300 mL) and washed with NaCl brine solution. The organic layer was dried over MgSO4, filtered and concentrated. The crude product (5-((2,4-dimethoxybenzyl)amino)-7-methoxyimidazo[1,2-c]quinazolin-2-yl)methanol was used in the next step without further purification. LC/MS=395 [M+1].

(Step 9) 2-(chloromethyl)-N-(2,4-dimethoxybenzyl)-7-methoxyimidazo[1,2-c]quinazolin-5-amine To a stirred suspension (5-((2,4-dimethoxybenzyl)amino)-7-methoxyimidazo[1,2-c]quinazolin-2-yl)methanol (578 mg, 0.983 mmol) in DCM (8932 μl) was added TEA (205 μl, 1.474 mmol) and methanesulfonyl chloride (92 μl, 1.179 mmol). The reaction mixture was stirred overnight (16 hrs), followed by the addition of saturated NaHCO₃(aq) and then extracted with DCM and washed with brine solution. The crude product was purified by column chromatography (EtOAc/Hex=30/70) to give white solid, 2-(chloromethyl)-N-(2,4-dimethoxybenzyl)-7-methoxyimidazo[1,2-c]quinazolin-5-amine (350 mg). LC/MS=412 [M+1].

(Step 10) 2-Benzyl-N-(2,4-dimethoxybenzyl)-7-methoxyimidazo[1,2-c]quinazolin-5-amine To a stirred solution of 2-(chloromethyl)-N-(2,4-dimethoxybenzyl)-7-methoxyimidazo[1,2-c]quinazolin-5-amine (100 mg, 0.261 mmol) in Dioxane (3918 μl) and Water (1306 μl) was added phenylboronic acid (96 mg, 0.784 mmol), potassium carbonate (217 mg, 1.567 mmol), and 1,1'-bis(diphenylphosphino)ferrocene-pallidium(II) dichloride/dichloromethane complex (53.3 mg, 0.065 mmol) at room temp. The reaction mixture was heated to 80° C. overnight, then the solvent was evaporated and DCM was added. The organic layer was washed with NaHCO3 and brine, dried over MgSO4, filtered, and concentrated. The crude product was purified by column chromatography on silica gel (Isco, 40 g) eluting with (EtOAc/Hexane=1/1) to give 101 mg of the product as a white solid, 2-benzyl-N-

(2,4-dimethoxybenzyl)-7-methoxyimidazo[1,2-c]quinazolin-5-amine (118 mg). LC/MS=455 [M+1].

(Step 11) 2-Benzyl-7-methoxyimidazo[1,2-c]quinazolin-5-amine Ex-01

Into a round bottom flask containing 2-benzyl-N-(2,4-dimethoxybenzyl)-7-methoxyimidazo[1,2-c]quinazolin-5-amine (118 mg, 0.278 mmol) was added TFA (2316 µl) and the reaction mixture was stirred for 16 hr at room temperature. The solvent was evaporated under reduced pressure and the mixture was redissolved in DCM. Into the reaction mixture was added 7N ammonia in MeOH until the mixture attained pH=8. The solvent was evaporated and the crude product was purified by column chromatography on silica gel (Isco, 40 g) eluting with (EtOAc/Hexane=1/1) to give 74.5 mg of the product as a white solid, 2-benzyl-7-methoxyimidazo[1,2-c]quinazolin-5-amine (78 mg). LC/MS=305 [M+1].

The compounds reported in Table 1 were prepared by using methods described in Examples 1 using appropriate reagents.

TABLE 1

| Ex No | Structure | Name | LC-MS |
| --- | --- | --- | --- |
| Ex-02 | 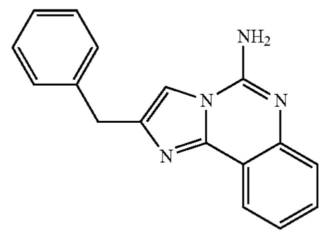 [SMILES: Nc1nc2ccccc2c2nc(Cc3ccccc3)cn12] | 2-benzylimidazo[1,2-c]quinazolin-5-amine | 275 [M + 1]. |
| Ex-03 | 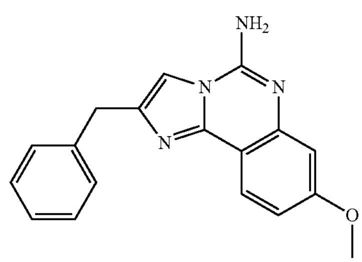 [SMILES: COc1ccc2c(c1)nc(N)n1cc(Cc3ccccc3)nc21] | 2-benzyl-8-methoxyimidazo[1,2-c]quinazolin-5-amine | 305 [M + 1]. |
| Ex-04 | 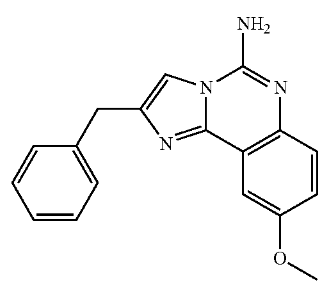 [SMILES: COc1ccc2nc(N)n3cc(Cc4ccccc4)nc3c2c1] | 2-benzyl-9-methoxyimidazo[1,2-c]quinazolin-5-amine | 305 [M + 1]. |
| Ex-05 | 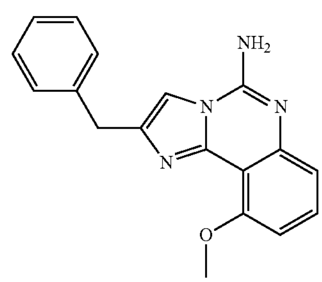 [SMILES: COc1cccc2nc(N)n3cc(Cc4ccccc4)nc3c12] | 2-benzyl-10-methoxyimidazo[1,2-c]quinazolin-5-amine | 305 [M + 1]. |
| Ex-06 | 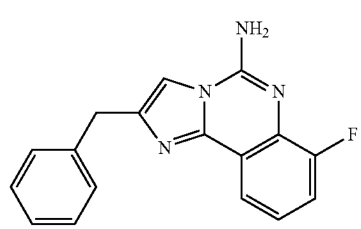 [SMILES: Nc1nc2c(F)cccc2c2nc(Cc3ccccc3)cn12] | 2-benzyl-7-fluoroimidazo[1,2-c]quinazolin-5-amine | 293 [M + 1]. |

TABLE 1-continued

| Ex No | Name | LC-MS |
|---|---|---|
| Ex-07 | 2-benzyl-8-fluoroimidazo[1,2-c]quinazolin-5-amine | 293 [M + 1]. |
| Ex-08 | 2-benzyl-9-fluoroimidazo[1,2-c]quinazolin-5-amine | 293 [M + 1]. |
| Ex-09 | 2-benzyl-10-fluoroimidazo[1,2-c]quinazolin-5-amine | 293 [M + 1]. |
| Ex-10 | 2-benzyl-7-(trifluoromethoxy)imidazo[1,2-c]quinazolin-5-amine | 359 [M + 1]. |
| Ex-11 | 2-benzyl-8-fluoro-7-methoxyimidazo[1,2-c]quinazolin-5-amine | 323 [M + 1]. |
| Ex-12 | 2-benzyl-10-bromo-7-fluoroimidazo[1,2-c]quinazolin-5-amine | 372 [M + 1]. |

TABLE 1-continued

| Ex No | Structure | Name | LC-MS |
|---|---|---|---|
| Ex-13 | 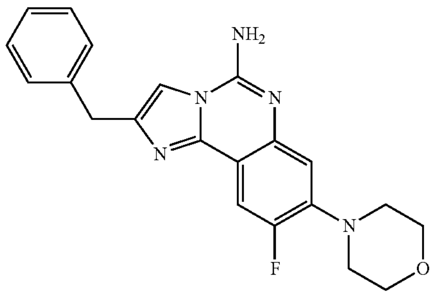 [SMILES: Nc1nc2cc(N3CCOCC3)c(F)cc2c2nc(Cc3ccccc3)cn12] | 2-benzyl-9-fluoro-8-morpholinoimidazo[1,2-c]quinazolin-5-amine | 378 [M + 1] |
| Ex-14 | 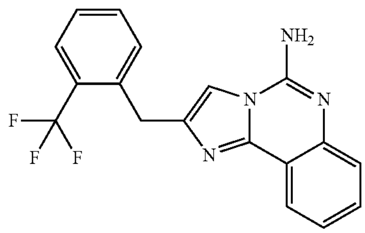 [SMILES: Nc1nc2ccccc2c2nc(Cc3ccccc3C(F)(F)F)cn12] | 2-(2-(trifluoromethyl)benzyl)imidazo[1,2-c]quinazolin-5-amine | 343 [M + 1]. |
| Ex-15 | 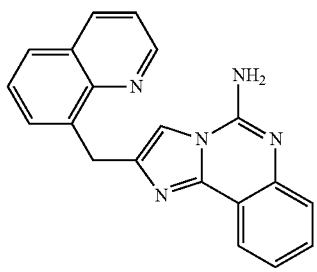 [SMILES: Nc1nc2ccccc2c2nc(Cc3cccc4cccnc34)cn12] | 2-(quinolin-8-ylmethyl)imidazo[1,2-c]quinazolin-5-amine | 326 [M + 1]. |
| Ex-16 | 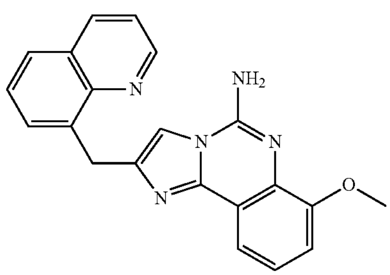 [SMILES: COc1cccc2c1nc(N)n1cc(Cc3cccc4cccnc34)nc21] | 7-methoxy-2-(quinolin-8-ylmethyl)imidazo[1,2-c]quinazolin-5-amine | 356 [M + 1]. |
| Ex-17 | 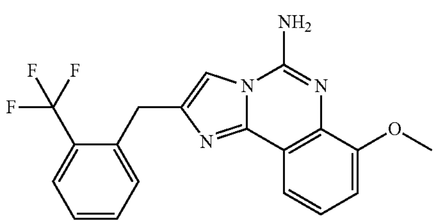 [SMILES: COc1cccc2c1nc(N)n1cc(Cc3ccccc3C(F)(F)F)nc21] | 7-methoxy-2-(2-(trifluoromethyl)benzyl)imidazo[1,2-c]quinazolin-5-amine | 373 [M + 1]. |
| Ex-18 | 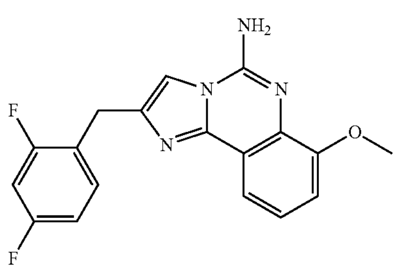 [SMILES: COc1cccc2c1nc(N)n1cc(Cc3ccc(F)cc3F)nc21] | 2-(2,4-difluorobenzyl)-7-methoxyimidazo[1,2-c]quinazolin-5-amine | 341 [M + 1]. |

TABLE 1-continued

| Ex No | Structure | Name | LC-MS |
|---|---|---|---|
| Ex-19 | 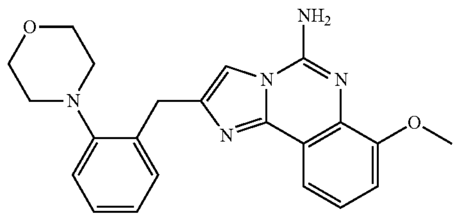 [SMILES: COc1cccc2c1nc(N)n1cc(Cc3ccccc3N3CCOCC3)nc21] | 7-methoxy-2-(2-morpholinobenzyl)imidazo[1,2-c]quinazolin-5-amine | 390 [M + 1]. |
| Ex-20 | 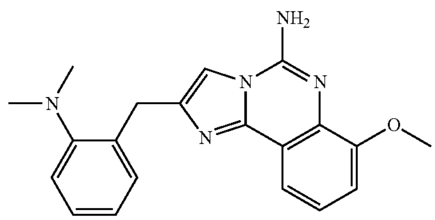 | 2-(2-(dimethylamino)benzyl)-7-methoxyimidazo[1,2-c]quinazolin-5-amine | 348 [M + 1]. |
| Ex-21 | 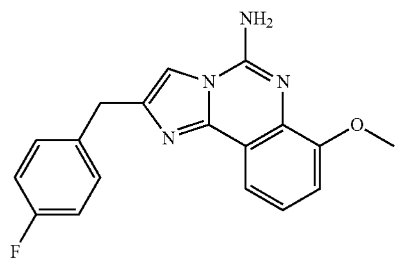 [SMILES: COc1cccc2c1nc(N)n1cc(Cc3ccc(F)cc3)nc21] | 2-(4-fluorobenzyl)-7-methoxyimidazo[1,2-c]quinazolin-5-amine | 323 [M + 1]. |
| Ex-22 | 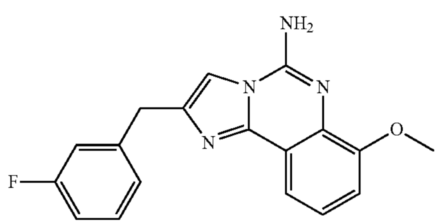 [SMILES: COc1cccc2c1nc(N)n1cc(Cc3cccc(F)c3)nc21] | 2-(3-fluorobenzyl)-7-methoxyimidazo[1,2-c]quinazolin-5-amine | 323 [M + 1] |
| Ex-23 | 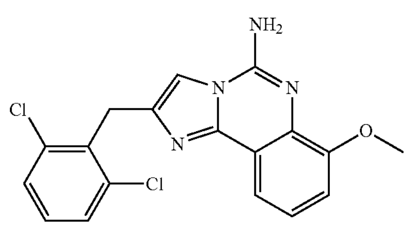 [SMILES: COc1cccc2c1nc(N)n1cc(Cc3c(Cl)cccc3Cl)nc21] | 2-(2,6-dichlorobenzyl)-7-methoxyimidazo[1,2-c]quinazolin-5-amine | 374 [M + 1]. |
| Ex-24 | 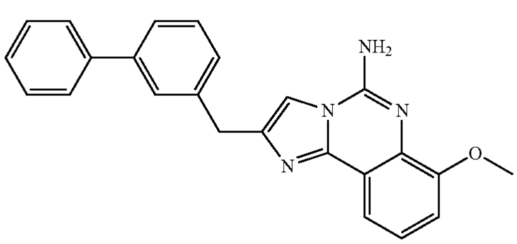 [SMILES: COc1cccc2c1nc(N)n1cc(Cc3cccc(-c4ccccc4)c3)nc21] | 2-([1,1'-biphenyl]-3-ylmethyl)-7-methoxyimidazo[1,2-c]quinazolin-5-amine | 381 [M + 1]. |

TABLE 1-continued

| Ex No | Structure | Name | LC-MS |
|---|---|---|---|
| Ex-25 | 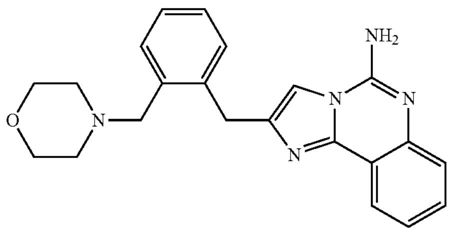 [SMILES: Nc1nc2ccccc2c2nc(Cc3ccccc3CN3CCOCC3)cn12] | 2-(2-(morpholinomethyl)benzyl)imidazo[1,2-c]quinazolin-5-amine | 374 [M + 1]. |
| Ex-26 | 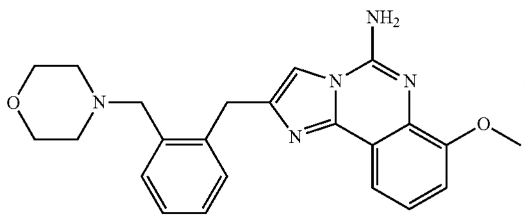 [SMILES: COc1cccc2c1nc(N)n1cc(Cc3ccccc3CN3CCOCC3)nc21] | 7-methoxy-2-(2-(morpholinomethyl)benzyl)imidazo[1,2-c]quinazolin-5-amine | 404 [M + 1]. |
| Ex-27 | 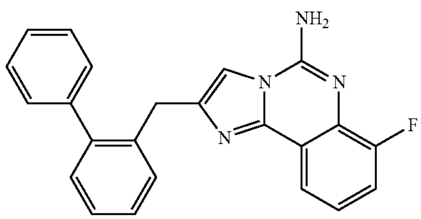 [SMILES: Nc1nc2c(F)cccc2c2nc(Cc3ccccc3-c3ccccc3)cn12] | 2-([1,1'-biphenyl]-2-ylmethyl)-7-fluoroimidazo[1,2-c]quinazolin-5-amine | 369 [M + 1]. |
| Ex-28 | 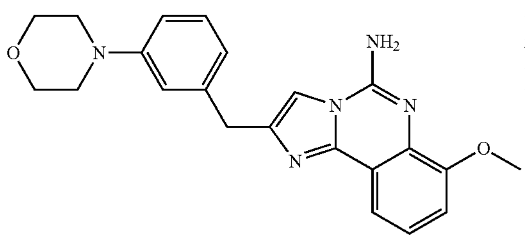 | 7-methoxy-2-(3-morpholinobenzyl)imidazo[1,2-c]quinazolin-5-amine | 390 [M + 1]. |
| Ex-29 | 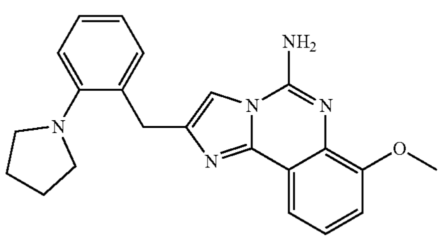 [SMILES: COc1cccc2c1nc(N)n1cc(Cc3ccccc3N3CCCC3)nc21] | 7-methoxy-2-(2-(pyrrolidin-1-yl)benzyl)imidazo[1,2-c]quinazolin-5-amine | 374 [M + 1]. |
| Ex-30 | 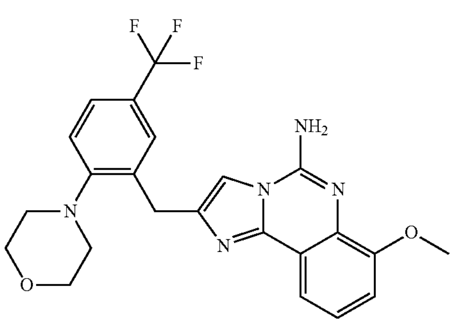 [SMILES: COc1cccc2c1nc(N)n1cc(Cc3cc(C(F)(F)F)ccc3N3CCOCC3)nc21] | 7-methoxy-2-(2-morpholino-5-(trifluoromethyl)benzyl)imidazo[1,2-c]quinazolin-5-amine | 458 [M + 1]. |

TABLE 1-continued

| Ex No | Structure | Name | LC-MS |
|---|---|---|---|
| Ex-31 | 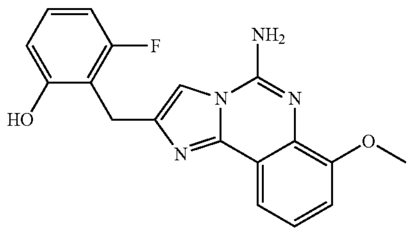 [SMILES: COc1cccc2c1nc(N)n1cc(Cc3c(O)cccc3F)nc21] | 2-((5-amino-7-methoxyimidazo[1,2-c]quinazolin-2-yl)methyl)-3-fluorophenol | 339 [M + 1]. |
| Ex-32 | 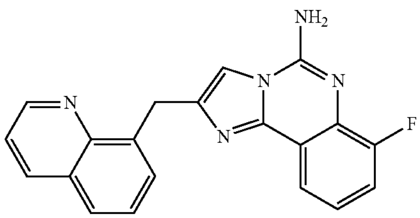 [SMILES: Nc1nc2c(F)cccc2c2nc(Cc3cccc4cccnc34)cn12] | 7-fluoro-2-(quinolin-8-ylmethyl)imidazo[1,2-c]quinazolin-5-amine | 344 [M + 1]. |
| Ex-33 | 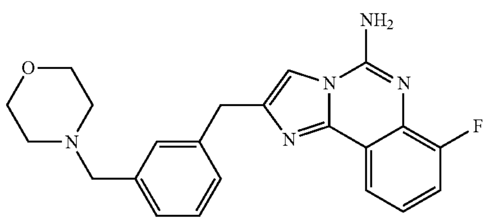 [SMILES: Nc1nc2c(F)cccc2c2nc(Cc3cccc(CN4CCOCC4)c3)cn12] | 7-fluoro-2-(3-(morpholinomethyl)benzyl)imidazo[1,2-c]quinazolin-5-amine | 392 [M + 1]. |
| Ex-34 | 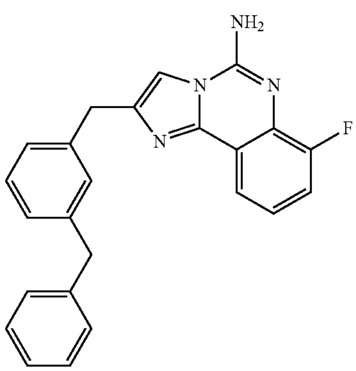 [SMILES: Nc1nc2c(F)cccc2c2nc(Cc3cccc(Cc4ccccc4)c3)cn12] | 2-(3-benzylbenzyl)-7-fluoroimidazo[1,2-c]quinazolin-5-amine | 383 [M + 1]. |
| Ex-35 | 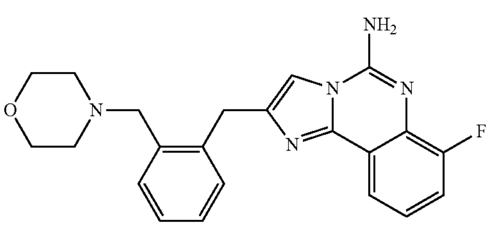 [SMILES: Nc1nc2c(F)cccc2c2nc(Cc3ccccc3CN3CCOCC3)cn12] | 7-fluoro-2-(2-(morpholinomethyl)benzyl)imidazo[1,2-c]quinazolin-5-amine | 392 [M + 1]. |
| Ex-36 | 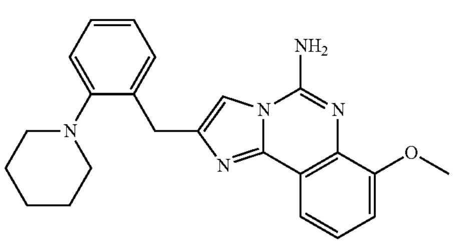 [SMILES: COc1cccc2c1nc(N)n1cc(Cc3ccccc3N3CCCCC3)nc21] | 7-methoxy-2-(2-(piperidin-1-yl)benzyl)imidazo[1,2-c]quinazolin-5-amine | 388 [M + 1]. |

TABLE 1-continued

| Ex No | Structure | Name | LC-MS |
|---|---|---|---|
| Ex-37 | 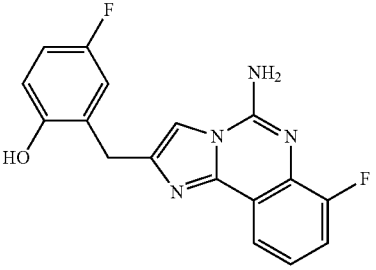 [SMILES: Nc1nc2c(F)cccc2c2nc(Cc3cc(F)ccc3O)cn12] | 2-((5-amino-7-fluoroimidazo[1,2-c]quinazolin-2-yl)methyl)-4-fluorophenol | 327 [M + 1]. |
| Ex-38 | 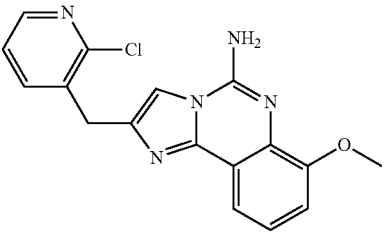 [SMILES: COc1cccc2c1nc(N)n1cc(Cc3cccnc3Cl)nc21] | 2-((2-chloropyridin-3-yl)methyl)-7-methoxyimidazo[1,2-c]quinazolin-5-amine | 340 [M + 1]. |
| Ex-39 | 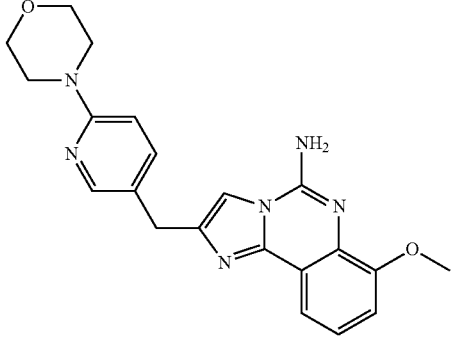 [SMILES: COc1cccc2c1nc(N)n1cc(Cc3ccc(N4CCOCC4)nc3)nc21] | 7-methoxy-2-((6-morpholinopyridin-3-yl)methyl)imidazo[1,2-c]quinazolin-5-amine | 391 [M + 1]. |
| Ex-40 | 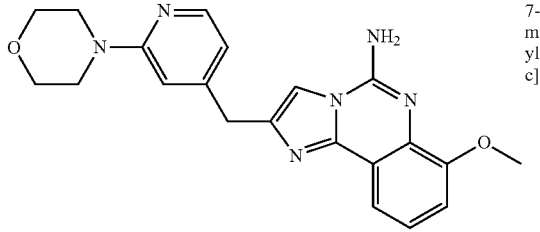 | 7-methoxy-2-((2-morpholinopyridin-4-yl)methyl)imidazo[1,2-c]quinazolin-5-amine | 391 [M + 1]. |
| Ex-41 | 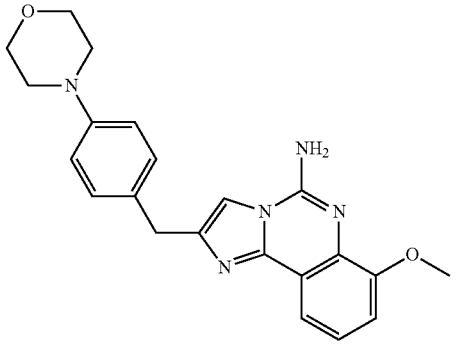 [SMILES: COc1cccc2c1nc(N)n1cc(Cc3ccc(N4CCOCC4)cc3)nc21] | 7-methoxy-2-(4-morpholinobenzyl)imidazo[1,2-c]quinazolin-5-amine | 390 [M + 1]. |

TABLE 1-continued

| Ex No | Structure | Name | LC-MS |
|---|---|---|---|
| Ex-42 | 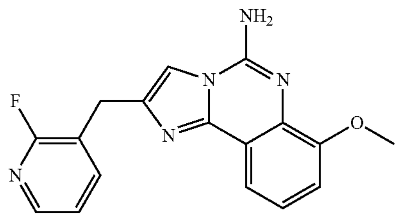 [SMILES: COc1cccc2c1nc(N)n1cc(Cc3cccnc3F)nc21] | 2-((2-fluoropyridin-3-yl)methyl)-7-methoxyimidazo[1,2-c]quinazolin-5-amine | 324 [M + 1]. |
| Ex-43 | 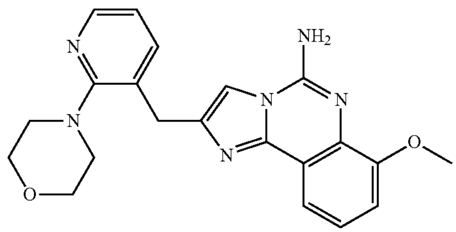 [SMILES: COc1cccc2c1nc(N)n1cc(Cc3cccnc3N3CCOCC3)nc21] | 7-methoxy-2-((2-morpholinopyridin-3-yl)methyl)imidazo[1,2-c]quinazolin-5-amine | 391 [M + 1]. |
| Ex-44 | 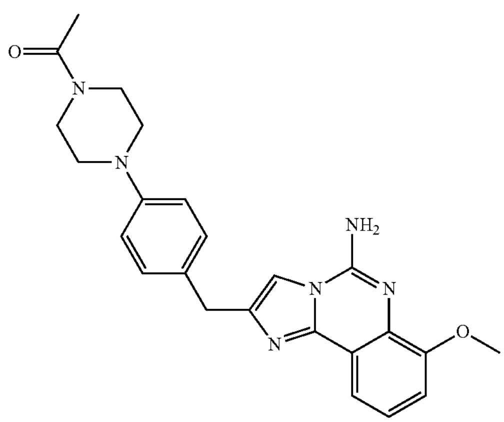 [SMILES: COc1cccc2c1nc(N)n1cc(Cc3ccc(N4CCN(C(C)=O)CC4)cc3)nc21] | 1-(4-(4-((5-amino-7-methoxyimidazo[1,2-c]quinazolin-2-yl)methyl)phenyl)piperazin-1-yl)ethan-1-one | 431 [M + 1]. |
| Ex-45 | 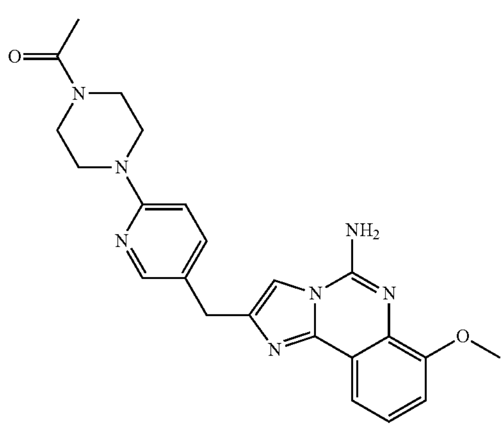 [SMILES: COc1cccc2c1nc(N)n1cc(Cc3ccc(N4CCN(C(C)=O)CC4)nc3)nc21] | 1-(4-(5-((5-amino-7-methoxyimidazo[1,2-c]quinazolin-2-yl)methyl)pyridin-2-yl)piperazin-1-yl)ethan-1-one | 432 [M + 1]. |

TABLE 1-continued

| Ex No | Name | LC-MS |
|---|---|---|
| Ex-46 | 1-(4-(4-((5-amino-7-methoxyimidazo[1,2-c]quinazolin-2-yl)methyl)pyridin-2-yl)piperazin-1-yl)ethan-1-one | 432 [M + 1]. |
| Ex-47 | 1-(6-((5-amino-7-fluoroimidazo[1,2-c]quinazolin-2-yl)methyl)-3,4-dihydroisoquinolin-2(1H)-yl)ethan-1-one | 390 [M + 1]. |
| Ex-48 | 1-(7-((5-amino-7-fluoroimidazo[1,2-c]quinazolin-2-yl)methyl)-3,4-dihydroisoquinolin-2(1H)-yl)ethan-1-one | 390 [M + 1]. |
| Ex-49 | 7-methoxy-2-((2-(pyrrolidin-1-yl)pyridin-3-yl)methyl)imidazo[1,2-c]quinazolin-5-amine | 375 [M + 1]. |
| Ex-50 | 7-methoxy-2-((2-(piperidin-1-yl)pyridin-3-yl)methyl)imidazo[1,2-c]quinazolin-5-amine | 389 [M + 1]. |

TABLE 1-continued

| Ex No | Structure | Name | LC-MS |
|---|---|---|---|
| Ex-51 | 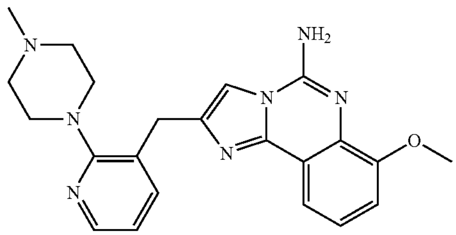 [SMILES: COc1cccc2c1nc(N)n1cc(Cc3cccnc3N3CCN(C)CC3)nc21] | 7-methoxy-2-((2-(4-methylpiperazin-1-yl)pyridin-3-yl)methyl)imidazo[1,2-c]quinazolin-5-amine | 404 [M + 1]. |
| Ex-52 | 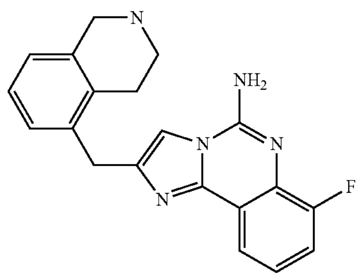 [SMILES: Nc1nc2c(F)cccc2c2nc(Cc3cccc4c3CCNC4)cn12] | 7-fluoro-2-((1,2,3,4-tetrahydroisoquinolin-5-yl)methyl)imidazo-[1,2-c]quinazolin-5-amine | 348 [M + 1]. |
| Ex-53 | 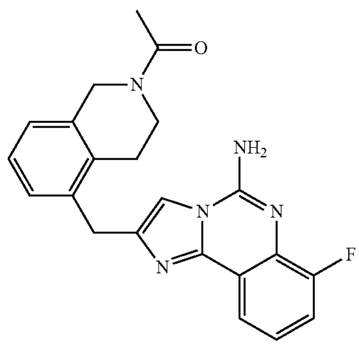 [SMILES: CC(=O)N1CCc2c(Cc3cn4c(N)nc5c(F)cccc5c4n3)cccc2C1] | 1-(5-((5-amino-7-fluoroimidazo[1,2-c]quinazolin-2-yl)methyl)-3,4-dihydroisoquinolin-2(1H)-yl)ethan-1-one | 390 [M + 1]. |
| Ex-54 | 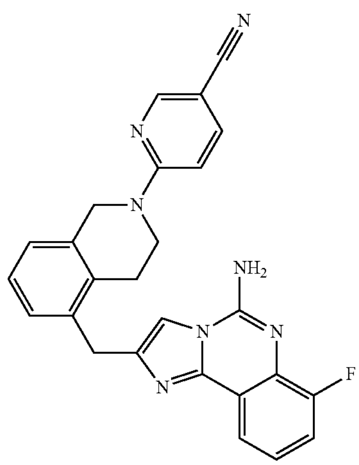 [SMILES: N#Cc1ccc(N2CCc3c(Cc4cn5c(N)nc6c(F)cccc6c5n4)cccc3C2)nc1] | 6-(5-((5-amino-7-fluoroimidazo[1,2-c]quinazolin-2-yl)methyl)-3,4-dihydroisoquinolin-2(1H)-yl)nicotinonitrile | 450 [M + 1]. |
| Ex-55 | 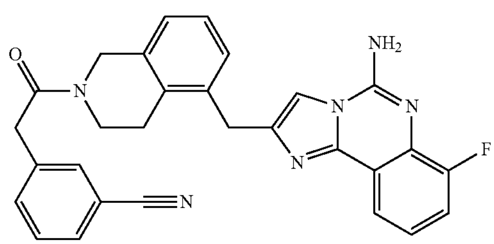 [SMILES: N#Cc1cccc(CC(=O)N2CCc3c(Cc4cn5c(N)nc6c(F)cccc6c5n4)cccc3C2)c1] | 3-(2-(5-((5-amino-7-fluoroimidazo[1,2-c]quinazolin-2-yl)methyl)-3,4-dihydroisoquinolin-2(1H)-yl)-2-oxoethyl)benzonitrile | 491 [M + 1]. |

TABLE 1-continued

| Ex No | Structure | Name | LC-MS |
|---|---|---|---|
| Ex-56 | 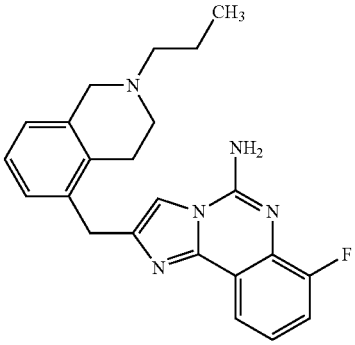 [SMILES: CCCN1CCc2c(Cc3cn4c(N)nc5c(F)cccc5c4n3)cccc2C1] | 7-fluoro-2-((2-propyl-1,2,3,4-tetrahydroisoquinolin-5-yl)melhyl)imidazo-[1,2-c]quinazolin-5-amine | 390 [M + 1]. |
| Ex-57 | 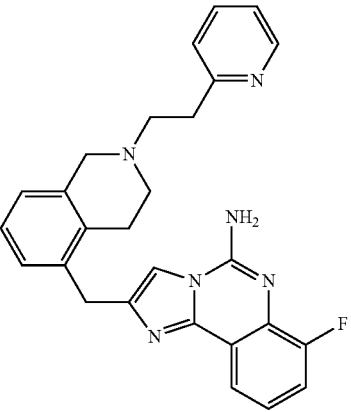 [SMILES: Nc1nc2c(F)cccc2c2nc(Cc3cccc4c3CCN(CCc3ccccn3)C4)cn12] | 7-fluoro-2-((2-(2-(pyridin-2-yl)ethyl)-1,2,3,4-tetrahydroisoquinolin-5-yl)methyl)imidazo[1,2-c]quinazolin-5-amine | 453 [M + 1]. |
| Ex-58 | 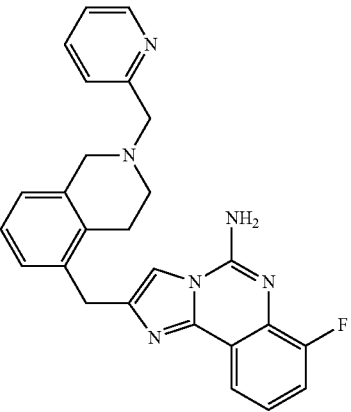 [SMILES: Nc1nc2c(F)cccc2c2nc(Cc3cccc4c3CCN(Cc3ccccn3)C4)cn12] | 7-fluoro-2-((2-(pyridin-2-ylmethyl)-1,2,3,4-tetrahydroisoquinolin-5-yl)methyl)imidazo[1,2-c]quinazolin-5-amine | 439 [M + 1]. |
| Ex-59 | 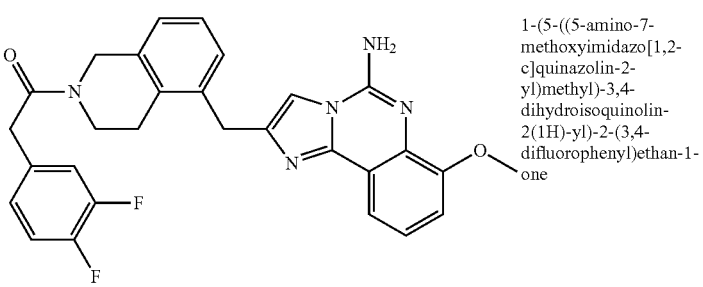 | 1-(5-((5-amino-7-methoxyimidazo[1,2-c]quinazolin-2-yl)methyl)-3,4-dihydroisoquinolin-2(1H)-yl)-2-(3,4-difluorophenyl)ethan-1-one | 514 [M + 1]. |

TABLE 1-continued

| Ex No | Structure | Name | LC-MS |
|---|---|---|---|
| Ex-60 | 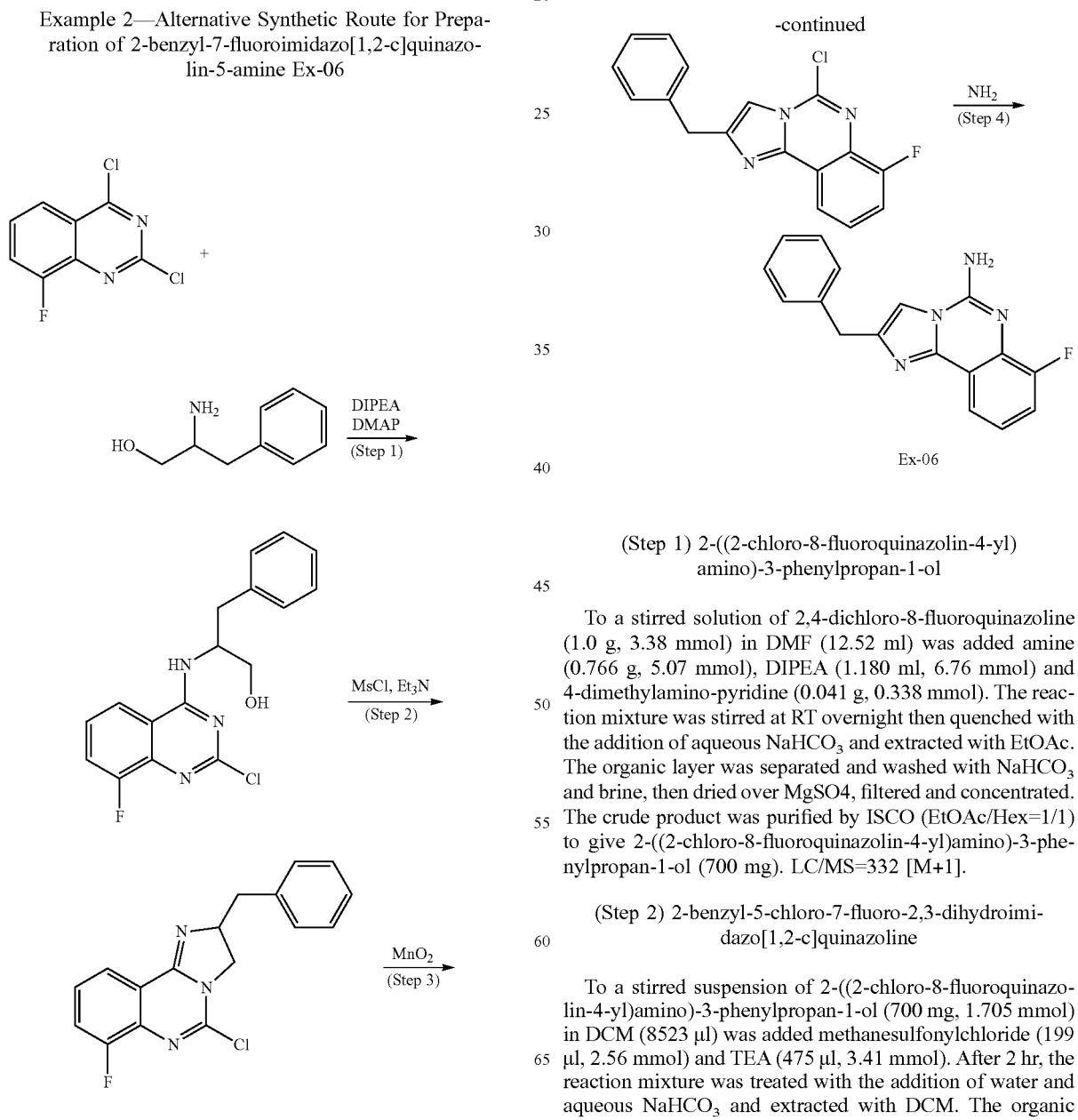 | 1-(5-((5-amino-7-methoxyimidazo[1,2-c]quinazolin-2-yl)methyl)-3,4-dihydroisoquinolin-2(1H)-yl)-4,4,4-trifluorobutan-1-one | 484 [M + 1]. |

Example 2—Alternative Synthetic Route for Preparation of 2-benzyl-7-fluoroimidazo[1,2-c]quinazolin-5-amine Ex-06

(Step 1) 2-((2-chloro-8-fluoroquinazolin-4-yl)amino)-3-phenylpropan-1-ol

To a stirred solution of 2,4-dichloro-8-fluoroquinazoline (1.0 g, 3.38 mmol) in DMF (12.52 ml) was added amine (0.766 g, 5.07 mmol), DIPEA (1.180 ml, 6.76 mmol) and 4-dimethylamino-pyridine (0.041 g, 0.338 mmol). The reaction mixture was stirred at RT overnight then quenched with the addition of aqueous NaHCO₃ and extracted with EtOAc. The organic layer was separated and washed with NaHCO₃ and brine, then dried over MgSO4, filtered and concentrated. The crude product was purified by ISCO (EtOAc/Hex=1/1) to give 2-((2-chloro-8-fluoroquinazolin-4-yl)amino)-3-phenylpropan-1-ol (700 mg). LC/MS=332 [M+1].

(Step 2) 2-benzyl-5-chloro-7-fluoro-2,3-dihydroimidazo[1,2-c]quinazoline

To a stirred suspension of 2-((2-chloro-8-fluoroquinazolin-4-yl)amino)-3-phenylpropan-1-ol (700 mg, 1.705 mmol) in DCM (8523 µl) was added methanesulfonylchloride (199 µl, 2.56 mmol) and TEA (475 µl, 3.41 mmol). After 2 hr, the reaction mixture was treated with the addition of water and aqueous NaHCO₃ and extracted with DCM. The organic layer was dried over MgSO4, filtered and concentrated. The crude product was purified by ISCO (EtOAc/Hex=1/1) to give 2-benzyl-5-chloro-7-fluoro-2,3-dihydroimidazo[1,2-c]quinazoline (650 mg). LC/MS=314 [M+1].

(Step 3) 2-benzyl-5-chloro-7-fluoroimidazo[1,2-c]quinazoline

To a stirred solution of 2-benzyl-5-chloro-7-fluoro-2,3-dihydroimidazo[1,2-c]quinazoline (650 mg, 1.655 mmol) in Toluene (3.31E+04 µl) and 5 mL CHCl₃ was added manganese dioxide (1439 mg, 16.55 mmol) and the reaction mixture was heated to 110° C. overnight. The reaction mixture was filtered through the short pad of Celite and the filtrate was evaporated. The crude product thus obtained was purified by ISCO (EtOAc/Hex=1/1) to give 2-benzyl-5-chloro-7-fluoroimidazo[1,2-c]quinazoline (178 mg). LC/MS=312 [M+1].

(Step 4) 2-benzyl-7-fluoroimidazo[1,2-c]quinazolin-5-amine

To a sealed tube of 2-benzyl-5-chloro-7-fluoroimidazo[1,2-c]quinazoline (178 mg, 0.456 mmol) was added 20 mm of ammonia as an isopropanol solution (10 ml of 2M solution) and the reaction mixture was heated to 110° C. overnight. The solvent was evaporated and the crude was purified by prep-TLC (10% MeOH/DCM) to give 2-benzyl-7-fluoroimidazo[1,2-c]quinazolin-5-amine (135 mg). LC/MS=293 [M+1].

Example 3—Preparation of 2-benzyl-9-fluoro-8-morpholinoimidazo[1,2-c]quinazolin-5-amine Ex-13

The compound of Ex-13 was synthesized using the procedure of Example 1 from the 6-fluoro-7-morpholinoquinazoline-2,4(1H,3H)-dione (intermediate of Step 2 in the scheme above) which was prepared using the following procedure (Step 1) 6,7-difluoroquinazoline-2,4(1H,3H)-dione To a suspension of 2-amino-4,5-diflurobenzoic acid (2 g, 11.55 mmol) in Water (64.2 ml) and acetic acid (0.708 ml, 12.36 mmol) at 40° C. was added a solution of KOCN (2.249 g, 27.7 mmol) in water (7 mL). After 30 min, NaOH (20.33 g, 508 mmol) was added. The reaction mixture was cooled to room temp. Conc. HCl was added to make pH 7 at OC. The precipitate generated was filtered and washed with water. The solid was dried in the air to give 6,7-difluoroquinazoline-2,4(1H,3H)-dione (1.05 g), LC/MS=199 [M+1]

(Step 2) 6-fluoro-7-morpholinoquinazoline-2,4(1H,3H)-dione

To a stirred suspension of 6,7-difluoroquinazoline-2,4(1H,3H)-dione (1.02 g, 5.15 mmol) in DMSO (5 ml) was added morpholine (2 ml, 22.96 mmol) at RT, then the reaction mixture was heated to 90° C. for 1 hr., then cooled down to ambient temperature and diluted with water. The mixture was acidified with the addition of conc. HCl and the resulting precipitates were filtered, washed with water and dried in vacuo to give 6-fluoro-7-morpholinoquinazoline-2,4(1H,3H)-dione (1 g). LC/MS=266 [M+1]

Example 4, Preparation of 5-(5-amino-2-benzyl-7-fluoroimidazo[1,2-c]quinazolin-10-yl-1-methylpyridin-2(1H)-one Ex-61

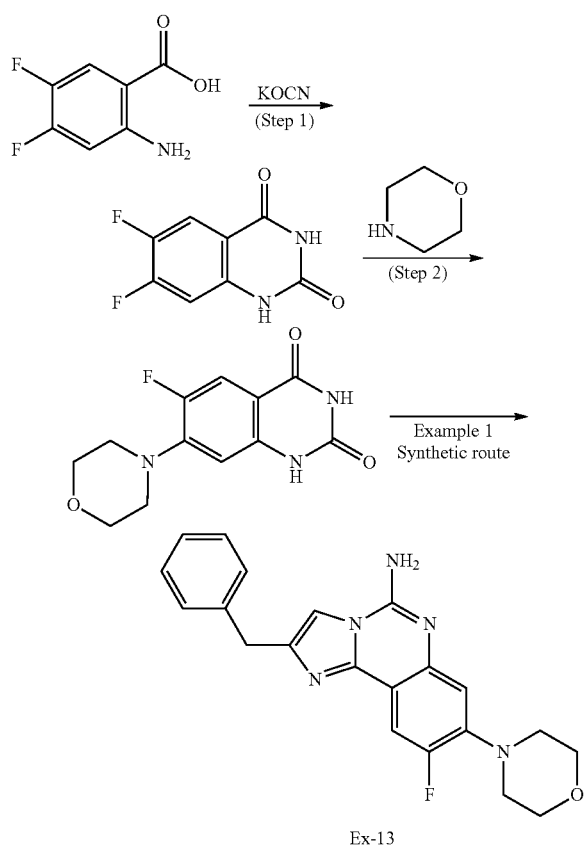

Ex-13

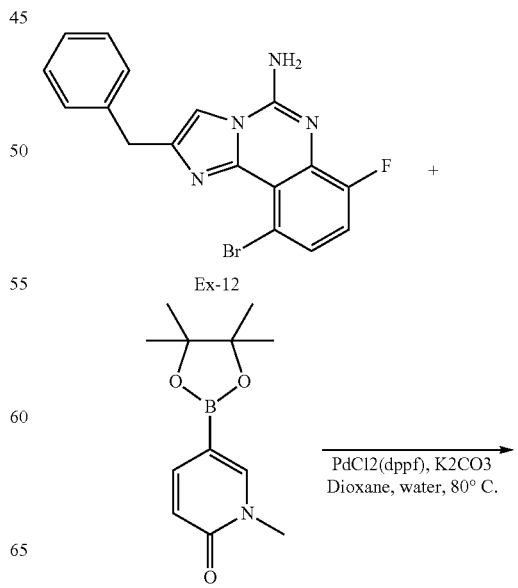

Ex-12

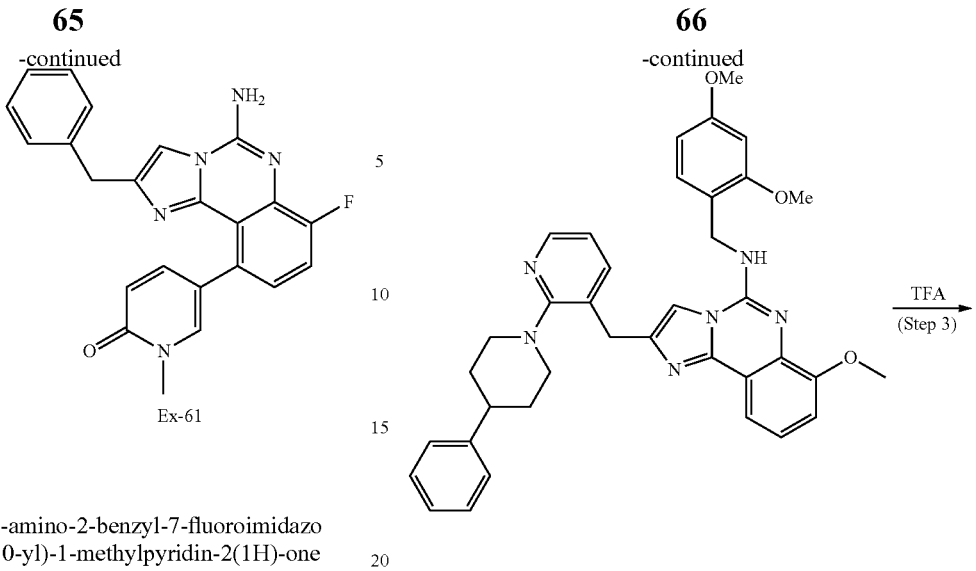

Ex-61

Preparation of 5-(5-amino-2-benzyl-7-fluoroimidazo[1,2-c]quinazolin-10-yl)-1-methylpyridin-2(1H)-one To a stirred solution of Ex-12 prepared in Example 1 (2-benzyl-10-bromo-7-fluoroimidazo[1,2-c]quinazolin-5-amine, 30 mg, 0.081 mmol) in Dioxane (1616 μl) was added boronic acid (38.0 mg, 0.162 mmol), $K_2CO_3$ (242 μl, 0.242 mmol), and 1,1'-bis(diphenylphosphino)ferrocene-palladium(II)dichloride/dichloromethane complex (herein, alternatively Pd(Cl)$_2$(dppf) complex, 16.50 mg, 0.020 mmol). The reaction mixture was heated to 88° C. for 2.5 hrs, then the solvent was evaporated and the crude was diluted with DCM. The organic layer was washed with NaHCO$_3$, dried over MgSO$_4$, filtered and concentrated. The crude product was purified by prep-TLC to yield 5-(5-amino-2-benzyl-7-fluoroimidazo[1,2-c]quinazolin-10-yl)-1-methylpyridin-2(1H)-one (Ex-61). LC/MS=400 [M+1].

Example 5, Preparation of 7-methoxy-2-((2-(4-phenylpiperidin-1-yl)pyridin-3-yl)methyl)-imidazo[1,2-c]quinazolin-5-amine (Ex-62

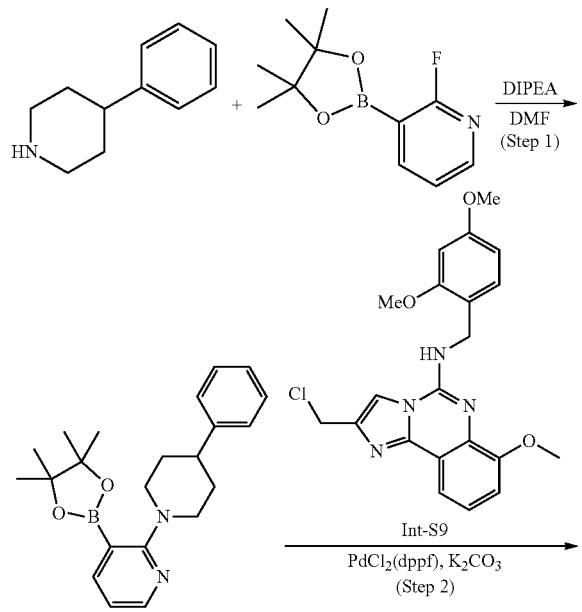

(Step 1) 2-(4-phenylpiperidin-1-yl)-3-(4,4,5,5-tetramethyl-1,3,2-dioxaborolan-2-yl)pyridine To a stirred solution of 2-fluoro-3-(4,4,5,5-tetramethyl-1,3,2-dioxaborolan-2-yl)pyridine (200 mg, 0.897 mmol) in DMF (1793 μl) was added DIPEA (626 μl, 3.59 mmol) and 4-phenylpiperidine (173 mg, 1.076 mmol). The reaction mixture was heated to 80° C. until LCMS determined that only hydrolyzed product was present (overnight), then the reaction mixture was quenched with. aqueous NaHCO$_3$ and extracted with EtOAc. The organic layer was washed with water, dried over MgSO4, filtered and concentrated to provide crude title compound which was used in the next step, LC/MS=365 [M+1].

(Step 2) N-(2,4-dimethoxybenzyl)-7-methoxy-2-((2-(4-phenylpiperidin-1-yl)pyridin-3-yl)methyl)imidazo[1,2-c]quinazolin-5-amine To a stirred solution of 2-(chloromethyl)-N-(2,4-dimethoxybenzyl)-7-methoxyimidazo[1,2-c]quinazolin-5-amine (Int-S9, prepared from Step 9 of Example 1 above, 200 mg, 0.261 mmol) in Dioxane (3918 μl) and Water (1306 μl) was added 2-(4-phenylpiperidin-1-yl)-3-(4,4,5,5-tetramethyl-1,3,2-dioxaborolan-2-yl)pyridine (207 mg, 0.784 mmol), potassium carbonate (217 mg, 1.567 mmol), and 1,1'-bis(diphenylphosphino)ferrocene-palladium(II)dichloride/dichloromethane complex (53.3 mg, 0.065 mmol) at room temp. The reaction mixture was heated to 80° C. overnight, the solvent evaporated and DCM added. The organic layer was separated, washed with NaHCO3 and brine, dried over MgSO$_4$, filtered, and concentrated. The crude product thus obtained was purified by column chromatography on silica gel (Isco, 40 g) eluting with (EtOAc/Hexane=1/1) to yield the title compound. LC/MS=615 [M+1].

(Step 3) 7-methoxy-2-((2-(4-phenylpiperidin-1-yl) pyridin-3-yl)methyl)imidazo[1,2-c]quinazolin-5-amine Ex-62

Into a round-bottom flask containing N-(2,4-dimethoxybenzyl)-7-methoxy-2-((2-(4-phenylpiperidin-1-yl)pyridin-3-yl)methyl)imidazo[1,2-c]quinazolin-5-amine prepared in the last step (189 mg, 0.278 mmol) was added TFA (2316 μl) and the reaction mixture was stirred for 16 hr at room temperature. The solvent was evaporated under reduced pressure and the mixture was redissolved in DCM. A methanolic ammonia solution (7N ammonia in MeOH) was added until the reaction mixture pH=8 then the solvent was evaporated and the crude product was purified by column chromatography on silica gel (Isco, 40 g) eluting with (EtOAc/Hexane=1/1) to give Ex-62 LC/MS=465 [M+1]. L-005079678, A2a Ki=2.2 nM.

The compound of Ex-63:

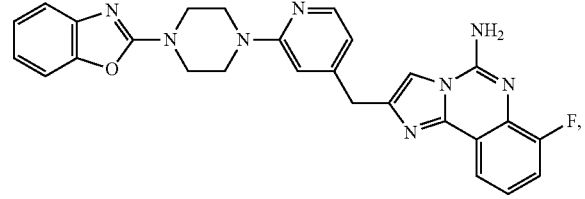 [SMILES: Nc1nc2c(F)cccc2c2nc(Cc3ccnc(N4CCN(c5nc6ccccc6o5)CC4)c3)cn12]

x-63, 2-((2-(4-(benzo[d]oxazol-2-yl)piperazin-1-yl)pyridin-4-yl)methyl)-7-fluoroimidazo[1,2-c]quinazolin-5-amine, was prepared using the methodology of Example 5 and appropriate reagents. LC/MS=495 [M+1].

The compound of Ex-64:

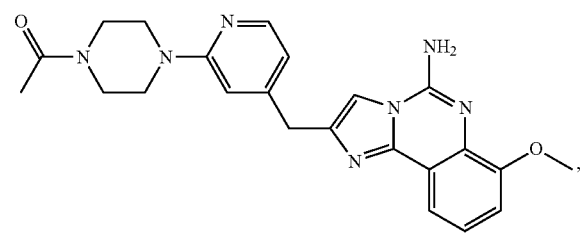 [SMILES: COc1cccc2c1nc(N)n1cc(Cc3ccnc(N4CCN(C(C)=O)CC4)c3)nc21]

Ex-64, 1-(4-(4-((5-amino-7-methoxyimidazo[1,2-c]quinazolin-2-yl)methyl)pyridin-2-yl)piperazin-1-yl)ethan-1-one, was prepared using the methodology of Example 5 and appropriate reagents. LC/MS=432 [M+1].

Example 6 Preparation 2-((2-benzylisoindolin-5-yl)methyl)-7-fluoroimidazo[1,2-c]quinazolin-5-amine (Ex-65

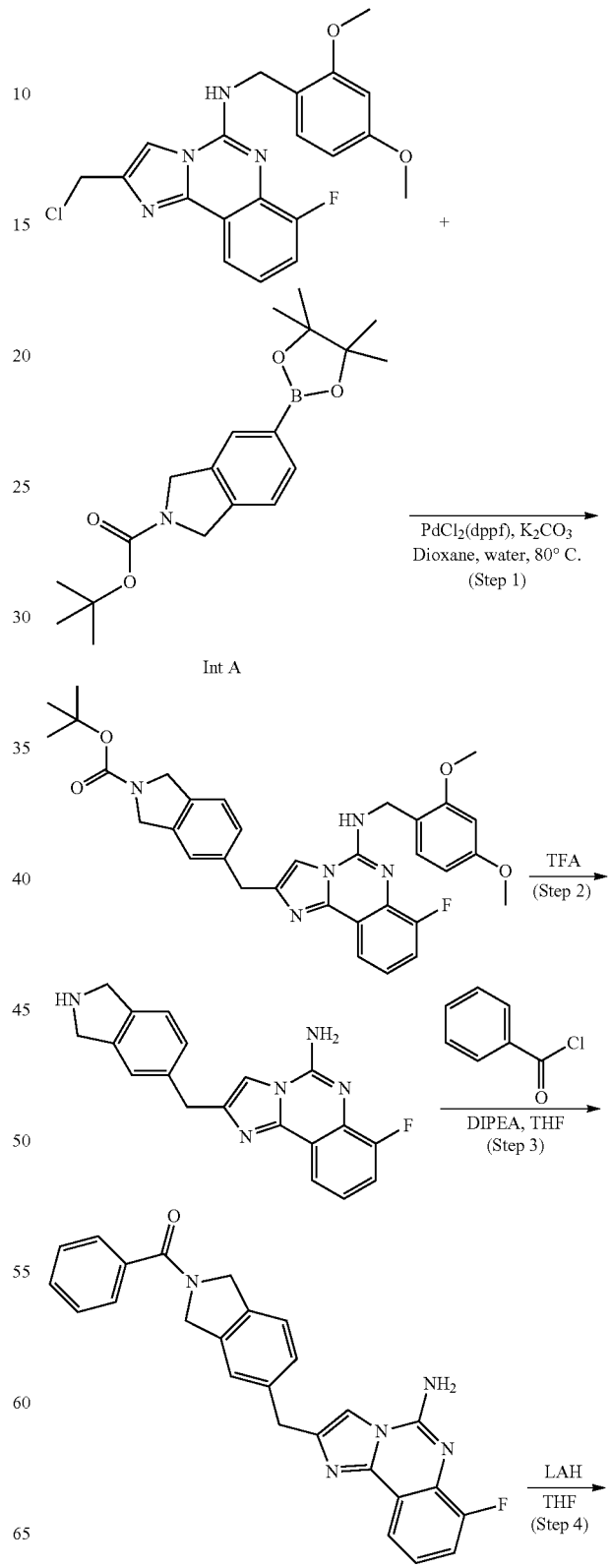

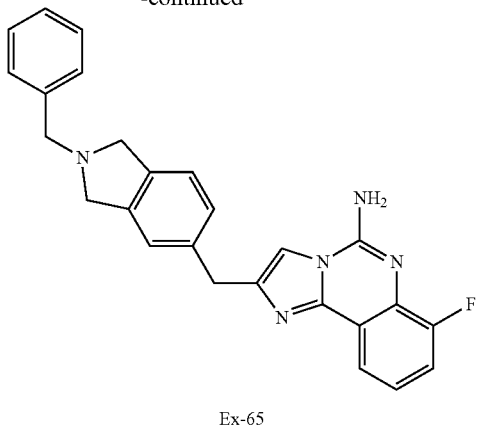

Ex-65

(Step 1) tert-butyl 5-((5-((2,4-dimethoxybenzyl)amino)-7-fluoroimidazo[1,2-c]quinazolin-2-yl)methyl)isoindoline-2-carboxylate To a stirred solution of 2-(chloromethyl)-N-(2,4-dimethoxybenzyl)-7-fluoroimidazo[1,2-c]quinazolin-5-amine prepared in accordance with the procedures of Example 1, steps 1 to 9 (100 mg, 0.249 mmol) in Dioxane (3742 µl) was added Int A (the 5-[4,4,5,5-pentamethyl-1,3,2-dioxaborolane] salt of tert-butyl isoindoline-2-carboxylate (172 mg, 0.499 mmol), K₂CO₃ (103 mg, 0.748 mmol), and Pd(Cl)₂(dppf) complex (50.9 mg, 0.062 mmol). The reaction mixture was heated to 87° C. for 3 hrs, then the solvent was evaporated and the mixture worked-up with EtOAc/NaHCO₃ (aqueous). The organic layer was washed with brine, dried over MgSO₄, filtered and concentrated. The crude product was purified by ISCO (EtOAc/Hex=1/1) to afford tert-butyl 5-((5-((2,4-dimethoxybenzyl)amino)-7-fluoroimidazo[1,2-c]quinazolin-2-yl)methyl)isoindoline-2-carboxylate (106.4 mg). LC/MS=584 [M+1].

(Step 2) 7-fluoro-2-(isoindolin-5-ylmethyl)imidazo[1,2-c]quinazolin-5-amine

To a rbf of tert-butyl 5-((5-((2,4-dimethoxybenzyl)amino)-7-fluoroimidazo[1,2-c]quinazolin-2-yl)methyl)isoindoline-2-carboxylate (106.4 mg, 0.182 mmol) was added TFA (1823 µl). The reaction was stirred overnight. TFA was evaporated. The crude was diluted with 10% MeOH/DCM. and work-up with NaHCO₃ (aq). The organic layer was dried over MgSO₄, filtered, and concentrated. The crude product was purified by prep-TLC (10% MeOH/DCM) to give 7-fluoro-2-(isoindolin-5-ylmethyl)imidazo[1,2-c]quinazolin-5-amine (47 mg), LC/MS=334 [M+1].

(Step 3) (5-((5-amino-7-fluoroimidazo[1,2-c]quinazolin-2-yl)methyl)isoindolin-2-yl)(phenyl)methanone To a stirred solution of 7-fluoro-2-(isoindolin-5-ylmethyl)imidazo[1,2-c]quinazolin-5-amine (47 mg, 0.141 mmol) in THF (1410 µl) was added DIPEA (49.2 µl, 0.282 mmol) and benzoylchloride (18.00 µl, 0.155 mmol). DCM/NaHCO₃ (aq) work-up. The organic layer was dried over MgSO4, filtered and concentrated.

The crude product was purified by prep-TLC (10% MeOH/DCM) to give (5-((5-amino-7-fluoroimidazo[1,2-c]quinazolin-2-yl)methyl)isoindolin-2-yl)(phenyl)methanone (47 mg). LC/MS=438 [M+1], L-005052550, A2a=8.4 nM (Step 4) 2-((2-benzylisoindolin-5-yl)methyl)-7-fluoroimidazo[1,2-c]quinazolin-5-amine To a stirred solution of (5-((5-amino-7-fluoroimidazo[1,2-c]quinazolin-2-yl)methyl)isoindolin-2-yl)(phenyl)methanone (41 mg, 0.094 mmol) in THF was added LAH (141 µl, 0.141 mmol). The reaction mixture was stirred at RT overnight. then refluxed for 3 hrs and cooled to 0° C. solid Na2SO4-10H2O was added slowly until frothing ceased. After extraction with DCM, the organic layer was dried over MgSO4, filtered and concentrated. The crude product was purified by prep-TLC (10% MeOH/DCM) to give 2-((2-benzylisoindolin-5-yl)methyl)-7-fluoroimidazo[1,2-c]quinazolin-5-amine (20 mg), LC/MS=424 [M+1].

Example 7 preparation of 7-methoxy-2-(2-((4-(4-(2-methoxyethoxy)phenyl)piperazin-1-yl)methyl)benzyl)imidazo[1,2-c]quinazolin-5-amine Ex-66

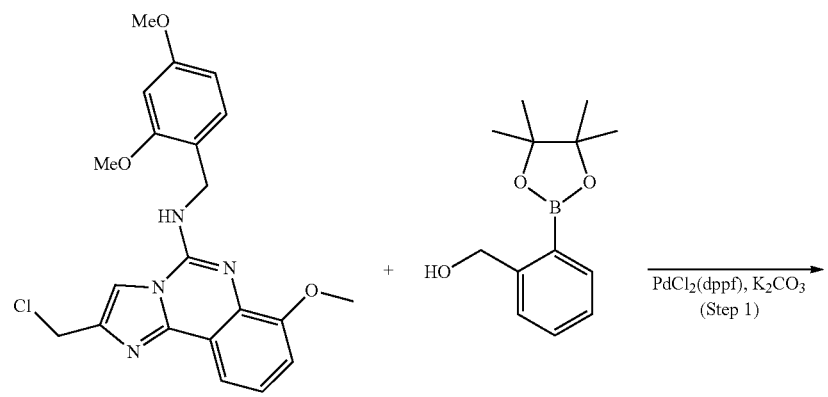

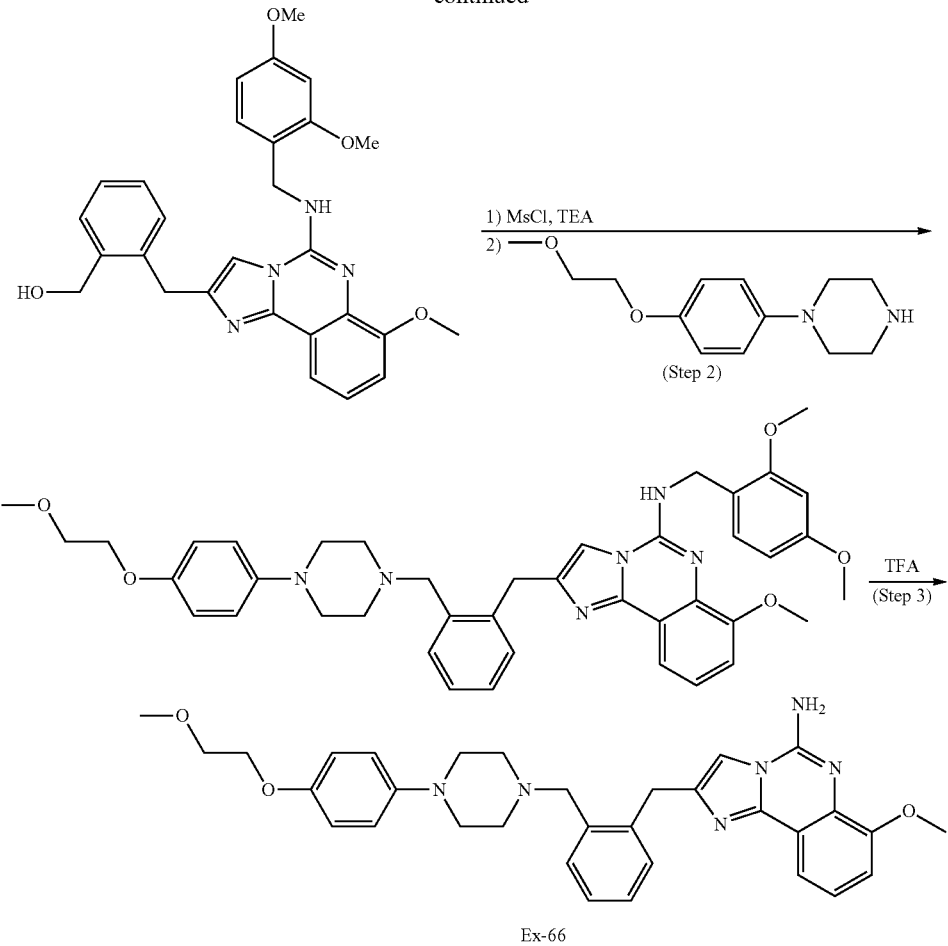

Ex-66

(Step 1) (2-((5-((2,4-dimethoxybenzyl)amino)-7-methoxyimidazo[1,2-c]quinazolin-2-yl)methyl)phenyl)methanol To a stirred solution of 2-(chloromethyl)-N-(2,4-dimethoxybenzyl)-7-methoxyimidazo[1,2-c]quinazolin-5-amine (100 mg, 0.242 mmol) in Dioxane (3633 µl) and Water (1211 µl) was added 2-(hydroxymethyl)phenylboronic acid (110 mg, 0.727 mmol), potassium carbonate (201 mg, 1.453 mmol), and Pd(Cl)$_2$(dppf) complex (49.4 mg, 0.061 mmol) at room temp. The reaction mixture was heated to 80° C. for 2 hrs. The solvent was evaporated and DCM was added. The organic layer was washed with NaHCO3 and brine, dried over MgSO4, filtered, and concentrated. The crude product was purified by column chromatography on silica gel (Isco, 40 g) eluting with (EtOAc/Hexane=1/1 to 100% EtOAc) to give (2-((5-((2,4-dimethoxybenzyl)amino)-7-methoxyimidazo[1,2-c]quinazolin-2-yl)methyl)phenyl)methanol of the product as a foam (112 mg). LC/MS=485 [M+1]

(Step 2) N-(2,4-dimethoxybenzyl)-7-methoxy-2-(2-((4-(4-(2-methoxyethoxy)phenyl)piperazin-1-yl)methyl)benzyl)imidazo[1,2-c]quinazolin-5-amine To a stirred solution of (2-((5-((2,4-dimethoxybenzyl)amino)-7-methoxyimidazo[1,2-c]quinazolin-2-yl)methyl)phenyl)methanol (48 mg, 0.099 mmol) in DCM (991 µl) was added methanesulfonyl chloride (9.26 µl, 0.119 mmol) and TEA (20.71 µl, 0.149 mmol) at 0° C. Generation of the mesylate was confirmed by TLC, then a solution of piperazine (234 mg, 0.991 mmol) in DCM was added, the DCM solvent was evaporated and DMF was added. The reaction mixture was heated to 70° C. for 16 hrs, then cooled to ambient and saturated aqueous NaHCO$_3$ was added. The resulting precipitate was collected by filtration, washed, dried, and purified by ISCO (10% MeOH/DCM) yielding the title compound which was confirmed by LC/MS=703 [M+1]

(Step 3) 7-methoxy-2-(2-((4-(4-(2-methoxyethoxy)phenyl)piperazin-1-yl)methyl)benzyl)imidazo[1,2-c]quinazolin-5-amine Ex-66

Into round bottom flask containing N-(2,4-dimethoxybenzyl)-7-methoxy-2-(2-((4-(4-(2-methoxyethoxy)phenyl)piperazin-1-yl)methyl)benzyl)imidazo[1,2-c]quinazolin-5-amine (67 mg, 0.095 mmol) was added TFA and the mixture was stirred for 16 hrs., then TFA was removed by evacuation. The crude product thus provided was redissolved in 10% MeOH/DCM and the organic layer was washed with NaHCO3(aq) to remove TFA salt. The organics were separated, dried over MgSO$_4$, filtered and concentrated. The crude product was purified by prep-TLC (10% MeOH in DCM) to give Ex-66 which was confirmed by LC/MS=553 [M+1].

The compounds of Table 2 were prepared by using methodology described in Example 7 and appropriate reagents.

TABLE 2

| Ex. No. | Structure | LC-MS | Name |
|---|---|---|---|
| Ex-67 | 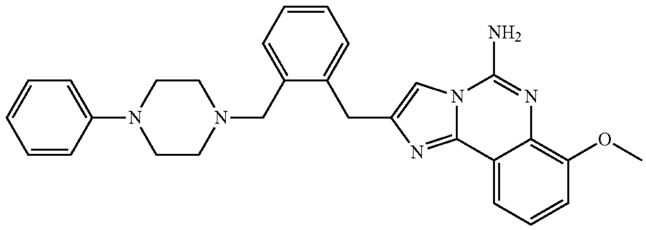 [SMILES: COc1cccc2c1nc(N)n1cc(Cc3ccccc3CN3CCN(c4ccccc4)CC3)nc21] | 479 [M + 1]. | 7-methoxy-2-(2-((4-(4-(2-methoxyethoxy)phenyl)piperazin-1-yl)methyl)benzyl)imidazo[1,2-c]quinazolin-5-amine |
| Ex-68 | 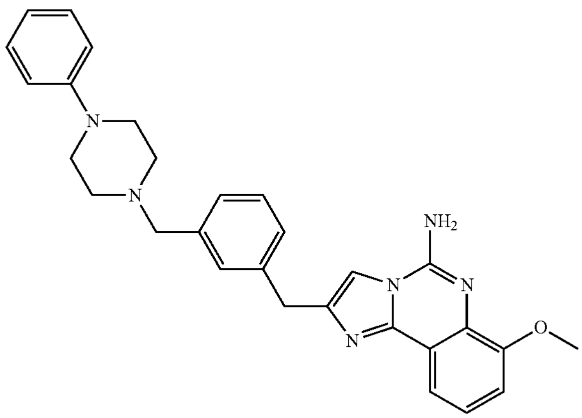 [SMILES: COc1cccc2c1nc(N)n1cc(Cc3cccc(CN4CCN(c5ccccc5)CC4)c3)nc21] | 479 [M + 1]. | 7-methoxy-2-(2-((4-phenylpiperazin-1-yl)methyl)benzyl)imidazo[1,2-c]quinazolin-5-amine |
| Ex-69 | 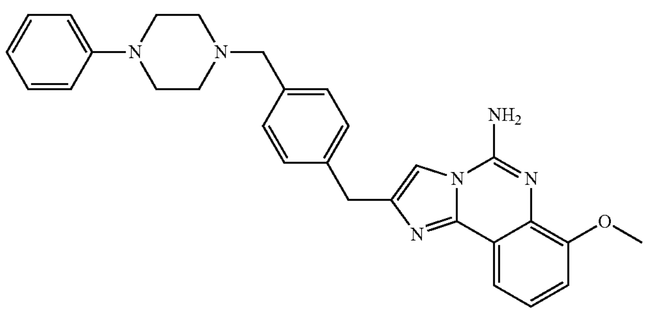 [SMILES: COc1cccc2c1nc(N)n1cc(Cc3ccc(CN4CCN(c5ccccc5)CC4)cc3)nc21] | 479 [M + 1]. | 7-methoxy-2-(3-((4-phenylpiperazin-1-yl)methyl)benzyl)imidazo[1,2-c]quinazolin-5-amine |
| Ex-71 | 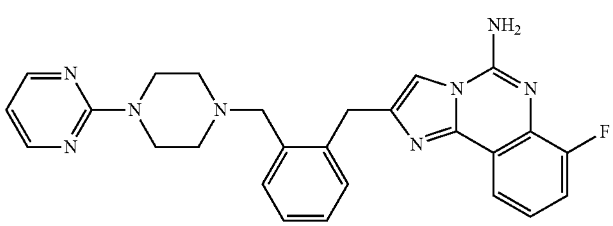 [SMILES: Nc1nc2c(F)cccc2c2nc(Cc3ccccc3CN3CCN(c4ncccn4)CC3)cn12] | 469 [M + 1]. | 7-fluoro-2-(2-((4-(pyrimidin-2-yl)piperazin-1-yl)methyl)benzyl)imidazo[1,2-c]quinazolin-5-amine |
| Ex-72 | 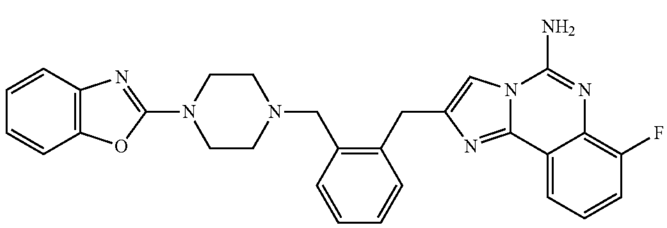 [SMILES: Nc1nc2c(F)cccc2c2nc(Cc3ccccc3CN3CCN(c4nc5ccccc5o4)CC3)cn12] | 508 [M + 1]. | 7-fluoro-2-(2-((4-(pyrimidin-2-yl)piperazin-1-yl)methyl)benzyl)imidazo[1,2-c]quinazolin-5-amine |

TABLE 2-continued

| Ex. No. | Structure | LC-MS | Name |
|---|---|---|---|
| Ex-73 | 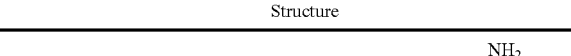 | 475 [M + 1]. | 2-(2-((4-(benzo[d]oxazol-2-yl)piperazin-1-yl)methyl)benzyl)-7-fluoroimidazo[1,2-c]quinazolin-5-amine |

Example 8 Preparation of 7-fluoro-2-(3-(pyridin-3-yl)benzyl)imidazo[1,2-c]quinazolin-5-amine Ex-74

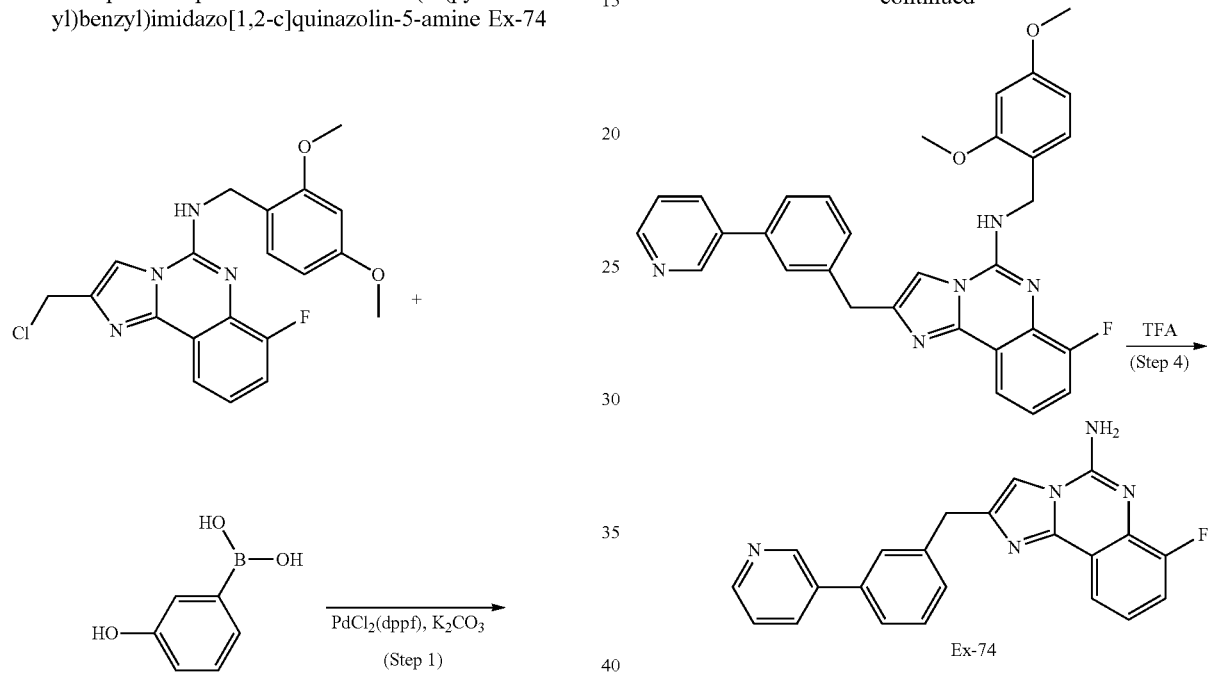

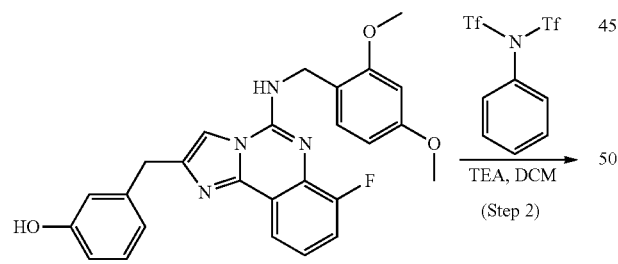

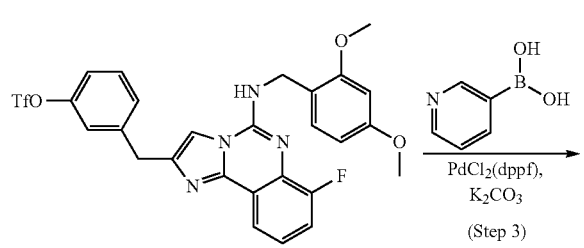

(Step 1) 3-((5-((2,4-dimethoxybenzyl)amino)-7-fluoroimidazo[1,2-c]quinazolin-2-yl)methyl)phenol To a stirred solution of 2-(chloromethyl)-N-(2,4-dimethoxybenzyl)-7-fluoroimidazo[1,2-c]quinazolin-5-amine (200 mg, 0.499 mmol) in Dioxane (7484 μl) and Water (2495 μl) was added 3-hydroxyphenylboronic acid (206 mg, 1.497 mmol), potassium carbonate (414 mg, 2.99 mmol), and Pd(Cl)$_2$(dppf) complex (102 mg, 0.125 mmol) at room temp. The reaction mixture was heated to 80° C. for 2 hrs. then solvent was evaporated and DCM was added. The organic layer was washed with NaHCO$_3$ and brine, dried over MgSO$_4$, filtered, and concentrated. The crude product was purified by column chromatography on silica gel (ISCO) eluting with (EtOAc/Hexane=1/1 to 100% EtOAc) to yield the title compound, which was confirmed by LC/MS=459 [M+1]

(Step 2) 3-((5-((2,4-dimethoxybenzyl)amino)-7-fluoroimidazo[1,2-c]quinazolin-2-yl)methyl)phenyl trifluoromethanesulfonate To a stirred solution of 3-((5-((2,4-dimethoxybenzyl)amino)-7-fluoroimidazo[1,2-c]quinazolin-2-yl)methyl)phenol (171.4 mg, 0.374 mmol) in CH2Cl2 (7477 μl) was added TEA (104 µl, 0.748 mmol) and N-Phenyl-bis(trifluoromethanesulfonimide) (174 mg, 0.486 mmol) at 0° C. The reaction was monitored by LCMS and TLC. The reaction was warmed to RT and stirred overnight (16 hrs). Water and NaHCO3(aq)/DCM work-up. The organic layer was dried over MgSO4, filtered and concentrated to yield the title compound as crude product, which was used in the next step without purification, LC/MS=591 [M+1].

(Step 3) N-(2,4-dimethoxybenzyl)-7-fluoro-2-(3-(pyridin-3-yl)benzyl)imidazo[1,2-c]quinazolin-5-amine To a stirred solution of 3-((5-((2,4-dimethoxybenzyl)amino)-7-fluoroimidazo[1,2-c]quinazolin-2-yl)methyl)phenyl trifluoromethanesulfonate in Dioxane (2896 µl) and Water (965 µl) was added pyridin-3-ylboronic acid, potassium carbonate (160 mg, 1.158 mmol), and Pd(Cl)$_2$(dppf) complex (39.4 mg, 0.048 mmol) at room temp. The reaction mixture was heated to 80° C. for 2 hrs. The solvent was evaporated and DCM was added. The organic layer was washed with NaHCO$_3$ and brine, dried over MgSO$_4$, filtered, and concentrated. The crude product was purified by ISCO (1/1EtOAC/HEx to 10% MeOH/DCM) to give the title compound which was confirmed using LC/MS=520 [M+1]

(Step 4) 7-fluoro-2-(3-(pyridin-3-yl)benzyl)imidazo[1,2-c]quinazolin-5-amine

To a rbf of N-(2,4-dimethoxybenzyl)-7-fluoro-2-(3-(pyridin-3-yl)benzyl)imidazo[1,2-c]quinazolin-5-amine (101 mg, 0.194 mmol) was added TFA (1944 µl). The reaction mixture was stirred overnight. TFA was evaporated and NaHCO$_3$ (aq) and 10% MeOH/DCM work-up. The organic layer was dried over MgSO$_4$ and filtered and concentrated. The crude product was purified by prep-TLC (10% MeOH/DCM) to give 7-fluoro-2-(3-(pyridin-3-yl)benzyl)imidazo[1,2-c]quinazolin-5-amine (Ex-74). LC/MS=370 [M+1].

The compounds reported in Table 3 were prepared by using methods described in Example 8 using appropriate reagents.

TABLE 3

| Ex-No | Structure | LCMS | Name |
|---|---|---|---|
| Ex-75 | 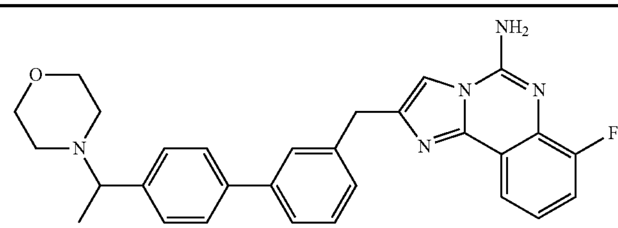 | 482 [M + 1] | 7-fluoro-2-((4'-(1-morpholinoethyl)-[1,1'-biphenyl]-3-yl)methyl)imidazo[1,2-c]quinazolin-5-amine |
| Ex-76 | 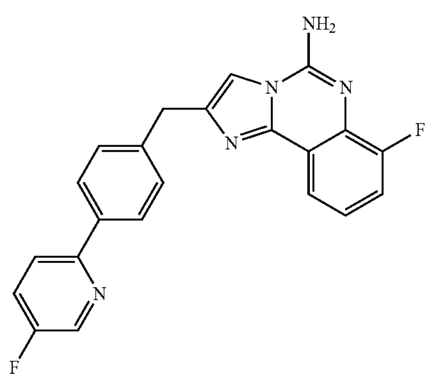 [SMILES: Nc1nc2c(F)cccc2c2nc(Cc3ccc(-c4ccc(F)cn4)cc3)cn12] | 388 [M + 1] | 7-fluoro-2-(4-(5-fluoropyridin-yl)benzyl)imidazo[1,2-c]quinazolin-5-amine |
| Ex-77 | 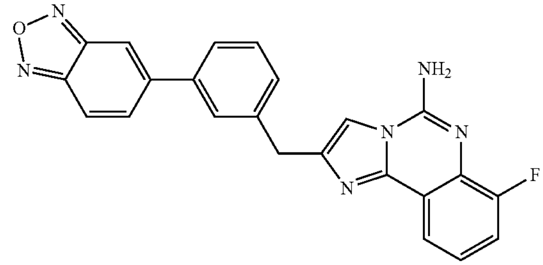 [SMILES: Nc1nc2c(F)cccc2c2nc(Cc3cccc(-c4ccc5nonc5c4)c3)cn12] | 411 [M + 1] | 2-(3-(benzo[c][1,2,5]oxadiazol-5-yl)benzyl)-7-fluoroimidazo[1,2-c]quinazolin-5-amine |

TABLE 3-continued

| Ex-No | Structure | LCMS | Name |
|---|---|---|---|
| Ex-78 | 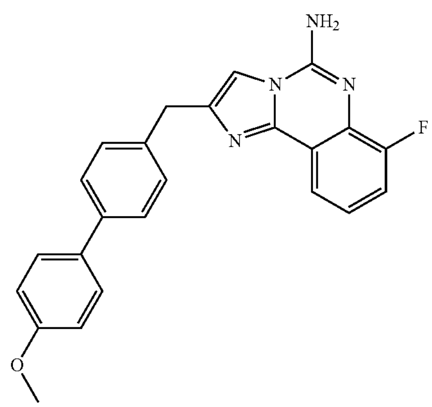 [SMILES: COc1ccc(-c2ccc(Cc3cn4c(N)nc5c(F)cccc5c4n3)cc2)cc1] | 399 [M + 1] | 7-fluoro-2-((4'-methoxy-[1,1'-biphenyl]-4-yl)melhyl)imidazo[1,2-c]quinazolin-5-amine |
| Ex-79 | 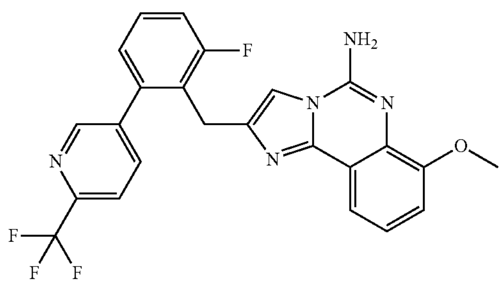 [SMILES: COc1cccc2c1nc(N)n1cc(Cc3c(F)cccc3-c3ccc(C(F)(F)F)nc3)nc21] | 468 [M + 1] | 2-(2-fluoro-6-(6-(trifluoromethyl)pyridin-3-yl)benzyl)-7-methoxyimidazo[1,2-c]quinazolin-5-amine |
| Ex-80 | 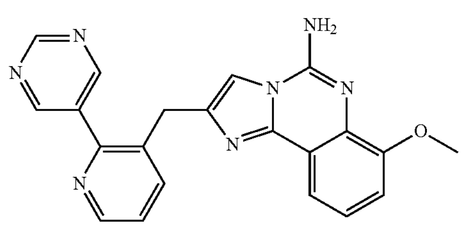 [SMILES: COc1cccc2c1nc(N)n1cc(Cc3cccnc3-c3cncnc3)nc21] | 384 [M + 1] | 7-methoxy-2-((2-(pyrimidin-5-yl)pyridin-3-yl)methyl)imidazo[1,2-c]quinazolin-5-amine |
| Ex-81 | 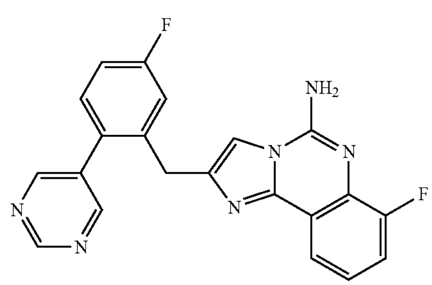 [SMILES: Nc1nc2c(F)cccc2c2nc(Cc3cc(F)ccc3-c3cncnc3)cn12] | 389 | 7-fluoro-2-(5-fluoro-2-(pyrimidin-5-yl)benzyl)imidazo[1,2-c]quinazolin-5-amine |
| Ex-82 | 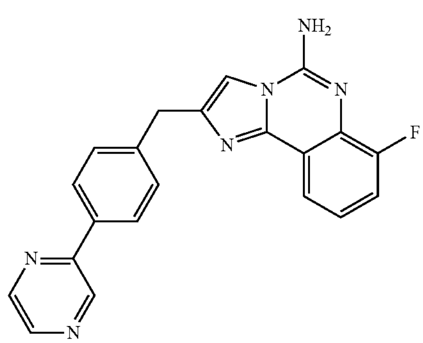 [SMILES: Nc1nc2c(F)cccc2c2nc(Cc3ccc(-c4cnccn4)cc3)cn12] | 371 | 7-fluoro-2-(4-(pyrazin-2-yl)benzyl)imidazo[1,2-c]quinazolin-5-amine |

TABLE 3-continued
| Ex-No | Structure | LCMS | Name |
|---|---|---|---|
| Ex-83 | 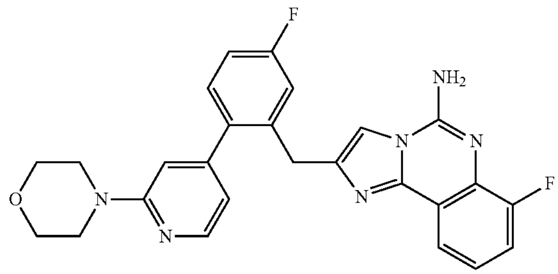 [SMILES: Nc1nc2c(F)cccc2c2nc(Cc3cc(F)ccc3-c3ccnc(N4CCOCC4)c3)cn12] | 473 | 7-fluoro-2-(5-fluoro-2-morpholinopyridin-4-yl)benzyl)imidazo[1,2-c]quinazolin-5-amine |
Example 9 PREPARATION of 4-((5-amino-7-fluoroimidazo[1,2-c]quinazolin-2-yl)methyl)-N-(pyridin-2-yl)benzamide Ex-84
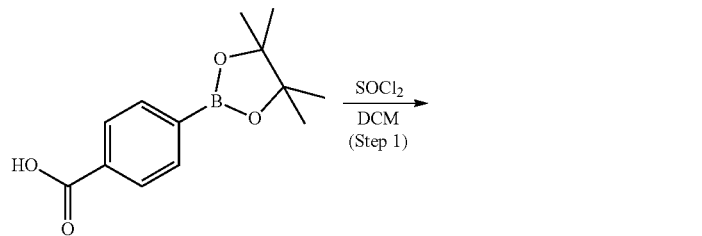
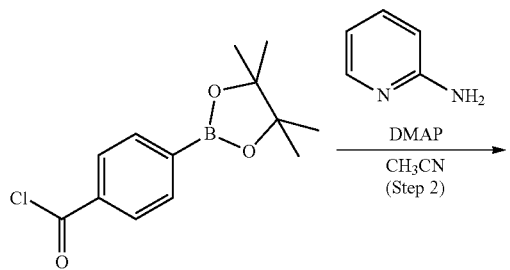
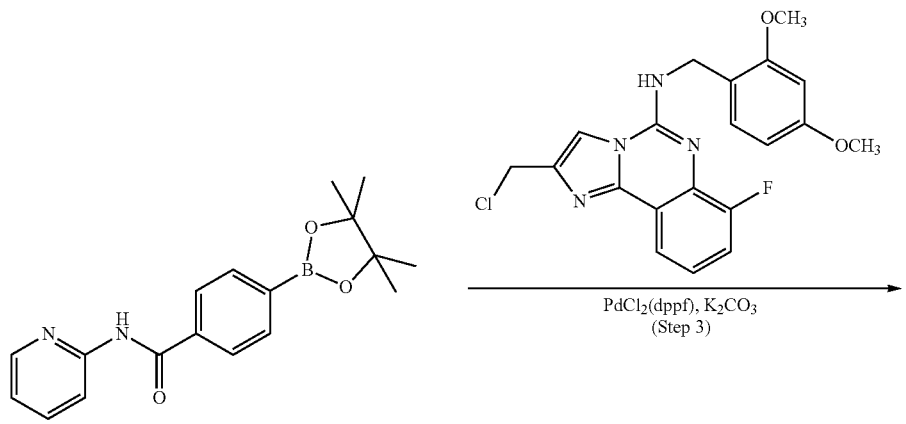

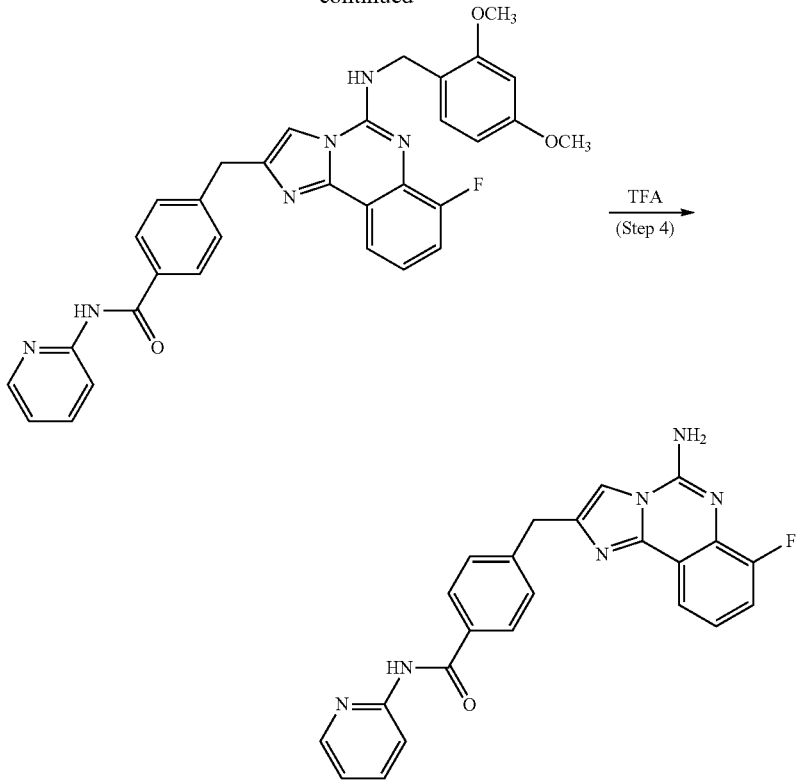

Ex-84

(Step 1) 4-(4,4,5,5-tetramethyl-1,3,2-dioxaborolan-2-yl)benzoyl chloride

To a stirred solution of 4-carboxyphenylboronic acid pinacol ester (2 g, 8.06 mmol) in DCM (16.12 ml) was added thionyl chloride (5.88 ml, 81 mmol) and a couple of drops of DMF (activation of the reaction), then the reaction mixture was stirred at reflux for 16 hrs. After 16 hours the reaction mixture was cooled from reflux and the solvent and $SOCl_2$ was evaporated in a rotary evaporator at 40° C. to yield the title compound as a solid product. LC/MS=267 [M+1]

(Step 2) [2-(chloromethyl)-N-(2,4-dimethoxybenzyl)-7-fluoroimidazo[1,2-c]quinazolin-5-amine To a stirred solution of 4-(4,4,5,5-tetramethyl-1,3,2-dioxaborolan-2-yl)benzoyl chloride (500 mg, 1.876 mmol) and DMAP (229 mg, 1.876 mmol) in acetonitrile (3752 μl) was added 2-aminopyridine (194 mg, 2.064 mmol) at RT. The reaction mixture was stirred for 2 hours, then the solvent was evaporated and partitioned between DCM and 0.2 N(aq) HCl. The aqueous phase was back extracted using DCM and combined the organic layers were combined, dried over $MgSO_4$, filtered, and evaporated to dryness to give the title product. LC/MS=325 [M+1]

(Step 3) 4-((5-((2,4-dimethoxybenzyl)amino)-7-fluoroimidazo[1,2-c]quinazolin-2-yl)methyl)-N-(pyridin-2-yl)benzamide To a stirred solution of [2-(chloromethyl)-N-(2,4-dimethoxybenzyl)-7-fluoroimidazo[1,2-c]quinazolin-5-amine in Dioxane (2994 μl) and water (998 μl) was added N-(pyridin-2-yl)-4-(4,4,5,5-tetramethyl-1,3,2-dioxaborolan-2-yl)benzamide, potassium carbonate (166 mg, 1.198 mmol), and $Pd(Cl)_2(dppf)$ complex (40.7 mg, 0.050 mmol) at room temp. The reaction mixture was heated to 80° C. for 2 hr., then the solvent was evaporated and DCM was added. The organic layer was washed with $NaHCO_3$ and brine, dried over $MgSO_4$, filtered, and concentrated. The crude product was purified by ISCO (1/1EtOAC/HEx to 100% EtOAc) to yield the title compound, confirmed using LC/MS=563 [M+1].

(Step 4) 4-((5-amino-7-fluoroimidazo[1,2-c]quinazolin-2-yl)methyl)-N-(pyridin-2-yl)benzamide (Ex-84

Into a round bottom flask containing 4-((5-((2,4-dimethoxybenzyl)amino)-7-fluoroimidazo[1,2-c]quinazolin-2-yl)methyl)-N-(pyridin-2-yl)benzamide from the previous step (73.6 mg, 0.131 mmol) was added TFA (1308 μl), and the reaction mixture was stirred overnight. TFA was evaporated and $NaHCO_3$ (aq) and 10% MeOH/DCM work-up. The organic layer was dried over $MgSO_4$ and filtered and concentrated. The crude product was purified by prep-TLC (10% MeOH/DCM) to yield the title product, the compound Ex-84, which was confirmed by LC/MS=413 [M+1].

The compounds reported in Table 4 were prepared by using methods described in Example 9 using appropriate reagents.

TABLE 4

| Ex-No | Structure | LCMS | Name |
|---|---|---|---|
| Ex-85 | 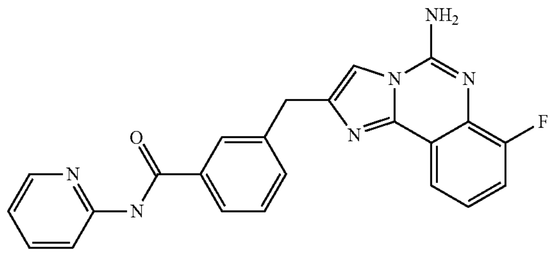 [SMILES: Nc1nc2c(F)cccc2c2nc(Cc3cccc(C(=O)Nc4ccccn4)c3)cn12] | 413 [M + 1] | 3-((5-amino-7-fluoroimidazo[1,2-c]quinazolin-2-yl)methyl)-N-(pyridin-2-yl)benzamide |
| Ex-86 | 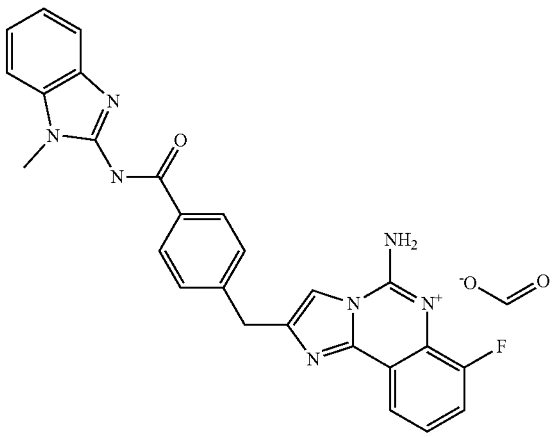 | 512 [M + 1] | 5-amino-7-fluoro-2-(4-((1-methyl-1H-benzo[d]imidazol-2-yl)carbamoyl)benzyl)imidazo[1,2-c]quinazolin-6-ium formate |
| Ex-87 | 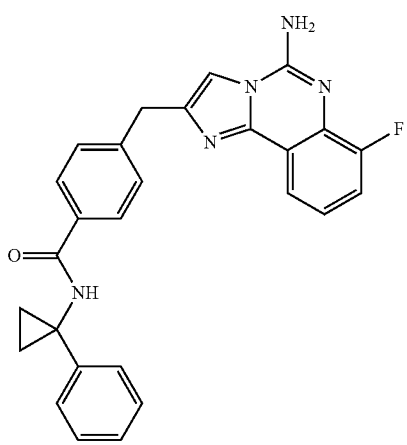 [SMILES: Nc1nc2c(F)cccc2c2nc(Cc3ccc(C(=O)NC4(c5ccccc5)CC4)cc3)cn12] | 452 | 4-((5-amino-7-fluoroimidazo[1,2-c]quinazolin-2-yl)methyl)-N-(1-phenylcyclopropyl)benzamide |
| Ex-88 | 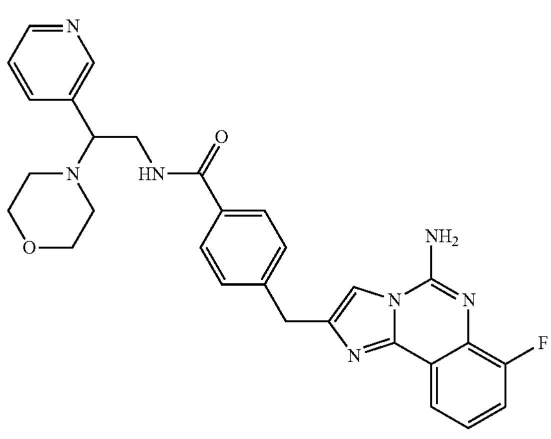 [SMILES: Nc1nc2c(F)cccc2c2nc(Cc3ccc(C(=O)NCC(c4cccnc4)N4CCOCC4)cc3)cn12] | 526 | 4-((5-amino-7-fluoroimidazo[1,2-c]quinazolin-2-yl)methyl)-N-(2-morpholino-2-(pyridin-3-yl)ethyl)benzamide |

TABLE 4-continued
| Ex-No | Structure | LCMS | Name |
|---|---|---|---|
| Ex-89 | 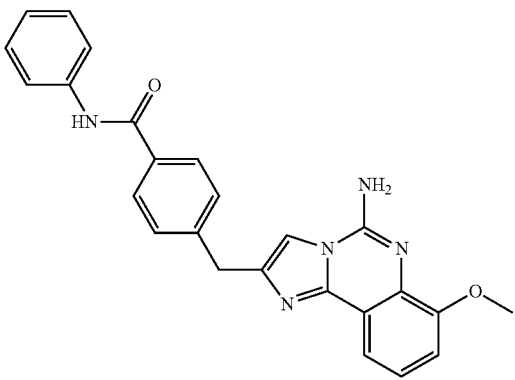 [SMILES: COc1cccc2c1nc(N)n1cc(Cc3ccc(C(=O)Nc4ccccc4)cc3)nc21] | 424 | 4-((5-amino-7-methoxyimidazo[1,2-c]quinazolin-2-yl)methyl)-N-phenylbenzamide |
| Ex-90 | 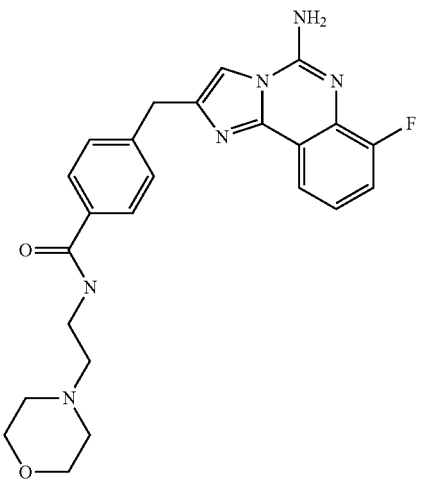 [SMILES: Nc1nc2c(F)cccc2c2nc(Cc3ccc(C(=O)NCCN4CCOCC4)cc3)cn12] | 449 | 4-((5-amino-7-fluoroimidazo[1,2-c]quinazolin-2-yl)methyl)-N-(2-morpholinoethyl)benzamide |
Example 10 Preparation of 7-fluoro-2-(4-(5-(morpholinomethyl)-1,3,4-oxadiazol-2-yl)benzyl)imidazo[1,2-c]quinazolin-5-amine Ex-91
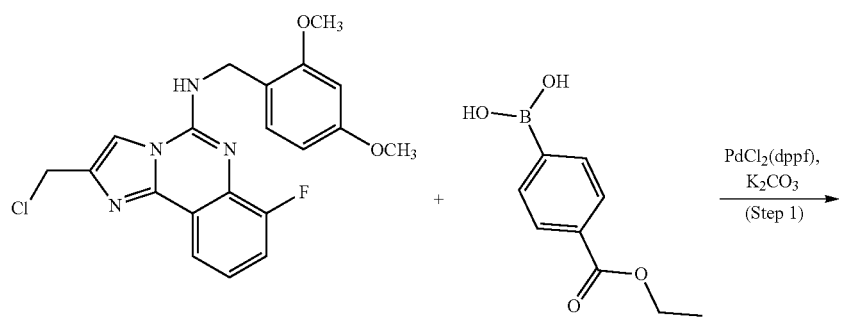

-continued
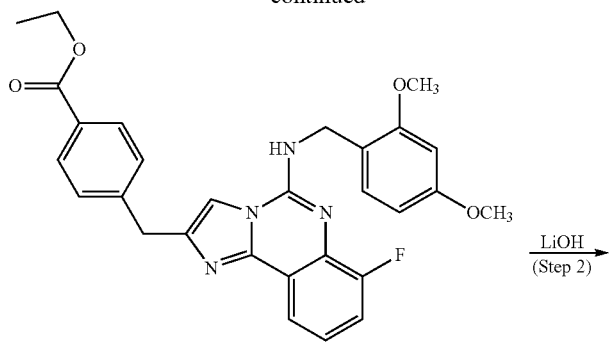
LiOH
(Step 2)
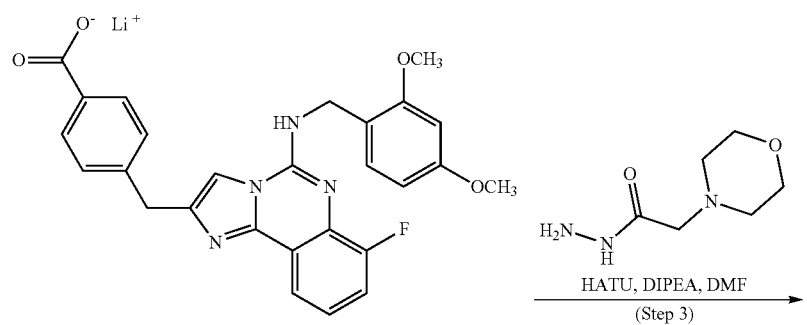
HATU, DIPEA, DMF
(Step 3)
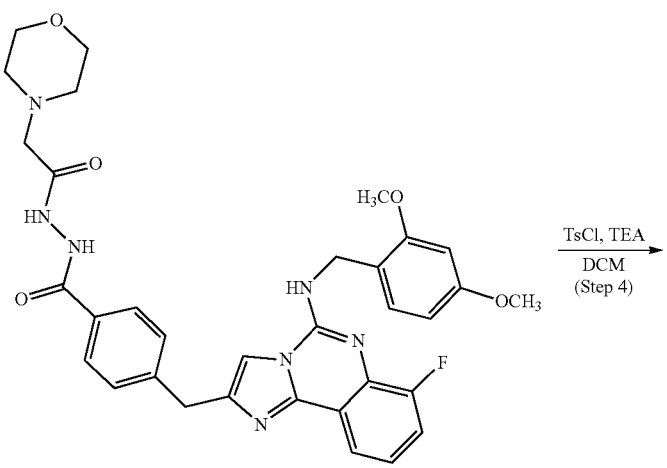
TsCl, TEA
DCM
(Step 4)
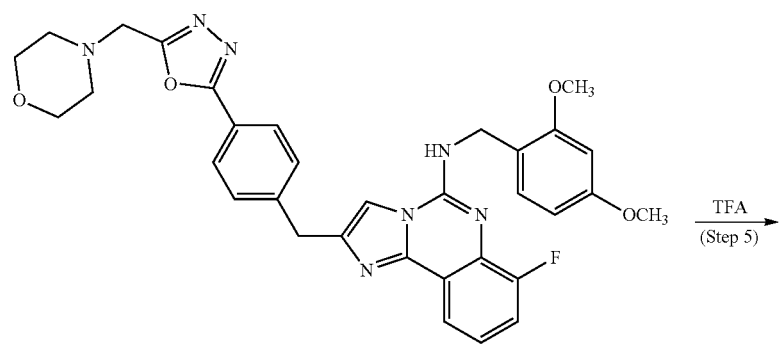
TFA
(Step 5)

-continued

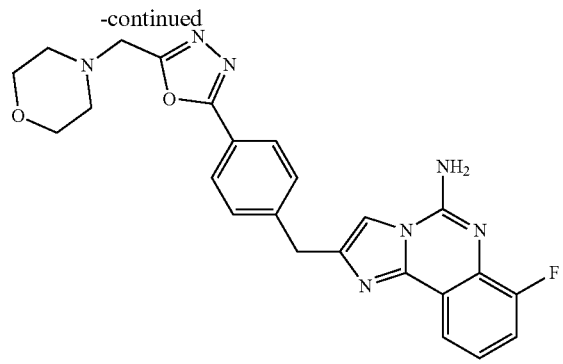

Ex-91

(Step 1) ethyl 4-((5-((2,4-dimethoxybenzyl)amino)-7-fluoroimidazo[1,2-c]quinazolin-2-yl)methyl)benzoate To a stirred solution of 2-(chloromethyl)-N-(2,4-dimethoxybenzyl)-7-fluoroimidazo[1,2-c]quinazolin-5-amine (100 mg, 0.249 mmol) in Dioxane (2994 μl) and water (998 μl) was added potassium carbonate (166 mg, 1.198 mmol), and Pd(Cl)$_2$(dppf) complex (40.7 mg, 0.050 mmol) at room temp. The reaction mixture was heated to 80° C. for 2 hrs. then the solvent was evaporated and DCM was added. The organic layer was washed with NaHCO$_3$ and brine, dried over MgSO$_4$, filtered, and concentrated. The crude product was purified by column chromatography on silica gel (ISCO, 40 g) eluting with (EtOAc/Hexane=1/1 to 100% EtOAc) to give the title product, which was confirmed by LC/MS=515 [M+1]

(Step 2) Lithium 4-((5-((2,4-dimethoxybenzyl)amino)-7-fluoroimidazo[1,2-c]quinazolin-2-yl)methyl)benzoate Into a vessel was placed a solution of ethyl 4-((5-((2,4-dimethoxybenzyl)amino)-7-fluoroimidazo[1,2-c]quinazolin-2-yl)methyl)benzoate (371.3 mg, 0.722 mmol) in THF (1984 μl) and methanol (902 μl), and added therein, at room temperature with stirring, lithium monohydrate (64.9 mg, 0.866 mmol) dissolved in water (722 μl). The reaction mixture was allowed to stir at RT overnight, then the solvents were evaporated off and the residue dried under vacuum for 1 hr to obtain white solid: lithium 4-((5-((2,4-dimethoxybenzyl)amino)-7-fluoroimidazo[1,2-c]quinazolin-2-yl)methyl)benzoate, used in the next step without purification. LC/MS=487 [M+1]

(Step 3) 4-((5-((2,4-dimethoxybenzyl)amino)-7-fluoroimidazo[1,2-c]quinazolin-2-yl)methyl)-N'-(2-morpholinoacetyl)benzohydrazide Into a 20 mL borosilicate glass vial fitted with a magnetic stir bar was placed lithium 4-((5-((2,4-dimethoxybenzyl)amino)-7-fluoroimidazo[1,2-c]quinazolin-2-yl)methyl)benzoate (177.5 mg, 0.360 mmol), HATU (206 mg, 0.541 mmol), and 2-morpholinoacetohydrazide (115 mg, 0.721 mmol) in DMF (1802 μl). Into the mixture was added DIEA (189 μl, 1.081 mmol) and the vial was capped with rubber septum screw cap and the mixture stirred at 60° C. overnight. The next day the mixture was diluted with DCM and washed 2x with ½ sat. aq. NaHCO$_3$, and the aqueous phase extracted with three aliquots of DCM. The organic layers were combined, dried over MgSO$_4$, filtered and evaporated to dryness. Thus obtained, the crude material was loaded onto a 40 g flash silica gel column and eluted first with Hex/EtOAc, followed by DCM/10% MeOH in DCM, and the appropriate fractions collected to yield the title compound, which was confirmed by LC/MS=628 [M+1]

(Step 4) N-(2,4-dimethoxybenzyl)-7-fluoro-2-(4-(5-(morpholinomethyl)-1,3,4-oxadiazol-2-yl)benzyl)imidazo[1,2-c]quinazolin-5-amine Into a vial fitted with a magnetic stir bar was dissolved 4-((5-((2,4-dimethoxybenzyl)amino)-7-fluoroimidazo[1,2-c]quinazolin-2-yl)methyl)-N'-(2-morpholinoacetyl)benzohydrazide (200 mg, 0.318 mmol) in DCE (635 μl) followed by the addition of TEA (89 μl, 0.635 mmol) and p-toluenesulfonyl chloride (91 mg, 0.476 mmol). The mixture was stirred at 45° C. overnight, cooled to RT, then diluted with ether. The DCE/ether solution was separated from insoluble material, the solution was filtered and the filtrate washed with ether. The organics thus obtained were washed with sat. aq. NaHCO$_3$ and water, then the aq. phase was back extracted with DCM 3x. Combined organics were worked up using a rotary evaporate and the solids thus obtained were loaded onto a 40 g ISCO gold flash silica gel column and eluted with A=DCM, B=DCM+10% MeOH yielding the title compound, the identity of which was confirmed by LC/MS=610 [M+1]

(Step 5) 7-fluoro-2-(4-(5-(morpholinomethyl)-1,3,4-oxadiazol-2-yl)benzyl)imidazo[1,2-c]quinazolin-5-amine Ex-91

Into a round bottom flask containing N-(2,4-dimethoxybenzyl)-7-fluoro-2-(4-(5-(morpholinomethyl)-1,3,4-oxadiazol-2-yl)benzyl)imidazo[1,2-c]quinazolin-5-amine (174 mg, 0.285 mmol) was added TFA (2854 μl) and the reaction mixture was stirred at RT overnight.

TFA was removed from the reaction mixture was evaporated on a rotary evaporator and the residue was redissolved in DCM with sufficient MeOH added (with continued stirring) to remove all coloration from reaction mixture. The reaction mixture was then washed with aq. sat. NaHCO$_3$ and the organics were separated, dried over MgSO$_4$, filtered and evaporated. The residue was loaded onto a 40 g ISCO gold flash silica gel column and eluted with Hex/EtOAc first, then DCM/10% MeOH in DCM second. Desired peak eluted as a sharp tall peak at 10% MeOH in DCM. Collected fractions were evaporated on a rotary evaporator to yield solids which were then further dried under vacuum overnight yielding the title compound, Ex-91, which was confirmed using LC/MS=460 [M+1].
Example 11 Preparation of 1-(8-((5-amino-7-fluoro-imidazo[1,2-c]quinazolin-2-yl)methyl)-2,3-dihydro-4H-benzo[b][1,4]oxazin-4-yl)-2-(pyridin-2-yl)ethan-1-one (Ex-92)
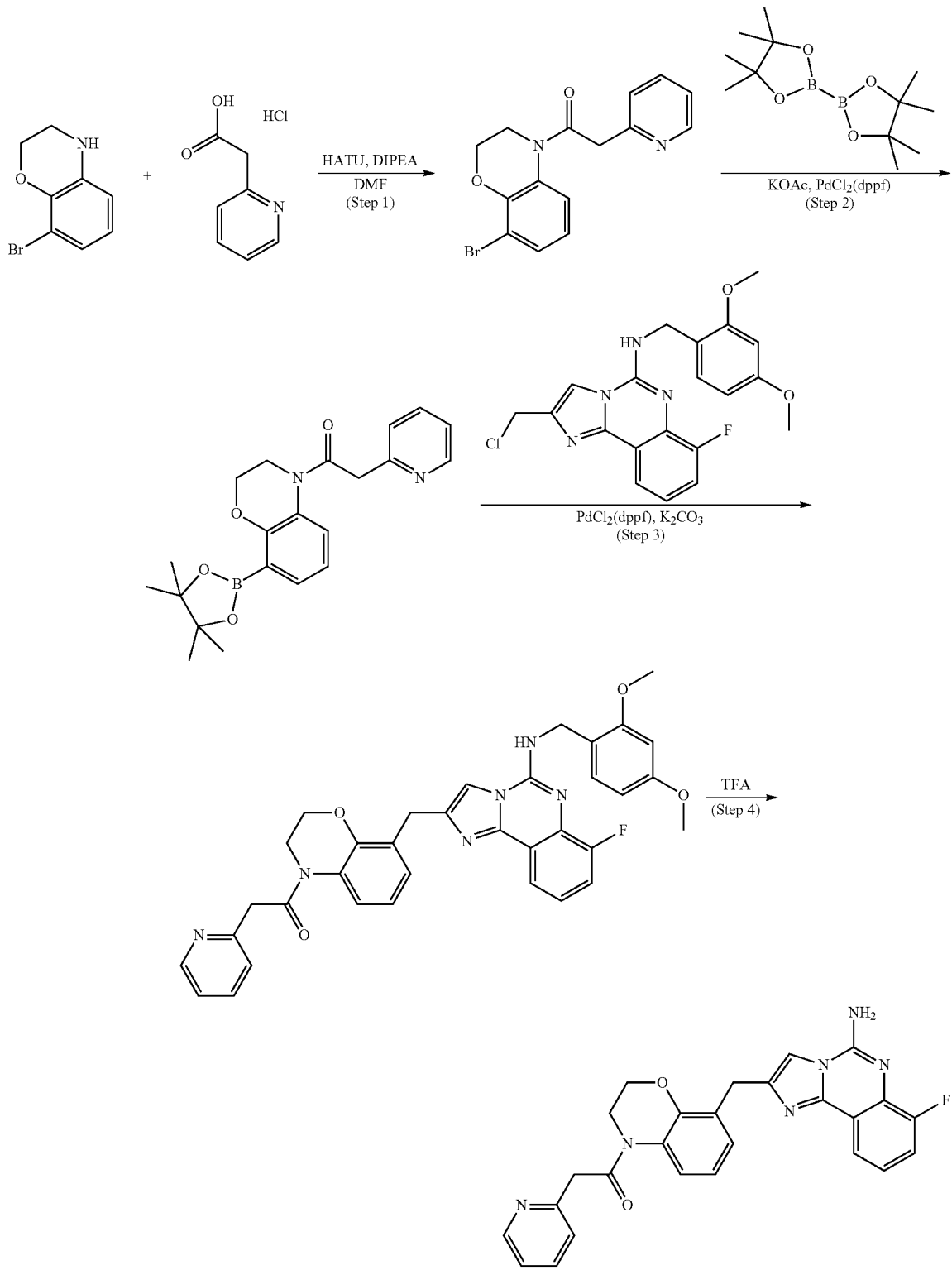
Ex-92

(Step 1) 1-(8-bromo-2H-benzo[b][1,4]oxazin-4(3H)-yl)-2-(pyridin-2-yl)ethanone

To a stirred solution of 8-bromo-3,4-dihydro-2H-benzo[b][1,4]oxazine (300 mg, 1.401 mmol) in DMF (1.40E+04 µl) was added 2-pyridylacetic acid (292 mg, 1.682 mmol), HATU (799 mg, 2.102 mmol) and DIPEA (734 µl, 4.20 mmol). The reaction was heated to 70° C. for 16 hrs then worked-up with EtOAC/NaHCO₃(aq). The organic layer was separated, washed with brine and dried over MgSO₄, filtered and concentrated. The crude product thus obtained was was purified by ISCO (40 g, 1/1EtOAC/Hex) to give the title compound which was confirmed using LC/MS=334 [M+1]

(Step 2) 2-(chloromethyl)-N-(2,4-dimethoxybenzyl)-7-fluoroimidazo[1,2-c]quinazolin-5-amine To a stirred solution of 1-(8-bromo-2H-benzo[b][1,4]oxazin-4(3H)-yl)-2-(pyridin-2-yl)ethanone (396 mg, 1.189 mmol) in Dioxane (5770 µl) was added diborane pinacol ester (362 mg, 1.426 mmol), Pd(Cl)₂(dppf) complex (243 mg, 0.297 mmol) and potassium acetate (350 mg, 3.57 mmol). The reaction mixture was stirred at 90° C. monitored by LCMS. After stirring overnight, LCMS confirmed the completion of the reaction and the crude reaction mixture was used in the next step without purification. LC/MS=381 [M+1]

(Step 3) 1-(8-((5-((2,4-dimethoxybenzyl)amino)-7-fluoroimidazo[1,2-c]quinazolin-2-yl)methyl)-2H-benzo[b][1,4]oxazin-4(3H)-yl)-2-(pyridin-2-yl)ethanone Ex-92

To a stirred solution of 2-(chloromethyl)-N-(2,4-dimethoxybenzyl)-7-fluoroimidazo[1,2-c]quinazolin-5-amine prepared in the previous step (120 mg, 0.299 mmol), dissolved in dioxane (4491 µl) and water (1497 µl), was added 2-(pyridin-2-yl)-1-(8-(4,4,5,5-tetramethyl-1,3,2-dioxaborolan-2-yl)-2H-benzo[b][1,4]oxazin-4(3H)-yl)ethanone, potassium carbonate (248 mg, 1.796 mmol), and Pd(Cl)₂(dppf) complex (61.1 mg, 0.075 mmol) at room temp. The reaction mixture was heated to 80° C. and stirred overnight, then the solvent was evaporated and DCM was added. The organic layer was separated, washed with NaHCO₃ and brine, dried over MgSO₄, filtered, and concentrated. The crude product was purified by column chromatography on silica gel (Isco, 40 g) eluting with (EtOAc/Hexane=1/1 to 10% MeOH/DCM to 100% MeOH) to yield the title compound which was confirmed using LC/MS=619 [M+1]

(Step 4) 1-(8-((5-amino-7-fluoroimidazo[1,2-c]quinazolin-2-yl)methyl)-2H-benzo[b][1,4]oxazin-4(3H)-yl)-2-(pyridin-2-yl)ethanone Ex-92

Into a round bottom flask was added 1-(8-((5-((2,4-dimethoxybenzyl)amino)-7-fluoroimidazo[1,2-c]quinazolin-2-yl)methyl)-2H-benzo[b][1,4]oxazin-4(3H)-yl)-2-(pyridin-2-yl)ethanone (55 mg, 0.089 mmol) and TFA (889 µl). The reaction mixture stirred overnight, the TFA was evaporated and the crude product was redissolved in 10% MeOH/DCM and washed with NaHCO₃(aq). The organic layer was separated, dried over MgSO₄, filtered and concentrated. The crude product was purified by dissolving in DMF and precipitating a solid which was filtered and washed with DCM to yield Ex-92, the identity of which was confirmed using LC/MS=469 [M+1].

Example 12 Preparation of 7-methoxy-2-((4-(4-methoxyphenyl)-1H-1,2,3-triazol-1-yl)methyl)imidazo[1,2-c]quinazolin-5-amine Ex-93

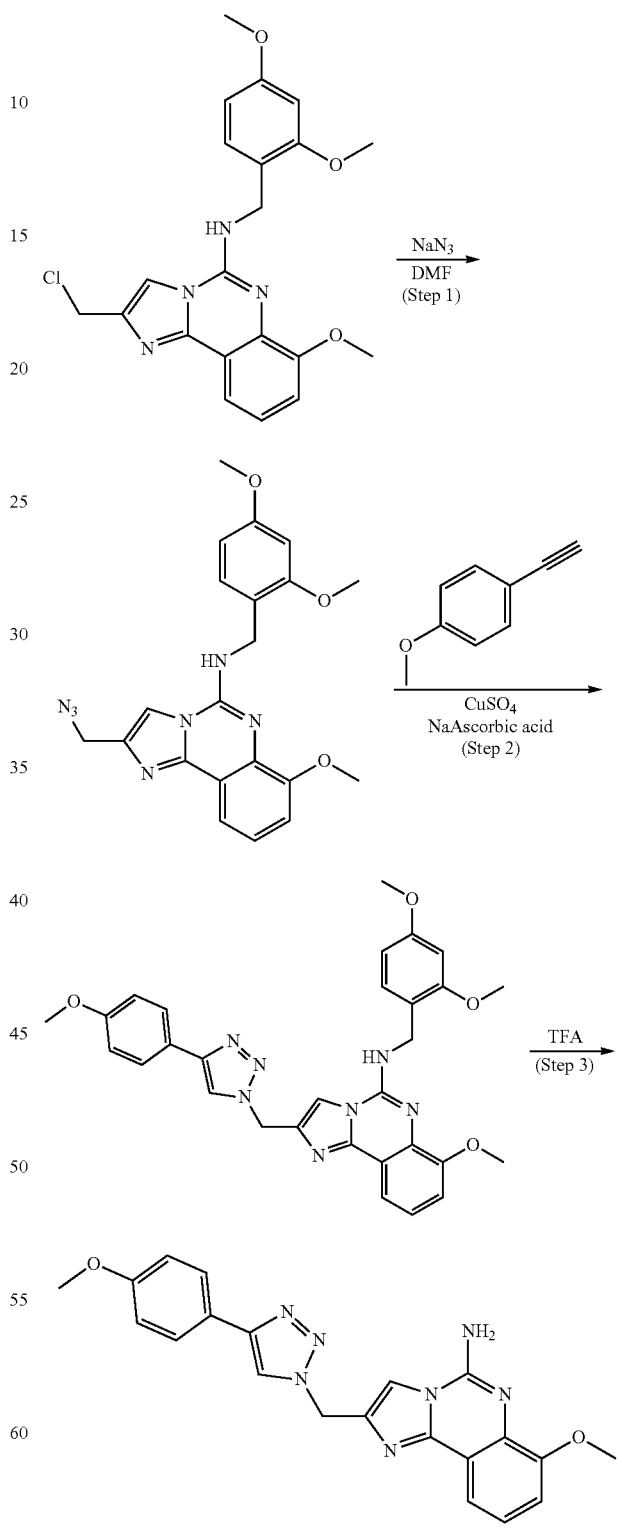

Ex-93

(Step 1) 2-(azidomethyl)-N-(2,4-dimethoxybenzyl)-
7-methoxyimidazo[1,2-c]quinazolin-5-amine To a stirred solution of 2-(chloromethyl)-N-(2,4-dimethoxybenzyl)-7-methoxyimidazo[1,2-c]quinazolin-5-amine (300 mg, 0.727 mmol) in DMF was added sodium azide (56.7 mg, 0.872 mmol) and the reaction mixture was heated to 70° C. overnight. The reaction mixture was used for the next step without purification. 2-(azidomethyl)-N-(2,4-dimethoxybenzyl)-7-methoxyimidazo[1,2-c]quinazolin-5-amine LC/MS=420 [M+1]

(Step 2) N-(2,4-dimethoxybenzyl)-7-methoxy-2-((4-(4-methoxyphenyl)-1H-1,2,3-triazol-1-yl)methyl)
imidazo[1,2-c]quinazolin-5-amine To a stirred solution of 2-(azidomethyl)-N-(2,4-dimethoxybenzyl)-7-methoxyimidazo[1,2-c]quinazolin-5-amine (150 mg, 0.358 mmol) in DMF (2 mL) was added 4-ethynylanisole (55.7 µl, 0.429 mmol), copper(II) sulfate pentahydrate (as a 1M solution in H2O) (8.93 mg, 0.036 mmol), and sodium ascorbate (1M solution in H$_2$O) (14.17 mg, 0.072 mmol). The reaction mixture was stirred at 45° C. overnight, then cooled to RT and water was added, generating a precipitate. The precipitate was washed with water redissolved in DCM and the organic layer was washed with EDTA(aq)/H$_2$O$_2$, then water, then dried over MgSO$_4$, filtered and concentrated. To yield the title compound as a crude product which was used for the next step without further purification LC/MS=552 [M+1].

(Step 3) 7-methoxy-2-((4-(4-methoxyphenyl)-1H-1,
2,3-triazol-1-yl)methyl)imidazo[1,2-c]quinazolin-5-
amine Ex-93

Into a round bottom flask containing N-(2,4-dimethoxybenzyl)-7-methoxy-2-((4-(4-methoxyphenyl)-1H-1,2,3-triazol-1-yl)methyl)imidazo[1,2-c]quinazolin-5-amine (169 mg, 0.306 mmol) was added TFA (2.5 mL). The reaction mixture was stirred overnight at room temperature, TFA was evaporated, and the crude product was diluted with DCM and neutralized with 7N NH$_3$ in MeOH. The solvent was evaporated and the residue was purified by prep-TLC (10% MeOH/DCM) to give the title compound (Ex-93). LC/MS=402 [M+1].

The compounds of Table 5 were prepared by using methodology described in Example 12 and appropriate reagents.

TABLE 5

| Ex-No. | Structure | LC-MS | Name |
|---|---|---|---|
| Ex-94 | 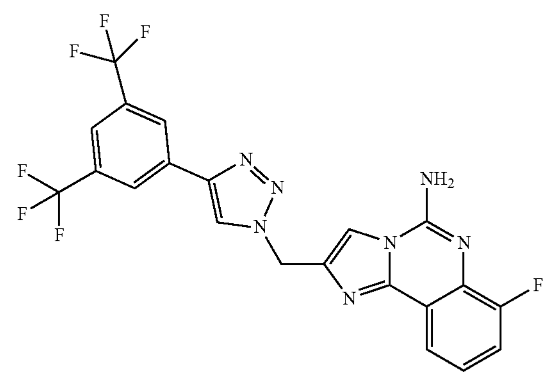 [SMILES: Nc1nc2c(F)cccc2c2nc(Cn3cc(-c4cc(C(F)(F)F)cc(C(F)(F)F)c4)nn3)cn12] | 496 [M + 1] | 2-((4-(3,5-bis(trifluoromethyl)phenyl)-1H-1,2,3-triazol-1-yl)methyl)-7-fluoroimidazo[1,2-c]quinazolin-5-amine |
| Ex-95 | 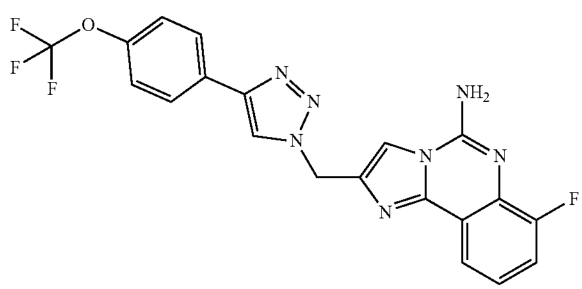 [SMILES: Nc1nc2c(F)cccc2c2nc(Cn3cc(-c4ccc(OC(F)(F)F)cc4)nn3)cn12] | 444 [M + 1] | 7-fluoro-2-((4-(4-(trifluoromethoxy)-phenyl)-1H-1,2,3-triazol-1-yl)methyl)-imidazo[1,2-c]-quinazolin-5-amine |
| Ex-96 | 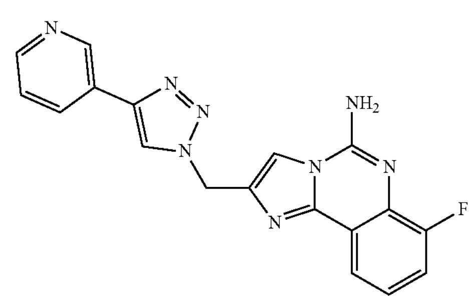 [SMILES: Nc1nc2c(F)cccc2c2nc(Cn3cc(-c4cccnc4)nn3)cn12] | 361 [M + 1] | 7-fluoro-2-((4-(pyridin-3-yl)-1H-1,2,3-triazol-1-yl)methyl)imidazo[1,2-c]quinazolin-5-amine |

TABLE 5-continued

| Ex-No. | Structure | LC-MS | Name |
|---|---|---|---|
| Ex-97 | 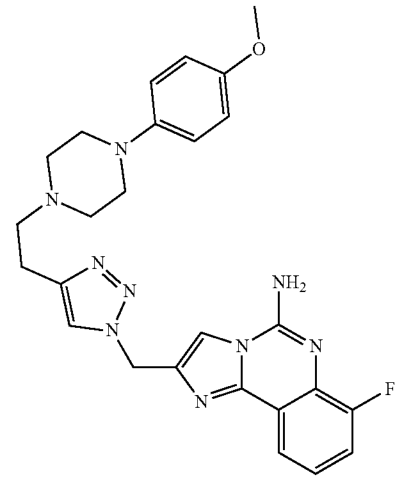 [SMILES: COc1ccc(N2CCN(CCc3cn(Cc4cn5c(N)nc6c(F)cccc6c5n4)nn3)CC2)cc1] | 502 [M + 1]. | 7-fluoro-2-((4-(2-(4-(4-methoxyphenyl)piperazin-1-yl)ethyl)-1H-1,2,3-triazol-1-yl)methyl)imidazo[1,2-c]quinazolin-5-amine |
| Ex-98 | 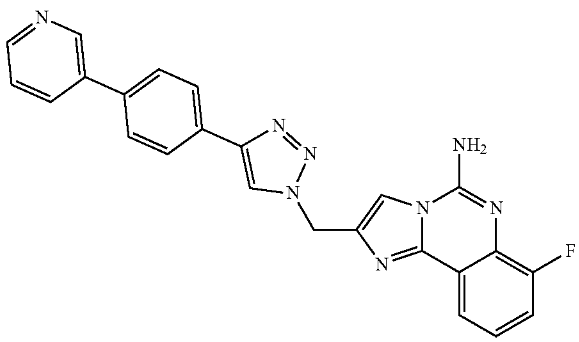 [SMILES: Nc1nc2c(F)cccc2c2nc(Cn3cc(-c4ccc(-c5cccnc5)cc4)nn3)cn12] | 437 [M + 1]. | 7-fluoro-2-((4-(4-(pyridin-3-yl)phenyl)-1H-1,2,3-triazol-1-yl)methyl)imidazo[1,2-c]quinazolin-5-amine |
| Ex-99 | 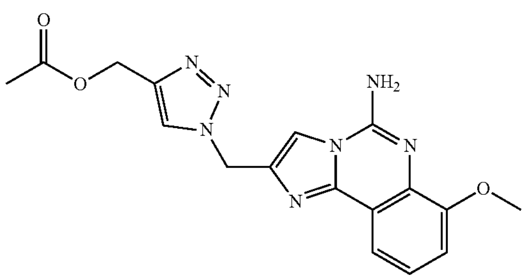 [SMILES: COc1cccc2c1nc(N)n1cc(Cn3cc(COC(C)=O)nn3)nc21] | 368 [M + 1]. | (1-((5-amino-7-methoxyimidazo[1,2-c]quinazolin-2-yl)methyl)-1H-1,2,3-triazol-4-yl)methyl acetate |

Example 13 Preparation of 7-fluoro-2-phenethyl-imidazo[1,2-c]quinazolin-5-amine Ex-100

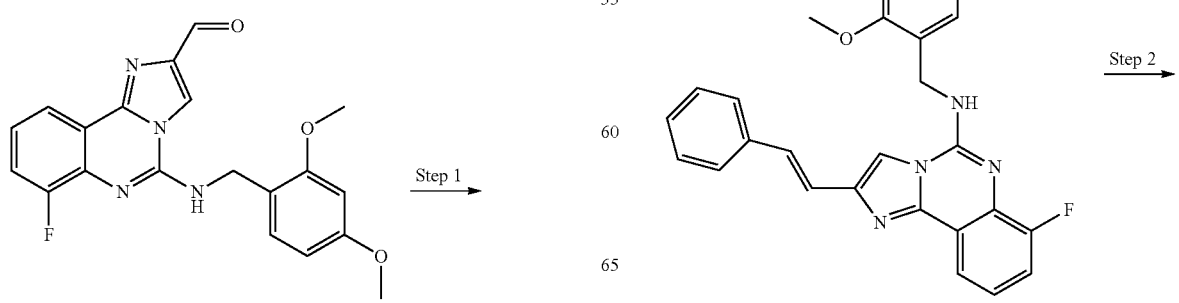

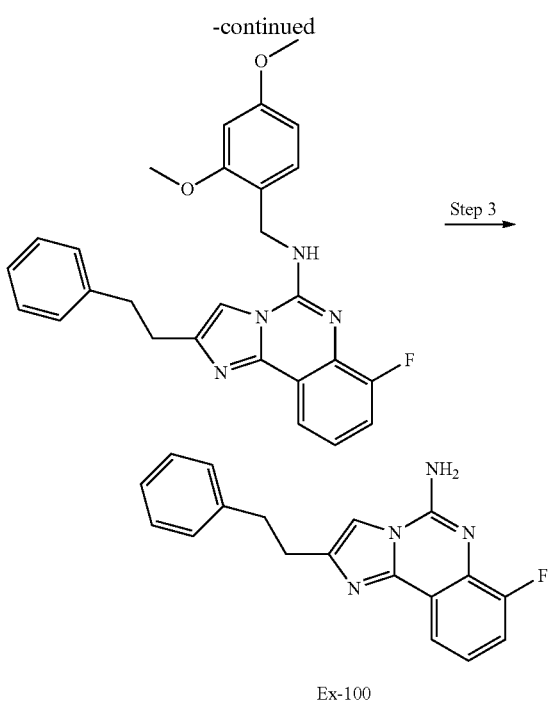

Ex-100

(Step 1) (E)-N-(2,4-dimethoxybenzyl)-7-fluoro-2-styrylimidazo[1,2-c]quinazolin-5-amine

To a stirred suspension of benzyltriphenylphosphonium chloride (204 mg, 0.526 mmol) in dry THF (5 ml) was added potassium tertiary butoxide (0.309 ml, 0.526 mmol) under nitrogen. The mixture was stirred for 1 h at rt, and 5-(2,4-dimethoxybenzylamino)-7-fluoroimidazo[1,2-c]quinazoline-2-carbaldehyde (100 mg, 0.263 mmol) was added at once as a solid. The reaction mixture was stirred at rt. until LCMS indicated full conversion to the title product (30 minutes) then the reaction mixture was poured all at once into water and extracted (3×50 mL EtOAc/water), dried over (Na$_2$SO$_4$), and concentrated on rotary evaporator.

(Step 2) N-(2,4-dimethoxybenzyl)-7-fluoro-2-phenethylimidazo[1,2-c]quinazolin-5-amine

(E)-N-(2,4-dimethoxybenzyl)-7-fluoro-2-styrylimidazo[1,2-c]quinazolin-5-amine (121 mg, 0.213 mmol) in EtOAc (30 ml) from the previous step was added with Pd/C (340 mg, 0.319 mmol) and reacted with H$_2$ gas under a balloon overnight at rt. whereupon LCMS showed full conversion to the title compound. The crude product was filtered through celite containing fritted funnel and concentrated on rotovap. and the crude material thus provided was used in the next step without purification.

(Step 3) 7-fluoro-2-phenethylimidazo[1,2-c]quinazolin-5-amine

Into a vessel was placed N-(2,4-dimethoxybenzyl)-7-fluoro-2-phenethylimidazo[1,2-c]quinazolin-5-amine (102 mg, 0.2 mmol) dichloromethane (2 ml), and trifluoroacetic acid (0.115 ml, 1.005 mmol) and the mixture was reacted in microwave at 85° C. for 1.5 h. Complete deprotection was confirmed using LCMS and the reaction mixture was basified with 7N methanolic ammonia (2 mL) then purified via prep TLC using 50% EtOAc/Hexanes and the residue thus obtained was subjected to a second purification via flash chromatography (combilfalshsystem) using 2% MeOH/DCM to yield Ex-100, the identity and purity of which was verified using LC/MS=307 [M+1].

The compounds of Table 6 were prepared by using methodology described in Example 13 and appropriate reagents.

TABLE 6

| Ex-No. | Structure | LC-MS [M + 1] | Name |
|---|---|---|---|
| Ex-101 | 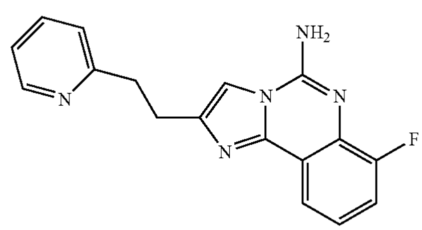 [SMILES: Nc1nc2c(F)cccc2c2nc(CCc3ccccn3)cn12] | 431 [M + 1]. | 7-fluoro-2-(2-(pyridin-2-yl)ethyl)imidazo[1,2-c]quinazolin-5-amine |
| Ex-102 | 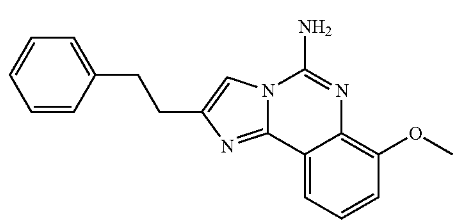 | 417 [M + 1]. | 7-methoxy-2-phenethylimidazo[1,2-c]quinazolin-5-amine |

Example 14 Preparation of (5-amino-7-methoxyimidazo[1,2-c]quinazolin-2-yl)(phenyl)methanone Ex-103

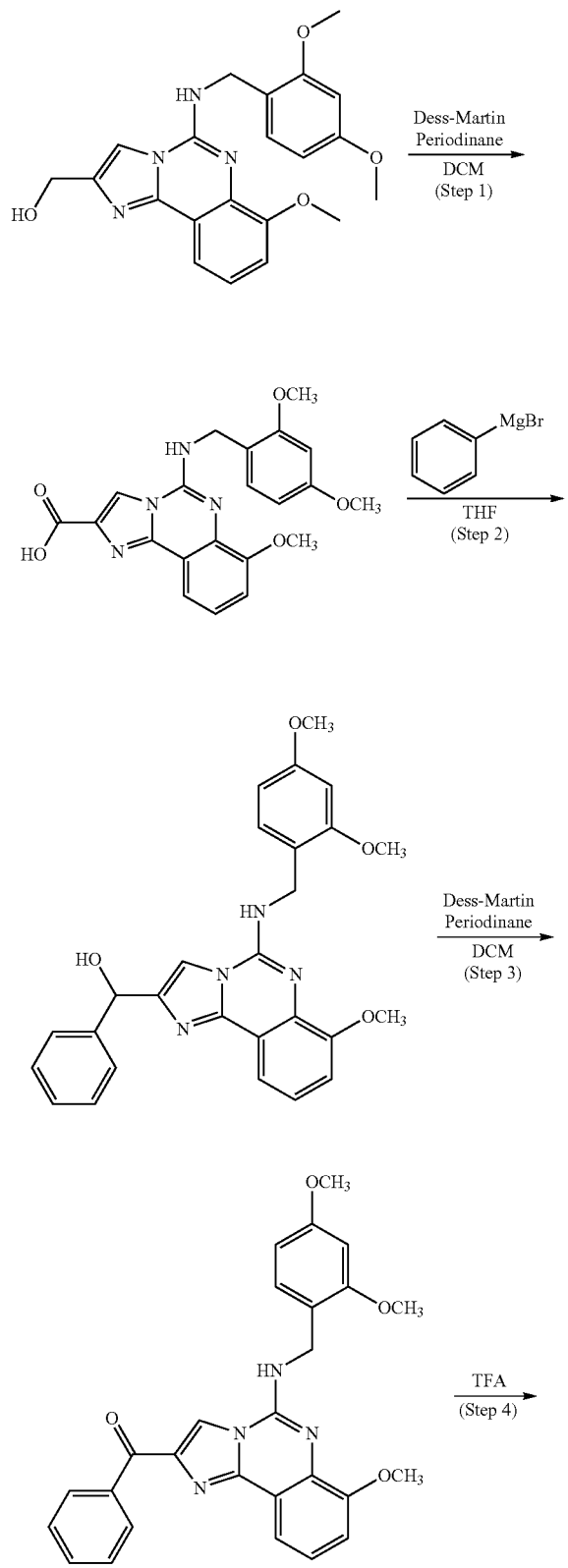

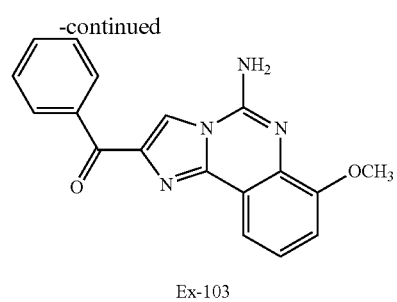

Ex-103

(Step 1) 5-((2,4-dimethoxybenzyl)amino)-7-methoxyimidazo[1,2-c]quinazoline-2-carbaldehyde To a stirred suspension of (5-((2,4-dimethoxybenzyl)amino)-7-methoxyimidazo[1,2-c]quinazolin-2-yl)methanol (517 mg, 1.311 mmol) in DCM (32.8 mL) was added Dess-MartinPeriodinane (667 mg, 1.573 mmol). After stirring at RT for 30-40 min the reaction was diluted by DCM and washed with $NaHCO_3$. The organic layer was dried over $MgSO_4$, filtered and concentrated and the crude product was purified by ISCO (1/1=EtOAc/Hex) to give the title compound which was verified using. LC/MS=393 [M+1]

(Step 2) (5-((2,4-dimethoxybenzyl)amino)-7-methoxyimidazo[1,2-c]quinazolin-2-yl)(phenyl)methanol To a stirred suspension of 5-((2,4-dimethoxybenzyl)amino)-7-methoxyimidazo[1,2-c]quinazoline-2-carbaldehyde (200 mg, 0.510 mmol) in THF was added phenylmagnesiumbromide (1019 µl, 1.019 mmol) at −78° C. dropwise. After stirring for 2 hr at −78° C., the reaction was warmed to 0° C. for one hour then the reaction mixture was warmed to RT and stirred overnight. The reaction mixture was cooled to 0° C. in an ice bath then aqueous ammonium chloride was added very slowly to quench access Grignard reagent and the crude mixture was extracted with EtOAc, washed with brine, the organic layer was dried over $MgSO_4$, filtered and concentrated. The crude product was purified by ISCO (1/1 EtOAc/Hex) to give the title product, LC/MS=471 [M+1]

(Step 3) (5-((2,4-dimethoxybenzyl)amino)-7-methoxyimidazo[1,2-c]quinazolin-2-yl)(phenyl)methanone To a stirred solution of (5-((2,4-dimethoxybenzyl)amino)-7-methoxyimidazo[1,2-c]quinazolin-2-yl)(phenyl)methanol (28 mg, 0.060 mmol) in DCM was added Dess-MartinPeriodinane (30.3 mg, 0.071 mmol). After 45 min, the reaction was quenched with $NaHCO_3$ and then extracted with DCM. The organic layer was dried over $MgSO_4$, filtered and concentrated. The crude material was used for the next step. LC/MS=469 [M+1]

(Step 4) (5-amino-7-methoxyimidazo[1,2-c]quinazolin-2-yl)(phenyl)methanone Ex-103

Into a round-bottom flask was placed (5-((2,4-dimethoxybenzyl)amino)-7-methoxyimidazo[1,2-c]quinazolin-2-yl)(phenyl)methanone from the previous step (32 mg, 0.068 mmol) and TFA was added (683 µl). The reaction mixture was stirred overnight, excess TFA was evaporated and the residue was redissolved in DCM and neutralized with methanolic ammonia. The solvent was evaporated and the crude product purified by prep-TLC (10% MeOH/DCM) to give Ex-103 LC/MS=319 [M+1].

Example 15 Preparation of 2-(4-bromophenyl)imidazo[1,2-c]quinazolin-5-amine Ex-104

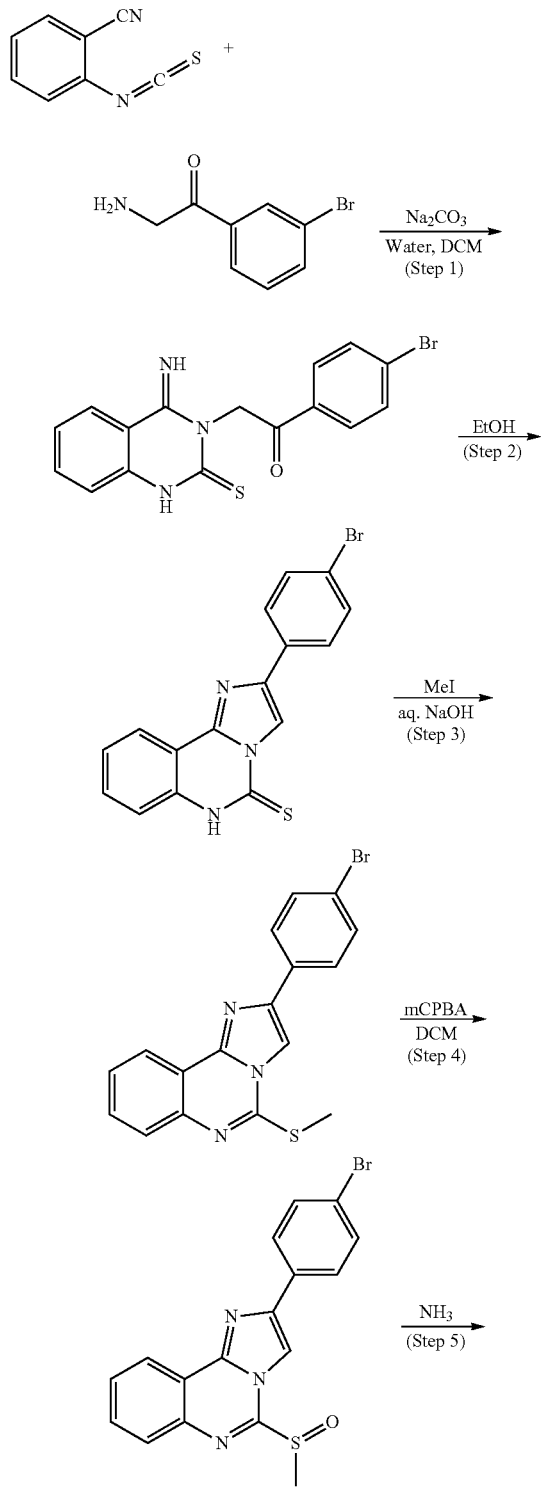

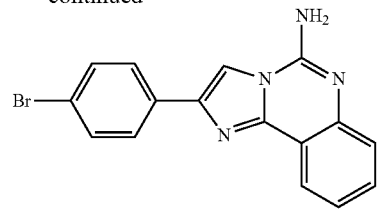

Ex-104

(Step 1) 1-(4-bromophenyl)-2-(4-imino-2-thioxo-1,2-dihydroquinazolin-3(4H)-yl)ethanone A solution of sodium carbonated (2.78 g, 26.2 mmol) dissolved in water (24 ml, 1332 mmol) was added to a stirred suspension of 2-isothiocyanatobenzonitrile (2 g, 12.48 mmol) and 2-amino-4'-bromoacetophenone (3.13 g, 12.48 mmol) in dichloromethane (78 ml) and the reaction mixture was stirred for 10 min at rt followed by an additional 10 min under refluxing conditions. After cooling to rt a colorless precipitated formed which was filtered off and set aside. Thus obtained, the organic and the aqueous layers of the filtrate were separated. The aqueous layer was extracted with DCM and the extract combined with the organics. The combined organic layers were dried over MgSO$_4$, filtered, concentrated at reduced pressure and the residue was combined with the precipitates and used in the next step without further purification. LC/MS=375 [M+1]

(Step 2) 2-(4-bromophenyl)imidazo[1,2-c]quinazoline-5(6H)-thione 1-(4-bromophenyl)-2-(4-imino-2-thioxo-1,2-dihydroquinazolin-3(4H)-yl)ethanone (4.67 g, 12.48 mmol) was suspended in EtOH (200 ml) and the mixture was refluxed for 16 hrs. After cooling down, the precipitate was filtered off and dried in vacuo and the filtrate concentrated at reduced pressure to give the title compound, LC/MS=357 [M+1]

(Step 3) 2-(4-bromophenyl)-5-(methylthio)imidazo[1,2-c]quinazoline 2-(4-bromophenyl)imidazo[1,2-c]quinazoline-5(6H)-thione (3.856 g, 10.82 mmol) was dissolved in an aqueous solution of NaOH (0.02M, 60 mL). The mixture was heated to 60° C. and methyl iodide was added dropwise over a period of 5 min. The reaction mixture was stirred at 60° C. for 2 hrs, precipitating a solid precipitated upon cooling, which was filtered off, washed with water and dried in air to provide the title compound, LC/MS=371 [M+1]

(Step 4) 2-(4-bromophenyl)-5-(methylsulfinyl)imidazo[1,2-c]quinazoline

To a stirred solution of 2-(4-bromophenyl)-5-(methylthio)imidazo[1,2-c]quinazoline (408 mg, 1.102 mmol) in DCM (10 mL) was added mCPBA (543 mg, 2.424 mmol) at rt. The reaction mixture was stirred at rt for 16 hrs., and the solvent evaporated to provide the title compound as crude product, used for the next step without purification, LC/MS=387 [M+1]

(Step 5) 2-(4-bromophenyl)imidazo[1,2-c]quinazolin-5-amine Ex-104

Into 5 mL tube was placed 2-(4-bromophenyl)-5-(methylsulfinyl)imidazo[1,2-c]quinazoline (100 mg, 0.091 mmol), a 2M isopropanol solution of ammonia (10 mL, 20.00 mmol), the tube was sealed and stirred at 100° C. for 16 hr. After cooling to ambient the solvent was evaporated and the residue purified on a 40 g flash silica gel column, eluting with A=Hexanes, B=Ethyl Acetate at 40 ml/min and the peak eluting at 95% B gave the title compound (Ex-104), LC/MS=340 [M+1].

The compounds of Table 7 were prepared by using methodology described in Example 15 and appropriate reagents.

TABLE 7

| Ex-No | Structure | LC-MS | Name |
| --- | --- | --- | --- |
| Ex-105 | 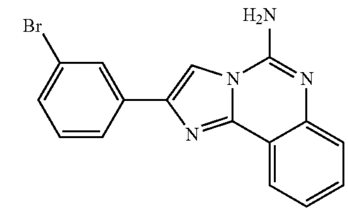 [SMILES: Nc1nc2ccccc2c2nc(-c3cccc(Br)c3)cn12] | 340 [M + 1]. | 2-(3-bromophenyl)imidazo[1,2-c]quinazolin-5-amine |
| Ex-106 | 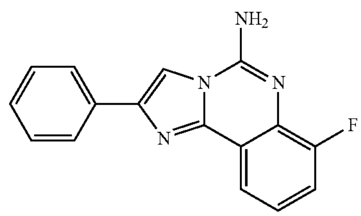 [SMILES: Nc1nc2c(F)cccc2c2nc(-c3ccccc3)cn12] | 279 [M + 1]. | 7-fluoro-2-phenylimidazo[1,2-c]quinazolin-5-amine |
| Ex-107 | 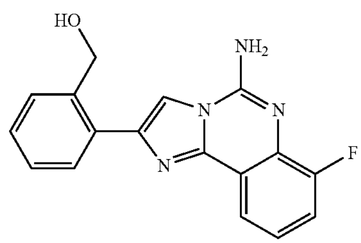 [SMILES: Nc1nc2c(F)cccc2c2nc(-c3ccccc3CO)cn12] | 309 [M + 1]. | (2-(5-amino-7-fluoroimidazo[1,2-c]quinazolin-2-yl)phenyl)methanol |
| Ex-108 | 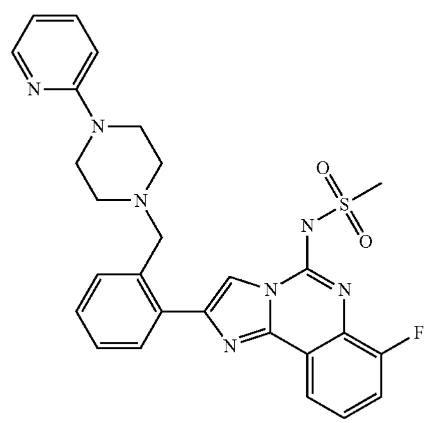 [SMILES: CS(=O)(=O)Nc1nc2c(F)cccc2c2nc(-c3ccccc3CN3CCN(c4ccccn4)CC3)cn12] | 532 [M + 1]. | N-(7-fluoro-2-(2-((4-(pyridin-2-yl)piperazin-1-yl)methyl)-phenyl)-imidazo[1,2-c]-quinazolin-5-yl)-methanesulfonamide |

Example 16 Preparation of 1-((5-aminoimidazo[1,2-c]quinazolin-2-yl)methyl)-4-methylpiperidin-4-ol Ex-109

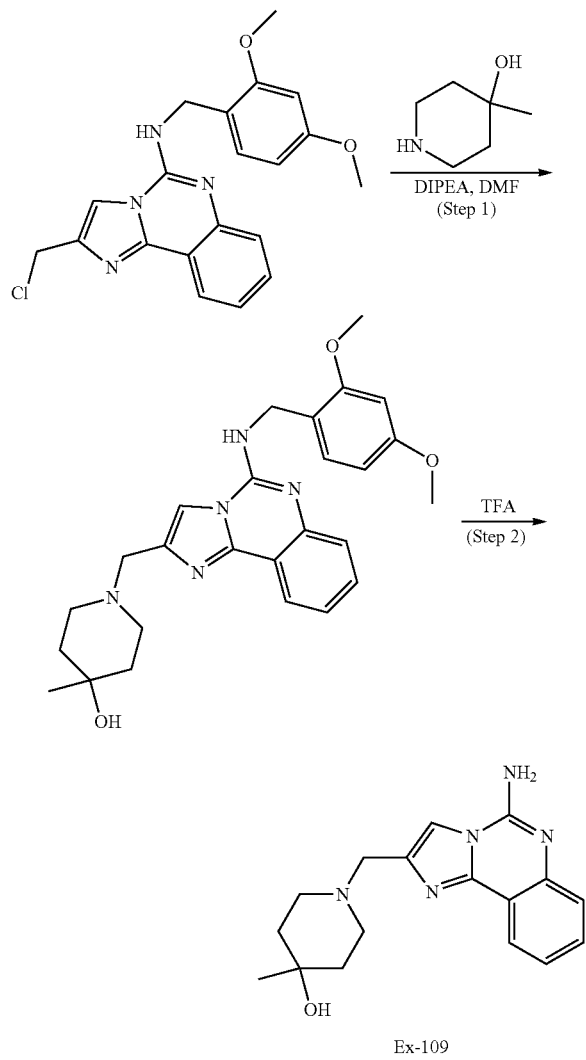

Ex-109

(Step 1) 1-((5-((2,4-dimethoxybenzyl)amino)imidazo[1,2-c]quinazolin-2-yl)methyl)-4-methylpiperidin-4-ol To a stirred solution of 2-(chloromethyl)-N-(2,4-dimethoxybenzyl)imidazo[1,2-c]quinazolin-5-amine (90 mg, 0.235 mmol) in acetonitrile (2351 μl) was added 4-methylpiperidin-4-ol (54.2 mg, 0.470 mmol) and potassium carbonate (97 mg, 0.705 mmol). The reaction mixture was heated to 80° C. with stirring for 4 hrs, then cooled to ambient and filtered. The solvent was evaporated and the residue was redissolved in DCM and washed with NaHCO₃ (aq) to give crude product which was used in the next step without purification, LC/MS=462 [M+1].

(Step 2) 1-((5-aminoimidazo[1,2-c]quinazolin-2-yl)methyl)-4-methylpiperidin-4-ol Ex-109

Into a round-bottom flask containing 1-((5-((2,4-dimethoxybenzyl)amino)imidazo[1,2-c]quinazolin-2-yl)methyl)-4-methylpiperidin-4-ol (101 mg, 0.219 mmol) was added TFA (2188 μl) and the reaction mixture was stirred for 16 hr at room temperature. The solvent was evaporated under reduced pressure and the mixture was redissolved in EtOAc and the organic layer was washed with NaHCO₃, dried over MgSO₄, filtered, and concentrated then the crude product was purified by column chromatography on silica gel (Isco, 40 g) eluting with (20% MeOH inDCM) to give the title compound, Ex-109, LC/MS=312 [M+1].

The compounds of Table 8 were prepared by using methodology described in Example 16 and appropriate reagents.

TABLE 8

| Ex-No | Structure | LCMS | Name |
|---|---|---|---|
| Ex-110 | 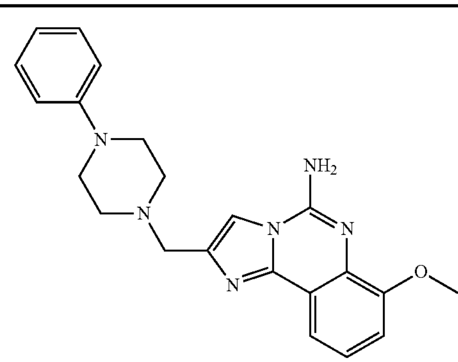 | 389 [M+ 1] | 7-methoxy-2-((4-phenylpiperazin-1-yl)methyl)imidazo[1,2-c]quinazolin-5-amine |

TABLE 8-continued

| Ex-No | LCMS | Name |
|---|---|---|
| Ex-111 | 391 | 2-((4-benzylpiperazin-1-yl)methyl)-7-fluoroimidazo[1,2-c]quinazolin-5-amine |
| Ex-112 | 329 | 2-((4-ethylpiperazin-1-yl)methyl)-7-fluoroimidazo[1,2-c]quinazolin-5-amine |
| Ex-113 | 405 | 7-fluoro-2-((4-phenethylpiperazin-1-yl)methyl)imidazo-[1,2-c]quinazolin-5-amine |
| Ex-114 | 390 | 2-((4-benzylpiperidin-1-yl)methyl)-7-fluoroimidazo[1,2-c]quinazolin-5-amine |
| Ex-115 | 302 | 7-fluoro-2-(morpholinomethyl)imidazo[1,2-c]quinazolin-5-amine |

TABLE 8-continued

| Ex-No | Structure | LCMS | Name |
|---|---|---|---|
| Ex-116 | 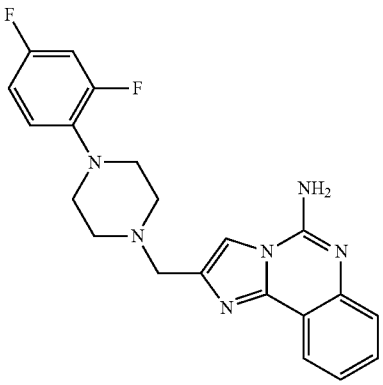 [SMILES: Nc1nc2ccccc2c2nc(CN3CCN(c4ccc(F)cc4F)CC3)cn12] | 395 | 2-((4-(2,4-difluorophenyl)piperazin-1-yl)methyl)imidazo[1,2-c]quinazolin-5-amine |
| Ex-117 | 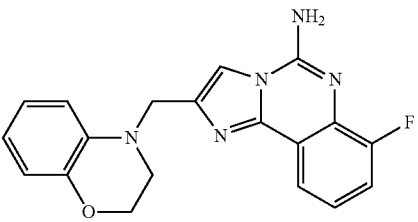 [SMILES: Nc1nc2c(F)cccc2c2nc(CN3CCOc4ccccc43)cn12] | 350 | 2-((2,3-dihydro-4H-benzo[b][1,4]oxazin-4-yl)methyl)-7-fluoroimidazo[1,2-c]quinazolin-5-amine |
| Ex-118 | 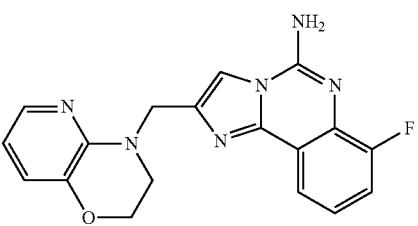 [SMILES: Nc1nc2c(F)cccc2c2nc(CN3CCOc4cccnc43)cn12] | 351 | 2-((2,3-dihydro-4H-pyrido[3,2-b][1,4]oxazin-4-yl)methyl)-7-fluoroimidazo[1,2-c]quinazolin-5-amine |
| Ex-119 | 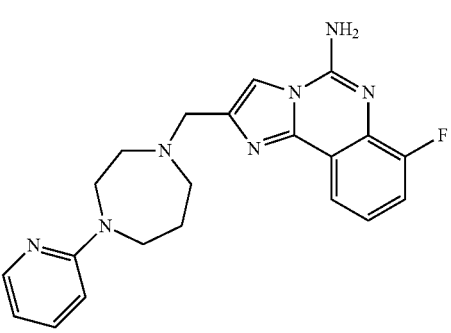 [SMILES: Nc1nc2c(F)cccc2c2nc(CN3CCCN(c4ccccn4)CC3)cn12] | 392 | 7-fluoro-2-((4-(pyridin-2-yl)-1,4-diazepan-1-yl)methyl)imidazo[1,2-c]quinazolin-5-amine |
| Ex-120 | 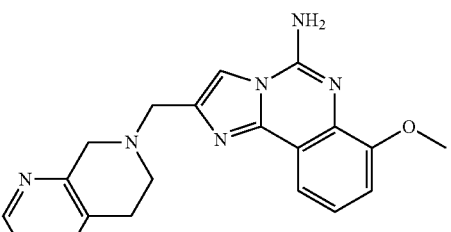 | 361 | 2-((5,8-dihydro-1,7-naphthyridin-7(6H)-yl)methyl)-7-methoxyimidazo[1,2-c]quinazolin-5-amine |

TABLE 8-continued

| Ex-No | Structure | LCMS | Name |
| --- | --- | --- | --- |
| Ex-121 | 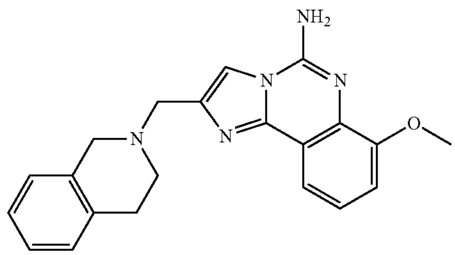 [SMILES: COc1cccc2c1nc(N)n1cc(CN3CCc4ccccc4C3)nc21] | 360 | 2-((3,4-dihydroisoquinolin-2(1H)-yl)methyl)-7-methoxyimidazo[1,2-c]quinazolin-5-amine |
| Ex-122 | 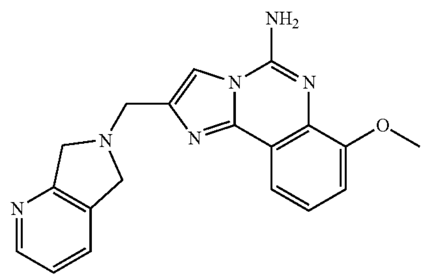 [SMILES: COc1cccc2c1nc(N)n1cc(CN3Cc4cccnc4C3)nc21] | 347 | 2-((5,7-dihydro-6H-pyrrolo[3,4-b]pyridin-6-yl)methyl)-7-methoxyimidazo[1,2-c]quinazolin-5-amine |
| Ex-123 | 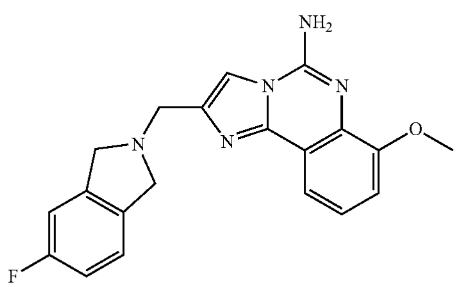 [SMILES: COc1cccc2c1nc(N)n1cc(CN3Cc4ccc(F)cc4C3)nc21] | 364 | 2-((5-fluoroisoindolin-2-yl)methyl)-7-methoxyimidazo[1,2-c]quinazolin-5-amine |
| Ex-124 | 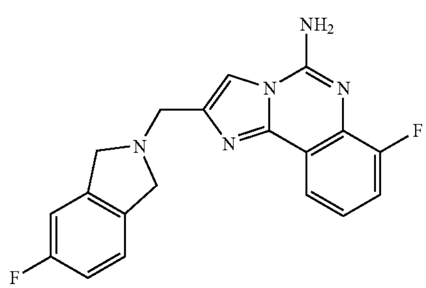 [SMILES: Nc1nc2c(F)cccc2c2nc(CN3Cc4ccc(F)cc4C3)cn12] | 352 | 7-fluoro-2-((5-fluoroisoindolin-2-yl)methyl)imidazo[1,2-c]quinazolin-5-amine |
| Ex-125 | 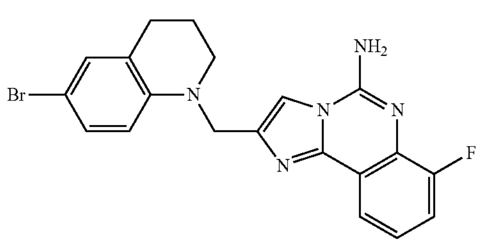 [SMILES: Nc1nc2c(F)cccc2c2nc(CN3CCCc4cc(Br)ccc43)cn12] | 427 | 2-((6-bromo-3,4-dihydroquinolin-1(2H)-yl)methyl)-7-fluoroimidazo[1,2-c]quinazolin-5-amine |

TABLE 8-continued

| Ex-No | Structure | LCMS | Name |
|---|---|---|---|
| Ex-126 | 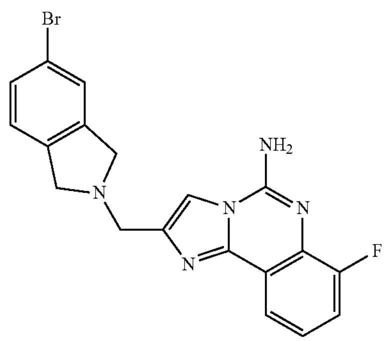 [SMILES: Nc1nc2c(F)cccc2c2nc(CN3Cc4ccc(Br)cc4C3)cn12] | 413 | 2-((5-bromoisoindolin-2-yl)methyl)-7-fluoroimidazo[1,2-c]quinazolin-5-amine |
| Ex-127 | 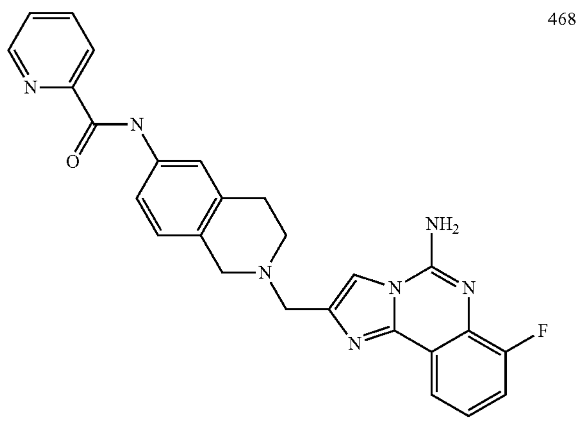 | 468 | N-(2-((5-amino-7-fluoroimidazo[1,2-c]quinazolin-2-yl)methyl)-1,2,3,4-tetrahydroisoquinolin-6-yl)picolinamide |
| Ex-128 | 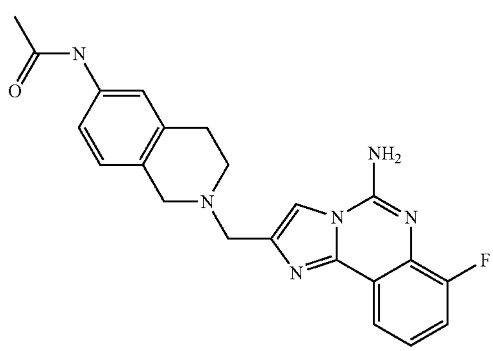 [SMILES: CC(=O)Nc1ccc2c(c1)CCN(Cc1cn3c(N)nc4c(F)cccc4c3n1)C2] | 405 | N-(2-((5-amino-7-fluoroimidazo[1,2-c]quinazolin-2-yl)methyl)-1,2,3,4-tetrahydroisoquinolin-6-yl)acetamide |
| Ex-129 | 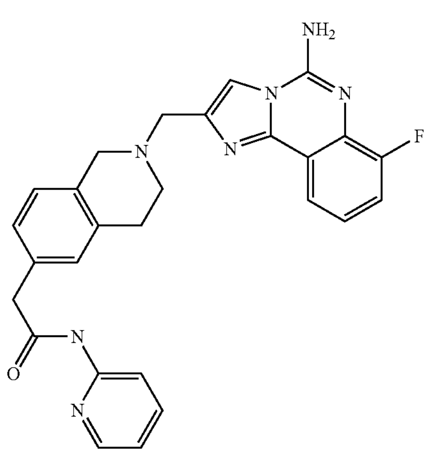 [SMILES: Nc1nc2c(F)cccc2c2nc(CN3CCc4cc(CC(=O)Nc5ccccn5)ccc4C3)cn12] | 482 | 2-(2-((5-amino-7-fluoroimidazo[1,2-c]quinazolin-2-yl)methyl)-1,2,3,4-tetrahydroisoquinolin-6-yl)-N-(pyridin-2-yl)acetamide |

TABLE 8-continued

| Ex-No | Structure | LCMS | Name |
|---|---|---|---|
| Ex-130 | 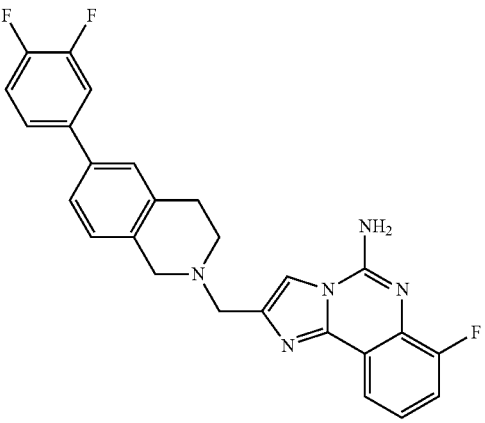 [SMILES: Nc1nc2c(F)cccc2c2nc(CN3CCc4cc(-c5ccc(F)c(F)c5)ccc4C3)cn12] | 460 | 2-((6-(3,4-difluorophenyl)-3,4-dihydroisoquinolin-2(1H)-yl)methyl)-7-fluoroimidazo[1,2-c]quinazolin-5-amine |
| Ex-131 | 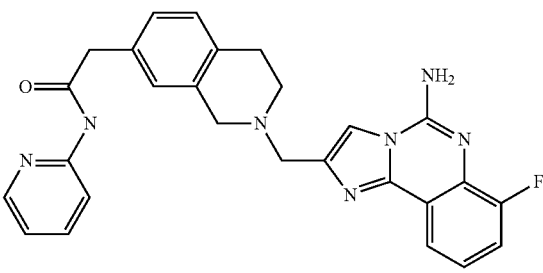 [SMILES: Nc1nc2c(F)cccc2c2nc(CN3CCc4ccc(CC(=O)Nc5ccccn5)cc4C3)cn12] | 482 | 2-(2-((5-amino-7-fluoroimidazo[1,2-c]quinazolin-2-yl)methyl)-1,2,3,4-tetrahydroisoquinolin-7-yl)-N-(pyridin-2-yl)acetamide |
| Ex-132 | 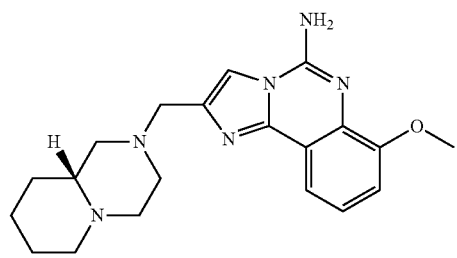 | 367 | (R)-7-methoxy-2-((octahydro-2H-pyrido[1,2-a]pyrazin-2-yl)methyl)imidazo[1,2-c]quinazolin-5-amine |
| Ex-133 | 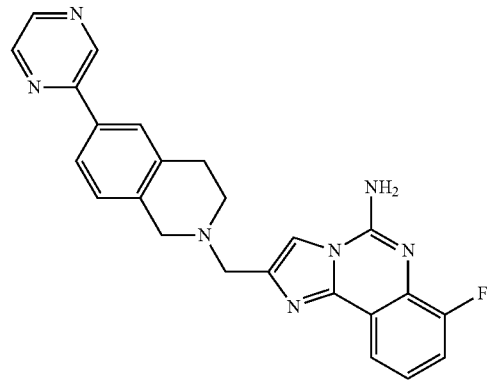 [SMILES: Nc1nc2c(F)cccc2c2nc(CN3CCc4cc(-c5cnccn5)ccc4C3)cn12] | 426 | 7-fluoro-2-((6-(pyrimidin-5-yl)-3,4-dihydroisoquinolin-2(1H)-yl)methyl)imidazo[1,2-c]quinazolin-5-amine |
| Ex-134 | 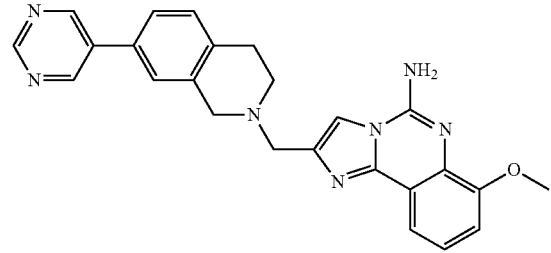 [SMILES: COc1cccc2c1nc(N)n1cc(CN3CCc4ccc(-c5cncnc5)cc4C3)nc21] | 438 | 7-methoxy-2-((7-(pyrimidin-5-yl)-3,4-dihydroisoquinolin-2(1H)-yl)methypimidazo[1,2-c]quinazolin-5-amine |

TABLE 8-continued

| Ex-No | Structure | LCMS | Name |
|---|---|---|---|
| Ex-135 | 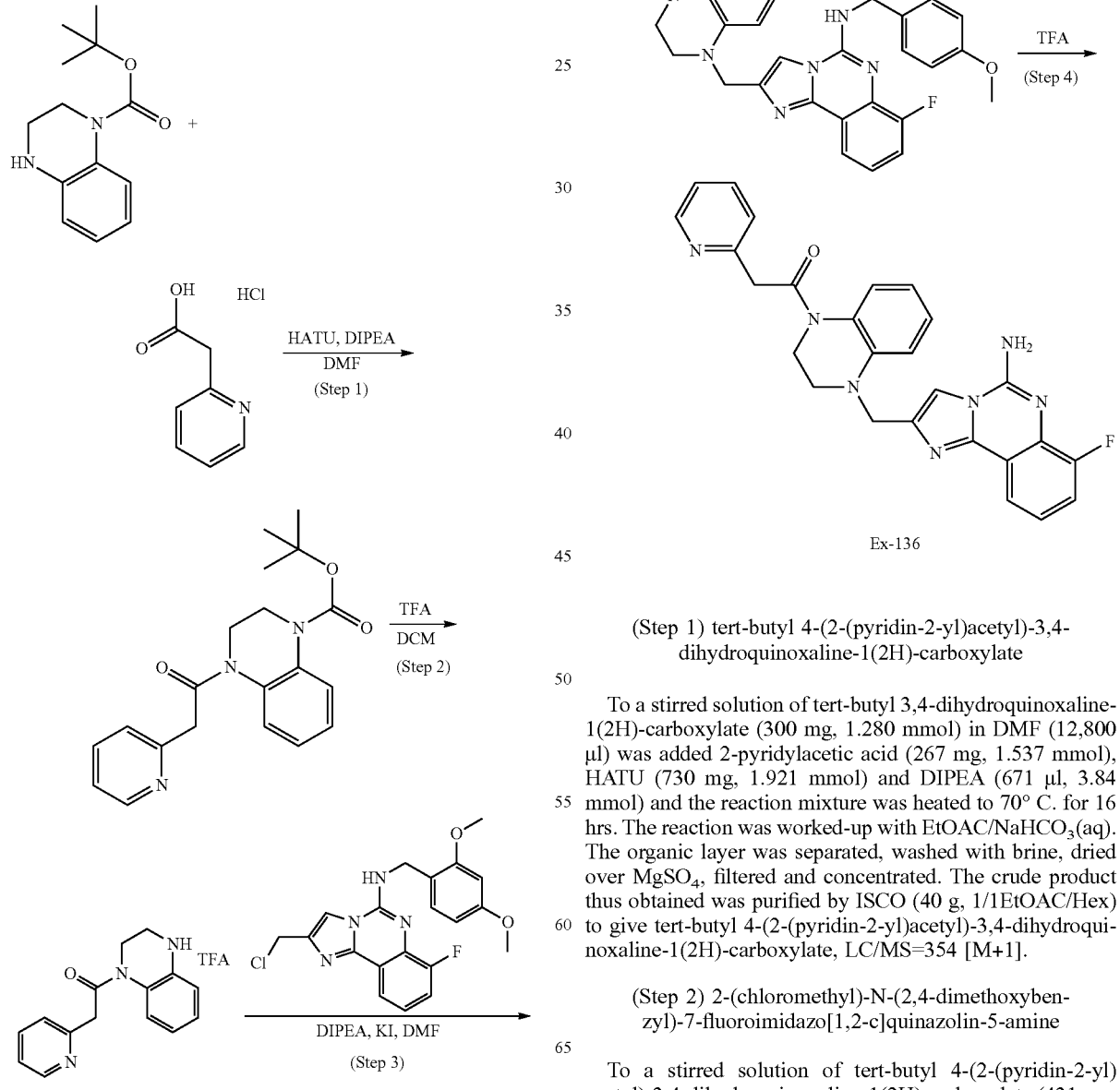 | 472 | 2-((7-(3,4-difluorophenyl)-3,4-dihydroisoquinolin-2(1H)-yl)methyl)-7-methoxyimidazo[1,2-c]quinazolin-5-amine |

Example 17 Preparation of 1-(4-((5-amino-7-fluoro-imidazo[1,2-c]quinazolin-2-yl)methyl)-3,4-dihydro-quinoxalin-1(2H)-yl)-2-(pyridin-2-yl)ethan-1-one Ex-136

(Step 1) tert-butyl 4-(2-(pyridin-2-yl)acetyl)-3,4-dihydroquinoxaline-1(2H)-carboxylate To a stirred solution of tert-butyl 3,4-dihydroquinoxaline-1(2H)-carboxylate (300 mg, 1.280 mmol) in DMF (12,800 µl) was added 2-pyridylacetic acid (267 mg, 1.537 mmol), HATU (730 mg, 1.921 mmol) and DIPEA (671 µl, 3.84 mmol) and the reaction mixture was heated to 70° C. for 16 hrs. The reaction was worked-up with EtOAC/NaHCO$_3$(aq). The organic layer was separated, washed with brine, dried over MgSO$_4$, filtered and concentrated. The crude product thus obtained was purified by ISCO (40 g, 1/1EtOAC/Hex) to give tert-butyl 4-(2-(pyridin-2-yl)acetyl)-3,4-dihydroquinoxaline-1(2H)-carboxylate, LC/MS=354 [M+1].

(Step 2) 2-(chloromethyl)-N-(2,4-dimethoxybenzyl)-7-fluoroimidazo[1,2-c]quinazolin-5-amine To a stirred solution of tert-butyl 4-(2-(pyridin-2-yl)acetyl)-3,4-dihydroquinoxaline-1(2H)-carboxylate (431 mg, 1.220 mmol) in methylene chloride (2439 μl) was added TFA (940 μl, 12.20 mmol) and the reaction mixture was stirred at RT until LCMS indicated the reaction was complete (9 hours), then the solvent was evaporated to give crude title compound and the crude residue was used in the next step without purification, LC/MS=254 [M+1]

(Step 3) 1-(4-((5-((2,4-dimethoxybenzyl)amino)-7-fluoroimidazo[1,2-c]quinazolin-2-yl)methyl)-3,4-dihydroquinoxalin-1(2H)-yl)-2-(pyridin-2-yl)ethanone To a stirred solution of 2-(chloromethyl)-N-(2,4-dimethoxybenzyl)-7-fluoroimidazo[1,2-c]quinazolin-5-amine (100 mg, 0.249 mmol) in DMF (2495 μl) was added DIPEA (87 μl, 0.499 mmol) and 1-(3,4-dihydroquinoxalin-1(2H)-yl)-2-(pyridin-2-yl)ethanone (183 mg, 0.499 mmol). The reaction mixture was stirred at 90° C. for 1 hour, then KI was added (83 mg, 0.499 mmol) and the reaction was stirred at 90° C. until the reaction initiated, then the temperature was reduced to 45° C. and stirred overnight. The reaction mixture was worked-up with EtOAc/NaHCO$_3$ (aq). The organic layer was separated, washed with brine, dried over MgSO$_4$, filtered and concentrated. The crude product was purified by ISCO (10% MeOH/DCM) to give the title compound LC/MS=618 [M+1].

(Step 4) 1-(4-((5-amino-7-fluoroimidazo[1,2-c]quinazolin-2-yl)methyl)-3,4-dihydroquinoxalin-1(2H)-yl)-2-(pyridin-2-yl)ethanone Ex-136

Into a round-bottom flask containing 1-(4-((5-((2,4-dimethoxybenzyl)amino)-7-fluoroimidazo[1,2-c]quinazolin-2-yl)methyl)-3,4-dihydroquinoxalin-1(2H)-yl)-2-(pyridin-2-yl)ethanone (74 mg, 0.120 mmol) was added TFA (1198 μl) and the mixture was stirred overnight. The TFA was evaporated and the crude residue was diluted with 10% MeOH/DCM. and work-up with NaHCO$_3$ (aq). The organic layer was separated and dried over MgSO$_4$, filtered, and concentrated, and the crude product was purified by prep-TLC (10% MeOH/DCM) to give the title compound, Ex-136, LC/MS=468 [M+1].

Example 18 Preparation of 2-(2-(5,7-dihydro-6H-pyrrolo[3,4-b]pyridin-6-yl)ethyl)-7-methoxyimidazo[1,2-c]quinazolin-5-amine (Ex-137

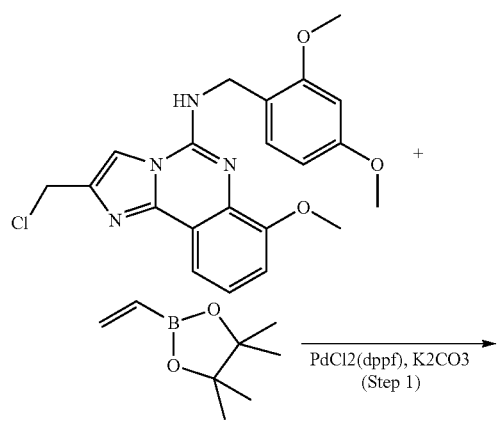

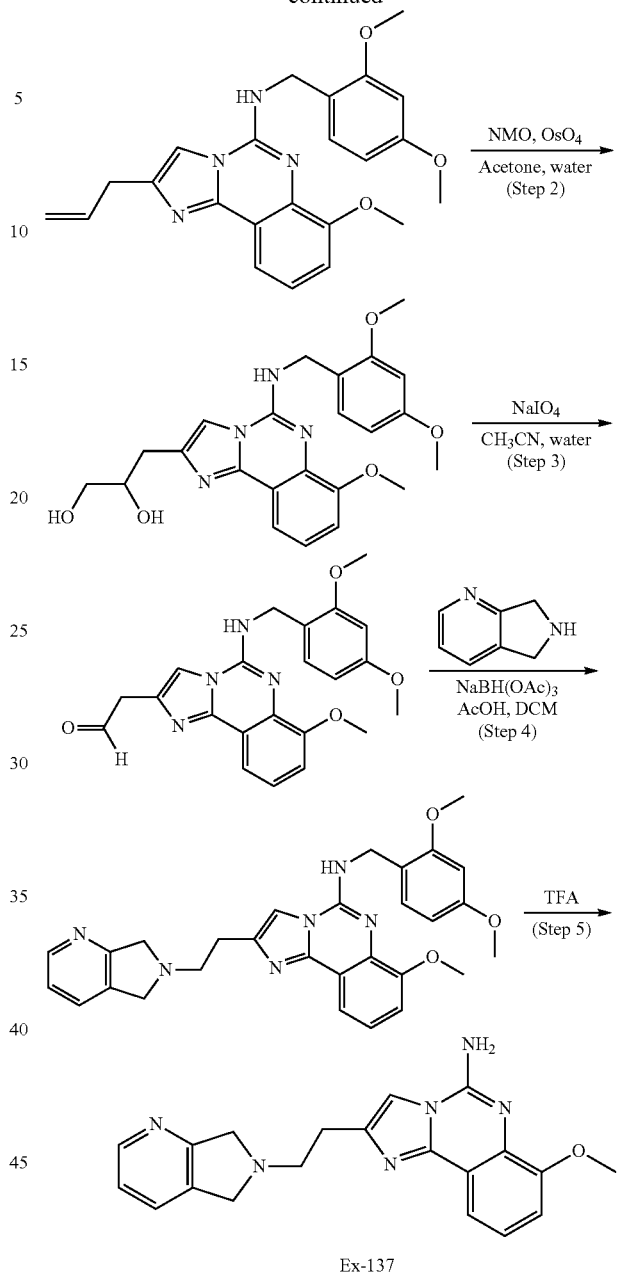

(Step 1) 2-allyl-N-(2,4-dimethoxybenzyl)-7-methoxyimidazo[1,2-c]quinazolin-5-amine To a stirred solution of 2-(chloromethyl)-N-(2,4-dimethoxybenzyl)-7-methoxyimidazo[1,2-c]quinazolin-5-amine (500 mg, 1.211 mmol) in 1,4-Dioxane (24.2 mL) was added vinyl boronic acid pinacol ester (373 mg, 2.422 mmol), K$_2$CO$_3$ (3633 μl, 3.63 mmol), and Pd(Cl)$_2$(dppf) complex (247 mg, 0.303 mmol). The reaction mixture was heated to 88° C. for 3 hrs, then solvent was evaporated and the crude was redissolved in EtOAc and worked up with aqueous NaHCO$_3$ and additional EtOAc extraction. The crude product thus obtained was purified by ISCO (EtOAc/Hex=1/1) to give the title compound, LC/MS=405 [M+1].

(Step 2) 3-(5-((2,4-dimethoxybenzyl)amino)-7-methoxyimidazo[1,2-c]quinazolin-2-yl)propane-1,2-diol To a stirred solution of 2-allyl-N-(2,4-dimethoxybenzyl)-7-methoxyimidazo[1,2-c]quinazolin-5-amine (360 mg, 0.890 mmol) in Acetone (4027 µl) and water (212 microliters) was added N-Methylmorpholine-N-Oxide (NMO, 115 mg, 0.979 mmol) and osmium tetroxide (34.9 µl, 4.45 µmol) and the reaction mixture was stirred at RT overnight, then the reaction was quenched with a sat. aq. $Na_2S_2O_3$, and the resulting precipitated solids were filtered and washed with water to give the title compound as a crude product, which was used for the next step without further purification, LC/MS=439 [M+1].

(Step 3) 2-(5-((2,4-dimethoxybenzyl)amino)-7-methoxyimidazo[1,2-c]quinazolin-2-yl)acetaldehyde To a stirred solution of 3-(5-((2,4-dimethoxybenzyl)amino)-7-methoxyimidazo[1,2-c]quinazolin-2-yl)propane-1,2-diol (382 mg, 0.871 mmol) in Acetonitrile (3630 µl) and Water (3630 µl) was added sodium periodate (280 mg, 1.307 mmol) at OC. The reaction mixture was allowed to reach RT and was stirred for overnight. 2 mL of THF was added because the reaction material was not soluble in CH3CN and water. The reaction was filtered through a short pd of silica gel (elution with $Et_2O$) allowed the removal of insoluble salts. The filtrate was then washed with water and brine, dried over MgSO4, filtered and concentrated to give 2-(5-((2,4-dimethoxybenzyl)amino)-7-methoxyimidazo[1,2-c]quinazolin-2-yl)acetaldehyde (352 mg). LC/MS=407 [M+1]

(Step 4) 2-(2-(5,7-dihydro-6H-pyrrolo[3,4-b]pyridin-6-yl)ethyl)-N-(2,4-dimethoxybenzyl)-7-methoxyimidazo[1,2-c]quinazolin-5-amine To a stirred solution of 2-(5-((2,4-dimethoxybenzyl)amino)-7-methoxyimidazo[1,2-c]quinazolin-2-yl)acetaldehyde (200 mg, 0.492 mmol) in DCM (5858 µl) was added 6,7-dihydro-5H-pyrrolo[3,4-b]pyridine (118 mg, 0.984 mmol) followed by AcOH (293 µl). The reaction mixture was stirred for 10 min, then sodium triacetoxyborohydride (261 mg, 1.230 mmol) was added and the reaction mixture was stirred at RT overnight. The reaction mixture was quenched with the addition of water and worked-up with $NaHCO_3$/DCM. The organic layer was separated, dried over $MgSO_4$, filtered and concentrated and the crude concentrate was purified by ISCO. EtOAC/Hex=1/1 to 10% MeOH/DCM to give the title compound, LC/MS=511 [M+1].

(Step 5) 2-(2-(5,7-dihydro-6H-pyrrolo[3,4-b]pyridin-6-yl)ethyl)-7-methoxyimidazo[1,2-c]quinazolin-5-amine Ex-137

Into a round-bottom flask containing 2-(2-(5,7-dihydro-6H-pyrrolo[3,4-b]pyridin-6-yl)ethyl)-N-(2,4-dimethoxybenzyl)-7-methoxyimidazo[1,2-c]quinazolin-5-amine (46.7 mg, 0.091 mmol) was added TFA (457 µl), and the mixture was stirred overnight. The TFA was evaporated and the residue diluted with DCM and neutralized with 7N methanolic $NH_3$ then the liquid was evaporated. The crude product thus obtained was purified by prep-TLC (10% MeOH/DCM) to give the title compound, Ex-137 which was verified by LC/MS=361 [M+1].

The compounds of Table 9 were prepared by using methodology described in Example 18 and appropriate reagents.

TABLE 9

| Ex No. | Structure | LC-MS | Name |
| --- | --- | --- | --- |
| Ex-138 | ![structure] | 392 [M + 1]. | 7-fluoro-2-(2-(4-(pyridin-2-yl)piperazin-1-yl)ethyl)imidazo[1,2-c]quinazolin-5-amine |

Example 19 Preparation of 7-bromo-2-((phenylamino)methyl)imidazo[1,2-c]quinazolin-5-amine (Ex-139)

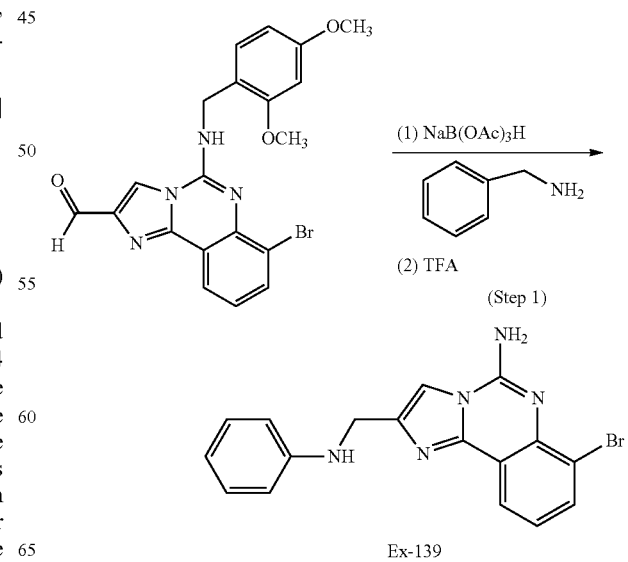

Ex-139

(Step 1) 2-((benzylamino)methyl)-7-bromoimidazo[1,2-c]quinazolin-5-amine

To a stirred solution of 7-bromo-5-((2,4-dimethoxybenzyl)amino)imidazo[1,2-c]quinazoline-2-carbaldehyde, prepared in accordance with the procedures of Example 16 and appropriate reagents (15 mg, 0.10 mmol), was added sodium triacetoxy borohydride (28 mg, 0.132 mmol) and benzylamine (20 mg, 0.187 mmol) in Methanol/CH$_2$Cl$_2$ v/v (4 ml, 1/1) at room temperature and the reaction mixture was stirred for 2 hrs at RT, following which, TFA (5 mL) was added into the reaction mixture and the reaction mixture was stirred for 2 hrs at RT. The solvent was evaporated and the residue was purified without aq. work-up by Prep TLC (2000 um; 20×20 cm$^{-1}$) eluting with 5% MeOH/MeCl$_2$/NH$_4$OH yielding the title compound (Ex-139), LCMS 369 [M+1].

The compounds of Table 10 were prepared by using methodology described in Example 19 and appropriate reagents.

TABLE 10

| Ex-No. | Structure | LCMS | Name |
| --- | --- | --- | --- |
| Ex-140 | 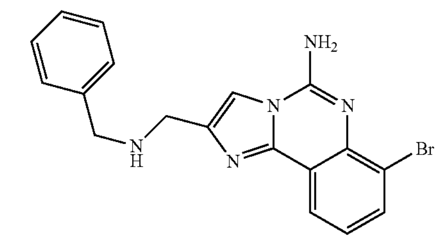 [SMILES: Nc1nc2c(Br)cccc2c2nc(CNCc3ccccc3)cn12] | 382 [M + 1] | 2-((benzylamino)methyl)-7-bromoimidazo[1,2-c]quinazolin-5-amine |
| Ex-141 | 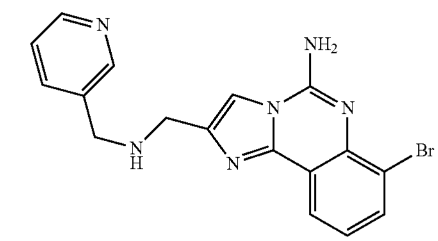 [SMILES: Nc1nc2c(Br)cccc2c2nc(CNCc3cccnc3)cn12] | 383 [M + 1] | 7-bromo-2-(((pyridin-3-ylmethyl)amino)methyl)imidazo[1,2-c]quinazolin-5-amine |
| Ex-142 | 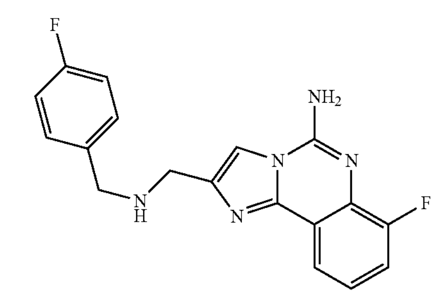 [SMILES: Nc1nc2c(F)cccc2c2nc(CNCc3ccc(F)cc3)cn12] | 340 [M + 1] | 7-fluoro-2-(((4-fluorobenzyeamino)methyl)imidazo[1,2-c]quinazolin-5-amine |
| Ex-143 | 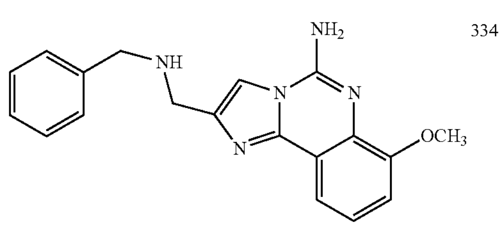 | 334 [M + 1] | 2-((benzylamino)-methyl)-7-methoxy-imidazo[1,2-c]-quinazolin-5-amine |

TABLE 10-continued
| Ex-No. | Structure | LCMS | Name |
|---|---|---|---|
| Ex-144 | 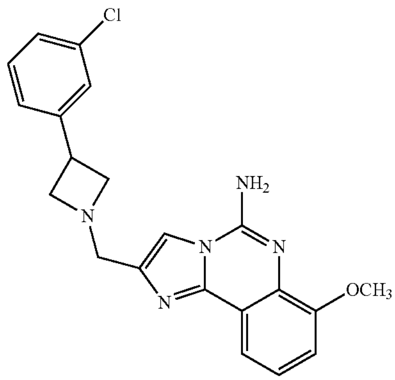 [SMILES: COc1cccc2c1nc(N)n1cc(CN3CC(c4cccc(Cl)c4)C3)nc21] | 394 [M + 1] | 2-((3-(3-chlorophenyl)azetidin-1-yl)methyl)-7-methoxyimidazo[1,2-c]quinazolin-5-amine |
| Ex-145 | 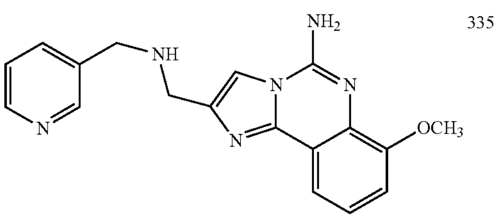 | 335 [M + 1] | 7-methoxy-2-(((pyridin-3-ylmethyl)amino)methyl)imidazo[1,2-c]quinazolin-5-amine |
Example 20 Preparation of 7-fluoro-2-(phenoxymethyl)imidazo[1,2-c]quinazolin-5-amine Ex-140
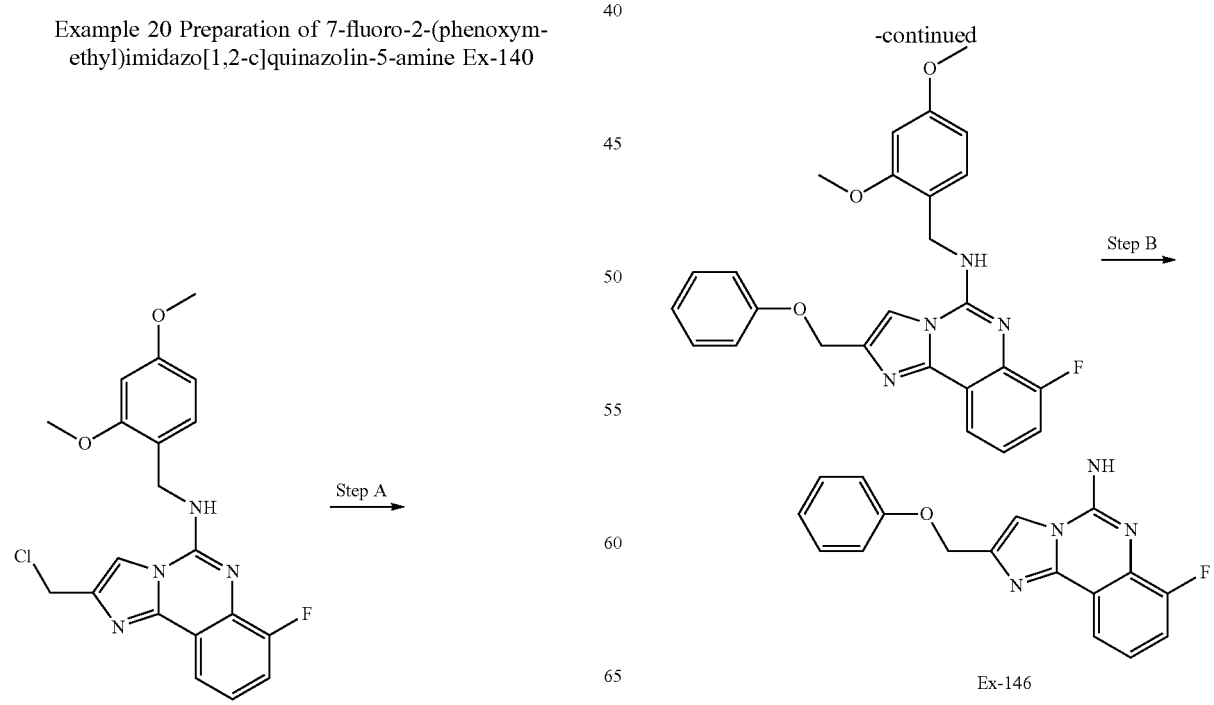

Step A: (N-(2,4-dimethoxybenzyl)-7-fluoro-2-(phenoxymethyl)imidazo[1,2-c]quinazolin-5-amine Into a dry THF solution of phenol (20.66 mg, 0.220 mmol) under N₂ atmosphere was added NaH (9.58 mg, 0.240 mmol). The reaction mixture was left to react for 30 minutes then 2-(chloromethyl)-N-(2,4-dimethoxybenzyl)-7-fluoroimidazo[1,2-c]quinazolin-5-amine (80 mg, 0.200 mmol) in dry THF was added and the reaction mixture was monitored by LCMS until it indicated that full conversion had occurred. The reaction mixture was quenched with water and diluted with EtOAC then extracted (3×50 mL ETOAc, water), dried over Na₂SO₄, and concentrated on rotary evaporator. The crude material thus obtained was purified by flash chromatography on a combiflash system using 10-50% EtOAc/Hexanes gradient to yield the title compound.

Step B: 7-fluoro-2-(phenoxymethyl)imidazo[1,2-c]quinazolin-5-amine Ex-146

N-(2,4-dimethoxybenzyl)-7-fluoro-2-(phenoxymethyl)imidazo[1,2-c]quinazolin-5-amine from the previous step (71 mg, 0.155 mmol) was added with CH₂Cl₂ (2 ml), TFA (0.088 ml, 0.774 mmol) and the mixture reacted in microwave at 85° C. for 1.5 hours, then the reaction mixture was concentrated in a rotary evaporator, diluted with DCM and basified with 7N NH₃ in MeOH. After neutralization, the mixture was again concentrated on a rotary evaporator. The crude material thus obtained was dissolve in DCM containing a few drops of MeOH and the mixture purified by flash chromatography (combiflash system) to yield the title product, Ex-146, LC/MS=309 [M+1].

The compounds of Table 11 were prepared by using methodology described in Example 20 and appropriate reagents.

TABLE 11

| Ex-No. | Structure | LC-MS | Name |
|---|---|---|---|
| Ex-147 | 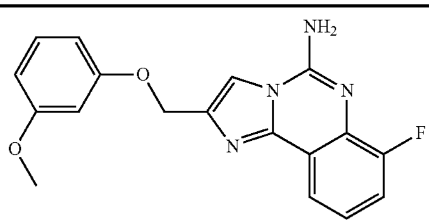 | 431 [M + 1]. | 7-fluoro-2-((3-methoxyphenoxy)methyl)-imidazo-[1,2-c]quinazolin-5-amine |

Example 21 Preparation of 7-(1-ethyl-1H-pyrazol-4-yl)-2-(((4-fluorobenzyl)amino)methyl)-imidazo[1,2-c]quinazolin-5-amine Ex-149

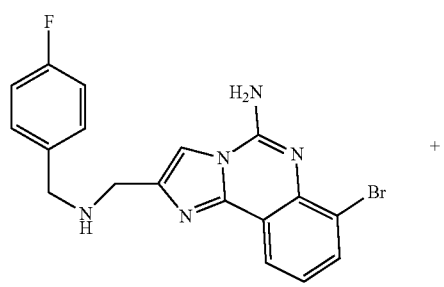

+

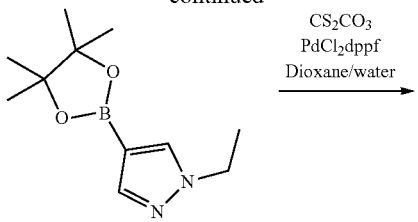

$\xrightarrow{\text{CS}_2\text{CO}_3,\ \text{PdCl}_2\text{dppf},\ \text{Dioxane/water}}$

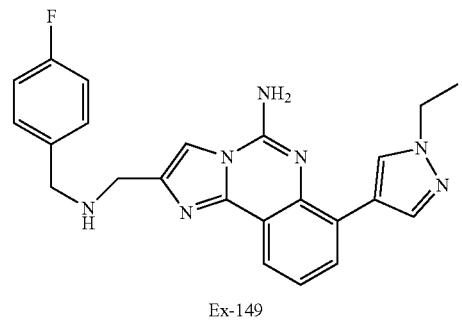

Ex-149

Preparation of 7-(1-ethyl-1H-pyrazol-4-yl)-2-((4-fluorobenzyl)amino)methyl)imidazo[1,2-c]quinazolin-5-amine Ex-149

Into a stirred mixture of 7-bromo-2-(((4-fluorobenzyl)amino)methyl)imidazo[1,2-c]quinazolin-5-amine, prepared in accordance with Example 22 and other procedures described herein using appropriate reagents, (12 mg, 0.031 mmol), was added cesium carbonate (15 mg, 0.046 mmol), 1-ethyl-4-(4,4,5,5-tetramethyl-1,3,2-dioxaborolan-2-yl)-1H-pyrazole and PdCl₂dppf (2 mg) in dioxane/Water v/v (3 ml/0.5 ml) and the reaction mixture was heated to 100° C. in a microwave oven for 1 hour, then solvent was evaporated and the crude residue purified using Analogix Redisep column eluting with 10% MeOH/MeCl₂/NH₄ OH yielding the title compound, Ex-149, LCMS 398 [M+1].

The compounds of Table 12 were prepared by using methodology described in Example 21 and appropriate reagents.

TABLE 12

| Ex-No | Structure | LCMS | Name |
|---|---|---|---|
| Ex-150 | 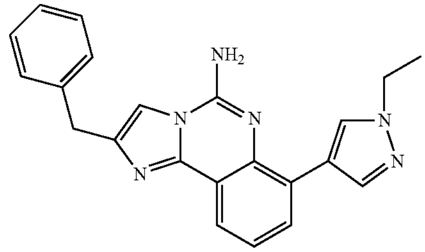 [SMILES: CCn1cc(-c2cccc3c2nc(N)n2cc(Cc4ccccc4)nc32)cn1] | 369 [M + 1] | 2-benzyl-7-(1-ethyl-1H-pyrazol-4-yl)imidazo[1,2-c]quinazolin-5-amine |
| Ex-151 | 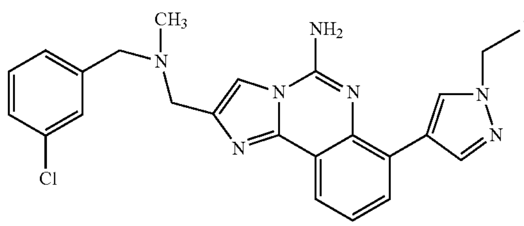 [SMILES: CCn1cc(-c2cccc3c2nc(N)n2cc(CN(C)Cc4cccc(Cl)c4)nc32)cn1] | 446 [M + 1] | 2-(((3-chlorobenzyl)-(methyl)amino)-methyl)-7-(1-ethyl-1H-pyrazol-4-yl)imidazo[1,2-c]-quinazolin-5-amine |
| Ex-152 | 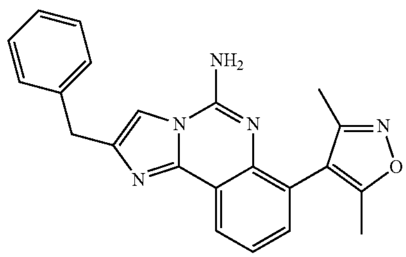 [SMILES: Cc1noc(C)c1-c1cccc2c1nc(N)n1cc(Cc3ccccc3)nc21] | 370 [M + 1] | 2-benzyl-7-(3,5-dimethylisoxazol-4-yl)imidazo[1,2-c]quinazolin-5-amine |
| Ex-153 | 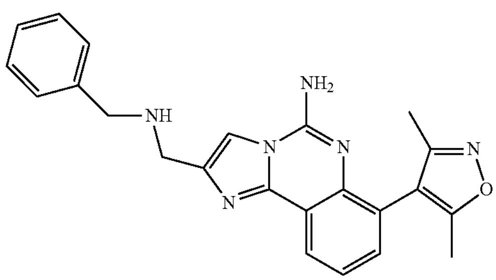 [SMILES: Cc1noc(C)c1-c1cccc2c1nc(N)n1cc(CNCc3ccccc3)nc21] | 399 [M + 1] | 2-((benzylamino)-methyl)-7-(3,5-dimethyl-isoxazol-4-yl)-imidazo[1,2-c]-quinazolin-5-amine |
| Ex-154 | 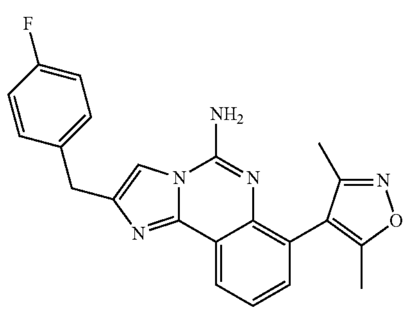 [SMILES: Cc1noc(C)c1-c1cccc2c1nc(N)n1cc(Cc3ccc(F)cc3)nc21] | 388 [M + 1] | 7-(3,5-dimethylisoxazol-4-yl)-2-(4-fluorobenzyl)imidazo[1,2-c]quinazolin-5-amine |
| Ex-155 | 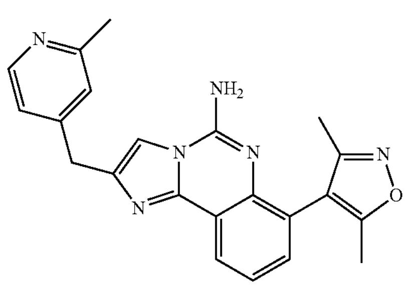 [SMILES: Cc1cc(Cc2cn3c(N)nc4c(-c5c(C)noc5C)cccc4c3n2)ccn1] | 385 [M + 1] | 7-(3,5-dimethylisoxazol-4-yl)-2-((2-methylpyridin-4-yl)methyl)imidazo[1,2-c]quinazolin-5-amine |

TABLE 12-continued

| Ex-No | Structure | LCMS | Name |
|---|---|---|---|
| Ex-156 | 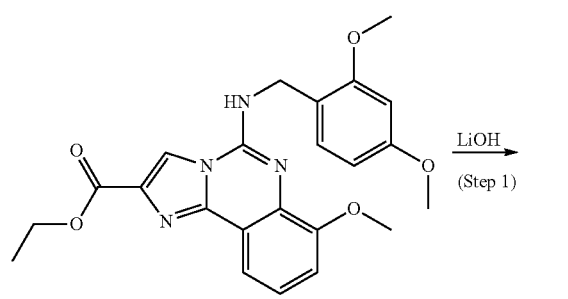 | 342 [M + 1] | 2-benzyl-7-(isoxazol-4-yl)imidazo[1,2-c]quinazolin-5-amine |

Example 22 Preparation of 5-amino-7-methoxy-N-(quinolin-8-ylmethyl)imidazo[1,2-c]quinazoline-2-carboxamide Ex-157

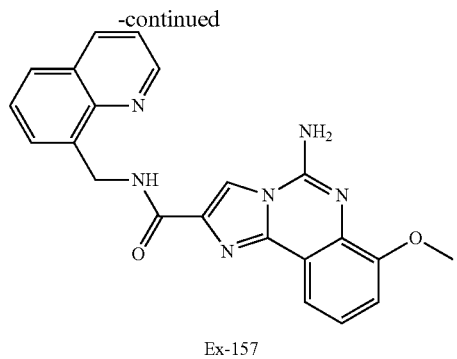

Ex-157

(Step 1) lithium 5-((2,4-dimethoxybenzyl)amino)-7-methoxyimidazo[1,2-c]quinazoline-2-carboxylate To a stirred suspension of ethyl 5-((2,4-dimethoxybenzyl)amino)-7-methoxyimidazo[1,2-c]quinazoline-2-carboxylate (prepared in accordance with Example 1 through Step 7, 312 mg, 0.715 mmol) in THF (3 ml) and MeOH (1.4 ml) was added a solution of lithium hydroxide monohydrate (64.3 mg, 0.858 mmol) in water (1 ml) at rt. The reaction mixture was stirred at rt for 16 hours then the solvent was evaporated and the residue dried under vacuum overnight to give the title product. The residue was used in the next step without further purification, LC/MS=409 [M+1]

(Step 2) 5-((2,4-dimethoxybenzyl)amino)-7-methoxy-N-(quinolin-8-ylmethyl)imidazo[1,2-c]quinazoline-2-carboxamide To a stirred solution of lithium 5-((2,4-dimethoxybenzyl)amino)-7-methoxyimidazo[1,2-c]quinazoline-2-carboxylate (100 mg, 0.241 mmol) in DMF (2413 µl) was added amine (94 mg, 0.483 mmol), HATU (138 mg, 0.362 mmol) and DIPEA (126 µl, 0.724 mmol). The reaction mixture was heated to 60° C. for four hours, then worked-up with NaHCO$_3$(aq) and DCM. The organic layer was separated, dried over MgSO$_4$, filtered and concentrated. The crude product thus provided was purified by flash silica column chromatography (10% MeOH/DCM) to give the title compound, LC/MS=549 [M+1].

(Step 3) 5-amino-7-methoxy-N-(quinolin-8-ylm-ethyl)imidazo[1,2-c]quinazoline-2-carboxamide Ex-157

Into a round-bottom flask containing 5-((2,4-dimethoxy-benzyl)amino)-7-methoxy-N-(quinolin-8-ylmethyl)imidazo[1,2-c]quinazoline-2-carboxamide (110 mg, 0.201 mmol) was added TFA (2005 μl) and the reaction mixture was stirred overnight. TFA was evaporated and the reaction was quenched with $NaHCO_3$ (aq) and extracted with 10% MeOH/DCM. The organic layer was separated, dried over $MgSO_4$, filtered, and concentrated. The crude product thus provided was dissolved in DCM, solids which precipitated were filtered and washed with DCM to give the title product, Ex-157, LC/MS=399 [M+1].

Example 23, General Procedure for Preparing Amide Analogs

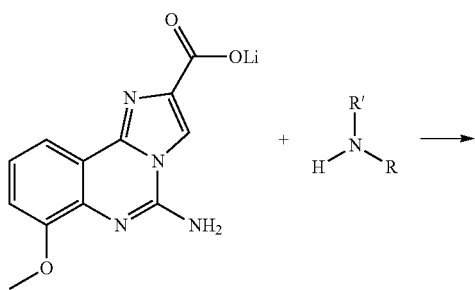

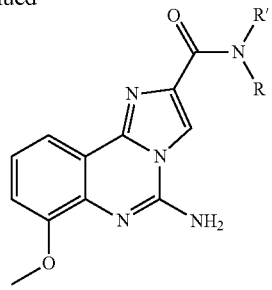

Additional amide analogs were prepared by adding 1.5 equivalents of an amine which will provide the desired substituents into a 1 dram vial (1.5 eq.) along with lithium 5-amino-7-methoxyimidazo[1,2-c]quinazoline-2-carboxylate (30 mg, 0.114 mmol) and a DMF solution (1.0 ml) solution of DIPEA (0.079 ml, 0.454 mmol), shaking the vial for 5 minutes in a Bohdan Miniblock Shaker and then adding 1-propanephosphonic acid cyclic anhydride (50% w/w in EtOAc, 64.7 μl, 0.109 mmol), and continuing to shake the vial at RT overnight. The completed reaction was quenched with 1.0 ml water and the organic layer separated by filtering through a Varian 2 ml Reservoir Frit and a Whatman 0.45 μm syringe filter to remove emulsion, followed by solvent removal using a Genevac. The crude residue was dissolved in 1.0 ml DMSO and purified by LC/MS.

The compounds of Table 13 were prepared by using methodology described herein with appropriate reagent substitutions.

TABLE 13

| Ex No | Structure | LCMS | Name |
| --- | --- | --- | --- |
| Ex-158 | 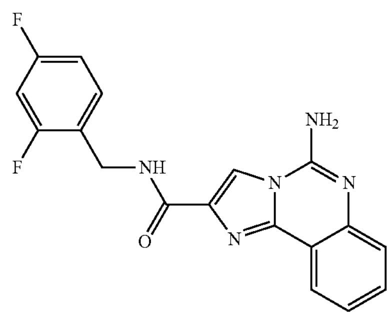 [SMILES: Nc1nc2ccccc2c2nc(C(=O)NCc3ccc(F)cc3F)cn12] | 354 [M + 1] | 5-amino-N-(2,4-difluorobenzyl)imidazo[1,2-c]quinazoline-2-carboxamide |
| Ex-159 | 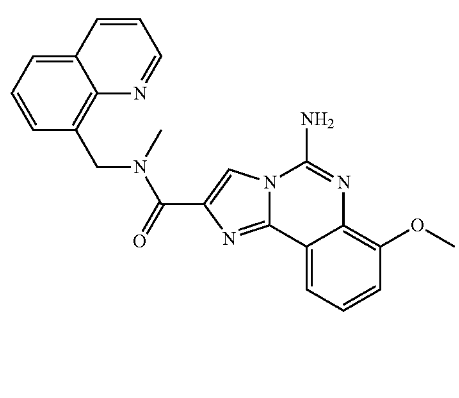 [SMILES: COc1cccc2c1nc(N)n1cc(C(=O)N(C)Cc3cccc4cccnc34)nc21] | 413 [M + 1] | 5-amino-7-methoxy-N-methyl-N-(quinolin-8-ylmethyl)imidazo[1,2-c]quinazoline-2-carboxamide |

TABLE 13-continued

| Ex No | Structure | LCMS | Name |
| --- | --- | --- | --- |
| Ex-160 | 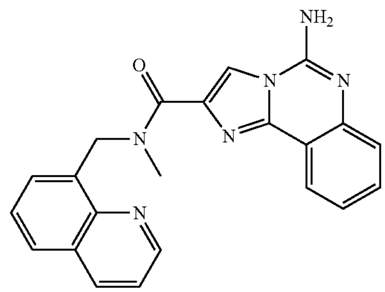 [SMILES: CN(Cc1cccc2cccnc12)C(=O)c1cn2c(N)nc3ccccc3c2n1] | 383 [M + 1] | 5-amino-N-methyl-N-(quinolin-8-ylmethyl)imidazo[1,2-c]quinazoline-2-carboxamide |
| Ex-161 | 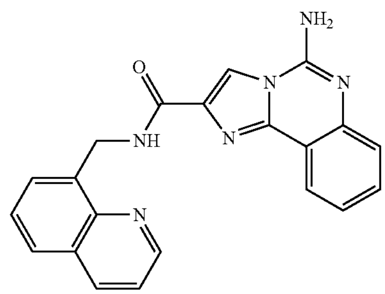 [SMILES: Nc1nc2ccccc2c2nc(C(=O)NCc3cccc4cccnc34)cn12] | 369 [M + 1] | 5-amino-N-(quinolin-8-ylmethyl)-imidazo-[1,2-c]-quinazoline-2-carboxamide |
| Ex-162 | 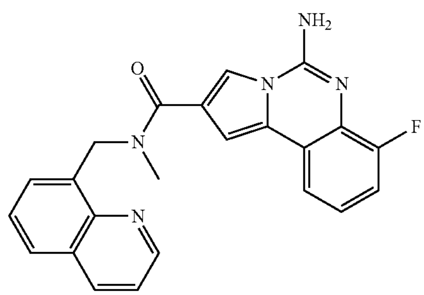 [SMILES: CN(Cc1cccc2cccnc12)C(=O)c1cc2c3cccc(F)c3nc(N)n2c1] | 401 | 5-amino-7-fluoro-N-methyl-N-(quinolin-8-ylmethyl)imidazo[1,2-c]quinazoline-2-carboxamide |
| Ex-163 | 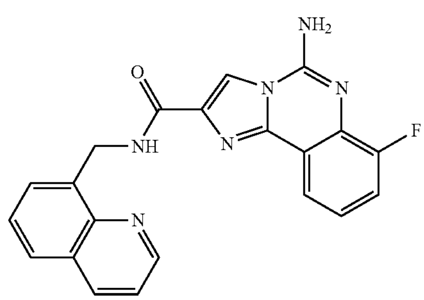 [SMILES: Nc1nc2c(F)cccc2c2nc(C(=O)NCc3cccc4cccnc34)cn12] | 387 | 5-amino-7-fluoro-N-(quinolin-8-ylmethyl)imidazo[1,2-c]quinazoline-2-carboxamide |
| Ex-164 | 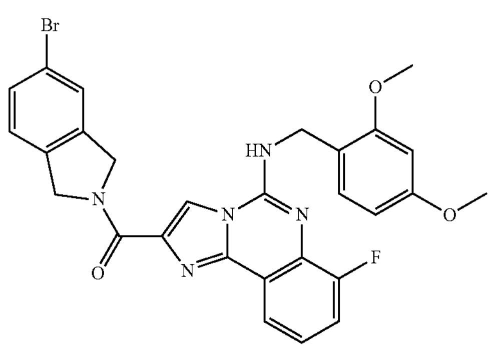 [SMILES: COc1ccc(CNc2nc3c(F)cccc3c3nc(C(=O)N4Cc5ccc(Br)cc5C4)cn23)c(OC)c1] | 576 | (5-bromoisoindolin-2-yl)(5-((2,4-dimethoxybenzyl)amino)-7-fluoroimidazo[1,2-c]quinazolin-2-yl)methanone |

TABLE 13-continued

| Ex No | Structure | LCMS | Name |
|---|---|---|---|
| Ex-165 | 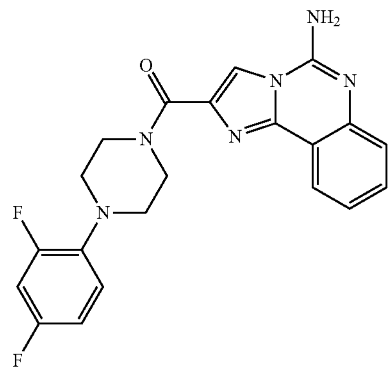 [SMILES: Nc1nc2ccccc2c2nc(C(=O)N3CCN(c4ccc(F)cc4F)CC3)cn12] | 409 | (5-aminoimidazo[1,2-c]quinazolin-2-yl)(4-(2,4-difluorophenyl)piperazin-1-yl)methanone |
| Ex-166 | 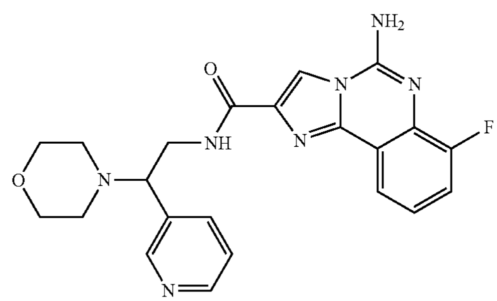 [SMILES: Nc1nc2c(F)cccc2c2nc(C(=O)NCC(c3cccnc3)N3CCOCC3)cn12] | 436 | 5-amino-7-fluoro-N-(2-morpholino-2-(pyridin-3-yl)ethyl)imidazo[1,2-c]quinazoline-2-carboxamide |
| Ex-167 | 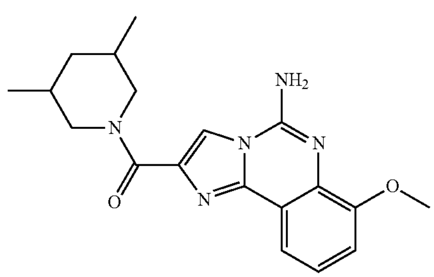 | 354.2 | (5-amino-7-methoxyimidazo[1,2-c]quinazolin-2-yl)(3,5-dimethylpiperidin-1-yl)methanone |
| Ex-168 | 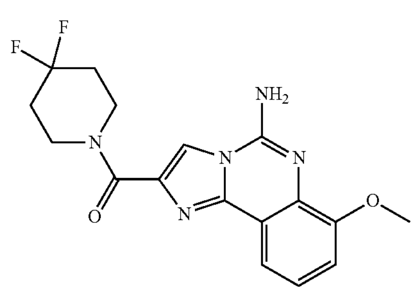 [SMILES: COc1cccc2c1nc(N)n1cc(C(=O)N3CCC(F)(F)CC3)nc21] | 362.1 | (5-amino-7-methoxyimidazo[1,2-c]quinazolin-2-yl)(4,4-difluoropiperidin-1-yl)methanone |
| Ex-169 | 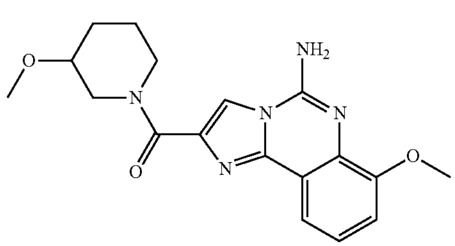 | 356.2 | (5-amino-7-methoxyimidazo[1,2-c]quinazolin-2-yl)(3-methoxypiperidin-1-yl)methanone |

TABLE 13-continued

| Ex No | Structure | LCMS | Name |
|---|---|---|---|
| Ex-170 | 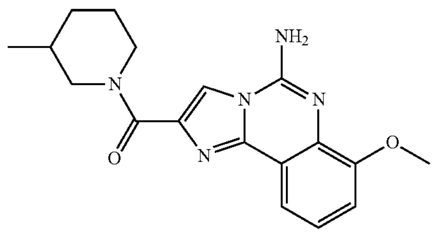 | 340.2 | (5-amino-7-methoxyimidazo[1,2-c]quinazolin-2-yl)(3-methylpiperidin-1-yl)methanone |
| Ex-171 | 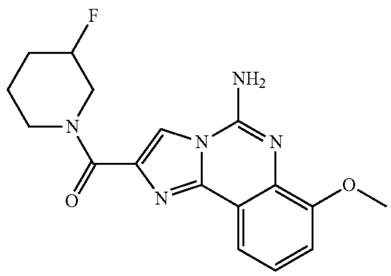 [SMILES: COc1cccc2c1nc(N)n1cc(C(=O)N3CCCC(F)C3)nc21] | 344.2 | (5-amino-7-methoxyimidazo[1,2-c]quinazolin-2-yl)(3-fluoropiperidin-1-yl)methanone |
| Ex-172 | 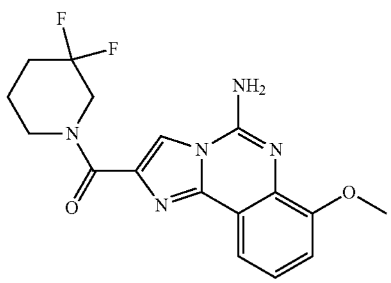 [SMILES: COc1cccc2c1nc(N)n1cc(C(=O)N3CCCC(F)(F)C3)nc21] | 362.1 | (5-amino-7-methoxyimidazo[1,2-c]quinazolin-2-yl)(3,3-difluoropiperidin-1-yl)methanone |
| Ex-173 | 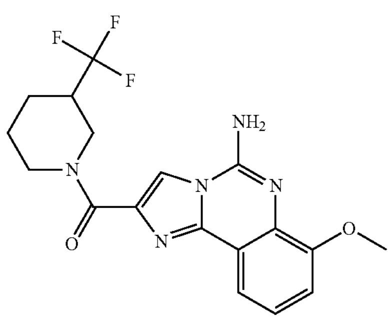 [SMILES: COc1cccc2c1nc(N)n1cc(C(=O)N3CCCC(C(F)(F)F)C3)nc21] | 394.1 | (5-amino-7-methoxyimidazo[1,2-c]quinazolin-2-yl)(3-(trifluoromethyl)piperidin-1-yl)methanone |
| Ex-174 | 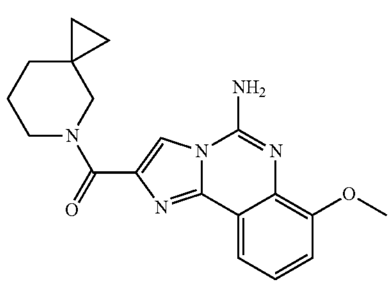 [SMILES: COc1cccc2c1nc(N)n1cc(C(=O)N3CCCC4(CC4)C3)nc21] | 352.2 | (5-amino-7-methoxyimidazo[1,2-c]quinazolin-2-yl)(5-azaspiro[2.5]octan-5-yl)methanone |

TABLE 13-continued

| Ex No | Structure | LCMS | Name |
| --- | --- | --- | --- |
| Ex-175 | 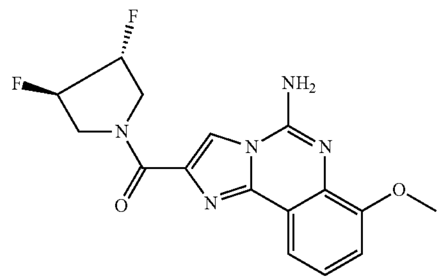 [SMILES: COc1cccc2c1nc(N)n1cc(C(=O)N3C[C@@H](F)[C@H](F)C3)nc21] | 348.1 | (5-amino-7-methoxyimidazo[1,2-c]quinazolin-2-yl)((3R,4R)-3,4-difluoropyrrolidin-1-yl)methanone |
| Ex-176 | 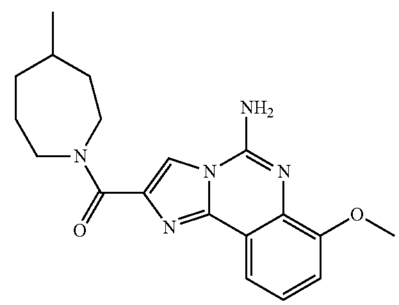 [SMILES: COc1cccc2c1nc(N)n1cc(C(=O)N3CCCC(C)CC3)nc21] | 354.2 | (5-amino-7-methoxyimidazo[1,2-c]quinazolin-2-yl)(4-methylazepan-1-yl)methanone |
| Ex-177 | 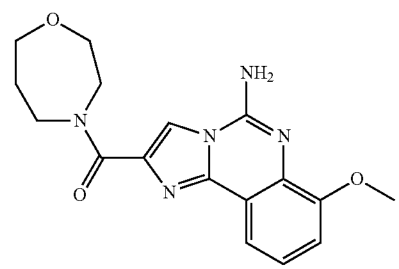 [SMILES: COc1cccc2c1nc(N)n1cc(C(=O)N3CCCOCC3)nc21] | 342.2 | (5-amino-7-methoxyimidazo[1,2-c]quinazolin-2-yl)(1,4-oxazepan-4-yl)methanone |
| Ex-178 | 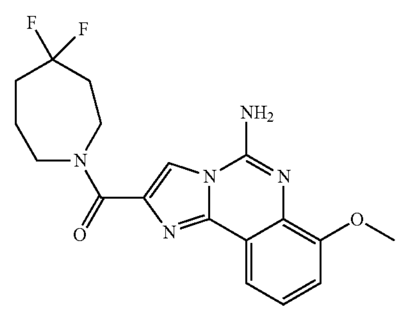 [SMILES: COc1cccc2c1nc(N)n1cc(C(=O)N3CCCC(F)(F)CC3)nc21] | 376.2 | (5-amino-7-methoxyimidazo[1,2-c]quinazolin-2-yl)(4,4-difluoroazepan-1-yl)methanone |
| Ex-179 | 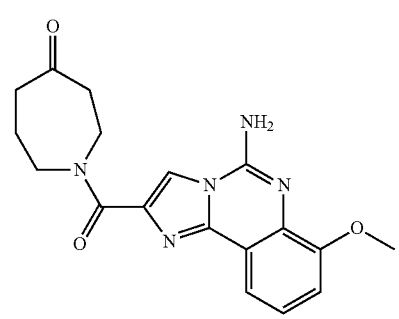 [SMILES: COc1cccc2c1nc(N)n1cc(C(=O)N3CCCC(=O)CC3)nc21] | 354.2 | 1-(5-amino-7-methoxyimidazo[1,2-c]quinazoline-2-carbonyl)azepan-4-one |

TABLE 13-continued

| Ex No | Structure | LCMS | Name |
|---|---|---|---|
| Ex-180 | 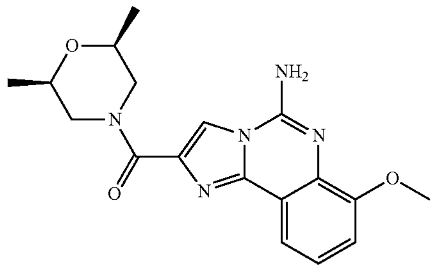 | 356.2 | (5-amino-7-methoxyimidazo[1,2-c]quinazolin-2-yl)((2R,6S)-2,6-dimethylmorpholino)methanone |
| Ex-181 | 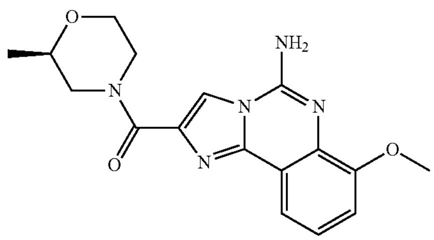 | 342.2 | (R)-(5-amino-7-methoxyimidazo[1,2-c]quinazolin-2-yl)(2-methylmorpholino)methanone |
| Ex-182 | 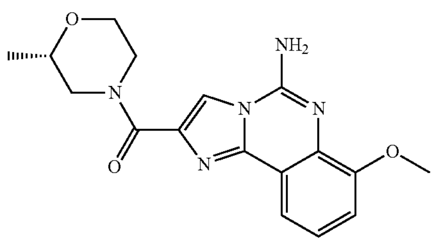 | 342.2 | (S)-(5-amino-7-methoxyimidazo[1,2-c]quinazolin-2-yl)(2-methylmorpholino)methanone |
| Ex-183 | 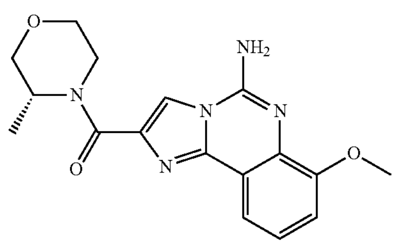 [SMILES: COc1cccc2c1nc(N)n1cc(C(=O)N3CCOC[C@H]3C)nc21] | 342.2 | (R)-(5-amino-7-methoxyimidazo[1,2-c]quinazolin-2-yl)(3-methylmorpholino)methanone |
| Ex-184 | 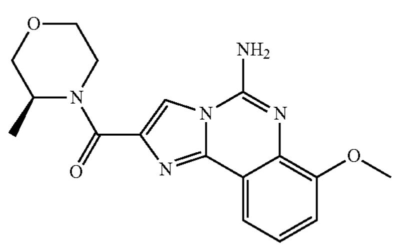 [SMILES: COc1cccc2c1nc(N)n1cc(C(=O)N3CCOC[C@@H]3C)nc21] | 342.2 | (S)-(5-amino-7-methoxyimidazo[1,2-c]quinazolin-2-yl)(3-methylmorpholino)methanone |
| Ex-185 | 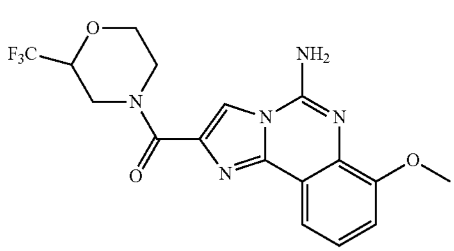 [SMILES: COc1cccc2c1nc(N)n1cc(C(=O)N3CCOC(C(F)(F)F)C3)nc21] | 396.1 | (5-amino-7-methoxyimidazo[1,2-c]quinazolin-2-yl)(2-(trifluoromethyl)morpholino)methanone |

TABLE 13-continued

| Ex No | Structure | LCMS | Name |
|---|---|---|---|
| Ex-186 | 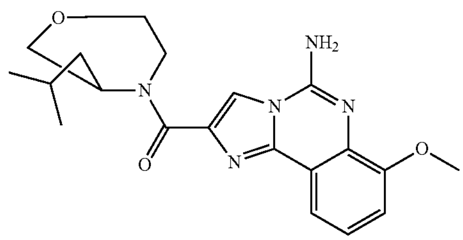 [SMILES: COc1cccc2c1nc(N)n1cc(C(=O)N3CCCOCCC3CC(C)C)nc21] | 384.2 | (5-amino-7-methoxyimidazo[1,2-c]quinazolin-2-yl)(3-isobutylmorpholino)methanone |
| Ex-187 | 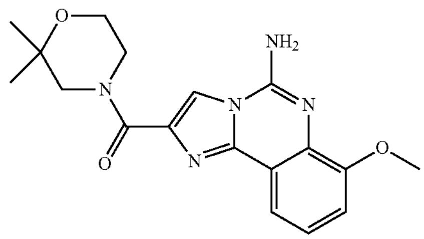 | 356.2 | (5-amino-7-methoxyimidazo[1,2-c]quinazolin-2-yl)(2,2-dimethylmorpholino)methanone |
| Ex-188 | 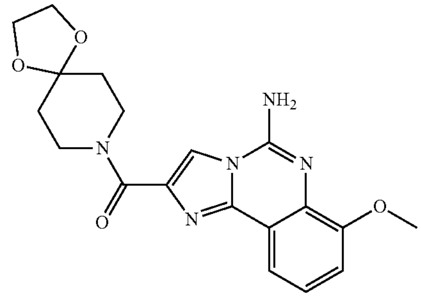 [SMILES: COc1cccc2c1nc(N)n1cc(C(=O)N3CCC4(CC3)OCCO4)nc21] | 384.2 | (5-amino-7-methoxyimidazo[1,2-c]quinazolin-2-yl)(1,4-dioxa-8-azaspiro[4.5]decan-8-yl)methanone |
| Ex-189 | 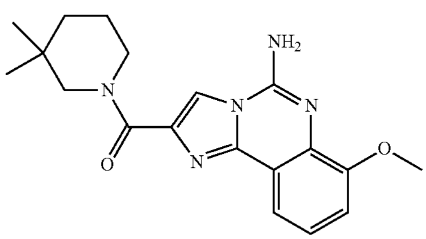 | 354.2 | (5-amino-7-methoxyimidazo[1,2-c]quinazolin-2-yl)(3,3-dimethylpiperidin-1-yl)methanone |
| Ex-190 | 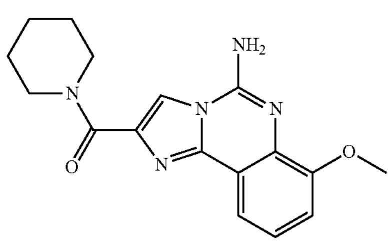 [SMILES: COc1cccc2c1nc(N)n1cc(C(=O)N3CCCCC3)nc21] | 326.2 | (5-amino-7-methoxyimidazo[1,2-c]quinazolin-2-yl)(piperidin-1-yl)methanone |
| Ex-191 | 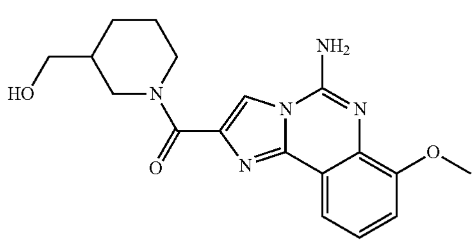 [SMILES: COc1cccc2c1nc(N)n1cc(C(=O)N3CCCC(CO)C3)nc21] | 356.2 | (5-amino-7-methoxyimidazo[1,2-c]quinazolin-2-yl)(3-(hydroxymethyl)piperidin-1-yl)methanone |

TABLE 13-continued

| Ex No | Structure | LCMS | Name |
|---|---|---|---|
| Ex-192 | 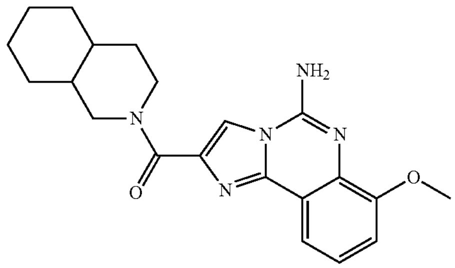 [SMILES: COc1cccc2c1nc(N)n1cc(C(=O)N3CCC4CCCCC4C3)nc21] | 380.2 | (5-amino-7-methoxyimidazo[1,2-c]quinazolin-2-yl)(octahydroisoquinolin-2(1H)-yl)methanone |
| Ex-193 | 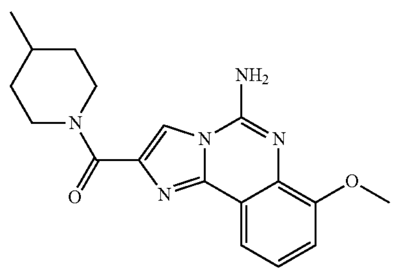 [SMILES: COc1cccc2c1nc(N)n1cc(C(=O)N3CCC(C)CC3)nc21] | 340.2 | (5-amino-7-methoxyimidazo[1,2-c]quinazolin-2-yl)(4-methylpiperidin-1-yl)methanone |
| Ex-194 | 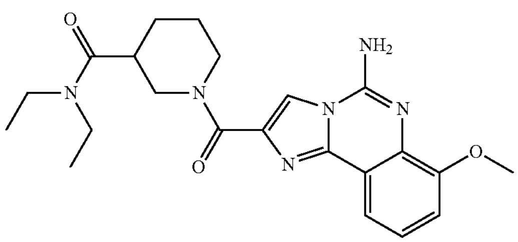 [SMILES: CCN(CC)C(=O)C1CCCN(C(=O)c2cn3c(N)nc4c(OC)cccc4c3n2)C1] | 425.2 | 1-(5-amino-7-methoxyimidazo[1,2-c]quinazoline-2-carbonyl)-N,N-diethylpiperidine-3-carboxamide |
| Ex-195 | 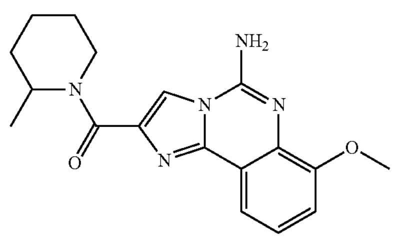 [SMILES: COc1cccc2c1nc(N)n1cc(C(=O)N3CCCCC3C)nc21] | 340.2 | (5-amino-7-methoxyimidazo[1,2-c]quinazolin-2-yl)(2-methylpiperidin-1-yl)methanone |
| Ex-196 | 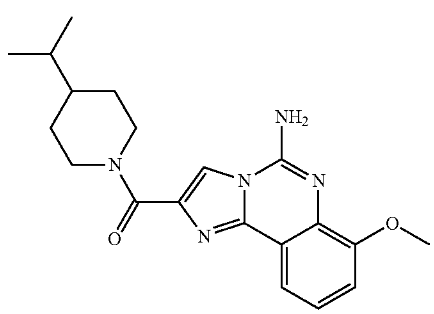 [SMILES: COc1cccc2c1nc(N)n1cc(C(=O)N3CCC(C(C)C)CC3)nc21] | 368.2 | (5-amino-7-methoxyimidazo[1,2-c]quinazolin-2-yl)(4-isopropylpiperidin-1-yl)methanone |

TABLE 13-continued

| Ex No | Structure | LCMS | Name |
|---|---|---|---|
| Ex-197 | 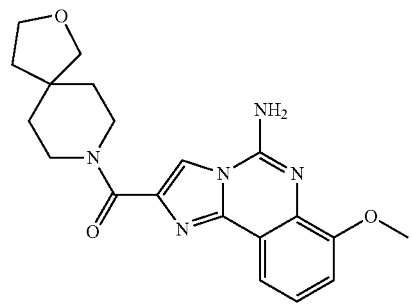 [SMILES: COc1cccc2c1nc(N)n1cc(C(=O)N3CCC4(CCOC4)CC3)nc21] | 382.2 | (5-amino-7-methoxyimidazo[1,2-c]quinazolin-2-yl)(2-oxa-8-azaspiro[4.5]decan-8-yl)methanone |
| Ex-198 | 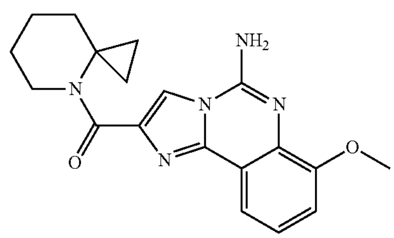 [SMILES: COc1cccc2c1nc(N)n1cc(C(=O)N3CCCCC34CC4)nc21] | 352.2 | (5-amino-7-methoxyimidazo[1,2-c]quinazolin-2-yl)(4-azaspiro[2.5]octan-4-yl)methanone |
| Ex-199 | 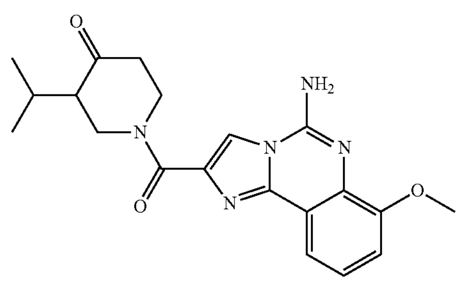 [SMILES: COc1cccc2c1nc(N)n1cc(C(=O)N3CCC(=O)C(C(C)C)C3)nc21] | 382.2 | 1-(5-amino-7-methoxyimidazo[1,2-c]quinazoline-2-carbonyl)-3-isopropylpiperidin-4-one |
| Ex-200 | 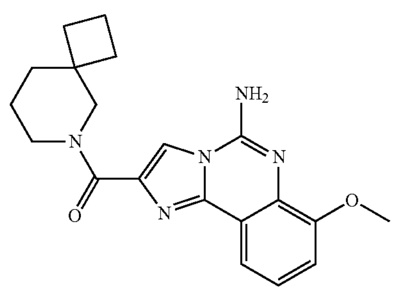 [SMILES: COc1cccc2c1nc(N)n1cc(C(=O)N3CCCC4(CCC4)C3)nc21] | 366.2 | (5-amino-7-methoxyimidazo[1,2-c]quinazolin-2-yl)(6-azaspiro[3.5]nonan-6-yl)methanone |
| Ex-201 | 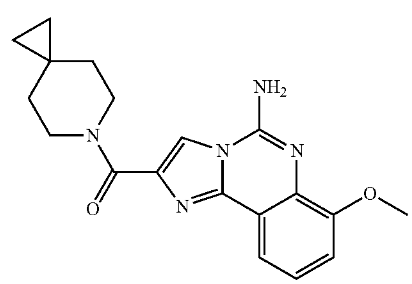 [SMILES: COc1cccc2c1nc(N)n1cc(C(=O)N3CCC4(CC3)CC4)nc21] | 352.2 | (5-amino-7-methoxyimidazo[1,2-c]quinazolin-2-yl)(6-azaspiro[2.5]octan-6-yl)methanone |

TABLE 13-continued

| Ex No | Structure | LCMS | Name |
|---|---|---|---|
| Ex-202 | 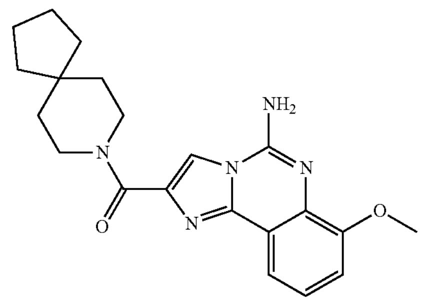 [SMILES: COc1cccc2c1nc(N)n1cc(C(=O)N3CCC4(CCCC4)CC3)nc21] | 380.2 | (5-amino-7-methoxyimidazo[1,2-c]quinazolin-2-yl)(8-azaspiro[4.5]decan-8-yl)methanone |
| Ex-203 | 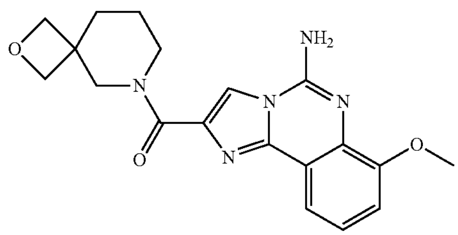 [SMILES: COc1cccc2c1nc(N)n1cc(C(=O)N3CCCC4(COC4)C3)nc21] | 368.2 | (5-amino-7-methoxyimidazo[1,2-c]quinazolin-2-yl)(2-oxa-6-azaspiro[3.5]nonan-6-yl)methanone |
| Ex-204 | 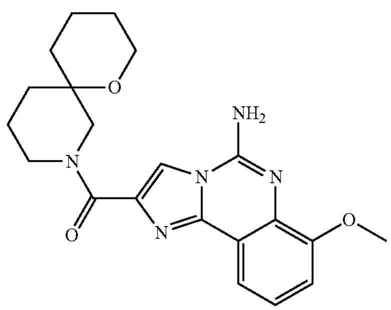 [SMILES: COc1cccc2c1nc(N)n1cc(C(=O)N3CCCC4(CCCCO4)C3)nc21] | 396.2 | (5-amino-7-methoxyimidazo[1,2-c]quinazolin-2-yl)(1-oxa-8-azaspiro[5.5]undecan-8-yl)methanone |
| Ex-205 | 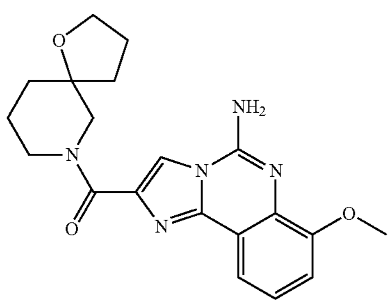 [SMILES: COc1cccc2c1nc(N)n1cc(C(=O)N3CCCC4(CCCO4)C3)nc21] | 382.2 | (5-amino-7-methoxyimidazo[1,2-c]quinazolin-2-yl)(1-oxa-7-azaspiro[4.5]decan-7-yl)methanone |
| Ex-206 | 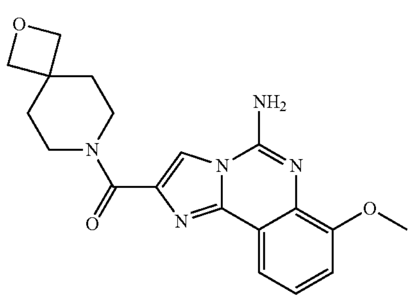 [SMILES: COc1cccc2c1nc(N)n1cc(C(=O)N3CCC4(CC3)COC4)nc21] | 368.2 | (5-amino-7-methoxyimidazo[1,2-c]quinazolin-2-yl)(2-oxa-7-azaspiro[3.5]nonan-7-yl)methanone |

TABLE 13-continued

| Ex No | Structure | LCMS | Name |
|---|---|---|---|
| Ex-207 | 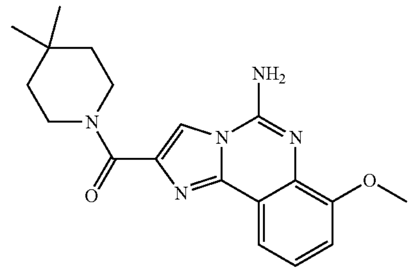 | 354.2 | (5-amino-7-methoxyimidazo[1,2-c]quinazolin-2-yl)(4,4-dimethylpiperidin-1-yl)methanone |
| Ex-208 | 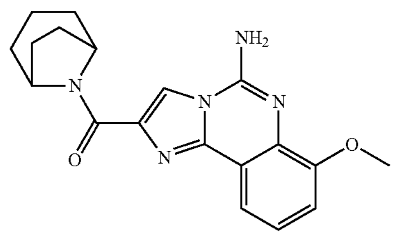 [SMILES: COc1cccc2c1nc(N)n1cc(C(=O)N3C4CCCC3CC4)nc21] | 352.2 | (5-amino-7-methoxyimidazo[1,2-c]quinazolin-2-yl)(8-azabicyclo[3.2.1]octan-8-yl)methanone |
| Ex-209 | 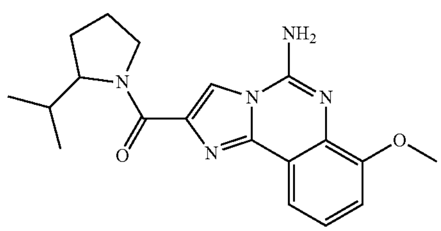 [SMILES: COc1cccc2c1nc(N)n1cc(C(=O)N3CCCC3C(C)C)nc21] | 354.2 | (5-amino-7-methoxyimidazo[1,2-c]quinazolin-2-yl)(2-isopropylpyrrolidin-1-yl)methanone |
| Ex-210 | 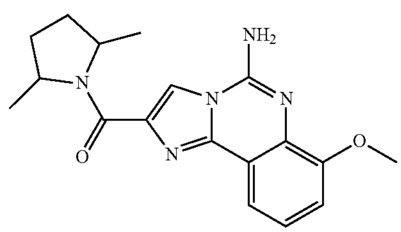 | 340.2 | (5-amino-7-methoxyimidazo[1,2-c]quinazolin-2-yl)(2,5-dimethylpyrrolidin-1-yl)methanone |
| Ex-211 | 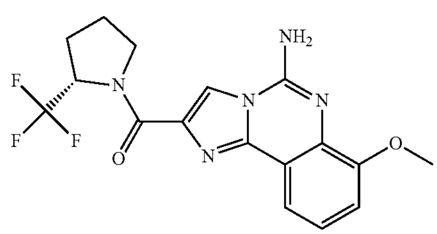 [SMILES: COc1cccc2c1nc(N)n1cc(C(=O)N3CCC[C@H]3C(F)(F)F)nc21] | 380.1 | (S)-(5-amino-7-methoxyimidazo[1,2-c]quinazolin-2-yl)(2-(trifluoromethyl)pyrrolidin-1-yl)methanone |
| Ex-212 | 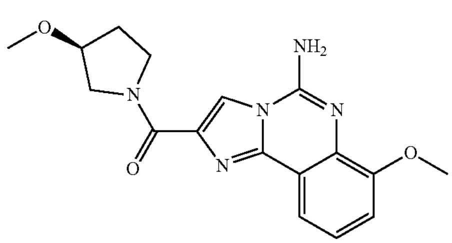 | 342.2 | (S)-(5-amino-7-methoxyimidazo[1,2-c]quinazolin-2-yl)(3-methoxypyrrolidin-1-yl)methanone |

TABLE 13-continued

| Ex No | Structure | LCMS | Name |
|---|---|---|---|
| Ex-213 | 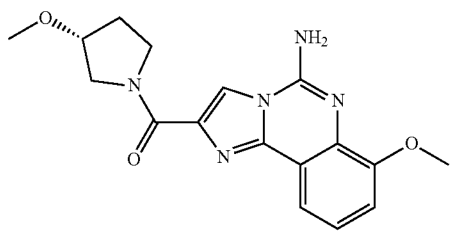 | 342.2 | (R)-(5-amino-7-methoxyimidazo[1,2-c]quinazolin-2-yl)(3-methoxypyrrolidin-1-yl)methanone |
| Ex-214 | 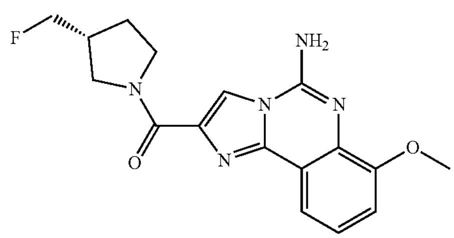 [SMILES: COc1cccc2c1nc(N)n1cc(C(=O)N3CC[C@@H](CF)C3)nc21] | 344.2 | (R)-(5-amino-7-methoxyimidazo[1,2-c]quinazolin-2-yl)(3-(fluoromethyl)pyrrolidin-1-yl)methanone |
| Ex-215 | 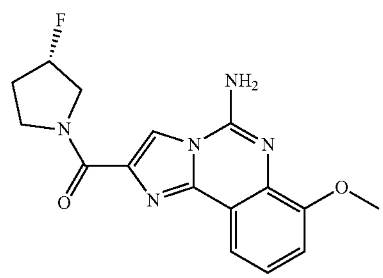 [SMILES: COc1cccc2c1nc(N)n1cc(C(=O)N3CC[C@H](F)C3)nc21] | 330.1 | (S)-(5-amino-7-methoxyimidazo[1,2-c]quinazolin-2-yl)(3-fluoropyrrolidin-1-yl)methanone |
| Ex-216 | 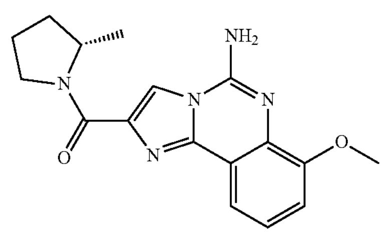 [SMILES: COc1cccc2c1nc(N)n1cc(C(=O)N3CCC[C@@H]3C)nc21] | 326.2 | (S)-(5-amino-7-methoxyimidazo[1,2-c]quinazolin-2-yl)(2-methylpyrrolidin-1-yl)methanone |
| Ex-217 | 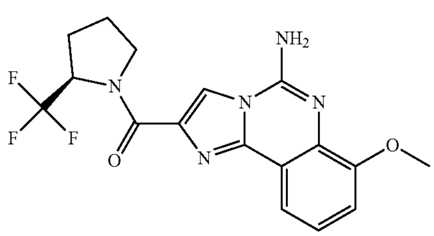 [SMILES: COc1cccc2c1nc(N)n1cc(C(=O)N3CCC[C@@H]3C(F)(F)F)nc21] | 380.1 | (R)-(5-amino-7-methoxyimidazo[1,2-c]quinazolin-2-yl)(2-(trifluoromethyl)pyrrolidin-1-yl)methanone |
| Ex-218 | 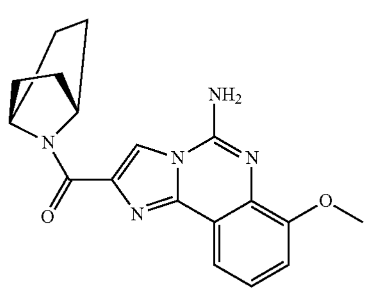 [SMILES: COc1cccc2c1nc(N)n1cc(C(=O)N3[C@@H]4CCC[C@H]3CC4)nc21] | 338.2 | (5-amino-7-methoxyimidazo[1,2-c]quinazolin-2-yl)((1s,4s)-7-azabicyclo[2.2.1]heptan-7-yl)methanone |

TABLE 13-continued

| Ex No | LCMS | Name |
|---|---|---|
| Ex-219 | 344.2 | (S)-(5-amino-7-methoxyimidazo[1,2-c]quinazolin-2-yl)(2-(fluoromethyl)pyrrolidin-1-yl)methanone |
| Ex-220 | 354.2 | (5-amino-7-methoxyimidazo[1,2-c]quinazolin-2-yl)(hexahydro-4H-furo[3,2-b]pyrrol-4-yl)methanone |
| Ex-221 | 348.1 | (5-amino-7-methoxyimidazo[1,2-c]quinazolin-2-yl)(3,3-difluoropyrrolidin-1-yl)methanone |
| Ex-222 | 366.2 | (5-amino-7-methoxyimidazo[1,2-c]quinazolin-2-yl)(2-azaspiro[4.4]nonan-2-yl)methanone |
| Ex-223 | 384.2 | (5-amino-7-methoxyimidazo[1,2-c]quinazolin-2-yl)(2,2,6,6-tetramethylmorpholino)methanone |
| Ex-224 | 354.2 | (5-amino-7-methoxyimidazo[1,2-c]quinazolin-2-yl)(3-oxa-8-azabicyclo[3.2.1]octan-8-yl)methanone |

TABLE 13-continued

| Ex No | LCMS | Name |
|---|---|---|
| Ex-225 | 340.1 | (5-amino-7-methoxyimidazo[1,2-c]quinazolin-2-yl)((1S,4S)-2-oxa-5-azabicyclo[2.2.1]heptan-5-yl)methanone |
| Ex-226 | 384.2 | methyl 1-(5-amino-7-methoxyimidazo[1,2-c]quinazoline-2-carbonyl)piperidine-4-carboxylate |
| Ex-227 | 396.2 | 8-(5-amino-7-methoxyimidazo[1,2-c]quinazoline-2-carbonyl)-1-oxa-8-azaspiro[4.5]decan-2-one |
| Ex-228 | 396.2 | 8-(5-amino-7-methoxyimidazo[1,2-c]quinazoline-2-carbonyl)-2-oxa-8-azaspiro[4.5]decan-1-one |
| Ex-229 | 424.2 | 7-(5-amino-7-methoxyimidazo[1,2-c]quinazoline-2-carbonyl)-3,3-dimethyl-2-oxa-7-azaspiro[4.5]decan-1-one |

TABLE 13-continued

| Ex No | Structure | LCMS | Name |
|---|---|---|---|
| Ex.-230 | 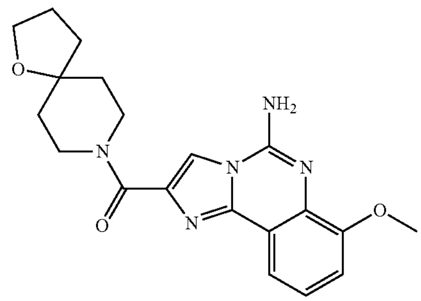 [SMILES: COc1cccc2c1nc(N)n1cc(C(=O)N3CCC4(CCCO4)CC3)nc21] | 382.2 | (5-amino-7-methoxyimidazo[1,2-c]quinazolin-2-yl)(1-oxa-8-azaspiro[4.5]decan-8-yl)methanone |
| Ex-231 | 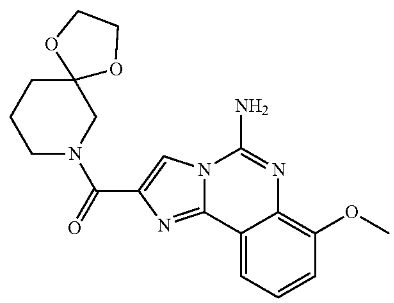 [SMILES: COc1cccc2c1nc(N)n1cc(C(=O)N3CCCC4(C3)OCCO4)nc21] | 384.2 | (5-amino-7-methoxyimidazo[1,2-c]quinazolin-2-yl)(1,4-dioxa-7-azaspiro[4.5]decan-7-yl)methanone |
| Ex-232 | 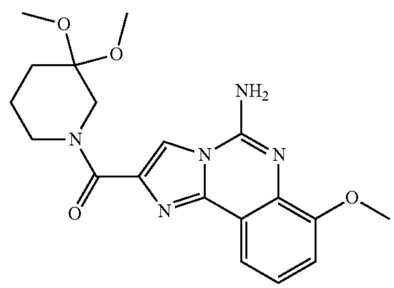 [SMILES: COc1cccc2c1nc(N)n1cc(C(=O)N3CCCC(OC)(OC)C3)nc21] | 386.2 | (5-amino-7-methoxyimidazo[1,2-c]quinazolin-2-yl)(3,3-dimethoxypiperidin-1-yl)methanone |
| Ex-233 | 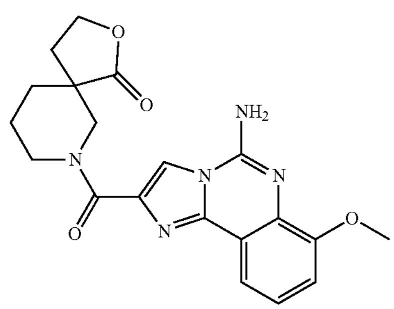 [SMILES: COc1cccc2c1nc(N)n1cc(C(=O)N3CCCC4(CCOC4=O)C3)nc21] | 396.2 | 7-(5-amino-7-methoxyimidazo[1,2-c]quinazoline-2-carbonyl)-2-oxa-7-azaspiro[4.5]decan-1-one |
| Ex-234 | 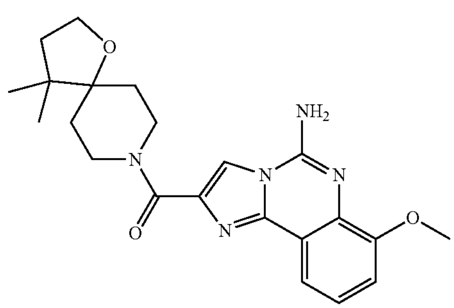 | 410.2 | (5-amino-7-methoxyimidazo[1,2-c]quinazolin-2-yl)(4,4-dimethyl-1-oxa-8-azaspiro[4.5]decan-8-yl)methanone |

TABLE 13-continued

| Ex No | Structure | LCMS | Name |
| --- | --- | --- | --- |
| Ex-235 | 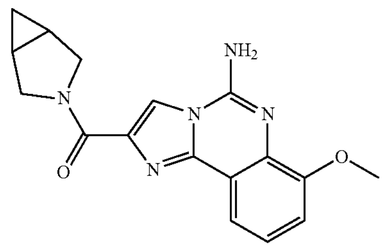 [SMILES: COc1cccc2c1nc(N)n1cc(C(=O)N3CC4CC4C3)nc21] | 324.1 | (5-amino-7-methoxyimidazo[1,2-c]quinazolin-2-yl)(3-azabicyclo[3.1.0]hexan-3-yl)methanone |
| Ex-236 | 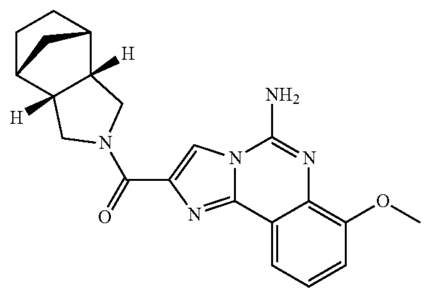 [SMILES: COc1cccc2c1nc(N)n1cc(C(=O)N3C[C@@H]4[C@@H]5CC[C@@H](C5)[C@@H]4C3)nc21] | 378.2 | (5-amino-7-methoxyimidazo[1,2-c]quinazolin-2-yl)((3aR,4R,7S,7aS)-octahydro-2H-4,7-methanoisoindol-2-yl)methanone |
| Ex-237 | 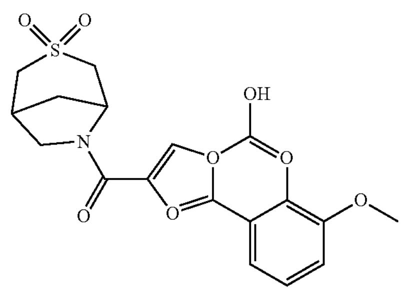 | 402.1 | (5-amino-7-methoxyimidazo[1,2-c]quinazolin-2-yl)(3,3-dioxido-3-thia-6-azabicyclo[3.2.1]octan-6-yl)methanone |
| Ex-238 | 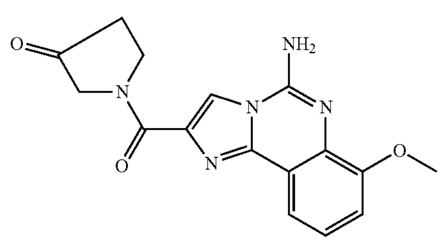 [SMILES: COc1cccc2c1nc(N)n1cc(C(=O)N3CCC(=O)C3)nc21] | 326.1 | 1-(5-amino-7-methoxyimidazo[1,2-c]quinazoline-2-carbonyl)pyrrolidin-3-one |
| Ex-239 | 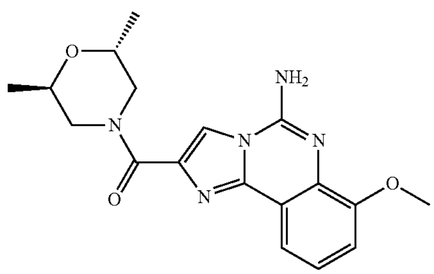 | 356.2 | (5-amino-7-methoxyimidazo[1,2-c]quinazolin-2-yl)((2R,6R)-2,6-dimethylmorpholino)methanone |

TABLE 13-continued

| Ex No | Structure | LCMS | Name |
|---|---|---|---|
| Ex-240 | 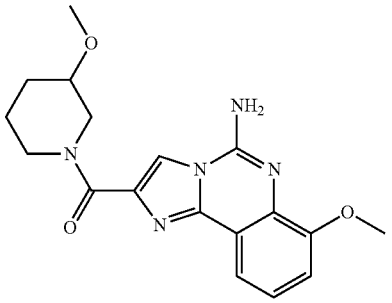 [SMILES: COc1cccc2c1nc(N)n1cc(C(=O)N3CCCC(OC)C3)nc21] | 356.2 | (5-amino-7-methoxyimidazo[1,2-c]quinazolin-2-yl)(3-methoxypiperidin-1-yl)methanone |
| Ex-241 | 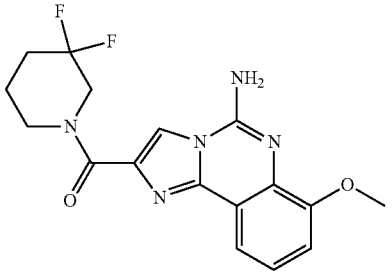 [SMILES: COc1cccc2c1nc(N)n1cc(C(=O)N3CCCC(F)(F)C3)nc21] | 362.1 | (5-amino-7-methoxyimidazo[1,2-c]quinazolin-2-yl)(3,3-difluoropiperidin-1-yl)methanone |
| Ex-242 | 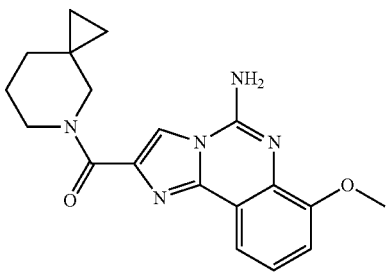 [SMILES: COc1cccc2c1nc(N)n1cc(C(=O)N3CCCC4(CC4)C3)nc21] | 352.2 | (5-amino-7-methoxyimidazo[1,2-c]quinazolin-2-yl)(5-azaspiro[2.5]octan-5-yl)methanone |
| Ex-243 | 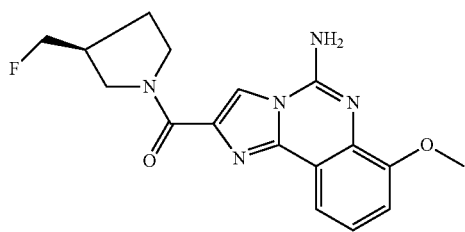 [SMILES: COc1cccc2c1nc(N)n1cc(C(=O)N3CC[C@H](CF)C3)nc21] | 344.2 | (S)-(5-amino-7-methoxyimidazo[1,2-c]quinazolin-2-yl)(3-(fluoromethyl)pyrrolidin-1-yl)methanone |
| Ex-244 | 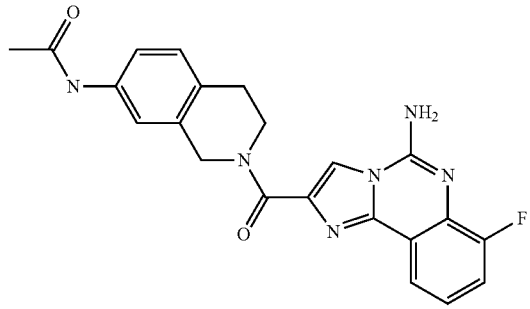 [SMILES: CC(=O)Nc1ccc2c(c1)CN(C(=O)c1cn3c(N)nc4c(F)cccc4c3n1)CC2] | 419 | N-(2-(5-amino-7-fluoroimidazo[1,2-c]quinazoline-2-carbonyl)-1,2,3,4-tetrahydroisoquinolin-7-yl)acetamide |

TABLE 13-continued

| Ex No | Structure | LCMS | Name |
|---|---|---|---|
| Ex-245 | 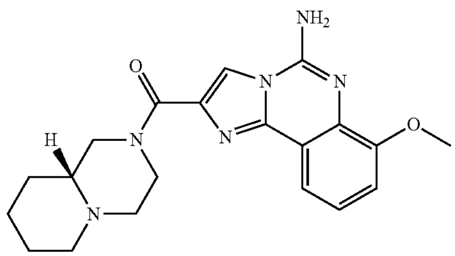 [SMILES: COc1cccc2c1nc(N)n1cc(C(=O)N3CCN4CCCC[C@@H]4C3)nc21] | 381 | (R)-(5-amino-7-methoxyimidazo[1,2-c]quinazolin-2-yl)(octahydro-2H-pyrido[1,2-a]pyrazin-2-yl)methanone |
| Ex-246 | 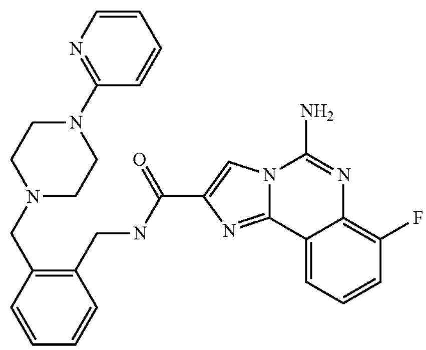 [SMILES: Nc1nc2c(F)cccc2c2nc(C(=O)NCc3ccccc3CN3CCN(c4ccccn4)CC3)cn12] | 511 | 5-amino-7-fluoro-N-(2-((4-(pyridin-2-yl)piperazin-1-yl)methyl)benzyl)imidazo[1,2-c]quinazoline-2-carboxamide |
| Ex-247 | 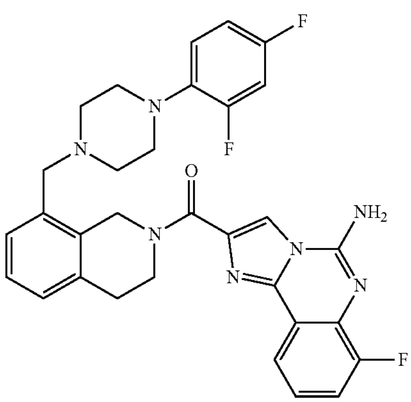 [SMILES: Nc1nc2c(F)cccc2c2nc(C(=O)N3CCc4cccc(CN5CCN(c6ccc(F)cc6F)CC5)c4C3)cn12] | 572 | (5-amino-7-fluoroimidazo[1,2-c]quinazolin-2-yl)(8-((4-(2,4-difluorophenye)piperazin-1-yl)methyl)-3,4-dihydroisoquinolin-2(1H)-yl)methanone |
| Ex-248 | 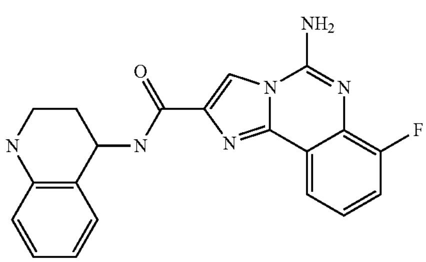 [SMILES: Nc1nc2c(F)cccc2c2nc(C(=O)NC3CCNc4ccccc43)cn12] | 377 | 5-amino-7-fluoro-N-(1,2,3,4-tetrahydroquinolin-4-yl)imidazo[1,2-c]quinazoline-2-carboxamide |

TABLE 13-continued

| Ex No | Structure | LCMS | Name |
|---|---|---|---|
| Ex-249 | 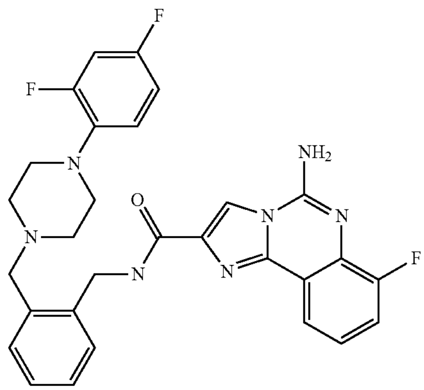 [SMILES: Nc1nc2c(F)cccc2c2nc(C(=O)NCc3ccccc3CN3CCN(c4ccc(F)cc4F)CC3)cn12] | 546 | 5-amino-N-(2-((4-(2,4-difluorophenyl)piperazin-1-yl)methyl)benzyl)-7-fluoroimidazo[1,2-c]quinazoline-2-carboxamide |
| Ex-250 | 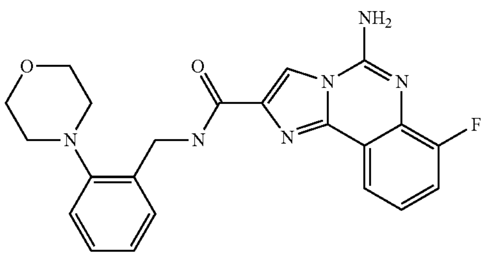 [SMILES: Nc1nc2c(F)cccc2c2nc(C(=O)NCc3ccccc3N3CCOCC3)cn12] | 421 | 5-amino-7-fluoro-N-(2-morpholinobenzyl)imidazo[1,2-c]quinazoline-2-carboxamide |
| Ex-251 | 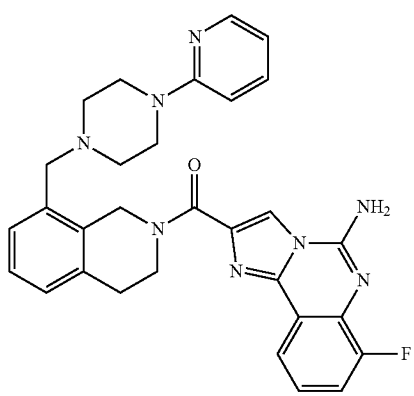 [SMILES: Nc1nc2c(F)cccc2c2nc(C(=O)N3CCc4cccc(CN5CCN(c6ccccn6)CC5)c4C3)cn12] | 537 | (5-amino-7-fluoroimidazo[1,2-c]quinazolin-2-yl)(8-((4-(pyridin-2-yl)piperazin-1-yl)methyl)-3,4-dihydroisoquinolin-2(1H)-yl)methanone |
| Ex-252 | 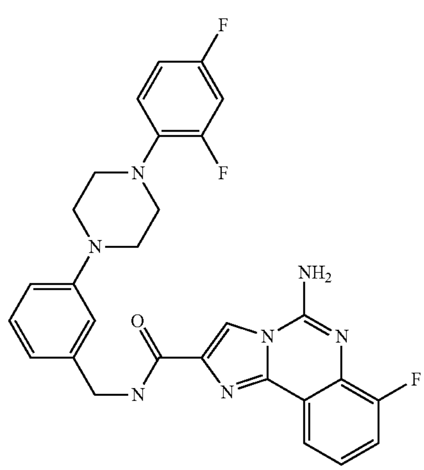 [SMILES: Nc1nc2c(F)cccc2c2nc(C(=O)NCc3cccc(N4CCN(c5ccc(F)cc5F)CC4)c3)cn12] | 532 | 5-amino-N-(3-(4-(2,4-difluorophenyl)piperazin-1-yl)benzyl)-7-fluoroimidazo[1,2-c]quinazoline-2-carboxamide |

TABLE 13-continued

| Ex No | Structure | LCMS | Name |
|---|---|---|---|
| Ex-253 | 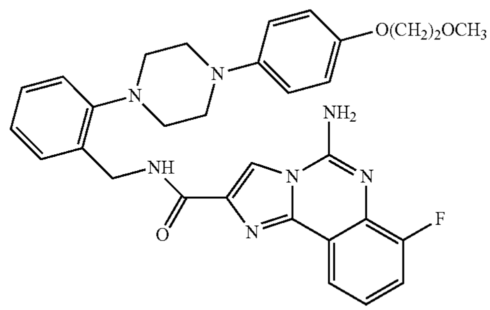 | 570 | 5-amino-7-fluoro-N-(2-(4-(4-(2-methoxyethoxy)phenyl)piperazin-1-yl)benzyl)imidazo[1,2-c]quinazoline-2-carboxamide |
| Ex-254 | 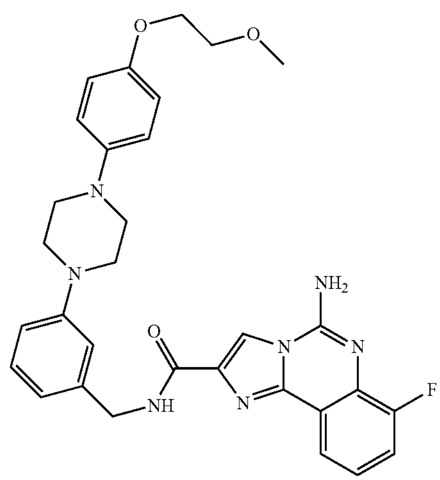 [SMILES: COCCOc1ccc(N2CCN(c3cccc(CNC(=O)c4cn5c(N)nc6c(F)cccc6c5n4)c3)CC2)cc1] | 570 | 5-amino-7-fluoro-N-(3-(4-(4-(2-methoxyethoxy)phenyl)piperazin-1-yl)benzyl)imidazo[1,2-c]quinazoline-2-carboxamide |
| Ex-255 | 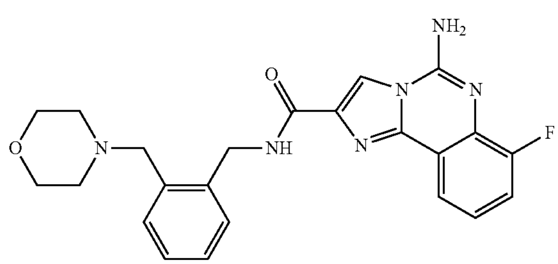 [SMILES: Nc1nc2c(F)cccc2c2nc(C(=O)NCc3ccccc3CN3CCOCC3)cn12] | 435 | 5-amino-7-fluoro-N-(2-(morpholinomethyl)benzyl)imidazo[1,2-c]quinazoline-2-carboxamide |
| Ex-256 | 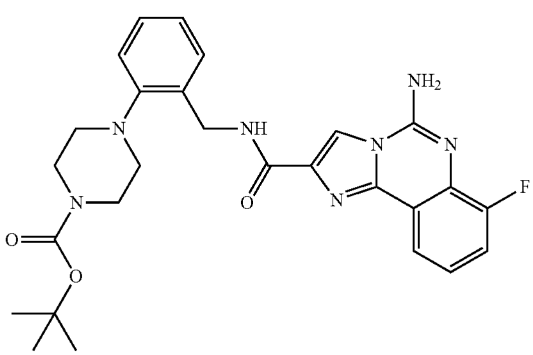 [SMILES: CC(C)(C)OC(=O)N1CCN(c2ccccc2CNC(=O)c2cn3c(N)nc4c(F)cccc4c3n2)CC1] | 520 | tert-butyl 4-(2-((5-amino-7-fluoroimidazo[1,2-c]quinazoline-2-carboxamido)methyl)phenyl)piperazine-1-carboxylate |

TABLE 13-continued

| Ex No | Structure | LCMS | Name |
| --- | --- | --- | --- |
| Ex-257 | 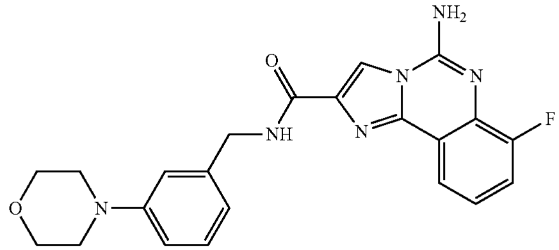 [SMILES: Nc1nc2c(F)cccc2c2nc(C(=O)NCc3cccc(N4CCOCC4)c3)cn12] | 421 | 5-amino-7-fluoro-N-(3-morpholino-benzyl)imidazo-[1,2-c]-quinazoline-2-carboxamide |
| Ex-258 | 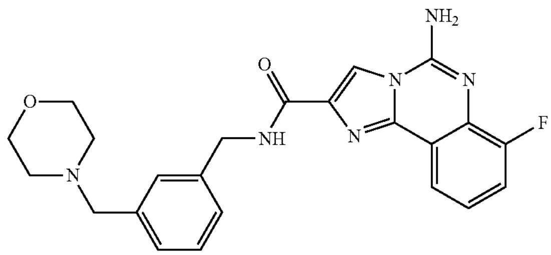 [SMILES: Nc1nc2c(F)cccc2c2nc(C(=O)NCc3cccc(CN4CCOCC4)c3)cn12] | 435 | 5-amino-7-fluoro-N-(3-(morpholinomethyl)benzyl)imidazo[1,2-c]quinazoline-2-carboxamide |
| Ex-259 | 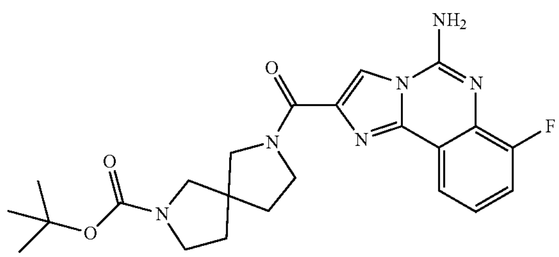 [SMILES: CC(C)(C)OC(=O)N1CCC2(CCN(C(=O)c3cn4c(N)nc5c(F)cccc5c4n3)C2)C1] | 455 | tert-butyl 7-(5-amino-7-fluoroimidazo[1,2-c]quinazoline-2-carbonyl)-2,7-diazaspiro[4.4]nonane-2-carboxylate |
| Ex-260 | 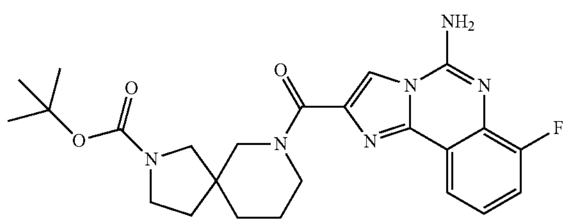 [SMILES: CC(C)(C)OC(=O)N1CCC2(CCCN(C(=O)c3cn4c(N)nc5c(F)cccc5c4n3)C2)C1] | 469 | tert-butyl 7-(5-amino-7-fluoroimidazo[1,2-c]quinazoline-2-carbonyl)-2,7-diazaspiro[4.5]decane-2-carboxylate |
| Ex-261 | 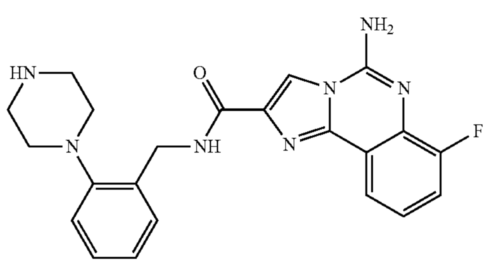 [SMILES: Nc1nc2c(F)cccc2c2nc(C(=O)NCc3ccccc3N3CCNCC3)cn12] | 420 | 5-amino-7-fluoro-N-(2-(piperazin-1-yl)benzyl)imidazo[1,2-c]quinazoline-2-carboxamide |
| Ex-262 | 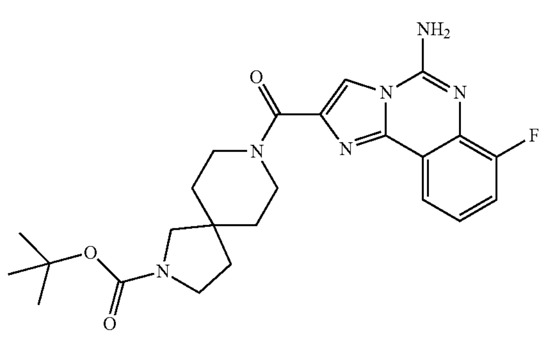 [SMILES: CC(C)(C)OC(=O)N1CCC2(CCN(C(=O)c3cn4c(N)nc5c(F)cccc5c4n3)CC2)C1] | 469 | tert-butyl 8-(5-amino-7-fluoroimidazo[1,2-c]quinazoline-2-carbonyl)-2,8-diazaspiro[4.5]decane-2-carboxylate |

TABLE 13-continued

| Ex No | Structure | LCMS | Name |
|---|---|---|---|
| Ex-263 | 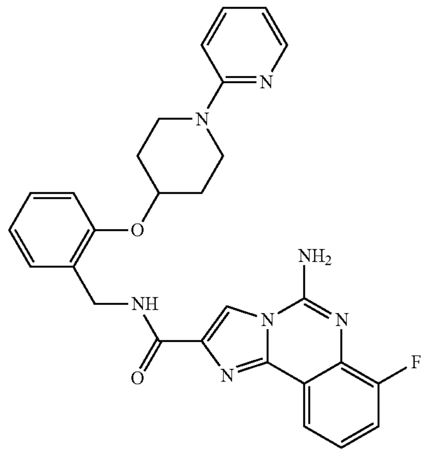 [SMILES: Nc1nc2c(F)cccc2c2nc(C(=O)NCc3ccccc3OC3CCN(c4ccccn4)CC3)cn12] | 512 | 5-amino-7-fluoro-N-(2-((1-(pyridin-2-yl)piperidin-4-yl)oxy)benzyl)imidazo[1,2-c]quinazoline-2-carboxamide |
| Ex-264 | 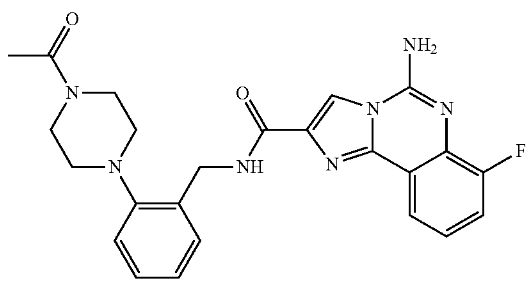 [SMILES: CC(=O)N1CCN(c2ccccc2CNC(=O)c2cn3c(N)nc4c(F)cccc4c3n2)CC1] | 462 | N-(2-(4-acetylpiperazin-1-yl)benzyl)-5-amino-7-fluoroimidazo[1,2-c]quinazoline-2-carboxamide |
| Ex-265 | 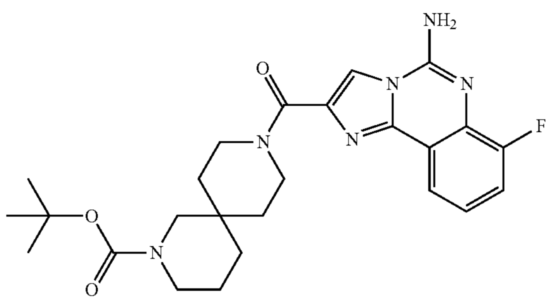 [SMILES: CC(C)(C)OC(=O)N1CCCC2(CCN(C(=O)c3cn4c(N)nc5c(F)cccc5c4n3)CC2)C1] | 483 | tert-butyl 9-(5-amino-7-fluoroimidazo[1,2-c]quinazoline-2-carbonyl)-2,9-diazaspiro[5.5]undecane-2-carboxylate |
| Ex-266 | 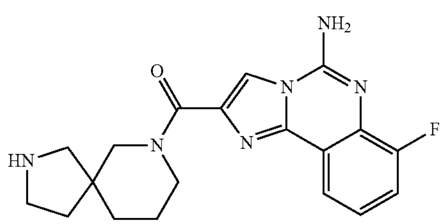 [SMILES: Nc1nc2c(F)cccc2c2nc(C(=O)N3CCCC4(CCNC4)C3)cn12] | 369 | (5-amino-7-fluoroimidazo[1,2-c]quinazolin-2-yl)(2,7-diazaspiro[4.5]decan-7-yl)methanone |
| Ex-267 | 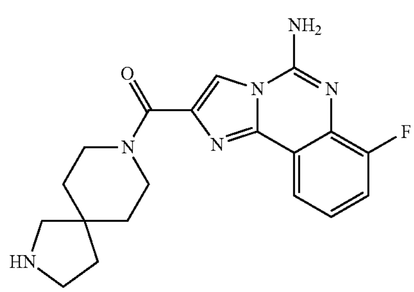 [SMILES: Nc1nc2c(F)cccc2c2nc(C(=O)N3CCC4(CCNC4)CC3)cn12] | 369 | (5-amino-7-fluoroimidazo[1,2-c]quinazolin-2-yl)(2,8-diazaspiro[4.5]decan-8-yl)methanone |

TABLE 13-continued

| Ex No | Structure | LCMS | Name |
|---|---|---|---|
| Ex-268 | 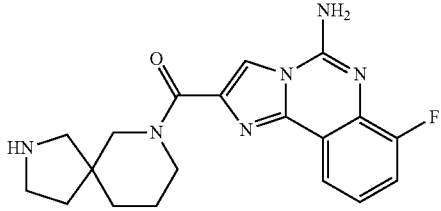 [SMILES: Nc1nc2c(F)cccc2c2nc(C(=O)N3CCCC4(CCNC4)C3)cn12] | 411 | (5-amino-7-fluoroimidazo[1,2-c]quinazolin-2-yl)(2,7-diazaspiro[4.5]decan-7-yl)methanone |
| Ex-269 | 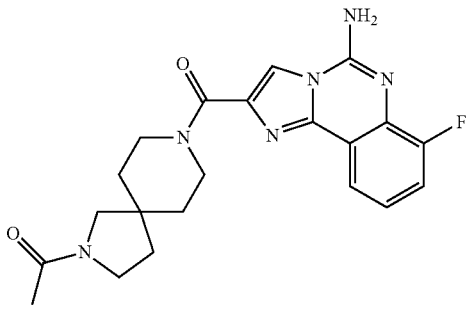 [SMILES: CC(=O)N1CCC2(CCN(C(=O)c3cn4c(N)nc5c(F)cccc5c4n3)CC2)C1] | 411 | 1-(8-(5-amino-7-fluoroimidazo[1,2-c]quinazoline-2-carbonyl)-2,8-diazaspiro[4.5]decan-2-yl)ethan-1-one |
| Ex-270 | 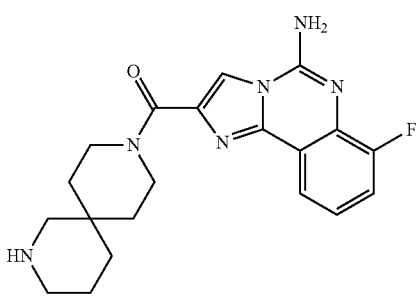 [SMILES: Nc1nc2c(F)cccc2c2nc(C(=O)N3CCC4(CCCNC4)CC3)cn12] | 383 | (5-amino-7-fluoroimidazo[1,2-c]quinazolin-2-yl)(2,9-diazaspiro[5.5]undecan-9-yl)methanone |
| Ex-271 | 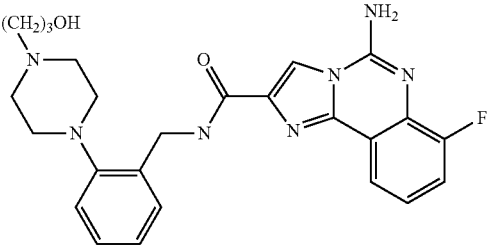 | 478 | 5-amino-7-fluoro-N-(2-(4-(3-hydroxypropyl)-piperazin-1-yl)benzyl)-imidazo[1,2-c]-quinazoline-2-carboxamide |
| Ex-272 | 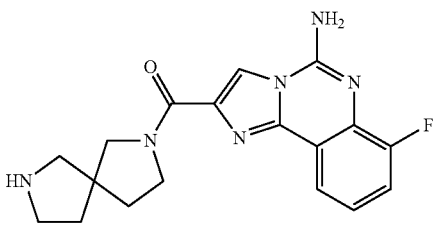 [SMILES: Nc1nc2c(F)cccc2c2nc(C(=O)N3CCC4(CCNC4)C3)cn12] | 355 | (5-amino-7-fluoroimidazo[1,2-c]quinazolin-2-yl)(2,7-diazaspiro[4.4]nonan-2-yl)methanone |
| Ex-273 | 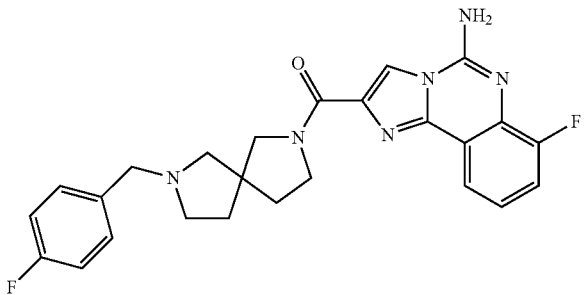 [SMILES: Nc1nc2c(F)cccc2c2nc(C(=O)N3CCC4(CCN(Cc5ccc(F)cc5)C4)C3)cn12] | 463 | (5-amino-7-fluoroimidazo[1,2-c]quinazolin-2-yl)(7-(4-fluorobenzyl)-2,7-diazaspiro[4.4]nonan-2-yl)methanone |

TABLE 13-continued

| Ex No | Structure | LCMS | Name |
|---|---|---|---|
| Ex-274 | 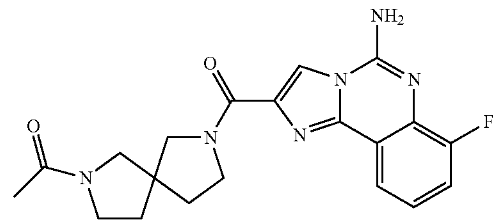 [SMILES: CC(=O)N1CCC2(CCN(C(=O)c3cn4c(N)nc5c(F)cccc5c4n3)C2)C1] | 397 | 1-(7-(5-amino-7-fluoroimidazo[1,2-c]quinazoline-2-carbonyl)-2,7-diazaspiro[4.4]nonan-2-yl)ethan-1-one |
| Ex-275 | 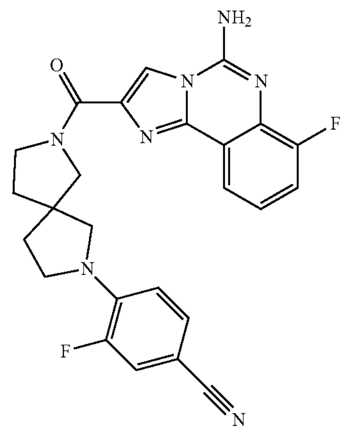 [SMILES: N#Cc1ccc(N2CCC3(CCN(C(=O)c4cn5c(N)nc6c(F)cccc6c5n4)C3)C2)c(F)c1] | 474 | 4-(7-(5-amino-7-fluoroimidazo[1,2-c]quinazoline-2-carbonyl)-2,7-diazaspiro[4.4]nonan-2-yl)-3-fluorobenzonitrile |
| Ex-276 | 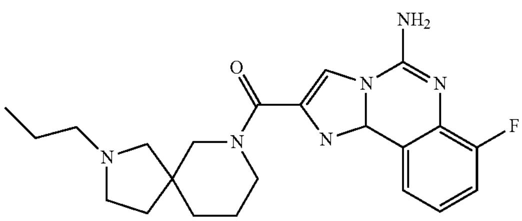 [SMILES: CCCN1CCC2(CCCN(C(=O)C3=CN4C(N)=Nc5c(F)cccc5C4N3)C2)C1] | 411 | (5-amino-7-fluoroimidazo[1,2-c]quinazolin-2-yl)(2-propyl-2,7-diazaspiro[4.5]decan-7-yl)methanone |
| Ex-277 | 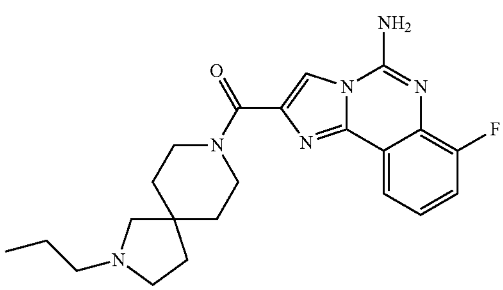 [SMILES: CCCN1CCC2(CCN(C(=O)c3cn4c(N)nc5c(F)cccc5c4n3)CC2)C1] | 411 | (5-amino-7-fluoroimidazo[1,2-c]quinazolin-2-yl)(2-propyl-2,8-diazaspiro[4.5]decan-8-yl)methanone |
| Ex-278 | 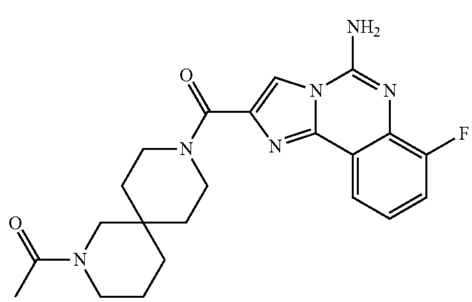 [SMILES: CC(=O)N1CCCC2(CCN(C(=O)c3cn4c(N)nc5c(F)cccc5c4n3)CC2)C1] | 425 | 1-(9-(5-amino-7-fluoroimidazo[1,2-c]quinazoline-2-carbonyl)-2,9-diazaspiro[5.5]undecan-2-yl)ethan-1-one |

TABLE 13-continued

| Ex No | Structure | LCMS | Name |
|---|---|---|---|
| Ex-279 | 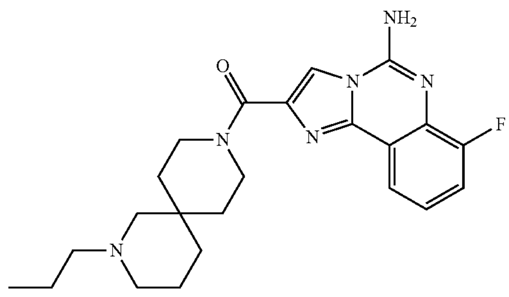 [SMILES: CCCN1CCCC2(CCN(C(=O)c3cn4c(N)nc5c(F)cccc5c4n3)CC2)C1] | 425 | (5-amino-7-fluoroimidazo[1,2-c]quinazolin-2-yl)(2-propyl-2,9-diazaspiro[5.5]undecan-9-yl)methanone |
| Ex-280 | 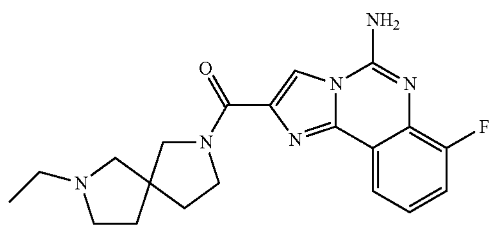 [SMILES: CCN1CCC2(CCN(C(=O)c3cn4c(N)nc5c(F)cccc5c4n3)C2)C1] | 383 | (5-amino-7-fluoroimidazo[1,2-c]quinazolin-2-yl)(7-ethyl-2,7-diazaspiro[4.4]nonan-2-yl)methanone |
| Ex-281 | 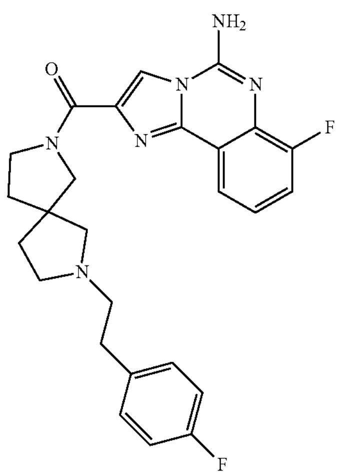 [SMILES: Nc1nc2c(F)cccc2c2nc(C(=O)N3CCC4(CCN(CCc5ccc(F)cc5)C4)C3)cn12] | 477 | (5-amino-7-fluoroimidazo[1,2-c]quinazolin-2-yl)(7-(4-fluorophenethyl)-2,7-diazaspiro[4.4]nonan-2-yl)methanone |
| Ex-282 | 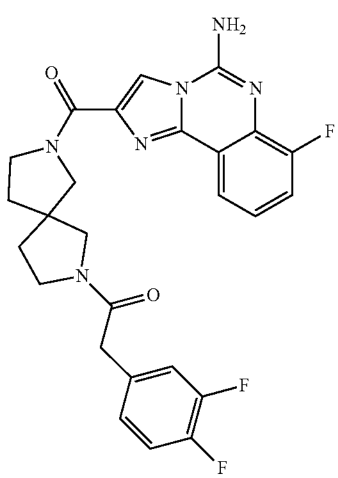 [SMILES: Nc1nc2c(F)cccc2c2nc(C(=O)N3CCC4(CCN(C(=O)Cc5ccc(F)c(F)c5)C4)C3)cn12] | 509 | 1-(7-(5-amino-7-fluoroimidazo[1,2-c]quinazoline-2-carbonyl)-2,7-diazaspiro[4.4]nonan-2-yl)-2-(3,4-difluorophenyl)ethan-1-one |

TABLE 13-continued

| Ex No | Structure | LCMS | Name |
|---|---|---|---|
| Ex-283 | 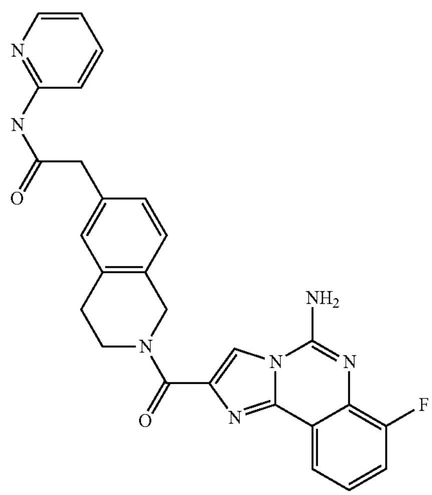 [SMILES: Nc1nc2c(F)cccc2c2nc(C(=O)N3CCc4cc(CC(=O)Nc5ccccn5)ccc4C3)cn12] | 496 | 2-(2-(5-amino-7-fluoroimidazo[1,2-c]quinazoline-2-carbonyl)-1,2,3,4-tetrahydroisoquinolin-6-yl)-N-(pyridin-2-yl)acetamide |
| Ex-284 | 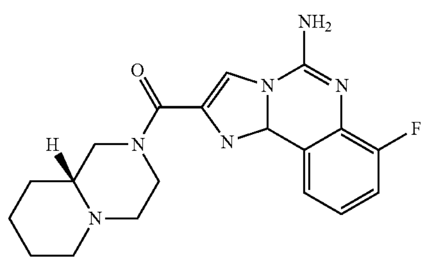 [SMILES: NC1=Nc2c(F)cccc2C2NC(C(=O)N3CCN4CCCC[C@@H]4C3)=CN12] | 369 | (R)-(5-amino-7-fluoroimidazo[1,2-c]quinazolin-2-yl)(octahydro-2H-pyrido[1,2-a]pyrazin-2-yl)methanone |
| Ex-285 | 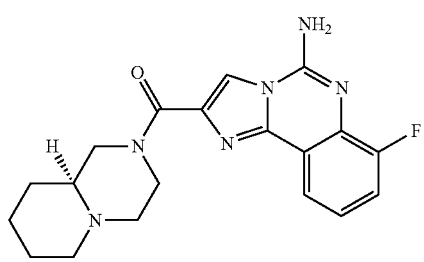 [SMILES: Nc1nc2c(F)cccc2c2nc(C(=O)N3CCN4CCCC[C@H]4C3)cn12] | 369 | (S)-(5-amino-7-fluoroimidazo[1,2-c]quinazolin-2-yl)(octahydro-2H-pyrido[1,2-a]pyrazin-2-yl)methanone |
| Ex-286 | 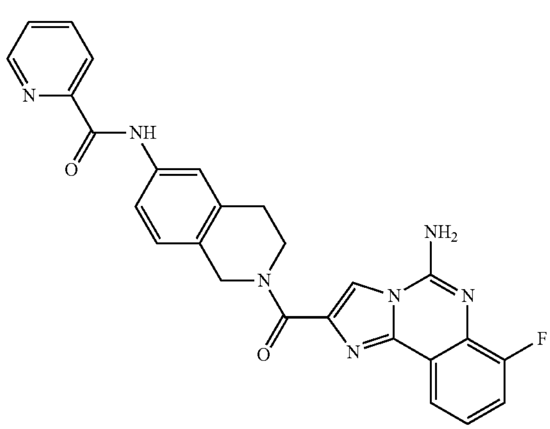 [SMILES: Nc1nc2c(F)cccc2c2nc(C(=O)N3CCc4cc(NC(=O)c5ccccn5)ccc4C3)cn12] | 482 | N-(2-(5-amino-7-fluoroimidazo[1,2-c]quinazoline-2-carbonyl)-1,2,3,4-tetrahydroisoquinolin-6-yl)picolinamide |

TABLE 13-continued

| Ex No | Structure | LCMS | Name |
| --- | --- | --- | --- |
| Ex-287 | 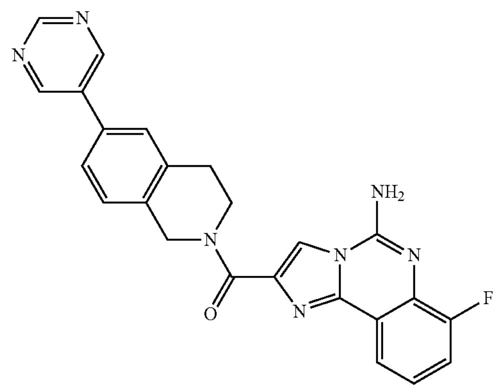 [SMILES: Nc1nc2c(F)cccc2c2nc(C(=O)N3CCc4cc(-c5cncnc5)ccc4C3)cn12] | 440 | (5-amino-7-fluoroimidazo[1,2-c]quinazolin-2-yl)(6-(pyrimidin-5-yl)-3,4-dihydroisoquinolin-2(1H)-yl)methanone |
| Ex-288 | 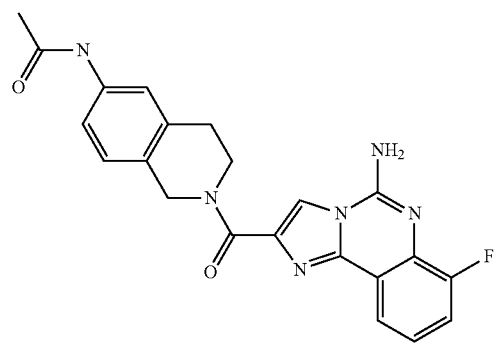 [SMILES: CC(=O)Nc1ccc2c(c1)CCN(C(=O)c1cn3c(N)nc4c(F)cccc4c3n1)C2] | 419 | N-(2-(5-amino-7-fluoroimidazo[1,2-c]quinazoline-2-carbonyl)-1,2,3,4-tetrahydroisoquinolin-6-yl)acetamide |
| Ex-289 | 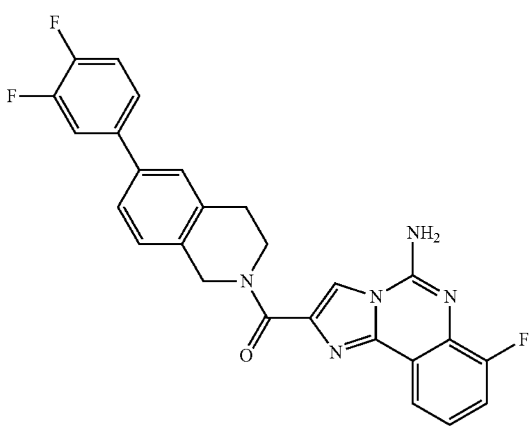 [SMILES: Nc1nc2c(F)cccc2c2nc(C(=O)N3CCc4cc(-c5ccc(F)c(F)c5)ccc4C3)cn12] | 474 | (5-amino-7-fluoroimidazo[1,2-c]quinazolin-2-yl)(6-(3,4-difluorophenyl)-3,4-dihydroisoquinolin-2(1H)-yl)methanone |
| Ex-290 | 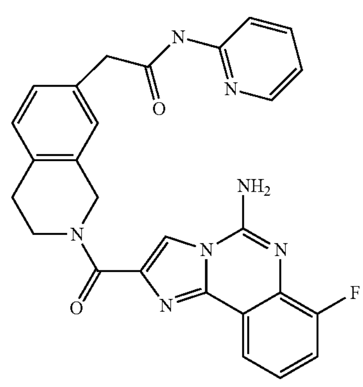 [SMILES: Nc1nc2c(F)cccc2c2nc(C(=O)N3CCc4ccc(CC(=O)Nc5ccccn5)cc4C3)cn12] | 496 | 2-(2-(5-amino-7-fluoroimidazo[1,2-c]quinazoline-2-carbonyl)-1,2,3,4-tetrahydroisoquinolin-7-yl)-N-(pyridin-2-yl)acetamide |

TABLE 13-continued

| Ex No | Structure | LCMS | Name |
| --- | --- | --- | --- |
| Ex-291 | 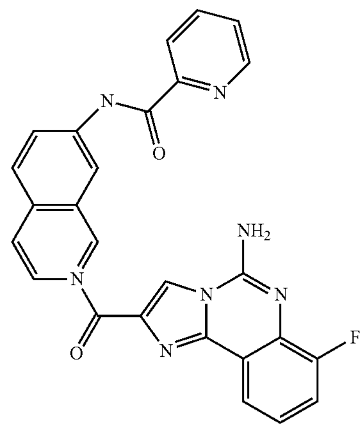 | 482 | N-(2-(5-amino-7-fluoroimidazo[1,2-c]quinazoline-2-carbonyl)-1,2,3,4-tetrahydroisoquinolin-7-yl)picolinamide |
| Ex-292 | 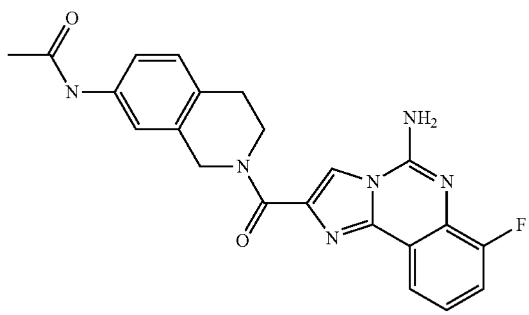 [SMILES: CC(=O)Nc1ccc2c(c1)CN(C(=O)c1cn3c(N)nc4c(F)cccc4c3n1)CC2] | 419 | N-(2-(5-amino-7-fluoroimidazo[1,2-c]quinazoline-2-carbonyl)-1,2,3,4-tetrahydroisoquinolin-7-yl)acetamide |
| Ex-293 | 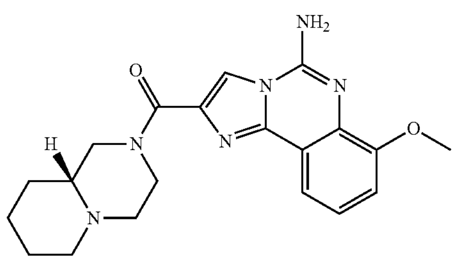 [SMILES: COc1cccc2c1nc(N)n1cc(C(=O)N3CCN4CCCC[C@@H]4C3)nc21] | 381 | (R)-(5-amino-7-methoxyimidazo[1,2-c]quinazolin-2-yl)(octahydro-2H-pyrido[1,2-a]pyrazin-2-yl)methanone |
| Ex-294 | 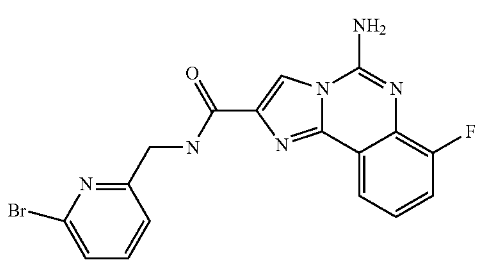 [SMILES: Nc1nc2c(F)cccc2c2nc(C(=O)NCc3cccc(Br)n3)cn12] | 415 [M + 1]/ 417 [M + 2] | 5-amino-N-((6-bromopyridin-2-yl)methyl)-7-fluoroimidazo[1,2-c]quinazoline-2-carboxamide |
| Ex-295 | 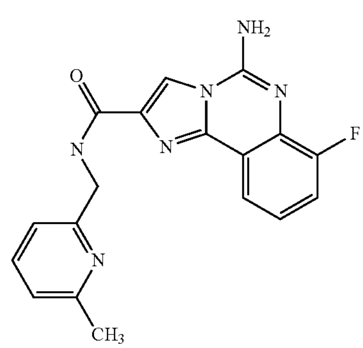 [SMILES: Cc1cccc(CNC(=O)c2cn3c(N)nc4c(F)cccc4c3n2)n1] | 351 (1.70) | 5-amino-7-fluoro-N-((6-methylpyridin-2-yl)methyl)imidazo[1,2-c]quinazoline-2-carboxamide |

TABLE 13-continued
| Ex No | Structure | LCMS | Name |
|---|---|---|---|
| Ex-296 | 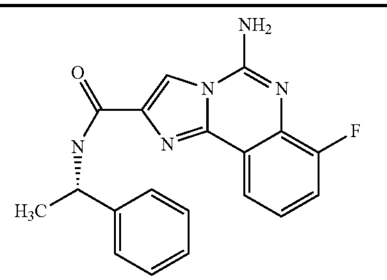 | 350 (2.18) | (S)-5-amino-7-fluoro-N-(1-phenylethyl)imidazo[1,2-c]quinazoline-2-carboxamide |
| Ex-297 | 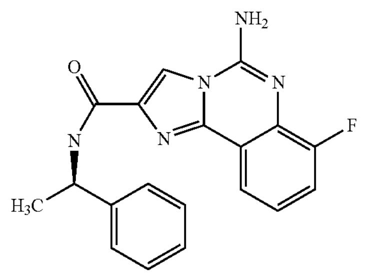 [SMILES: C[C@@H](NC(=O)c1cn2c(N)nc3c(F)cccc3c2n1)c1ccccc1] | 350 (2.18) | (R)-5-amino-7-fluoro-N-(1-phenylethyl)imidazo[1,2-c]quinazoline-2-carboxamide |
| Ex-298 | 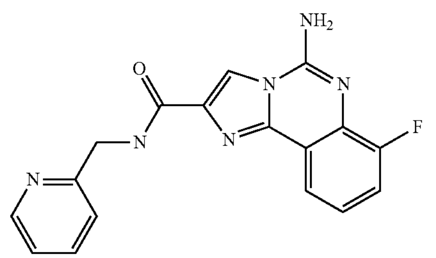 [SMILES: Nc1nc2c(F)cccc2c2nc(C(=O)NCc3ccccn3)cn12] | 337 (1.67) | 5-amino-7-fluoro-N-(pyridin-2-ylmethyl)imidazo[1,2-c]quinazoline-2-carboxamide |
Example 24, Preparation of 7-fluoro-2-(piperidin-4-ylmethyl)imidazo[1,2-c]quinazolin-5-amine Ex-299
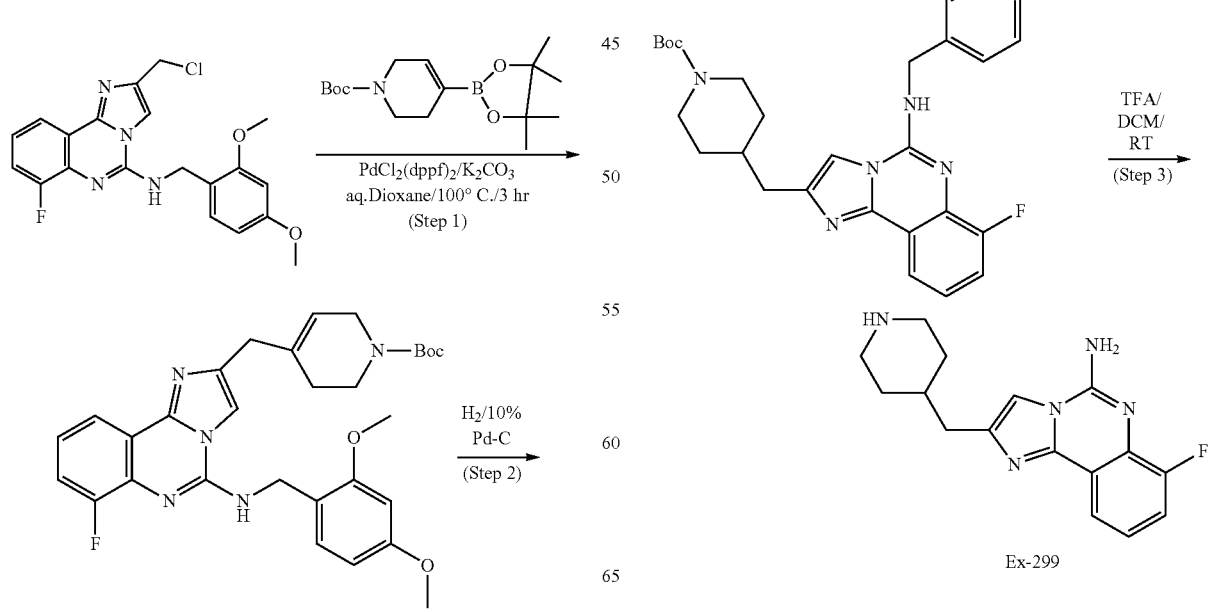

(Step 1) tert-butyl 4-((5-((2,4-dimethoxybenzyl)amino)-7-fluoroimidazo[1,2-c]quinazolin-2-yl)methyl)-5,6-dihydropyridine-1(2H)-carboxylate Into a round bottle was added 2-(chloromethyl)-N-(2,4-dimethoxybenzyl)-7-fluoroimidazo[1,2-c]quinazolin-5-amine (163 mg, 0.407 mmol), tert-butyl 4-(4,4,5,5-tetramethyl-1,3,2-dioxaborolan-2-yl)-5,6-dihydropyridine-1(2H)-carboxylate (189 mg, 0.610 mmol), potassium carbonate (169 mg, 1.220 mmol) and Pd(Cl)$_2$(dppf) complex (83 mg, 0.102 mmol). The reaction mixture was degassed and the vessel filled with N$_2$, then 4 ml of Dioxanes and 1 ml of H$_2$O were added and the reaction mixture was stirred at 100° C. for 3 hr, then cooled to R/T and stirred at R/T overnight. The solvent was evaporated and the crude product was purified by prep-TLC by CH$_2$Cl$_2$/EtOAc=1:1.5 to give tert-butyl 4-((5-((2,4-dimethoxybenzyl)amino)-7-fluoroimidazo[1,2-c]quinazolin-2-yl)methyl)-5,6-dihydropyridine-1(2H)-carboxylate. LCMS 548 [M+1].

(Step 2) tert-butyl 4-((5-((2,4-dimethoxybenzyl)amino)-7-fluoroimidazo[1,2-c]quinazolin-2-yl)methyl)piperidine-1-carboxylate To a solution of tert-butyl 4-((5-((2,4-dimethoxybenzyl)amino)-7-fluoroimidazo[1,2-c]quinazolin-2-yl)methyl)-5,6-dihydropyridine-1(2H)-carboxylate (168 mg, 0.307 mmol) in 3 ml of MeOH, was added Pd/C (20 mg), then fitted with a balloon and filled with hydrogen. The reaction mixture was stirred at RT overnight, then the mixture was filtered through a short pad of Celite, washed with MeOH, an concentrated to give the title compound, LCMS 550 [M+1].

(Step 3) 7-fluoro-2-(piperidin-4-ylmethyl)imidazo[1,2-c]quinazolin-5-amine

A solution of tert-butyl 4-((5-((2,4-dimethoxybenzyl)amino)-7-fluoroimidazo[1,2-c]quinazolin-2-yl)methyl)piperidine-1-carboxylate (177 mg, 0.322 mmol) in 3 ml of TFA was stirred at RT for 4 hr. The reaction mixture was diluted with 3 ml of dichloromethane and 2 ml MeOH, basified with 3N NaOH aq to PH=10, then evaporated, filtered, washed with H$_2$O, and the solids collected. The crude product thus provided was purified by prep-TLC (CH$_2$Cl$_2$/MeOH 7N Ammonium solution, 7:1 vol/vol) to give the title product, LCMS [M+1] 300.

Example 25, Preparation of 7-fluoro-2-((1-(5-fluoropyrimidin-2-yl)piperidin-4-yl)methyl)imidazo[1,2-c]quinazolin-5-amine Ex-300

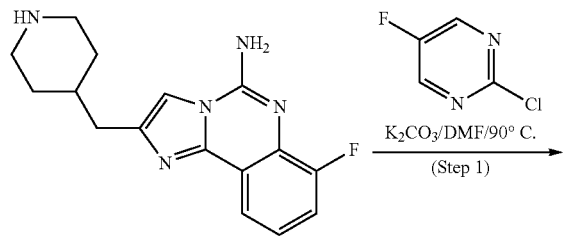

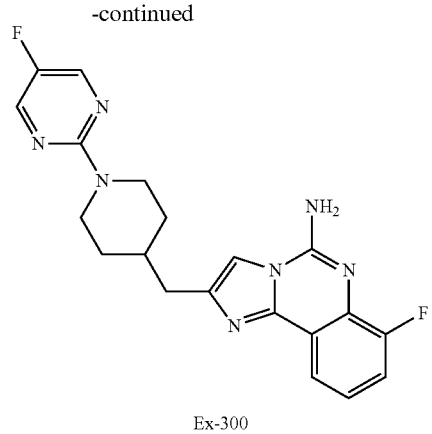

Ex-300

(Step 1) 7-fluoro-2-((1-(5-fluoropyrimidin-2-yl)piperidin-4-yl)methyl)imidazo[1,2-c]quinazolin-5-amine Into 1.0 ml of DMF was dissolved 7-fluoro-2-(piperidin-4-ylmethyl)imidazo[1,2-c]quinazolin-5-amine (10 mg, 0.033 mmol), 2-chloro-5-fluoropyrimidin (5.31 mg, 0.040 mmol) and potassium carbonate (9.23 mg, 0.067 mmol), and the solution was stirred at 90° C. for 3 hours, then the reaction mixture was evaporated. The crude product thus obtained was purified by prep-TLC eluting with 15:1 vol:vol CH$_2$Cl$_2$/7 N methanolic ammonia solution to give the title product, Ex-300, LCMS [M+1] 396.

Example 26, Preparation of 7-fluoro-2-((1-(thiophen-2-ylmethyl)piperidin-4-yl)methyl)imidazo[1,2-c]quinazolin-5-amine Ex-301

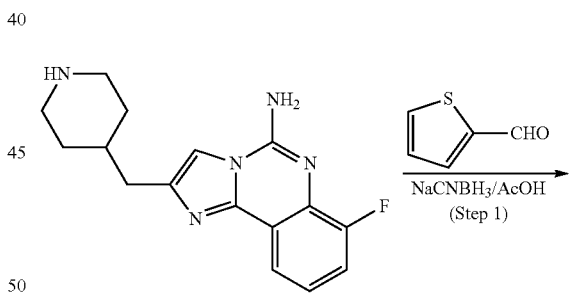

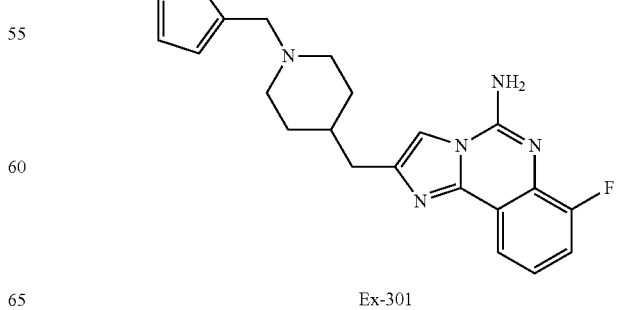

Ex-301

(Step 1) 7-fluoro-2-((1-(thiophen-2-ylmethyl)piperidin-4-yl)methyl)imidazo[1,2-c]quinazolin-5-amine Into a mixture of 0.4 ml of CH₂Cl₂ and 0.4 ml of MeOH was dissolved 7-fluoro-2-(piperidin-4-ylmethyl)imidazo[1,2-c]quinazolin-5-amine (10 mg, 0.033 mmol) and 2-thiophene-carboxaldehyde (18.7 mg) was added acetic acid (0.028 mL), and the reaction mixture was stirred at R/T for 10 min, followed by addition of sodium cyanoborohydride (10.5 mg), then the reaction mixture was stirred at RT overnight. The reaction mixture was evaporated and the crude product was purified by prep-TLC eluting with 15:1 vol:vol CH₂Cl₂/7 N methanolic ammonia solution to give the title product, Ex-301, LCMS [M+1] 396.

Example 27, Preparation of (4-((5-amino-7-fluoro-imidazo[1,2-c]quinazolin-2-yl)methyl)piperidin-1-yl)(pyridin-3-yl)methanone Ex-302

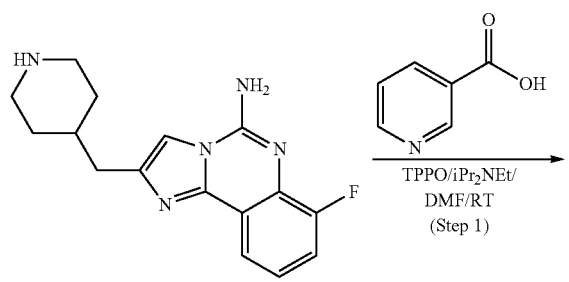

Ex-302

(Step 1)(4-((5-amino-7-fluoroimidazo[1,2-c]quinazolin-2-yl)methyl)piperidin-1-yl)(pyridin-3-yl)methanone Into a solution of 7-fluoro-2-(piperidin-4-ylmethyl)imidazo[1,2-c]quinazolin-5-amine (10 mg, 0.033 mmol), nicotinic acid (4.94 mg, 0.040 mmol) and N, N-disopropylethylamine (34.1 µl, 0.200 mmol) dissolved in 0.5 ml of DMF, was added 2,4,6-tripropyl-1,3,5,2,4,6-trioxatriphosphorinane-2,4,6-trioxide (9.91 µl, 0.050 mmol), and the reaction mixture was stirred at RT for 3 hours, then the reaction mixture was evaporated and the crude product was purified by prep-TLC eluting with 15:1 vol:vol CH₂Cl₂/7 N methanolic ammonia solution to give the title product, Ex-302, LCMS [M+1] 405.

The compounds of Table 14 were prepared by using methodology described herein with appropriate reagent substitutions.

TABLE 14

| Ex No | Structure | LCMS | Name |
|---|---|---|---|
| Ex-303 | 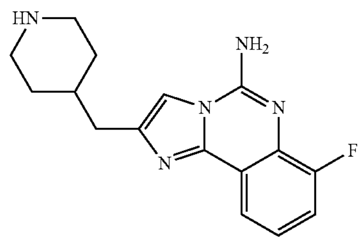 [SMILES: Nc1nc2c(F)cccc2c2nc(CC3CCNCC3)cn12] | 300 (1.01) | 7-fluoro-2-(piperidin-4-ylmethyl)imidazo-[1,2-c]quinazolin-5-amine |
| Ex-304 | 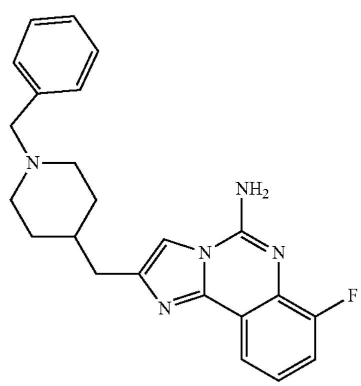 [SMILES: Nc1nc2c(F)cccc2c2nc(CC3CCN(Cc4ccccc4)CC3)cn12] | 390 (1.77) | 2-((1-benzylpiperidin-4-yl)methyl)-7-fluoro-imidazo[1,2-c]quinazolin-5-amine |

TABLE 14-continued

| Ex No | Structure | LCMS | Name |
|---|---|---|---|
| Ex-305 | 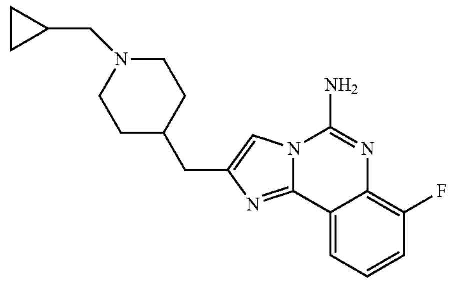 [SMILES: Nc1nc2c(F)cccc2c2nc(CC3CCN(CC4CC4)CC3)cn12] | 354 (1.66) | 2-((1-(cyclopropyl-methyl)piperidin-4-yl)methyl)-7-fluoro-imidazo[1,2-c]quina-zolin-5-amine |
| Ex-306 | 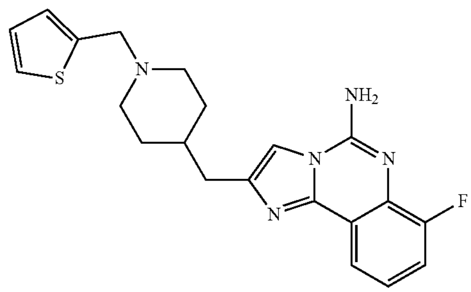 [SMILES: Nc1nc2c(F)cccc2c2nc(CC3CCN(Cc4cccs4)CC3)cn12] | 396 (1.73) | 7-fluoro-2-((1-(thio-phen-2-ylmethyl)-piperidin-4-yl)methyl)-imidazo[1,2-c]quina-zolin-5-amine |
| Ex-307 | 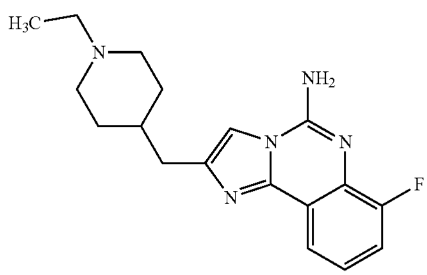 [SMILES: CCN1CCC(Cc2cn3c(N)nc4c(F)cccc4c3n2)CC1] | 328 (1.50) | 2-((1-ethyl-piperidin-4-yl)methyl)-7-fluoro-imidazo[1,2-c]quina-zolin-5-amine |
| Ex-308 | 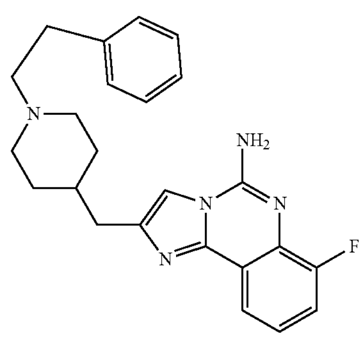 [SMILES: Nc1nc2c(F)cccc2c2nc(CC3CCN(CCc4ccccc4)CC3)cn12] | 404 (1.34) | 7-fluoro-2-((1-phen-ethylpiperidin-4-yl)-methyl)imidazo[1,2-c]quinazolin-5-amine |
| Ex-309 | 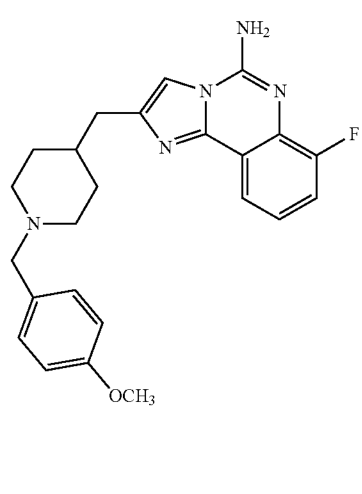 [SMILES: COc1ccc(CN2CCC(Cc3cn4c(N)nc5c(F)cccc5c4n3)CC2)cc1] | 420 (1.31) | 7-fluoro-2-((1-(4-methoxybenzyl)-piperidin-4-yl)-methyl)imidazo-[1,2-c]quinazolin-5-amine |

TABLE 14-continued

| Ex No | Structure | LCMS | Name |
|---|---|---|---|
| Ex-310 | 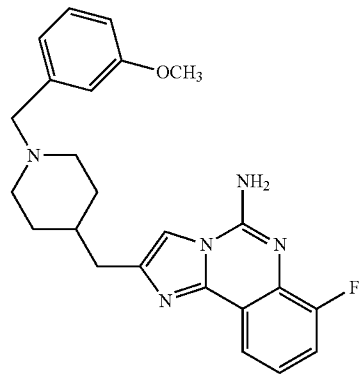 [SMILES: COc1cccc(CN2CCC(Cc3cn4c(N)nc5c(F)cccc5c4n3)CC2)c1] | 420 (1.84) | 7-fluoro-2-((1-(3-methoxybenzyl)-piperidin-4-yl)-methyl)imidazo-[1,2-c]quinazolin-5-amine |
| Ex-311 | 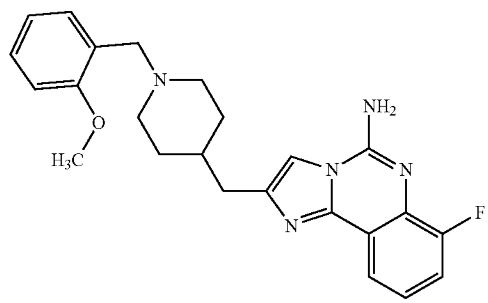 [SMILES: COc1ccccc1CN1CCC(Cc2cn3c(N)nc4c(F)cccc4c3n2)CC1] | 420 (1.85) | 7-fluoro-2-((1-(2-methoxybenzyl)-piperidin-4-yl)-methyl)imidazo-[1,2-c]quinazolin-5-amine |
| Ex-312 | 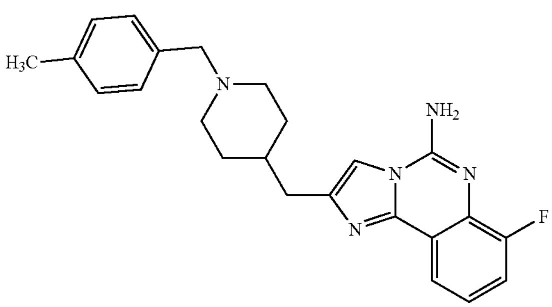 [SMILES: Cc1ccc(CN2CCC(Cc3cn4c(N)nc5c(F)cccc5c4n3)CC2)cc1] | 404 (1.87) | 7-fluoro-2-((1-(4-methylbenzyl)piperidin-4-yl)methyl)-imidazo-[1,2-c]-quinazolin-5-amine |
| Ex-313 | 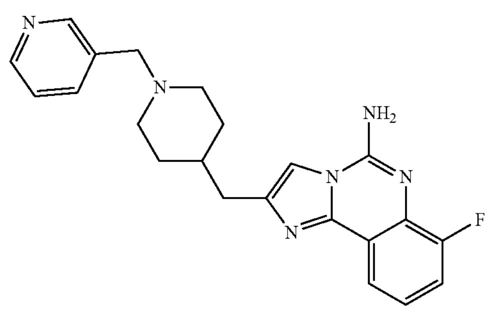 [SMILES: Nc1nc2c(F)cccc2c2nc(CC3CCN(Cc4cccnc4)CC3)cn12] | 391 (1.26) | 7-fluoro-2-((1-(pyridin-3-yl-methyl)piperidin-4-yl)methyl)imidazo-[1,2-c]quinazolin-5-amine |
| Ex-315 | 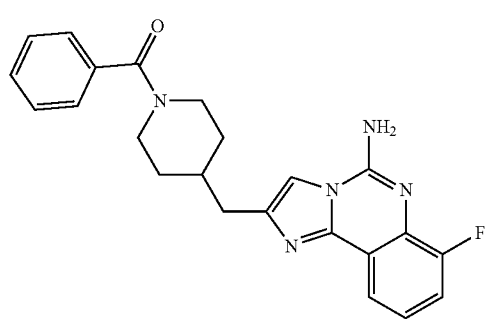 | 404 (1.42) | (4-((5-amino-7-fluoro-imidazo[1,2-c]quina-zolin-2-yl)methyl)-piperidin-1-yl)-(phenyl)methanone |

TABLE 14-continued

| Ex No | Structure | LCMS | Name |
| --- | --- | --- | --- |
| Ex-316 | 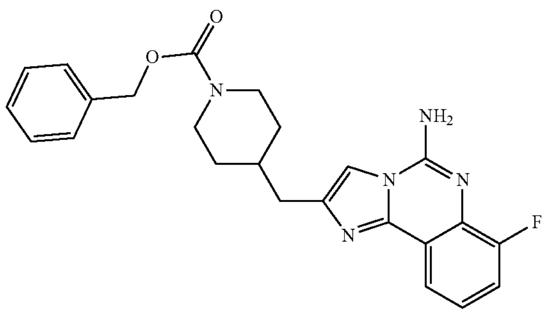 [SMILES: Nc1nc2c(F)cccc2c2nc(CC3CCN(C(=O)OCc4ccccc4)CC3)cn12] | 434 (1.61) | benzyl 4-((5-amino-7-fluoroimidazo[1,2-c]quinazolin-2-yl)methyl)piperidine-1-carboxylate |
| Ex-317 | 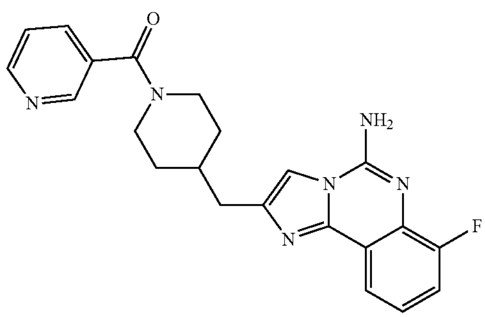 [SMILES: Nc1nc2c(F)cccc2c2nc(CC3CCN(C(=O)c4cccnc4)CC3)cn12] | 405 (1.66) | (4-((5-amino-7-fluoroimidazo-[1,2-c]quinazolin-2-yl)methyl)piperidin-1-yl)(pyridin-3-yl)-methanone |
| Ex-318 | 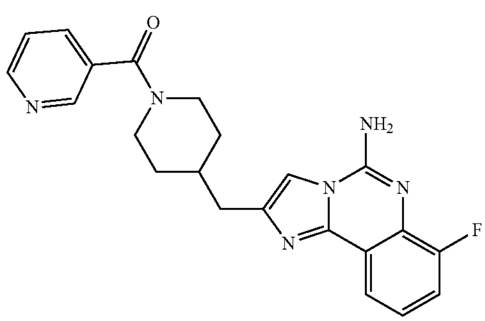 [SMILES: Nc1nc2c(F)cccc2c2nc(CC3CCN(C(=O)c4cccnc4)CC3)cn12] | 405 (1.24) | (4-((5-amino-7-fluoroimidazo[1,2-c]quinazolin-2-yl)methyl)piperidin-1-yl)(pyridin-2-yl)-methanone |
| Ex-319 | 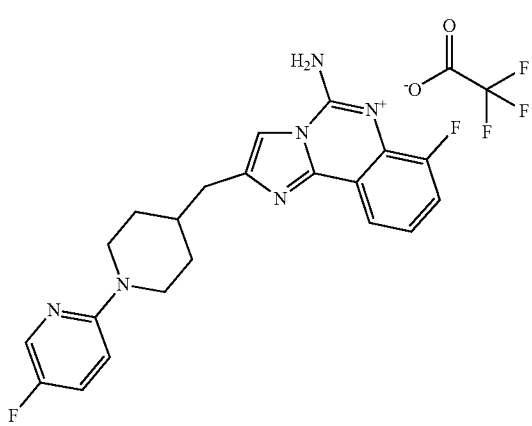 | 395 (1.75) | 5-amino-7-fluoro-2-((1-(5-fluoropyridin-2-yl)piperidin-4-yl)methyl)imidazo[1,2-c]quinazolin-6-ium 2,2,2-trifluoroacetate |

TABLE 14-continued

| Ex No | Structure | LCMS | Name |
|---|---|---|---|
| Ex-320 | 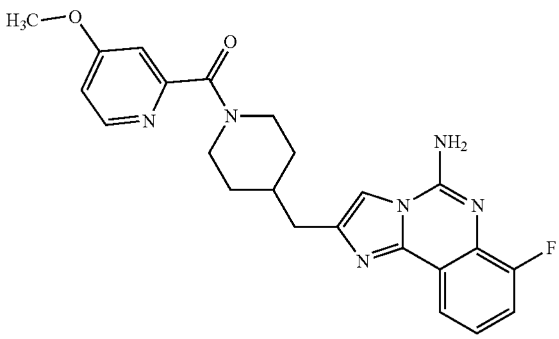 [SMILES: COc1ccnc(C(=O)N2CCC(Cc3cn4c(N)nc5c(F)cccc5c4n3)CC2)c1] | 435 (1.74) | (4-((5-amino-7-fluoroimidazo[1,2-c]quinazolin-2-yl)-methyl)piperidin-1-yl)(4-methoxypyridin-2-yl)methanone |
| Ex-321 | 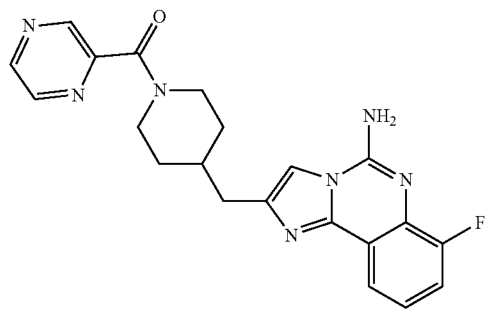 [SMILES: Nc1nc2c(F)cccc2c2nc(CC3CCN(C(=O)c4cnccn4)CC3)cn12] | 406 (1.76) | (4-((5-amino-7-fluoroimidazo[1,2-c]quinazolin-2-yl)-methyl)piperidin-1-yl)(pyrazin-2-yl)-methanone |
| Ex-322 | 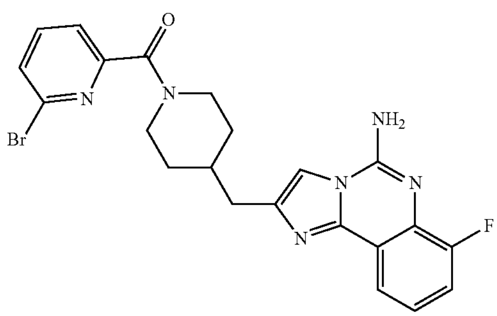 [SMILES: Nc1nc2c(F)cccc2c2nc(CC3CCN(C(=O)c4cccc(Br)n4)CC3)cn12] | 485 (1.91) | (4-((5-amino-7-fluoroimidazo[1,2-c]quinazolin-2-yl)-methyl)piperidin-1-yl)(6-bromopyridin-2-yl)methanone |
| Ex-323 | 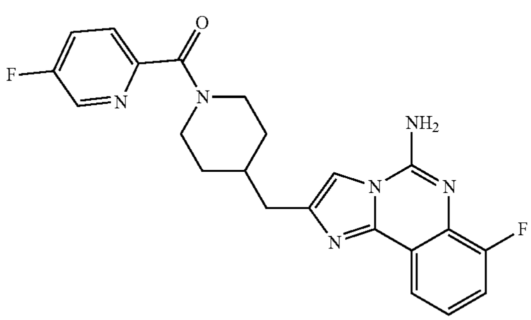 [SMILES: Nc1nc2c(F)cccc2c2nc(CC3CCN(C(=O)c4ccc(F)cn4)CC3)cn12] | 423 (1.83) | (4-((5-amino-7-fluoroimidazo[1,2-c]quinazolin-2-yl)-methyl)piperidin-1-yl)(5-fluoropyridin-2-yl)methanone |
| Ex-324 | 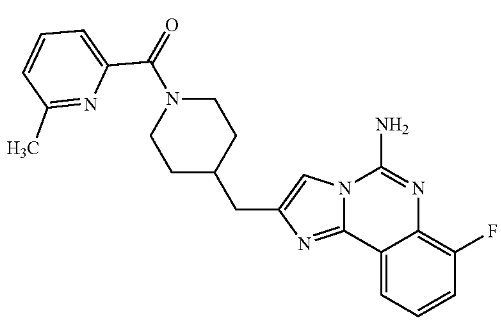 [SMILES: Cc1cccc(C(=O)N2CCC(Cc3cn4c(N)nc5c(F)cccc5c4n3)CC2)n1] | 419 (1.77) | (4-((5-amino-7-fluoroimidazo[1,2-c]quinazolin-2-yl)-methyl)piperidin-1-yl)(6-methylpyridin-2-yl)methanone |

TABLE 14-continued

| Ex No | Structure | LCMS | Name |
|---|---|---|---|
| Ex-325 | 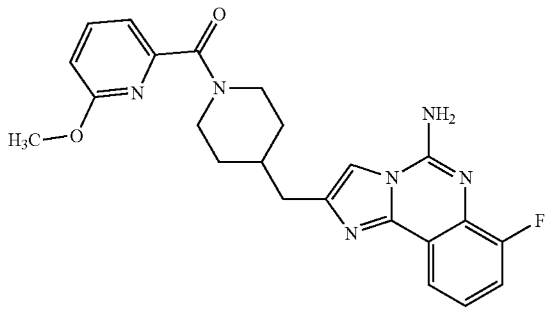 [SMILES: COc1cccc(C(=O)N2CCC(Cc3cn4c(N)nc5c(F)cccc5c4n3)CC2)n1] | 435 (1.89) | (4-((5-amino-7-fluoroimidazo[1,2-c]-quinazolin-2-yl)-methyl)piperidin-1-yl)(6-methoxypyridin-2-yl)methanone |
| Ex-326 | 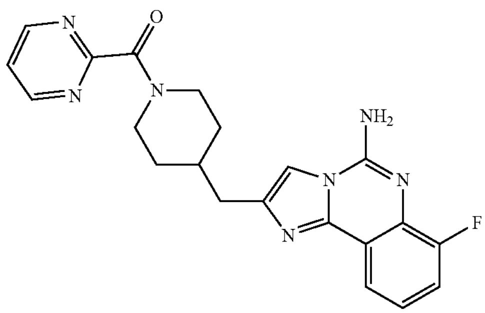 [SMILES: Nc1nc2c(F)cccc2c2nc(CC3CCN(C(=O)c4ncccn4)CC3)cn12] | 406 (1.2) | (4-((5-amino-7-fluoroimidazo[1,2-c]quinazolin-2-yl)-methyl)piperidin-1-yl)(pyrimidin-2-yl)-methanone |
| Ex-327 | 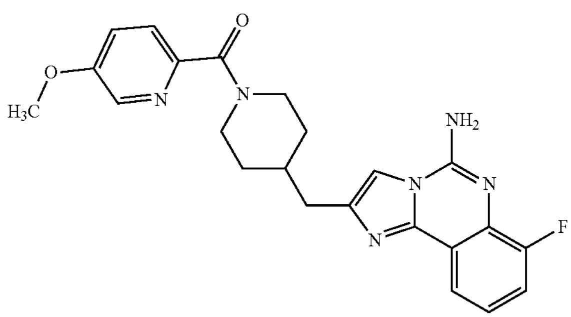 [SMILES: COc1ccc(C(=O)N2CCC(Cc3cn4c(N)nc5c(F)cccc5c4n3)CC2)nc1] | 435 (1.34) | (4-((5-amino-7-fluoroimidazo[1,2-c]quinazolin-2-yl)-methyl)piperidin-1-yl)(5-methoxypyridin-2-yl)methanone |

A2a Activity of Compounds of the Invention

Binding affinities of compounds of the invention for the human A2a receptor were determined in a competition binding assay using Scintillation Proximity technology. Thus, 0.3 µg of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 100 µg of wheat germ agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination:

Materials

HEK293 cells expressing the human, rat, dog or monkey adenosine 2a receptor (Purchased from Perkin-Elmer #RBHA2AM400UA).

The Tritiated compound was prepared according to published methods.

Wheat germ agglutinin-coated yttrium silicate SPA beads (GE Healthcare #RPNQ0023). Dilute to 25 mg/ml in assay buffer.

Assay Buffer was prepared using Dulbecco's calcium and magnesium free phosphate buffered saline+10 mMMgCl$_2$ Adenosine deaminase from calf intestine, 10 mg/2 ml (Roche #10 102 105 001).

DMSO

A2a antagonist standard (9-chloro-1-(2-furanyl)-[1,2,4]triazolo1,5-c]quinazolin-5-amine from Tocris Bioscience)

Compound Dilution

Make eight 1:3 serial dilutions in 100% DMSO from a 3 mM compound stock

Transfer 50 nl of compound into a 384-well OptiPlate (Perkin Elmer).

Typically, final concentrations of compound used in the assay ranged from 3000 nM to 0.152 nM.

Radioisotope

Dilute a solution of the Tritiated compound to 1.25 nM in assay buffer. This is a 2.5× solution. The final concentration in the assay is 0.5 nM. Calculate the concentration by counting two 5 µl aliquots.

Membrane Preparation

Use 0.25 ug of membrane/well. Dilute membranes to 9.7 µg/ml in assay buffer. Treat with 20 ug/ml adenosine deaminase (ADA) for 15 minutes at room temperature to degrade endogenous adenosine.

Membrane-Bead Mixture

Use 100 µg/well wheat germ agglutinin-coated yttrium silicate SPA beads.

Mix ADA-treated membranes and SPA beads together for 30 min prior to assay.

Assay Assembly

To the Perkin-Elmer Optiplate-384 containing the compound titration add 20 µl of 2.5× solution of the Tritiated compound and 30 µl of the membrane-bead mixture. Incubate for one hour at room temperature with agitation.

Include total binding (assay buffer+1% DMSO) and non-specific binding (CGS15943, 1 µM) wells.

Counting

Allow the beads to settle for one hour.

Count in TopCount.

Calculations

A curve fitting program (i.e., Prism, Activity Base, Chemcart) is used to determine the EC50. The Ki value is calculated using the Cheng-Prusoff equation.

$$Ki = EC50/(1+(\text{radioligand concentration}/Kd))$$

Using the foregoing assay method, the following results were obtained using various of the compounds of the invention described herein. Each example compound tested is reported in the following format: Ex-No.: A2a (EC50 value reported in nM). Thus, for example, the compound Ex-2 from Example 1 was determined to have an EC50 using the above-described assay, of 20 nM, and is accordingly reported as "Ex-2: A2a Ki=20":

Ex-01 A2a Ki=0.4; Ex-02 A2a Ki=5.8; Ex-03 A2a Ki=2.6; Ex-04 A2a Ki=89.6; Ex-05 A2a Ki=642; Ex-06 A2a Ki=0.9; Ex-07 A2a Ki=4.6; Ex-08 A2a Ki=3.6; Ex-09 A2a Ki=6.3; Ex-10 A2a Ki=6.2; Ex-11 A2a Ki=2.0; Ex-12 A2a Ki=7.7; Ex-13 A2a Ki=920; Ex-14 A2a Ki=2.3; Ex-15 A2a Ki=2.0; Ex-16 A2a Ki=0.3; Ex-17 A2a Ki=0.8; Ex-18 A2a Ki=1.0; Ex-19 A2a Ki=4.5; Ex-20 A2a Ki=1.4; Ex-21 A2a Ki=0.8; Ex-22 A2a Ki=1.9; Ex-23 A2a Ki=2.1; Ex-24 A2a Ki=10; Ex-25 A2a Ki=10.2; Ex-26 A2a Ki=0.4; Ex-27 A2a Ki=2.6; Ex-28 A2a Ki=2.1; Ex-29 A2a Ki=1.6; Ex-30 A2a Ki=38; Ex-31 A2a Ki=2.1; Ex-32 A2a Ki=2.0; Ex-33 A2a Ki=3.0; Ex-34 A2a Ki=21; Ex-35 A2a Ki=6.0; Ex-36 A2a Ki=2.8; Ex-37 A2a Ki=18; Ex-38 A2a Ki=2.3; Ex-39 A2a Ki=9.8; Ex-40 A2a Ki=10; Ex-41 A2a Ki=15; Ex-42 A2a Ki=2.8; Ex-43 A2a Ki=5.2; Ex-44 A2a Ki=14; Ex-45 A2a Ki=4.6; Ex-46 A2a Ki=7.4; Ex-47 A2a Ki=5.9; Ex-48 A2a Ki=3.0; Ex-49 A2a Ki=6.2; Ex-50 A2a Ki=3.7; Ex-51 A2a Ki=23.9; Ex-52 A2a Ki=11; Ex-53 A2a Ki=3.7; Ex-54 A2a Ki=3.8; Ex-55 A2a Ki=5.1; Ex-56 A2a Ki=16; Ex-57 A2a Ki=18; Ex-58 A2a Ki=9.9; Ex-59 A2a Ki=2.9; Ex-60 A2a Ki=2.0; Ex-61 A2a Ki=27; Ex-62 A2a Ki=2.2; Ex-63 A2a Ki=102; Ex-64 A2a Ki=7.4; Ex-65 A2a Ki=5.1; Ex-66 A2a Ki=11.5; [Same as Ex-70] Ex-67 A2a Ki=2.2; Ex-68 A2a Ki=7.8; Ex-69 A2a Ki=35.6; Ex-70 A2a Ki=11.5 [Same as Ex-66] Ex-71 A2a Ki=5.3; Ex-72 A2a Ki=20.0; Ex-73 A2a Ki=4.2; Ex-74 A2a Ki=4.5; Ex-75 A2a Ki=6.0; Ex-76 A2a Ki=10.0; Ex-77 A2a Ki=12.0; Ex-78 A2a Ki=120; Ex-79 A2a Ki=2.4; Ex-80 A2a Ki=11; Ex-81 A2a Ki=14; Ex-82 A2a Ki=27; Ex-83 A2a Ki=6.9; Ex-84 A2a Ki=3.8; Ex-85 A2a Ki=9.7; Ex-86 A2a Ki=44; Ex-87 A2a Ki=40; Ex-88 A2a Ki=84; Ex-89 A2a Ki=6.3; Ex-90 A2a Ki=66; Ex-91 A2a Ki=65; Ex-92 A2a Ki=13; Ex-93 A2a Ki=2.5; Ex-94 A2a Ki=150; Ex-95 A2a Ki=6.8; Ex-96 A2a Ki=36; Ex-97 A2a Ki=96; Ex-98 A2a Ki=6.7; Ex-99 A2a Ki=11.2; Ex-100 A2a Ki=4.4; Ex-101 A2a Ki=8.5; Ex-102 A2a Ki=3.8; Ex-103 A2a Ki=26.4; Ex-104 A2a Ki=407; Ex-105 A2a Ki=159.9; Ex-106 A2a Ki=7.1; Ex-107 A2a Ki=4.3; Ex-108 A2a Ki=130; Ex-109 A2a Ki=2463; Ex-110 A2a Ki=53.2; Ex-111 A2a Ki=160; Ex-112 A2a Ki=520; Ex-113 A2a Ki=76; Ex-114 A2a Ki=130; Ex-115 A2a Ki=380; Ex-116 A2a Ki=1000; Ex-117 A2a Ki=4.0; Ex-118 A2a Ki=3.9; Ex-119 A2a Ki=210; Ex-120 A2a Ki=4.2; Ex-121 A2a Ki=3.7; Ex-122 A2a Ki=11; Ex-123 A2a Ki=9.2; Ex-124 A2a Ki=18; Ex-125 A2a Ki=8.1; Ex-126 A2a Ki=38; Ex-127 A2a Ki=64; Ex-128 A2a Ki=97; Ex-129 A2a Ki=51; Ex-130 A2a Ki=46; Ex-131 A2a Ki=8.4; Ex-132 A2a Ki=150; Ex-133 A2a Ki=22.2; Ex-134 A2a Ki=7.9; Ex-135 A2a Ki=10.4; Ex-136 A2a Ki=12; Ex-137 A2a Ki=13.1; Ex-138 A2a Ki=28; Ex-139 A2a Ki=No data-specifically exemplified; Ex-140 A2a Ki=9.1; Ex-141 A2a Ki=9.5; Ex-142 A2a Ki=130; Ex-143 A2a Ki=4.0; Ex-144 A2a Ki=13; Ex-145 A2a Ki=28; Ex-146 A2a Ki=33; Ex-147 A2a Ki=54; Ex-149 A2a Ki=>2200; Ex-150 A2a Ki=760; Ex-151 A2a Ki=>2200; Ex-152 A2a Ki=35; Ex-153 A2a Ki=>2200; Ex-154 A2a Ki=48; Ex-155 A2a Ki=130; Ex-156 A2a Ki=28; Ex-157 A2a Ki=1.5; Ex-158 A2a Ki=33.9; Ex-159 A2a Ki=5.9; Ex-160 A2a Ki=80.6; Ex-161 A2a Ki=39.4; Ex-162 A2a Ki=29.7; Ex-163 A2a Ki=12.8; Ex-164 A2a Ki=>2200; Ex-165 A2a Ki=10000; Ex-166 A2a Ki=1400; Ex-167 A2a Ki=16; Ex-168 A2a Ki=81; Ex-169 A2a Ki=34; Ex-170 A2a Ki=11.5; Ex-171 A2a Ki=20; Ex-172 A2a Ki=18; Ex-173 A2a Ki=31; Ex-174 A2a Ki=2.3; Ex-175 A2a Ki=21; Ex-176 A2a Ki=10; Ex-177 A2a Ki=49; Ex-178 A2a Ki=27; Ex-179 A2a Ki=31; Ex-180 A2a Ki=53; Ex-181 A2a Ki=110; Ex-182 A2a Ki=75; Ex-183 A2a Ki=125.9; Ex-184 A2a Ki=90; Ex-185 A2a Ki=65; Ex-186 A2a Ki=53.8; Ex-187 A2a Ki=190.2; Ex-188 A2a Ki=54; Ex-189 A2a Ki=4.5; Ex-190 A2a Ki=21; Ex-191 A2a Ki=23; Ex-192 A2a Ki=11; Ex-193 A2a Ki=13; Ex-194 A2a Ki=21; Ex-195 A2a Ki=10; Ex-196 A2a Ki=11; Ex-197 A2a Ki=22; Ex-198 A2a Ki=5.6; Ex-199 A2a Ki=260; Ex-200 A2a Ki=4.6; Ex-201 A2a Ki=14; Ex-202 A2a Ki=5.2; Ex-203 A2a Ki=11; Ex-204 A2a Ki=12; Ex-205 A2a Ki=13; Ex-206 A2a Ki=110; Ex-207 A2a Ki=2.1; Ex-208 A2a Ki=3.2; Ex-209 A2a Ki=2.9; Ex-210 A2a Ki=6.1; Ex-211 A2a Ki=14; Ex-212 A2a Ki=5.5; Ex-213 A2a Ki=10; Ex-214 A2a Ki=11; Ex-215 A2a Ki=7.4; Ex-216 A2a Ki=10; Ex-217 A2a Ki=7.8; Ex-218 A2a Ki=6.1; Ex-219 A2a Ki=3.6; Ex-220 A2a Ki=24; Ex-221 A2a Ki=6.6; Ex-222 A2a Ki=11; Ex-223 A2a Ki=210; Ex-224 A2a Ki=8.2; Ex-225 A2a Ki=35; Ex-226 A2a Ki=29; Ex-227 A2a Ki=240; Ex-228 A2a Ki=180; Ex-229 A2a Ki=15; Ex-230 A2a Ki=61.1; Ex-231 A2a Ki=10; Ex-232 A2a Ki=18; Ex-233 A2a Ki=10; Ex-234 A2a Ki=2.6; Ex-235 A2a Ki=2.8; Ex-236 A2a Ki=6.4; Ex-237 A2a Ki=37; Ex-238 A2a Ki=170; Ex-239 A2a Ki=130; Ex-240 A2a Ki=30.6; Ex-241 A2a Ki=13; Ex-242 A2a Ki=4.3; Ex-243 A2a Ki=ND; Ex-244 A2a Ki=49.6; Ex-245 A2a Ki=151.6; Ex-246 A2a Ki=21; Ex-247 A2a Ki=120; Ex-248 A2a Ki=9; Ex-249 A2a Ki=18; Ex-250 A2a Ki=2.0; Ex-251 A2a Ki=91; Ex-252 A2a Ki=7.2; Ex-253 A2a Ki=3.7; Ex-254 A2a Ki=5.1; Ex-255 A2a Ki=6.1; Ex-256 A2a Ki=4.5; Ex-257 A2a Ki=3.6; Ex-258 A2a Ki=2.3; Ex-259 A2a Ki=29; Ex-260 A2a Ki=15; Ex-261 A2a Ki=5.4; Ex-262 A2a Ki=53; Ex-263 A2a Ki=2.9; Ex-264 A2a Ki=2.5; Ex-265 A2a Ki=86; Ex-266 A2a Ki=220; Ex-267 A2a Ki=710; Ex-268 A2a Ki=66; Ex-269 A2a Ki=200; Ex-270 A2a Ki=100; Ex-271 A2a Ki=12; Ex-272 A2a Ki=380; Ex-273 A2a Ki=110; Ex-274 A2a Ki=32; Ex-275 A2a Ki=43; Ex-276 A2a Ki=130; Ex-277 A2a Ki=430; Ex-278 A2a Ki=61; Ex-279 A2a Ki=34; Ex-280 A2a Ki=100; Ex-281 A2a Ki=170; Ex-282 A2a Ki=32; Ex-283 A2a Ki=21; Ex-284 A2a Ki=33; Ex-285 A2a Ki=40; Ex-286 A2a Ki=19; Ex-287 A2a Ki=35; Ex-288 A2a Ki=55; Ex-289 A2a Ki=640; Ex-290 A2a Ki=46; Ex-291 A2a Ki=47; Ex-292 A2a Ki=49.6; Ex-293 A2a Ki=151.6; Ex-294 A2a Ki=5.3; Ex-295 A2a Ki=6.2; Ex-296 A2a Ki=28; Ex-297 A2a Ki=2.3; Ex-298 A2a Ki=14; Ex-299 A2a Ki=ND; Ex-300 A2a Ki=(Same as Ex-314) 12; Ex-301 A2a Ki=ND; Ex-302 A2a Ki=ND; Ex-303 A2a Ki=170; Ex-304 A2a Ki=45; Ex-305 A2a Ki=220; Ex-306 A2a Ki=45; Ex-307 A2a Ki=120; Ex-308 A2a Ki=300; Ex-309 A2a Ki=150; Ex-310 A2a Ki=56; Ex-311 A2a Ki=94; Ex-312 A2a Ki=48; Ex-313 A2a Ki=310; Ex-314 [same as Ex300] A2a Ki=12; Ex-315 A2a Ki=82; Ex-316 A2a Ki=30; Ex-317 A2a Ki=100; Ex-318 A2a Ki=41; Ex-319 A2a Ki=31; Ex-320 A2a Ki=30; Ex-321 A2a Ki=34; Ex-322 A2a Ki=26 Ex-323 A2a Ki=17 Ex-324 A2a Ki=44; Ex-325 A2a Ki=54; Ex-326 A2a Ki=47; Ex-327 A2a Ki=21;

What is claimed is:
1. A compound of Formula I:

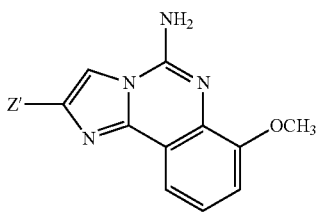

Formula I or a pharmaceutically acceptable salt thereof, wherein:
Z' is CH$_2$-phenyl, wherein the phenyl is optionally substituted with one or two R$^{2a}$ substituents;
each R$^{2a}$ is independently halogen, C$_{1-5}$ alkyl, CH$_2$-piperazin-1-yl, CH$_2$-phenyl, C(O)R$^{2i}$, N(R$^{2c}$)$_2$, OH, pyrrolidin-1-yl, piperidin-1-yl, piperazin-1-yl, 1-(acetyl)piperazin-4-yl, morpholin-4-yl, phenyl, pyridinyl, pyrazin-2-yl, pyrimidinyl, benzo[c][1,2,5]oxadiazol-4-yl, or benzo[c][1,2,5]oxadiazol-5-yl;
wherein each C$_{1-5}$ alkyl is optionally and independently substituted with one or more substituents independently selected from the group consisting of F, OH, and morpholin-4-yl;
wherein each pyrrolidin-1-yl and piperidin-1-yl is optionally and independently substituted with one R$^{2d}$ substituent;
wherein each piperazin-1-yl is optionally and independently substituted with one R$^{2e}$ substituent;
wherein each phenyl is optionally and independently substituted with one R$^{2b}$ substituent; and
wherein each pyridinyl is optionally and independently substituted with one R$^g$ substituent;

each R$^{2b}$ is independently OCH$_3$ or 4-[CH(CH$_3$)morpholin-4-yl];
each R$^{2c}$ is independently H or CH$_3$;
each R$^{2d}$ is independently morpholin-4-yl;
each R$^{2e}$ is independently CH$_2$C(O)CH$_3$, phenyl, pyrimidin-2-yl, or benzo[d]oxazol-2-yl, wherein each phenyl is optionally and independently substituted with one R$^{2f}$ substituent;
each R$^{2f}$ is independently OCH$_2$CH$_2$OCH$_3$;
each R$^g$ is independently F, CF$_3$, or morpholin-4-yl; and
each R$^{2i}$ is independently NH—CH$_2$CH$_2$-morpholin-4-yl, NH—CH$_2$CH(morpholin-4-yl)(pyridin-3-yl), NH-(1,1-cyclopropylene)-phenyl, NH-phenyl, NH-pyridinyl, NH-(1-methylbenzo [d]imidazol-2-ye, or 5-(CH$_2$-morpholin-4-yl)-1,3,4-oxadiazol-2-yl.

2. A compound selected from the group consisting of:

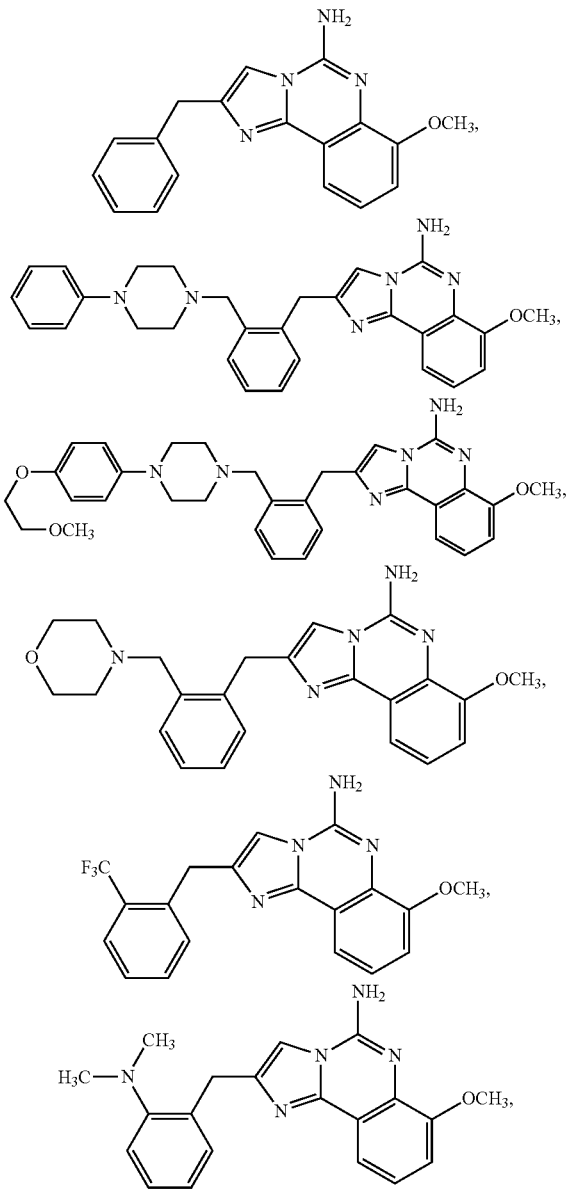

-continued
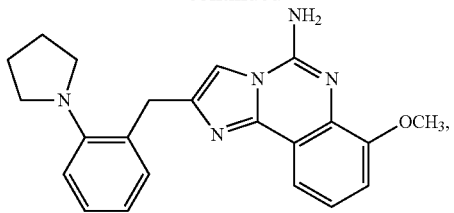
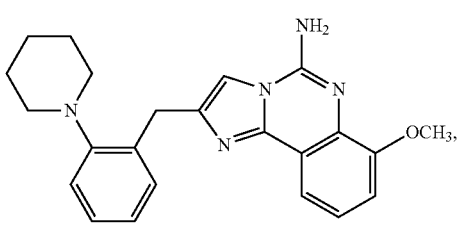
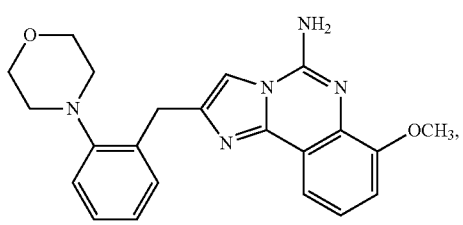
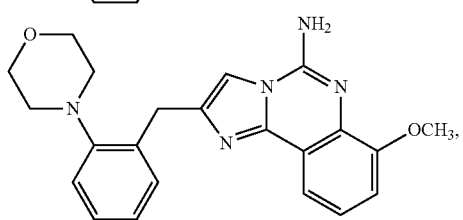
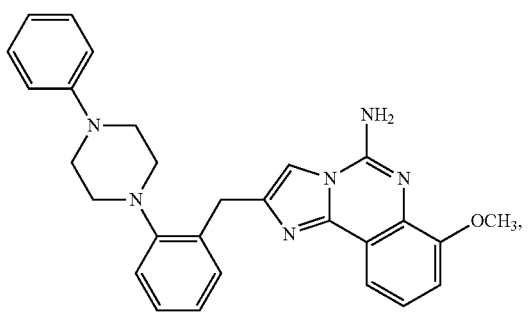
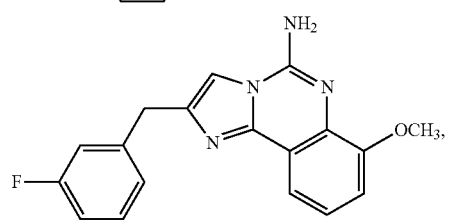
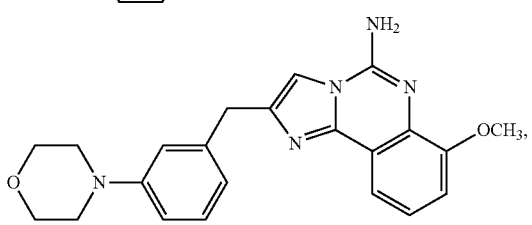
-continued
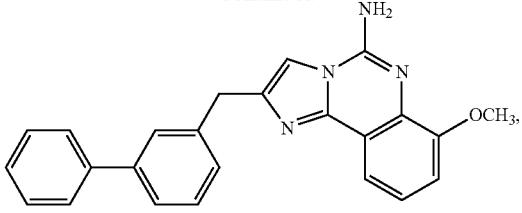
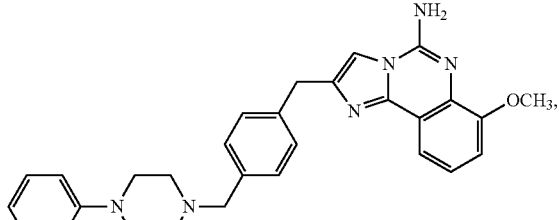
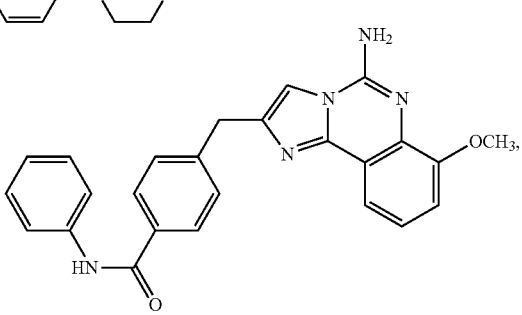
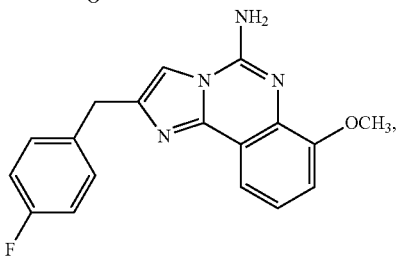
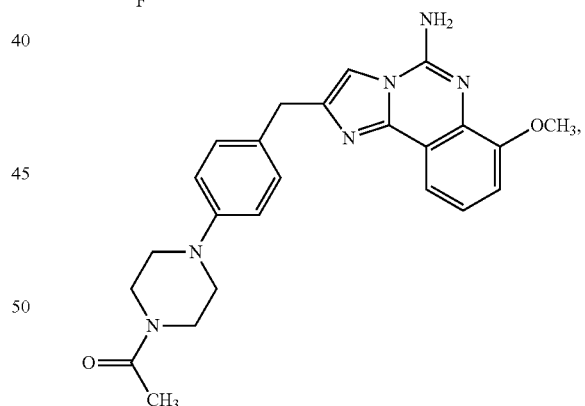
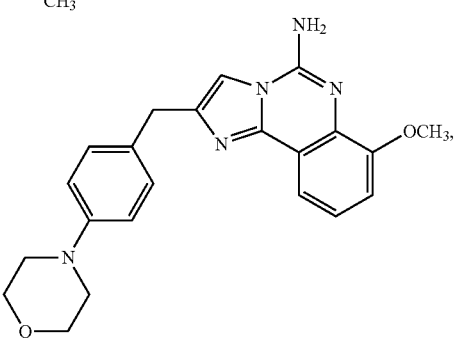

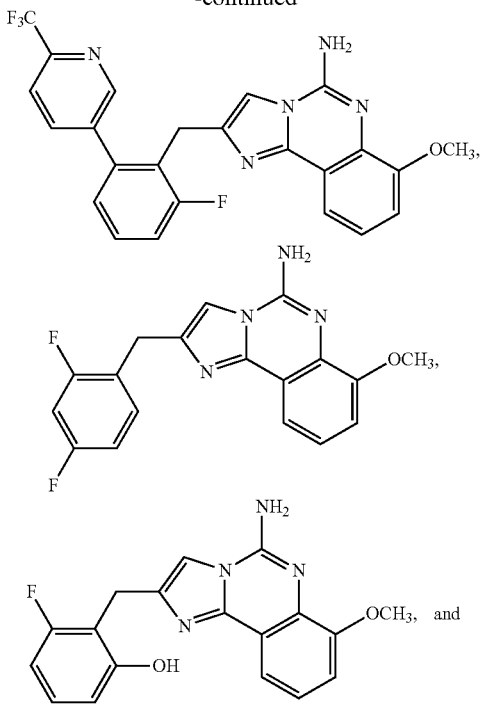

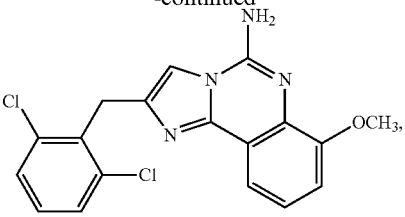

or a pharmaceutically acceptable salt thereof.

3. A pharmaceutical composition comprising at least one pharmaceutically acceptable excipient and a compound of claim 2, or a pharmaceutically acceptable salt thereof.

4. A method for inhibiting adenosine signaling in tumor immunosuppression in a patient, wherein the method comprises administering to the patient in need thereof an effective amount of a compound of claim 2, or a pharmaceutically acceptable salt thereof.

5. A method for treating a central nervous system disorder in a patient, wherein the method comprises administering to the patient in need thereof an effective amount of a compound of claim 2, or a pharmaceutically acceptable salt thereof.

* * * * *